US008435494B2

(12) United States Patent
Gelfand

(10) Patent No.: US 8,435,494 B2
(45) Date of Patent: May 7, 2013

(54) MESOTHELIN ANTIBODY PROTEIN FUSIONS AND METHODS OF USE

(75) Inventor: Jeffrey A. Gelfand, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/107,624

(22) Filed: May 13, 2011

(65) Prior Publication Data

US 2012/0134992 A1 May 31, 2012

Related U.S. Application Data

(63) Continuation of application No. 12/291,104, filed on Nov. 6, 2008, now Pat. No. 7,943,133.

(51) Int. Cl.

| | |
|---|---|
| ***A61K 49/00*** | (2006.01) |
| ***A61K 39/00*** | (2006.01) |
| ***A61K 39/38*** | (2006.01) |

(52) U.S. Cl.

USPC ....... 424/9.1; 424/9.2; 424/133.1; 424/134.1; 424/135.1; 424/136.1; 424/184.1; 424/185.1

(58) Field of Classification Search .................. 424/9.1, 424/9.2, 133.1, 134.1, 135.1, 136.1, 184.1, 424/185.1

See application file for complete search history.

(56) References Cited

U.S. PATENT DOCUMENTS

| | | | |
|---|---|---|---|
| 6,338,952 | B1 | 1/2002 | Young |
| 7,189,396 | B1 | 3/2007 | Weisbart |
| 2005/0221395 | A1 | 10/2005 | Zabrecky et al. |
| 2009/0068184 | A1 | 3/2009 | Gelfand |

FOREIGN PATENT DOCUMENTS

| | | | |
|---|---|---|---|
| WO | 2006099141 | A2 | 9/2006 |
| WO | 2007136892 | A2 | 11/2007 |

OTHER PUBLICATIONS

S. Dubel et al., "Bifunctional and Multimeric complexes of streptavidin fused to single chain antibodies (scFv)", J. Immunol. Methods, 178(2), pp. 201-209 (1995). [Abstract only].

W. Ito et al., "Development of an Artificial Antibody System with Multiple Valency Using an Fv Fragment Fused to a Fragment of Protein A", The Journal of Biological Chemistry, 268(27), pp. 20668-20675 (1993).

J. Goncalves et al., "Functional Neutralization of HIV-1 Vif Protein by Intracellular Immunization Inhibits Reverse Transcription and Viral Replication", The Journal of Biological Chemisty, 277(35), pp. 32036-32045 (2002).

R. Hassan et al., "Mesothelin targeted cancer immunotherapy", Eur. J. Cancer, 44(1), pp. 46-53 (2008).

J.E. Hansen et al., "Antibody-Mediated Transduction of Therapeutic Proteins into Living Cells", The Scientific World Journal, vol. 5, pp. 782-788 (2005).

J.E. Hansen et al., "Antibody-mediated Hsp70 Protein Therapy", Brain Research, vol. 1088, pp. 187-196 (2006).

B. Cochlovius et al., "Cure of Burkitt's Lymphoma in Severe Combined Immunodeficiency Mice by T Cells, Tetravalent CD3×CD19 Tandem Diabody, and CD28 Costimulation", Cancer Research, vol. 60, pp. 4336-4341 (2000).

International Search Report and Written Opinion from PCT/US09/05991.

*Primary Examiner* — Rodney P. Swartz

(74) *Attorney, Agent, or Firm* — Edwards Wildman Palmer LLP; Peter C. Lauro, Esq.; Elbert Chiang

(57) ABSTRACT

The invention relates to fusion proteins comprising a stress protein fused with an engineered antibody or fragment that binds to mesothelin, or a stress protein fused with a biotin-binding protein in combination with a biotinylated engineered antibody or fragment that binds to mesothelin. The invention also relates to fusion proteins comprising a stress protein fused with an antibody binding protein in combination with an engineered antibody or fragment that binds to mesothelin. The invention also relates to fusion proteins comprising an engineered antibody or fragment that binds specifically to mesothelin fused in frame with a biotin binding protein. The invention also provides fusion proteins comprising an engineered antibody or fragment, that binds to mesothelin, fused with an antibody binding protein. The invention also relates to methods of using fusion proteins of the invention to induce an immune response to mesothelin and to treat disease.

24 Claims, 59 Drawing Sheets

Nucleic Acid and Amino Acid sequences of MTBHSP70 (C) hinge anti-mesothelin scFv His-tag
+1 M A H H H H H H H H H H G A L E V L F Q G P G Y·
1 ATGGCACATC ACCACCATCA TCACCATCAC CACCACGGTG CACTTGAAGT CCTCTTTCAG GGACCCGGGT His-tag
MTBHSP70sk
+1 ·Y Q D P V Q V D A A A M A R A V G I D L G T T N·
71 ACCAGGATCC TGTACAAGTC GACGCGGCCG CAATGGCTCG TGCGGTCGGG ATCGACCTCG GGACCACCAA MTBHSP70sk
+1 ·N S V V S V L E G G D P V V V A N S E G S R T T
141 CTCCGTCGTC TCGGTTCTGG AAGGTGGCGA CCCGGTCGTC GTCGCCAACT CCGAGGGCTC CAGGACCACC MTBHSP70sk
+1 P S I V A F A R N G E V L V G Q P A K N Q A V T·
211 CCGTCAATTG TCGCGTTCGC CCGCAACGGT GAGGTGCTGG TCGGCCAGCC CGCCAAGAAC CAGGCGGTGA MTBHSP70sk
+1 ·T N V D R T V R S V K R M G S D W S I E I D G·
281 CCAACGTCGA TCGCACCGTG CGCTCGGTCA AGCGACACAT GGGCAGCGAC TGGTCCATAG AGATTGACGG MTBHSP70sk
+1 ·G K K Y T A P E I S A R I L M K L K R D A E A Y
351 CAAGAAATAC ACCGCGCCGG AGATCAGCGC CCGCATTCTG ATGAAGCTGA AGCGCGACGC CGAGGCCTAC MTBHSP70sk
+1 L G E D I T D A V I T T P A Y F N D A Q R Q A T·
421 CTCGGTGAGG ACATTACCGA CGCGGTTATC ACGACGCCCG CCTACTTCAA TGACGCCCAG CGTCAGGCCA

FIG. 2

Nucleic Acid and Amino Acid sequences of MTBHSP70 (C) hinge anti-mesothelin scFv

```
                                    MTBHSP70sk
 +1  ·T K D A G Q I A G L N V L R I V N E P T A A L·
491  CCAAGGACGC CGGCCAGATC GCCGGCCTCA ACGTGCTGCG GATCGTCAAC GAGCCGACCG CTGCAGCGCT
                                    MTBHSP70sk
 +1  ·L A Y G L D K G E K E Q R I L V F D L G G G T F
561  GGCCTACGGC CTCGACAAGG GCGAGAAGGA GCAGCGAATC CTGGTCTTCG ACTTGGGTGG TGGCACTTTC
                                    MTBHSP70sk
 +1   D V S L L E I G E G V V E V R A T S G D N H L G·
631  GACGTTTCCC TGCTGGAGAT CGGCGAGGGT GTGGTTGAGG TCCGTGCCAC TTCGGGTGAC AACCACCTCG
                                    MTBHSP70sk
 +1  ·G G D D W D Q R V V D W L V D K F K G T S G I D·
701  GCGGCGACGA CTGGGACCAG CGGGTCGTCG ATTGGCTGGT GGACAAGTTC AAGGGCACCA GCGGCATCGA
                                    MTBHSP70sk
 +1  ·D L T K D K M A M Q R L R E A A E K A K I E L S
771  TCTGACCAAG GACAAGATGG CGATGCAGCA GCTGCGGGAA GCCGCCGAGA AAGCAAAGAT CGAGCTGAGT
                                    MTBHSP70sk
 +1   S S Q S T S I N L P Y I T V D A D K N P L F L D·
841  TCGAGTCAGT CCACCTCGAT CAACCTGCCC TACATCACCG TCGACGCCGA CAAGAACCCG TTGTTCTTAG
                                    MTBHSP70sk
 +1  ·D E Q L T R A E F Q R I T Q D L L D R T R K P F·
911  ACGAGCAGCT GACCCGCGCG GAGTTCCAAC GGATCACTCA GGACCTGCTG GACCGCACTC GCAAGCCGTT
```

FIG. 2 CONT.

Nucleic Acid and Amino Acid sequences of MTBHSP70 (C) hinge anti-mesothelin scFv

```
                                        MTBHSP70sk
  +1 ·F Q  S   V   I   A   D   T   G   I   S   V   S   E   I   D   H   V   V   L   V   G   G   S
 981  CCAGTCGGTG ATCGCTGACA CCGGCATTTC GGTGTCGGAG ATCGATCACG TTGTGCTCGT GGGTGGTTCG

                                        MTBHSP70sk
  +1   T  R  M   P   A   V   T   D   L   V   K   E   L   T   G   G   K   E   P   N   K   G   V  N·
1051  ACCCGGATGC CCGCGGTGAC CGATCTGGTC AAGGAACTCA CCGGCGGCAA GGAACCCAAC AAGGGCGTCA

                                        MTBHSP70sk
  +1 ·N  P  D   E   V   V   A   V   G   A   A   L   Q   A   G   V   L   K   G   E   V   K   D  V·
1121  ACCCCGATGA GGTTGTCGCG GTGGGAGCCG CTCTGCAGGC CGGCGTCCTC AAGGGCGAGG TGAAAGACGT

                                        MTBHSP70sk
  +1 ·V L  L   L   D   V   T   P   L   S   L   G   I   E   T   K   G   G   V   M   T   R   L   I
1191  TCTGCTGCTT GATGTTACCC CGCTGAGCCT GGGTATCGAG ACCAAGGGCG GGGTGATGAC CAGGCTCATC

                                        MTBHSP70sk
  +1   E  R  N   T   T   I   P   T   K   R   S   E   S   F   T   T   A   D   D   N   Q   P   S  V·
1261  GAGCGCAACA CCACGATCCC CACCAAGCGG TCGGAGTCTT TCACCACCGC CGACGACAAC CAACCGTCGG

                                        MTBHSP70sk
  +1 ·V  Q  I   Q   V   Y   Q   G   E   R   E   I   A   A   H   N   K   L   L   G   S   F   E  L·
1331  TGCAGATCCA GGTCTATCAG GGGGAGCGTG AGATCGCCGC GCACAACAAG TTGCTCGGGT CCTTCGAGCT

                                        MTBHSP70sk
  +1 ·L T  G   I   P   P   A   P   R   G   I   P   Q   I   E   V   T   F   D   I   D   A   N   G
1401  GACCGGCATC CCGCCGGCGC CGCGGGGGAT TCCGCAGATC GAGGTCACTT TCGACATCGA CGCCAACGGC
```

FIG. 2 CONT.

Nucleic Acid and Amino Acid sequences of MTBHSP70 (C) hinge anti-mesothelin scFv

```
                                   MTBHSP70sk
  +1  I  V  H  V  T  A  K  D  K  G  T  G  K  E  N  T  I  R  I  Q  E  G  S  G·
1471 ATTGTGCACG TCACCGCCAA GGACAAGGGC ACCGGCAAGG AGAACACGAT CCGAATCCAG GAAGGCTCGG
                                   MTBHSP70sk
  +1 ·G  L  S  K  E  D  I  D  R  M  I  K  D  A  E  A  H  A  E  E  D  R  K  R·
1541 GCCTGTCCAA GGAAGACATT GACCGCATGA TCAAGGACGC CGAAGCGCAC GCCGAGGAGG ATCGCAAGCG
                                   MTBHSP70sk
  +1 ·R  R  E  E  A  D  V  R  N  Q  A  E  T  L  V  Y  Q  T  E  K  F  V  K  E
1611 TCGCGAGGAG GCCGATGTTC GTAATCAAGC CGAGACATTG GTCTACCAGA CGGAGAAGTT CGTCAAAGAA
                                   MTBHSP70sk
  +1  Q  R  E  A  E  G  G  S  K  V  P  E  D  T  L  N  K  V  D  A  A  V  A  E·
1681 CAGCGTGAGG CCCAGGGTGG TTCGAAGGTA CCTGAAGACA CGCTGAACAA GGTTGATGCC GCGGTGGCGG
                                   MTBHSP70sk
  +1 ·E  A  K  A  A  L  G  G  S  D  I  S  A  I  K  S  A  M  E  K  L  G  Q  E·
1751 AAGCGAAGGC GGCACTTGGC GGATCGGATA TTTCGGCCAT CAAGTCGGCG ATGGAGAAGC TGGGCCAGGA
                                   MTBHSP70sk
  +1 ·E  S  Q  A  L  G  Q  A  I  Y  E  A  A  Q  A  A  S  Q  A  T  G  A  A  H
1821 GTCGCAGGCT CTGGGGCAAG CGATCTACGA AGCAGCTCAG GCTGCGTCAC AGGCCACTGG CGCTGCCCAC
                                   MTBHSP70sk
  +1  P  G  G  E  P  G  G  A  H  P  G  S  A  D  D  V  V  D  A  E  V  V  D  D·
1891 CCCGGCGGCG AGCCGGGCGG TGCCCACCCC GGCTCGGCTG ATGACGTTGT GGACGCGGAG GTGGTCGACG
```

FIG. 2 CONT.

Nucleic Acid and Amino Acid sequences of MTBHSP70 (C) hinge anti-mesothelin scFv

```
              MTBHSP70sk
                                              Linker (hinge N. Scholler)
  +1  ·D G  R  E  A  K  P  S  T  P  P  T  P  S  P  S  T  P  P  T  P  S  P  S·
1961  ACGGCCGGGA GGCCAAGCCA TCAACACCAC CAACTCCAAG TCCTTCTACT CCTCCTACAC CTTCACCATC

 Linker (hinge N. Scholler)
                                                  VH
  +1  ·S G  L  N  D  I  S  Q  V  Q  L  Q  Q  S  G  P  G  L  V  T  P  S  Q  T
2031  AGGTTTGAAT GATATTAGCC AGGTACAGCT GCAGCAGTCA GGTCCAGGAC TCGTGACGCC CTCGCAGACC

                                          VH
  +1   L  S  L  T  C  A  I  S  G  D  S  V  S  S  N  S  A  T  W  N  W  I  R Q·
2101  GTCTCACTCA CCTGTGCCAT CTCCGGGGAC AGTGTCTCTA GCAACAGTGC TACTTGGAAC TGGATCAGGC

                                          VH
  +1  ·Q S  P  S  R  G  L  E  W  L  G  R  T  V  Y  R  S  K  W  Y  N  D  Y A·
2171  AGTCCCCATC GAGAGGCCTT GAGTGGCTGG GAAGGACATA CTACAGGTCC AAGTGGTATA ACGACTATGC

                                          VH
  +1  ·A V  S  V  K  S  R  M  S  I  N  P  D  T  S  K  N  Q  F  S  L  Q  L  N
2241  AGTATCTGTG AAAAGTCGAA TGAGCATCAA CCCAGACACA TCCAAGAACC AGTTCTCCCT GCAGCTGAAC

                                          VH
  +1   S  V  T  P  E  D  T  A  V  Y  Y  C  A  R  G  M  M  T  Y  Y  Y  G  M D·
2311  TCTGTGACTC CCGAGGACAC GGCTGTGTAT TACTGTGCAA GAGGAATGAT GACTTACTAT TACGGTATGG
```

FIG. 2 CONT.

Nucleic Acid and Amino Acid sequences of MTBHSP70 (C) hinge anti-mesothelin scFv

```
                              VH                                   Linker
+1    ·D V W G Q G T T V T V S S G I L G S G G G G S G·
2381  ACGTCTGGGG CCAAGGGACC ACGGTCACCG TCTCCTCAGG AATTCTAGGA TCCGGTGGCG GTGGCAGCGG

                                               VL
           Linker
+1    ·G G G G S G G G G S Q P V L T Q S S S L S A S P
2451  CGGTGGTGGT TCCGGAGGCG GCGGTTCTCA GCCTGTGCTG ACTCAGTCGT CTTCCCTCTC TGCATCTCCT

                                  VL
+1     G A S A S L T C T L R S G I N V G P Y R I Y W Y·
2521  GGAGCATCAG CCAGTCTCAC CTGCACCTTG CGCAGTGGCA TCAATGTTGG TCCCTACAGG ATATACTGGT

                                  VL
+1    ·Y Q Q K P G S P P Q Y L L N Y K S D S D K Q Q G·
2591  ACCAGCAGAA GCCAGGGAGT CCTCCCCAGT ATCTCCTGAA CTACAAATCA GACTCAGATA AGCAGCAGGG

                                  VL
+1    ·G S G V P S R F S G S K D A S A N A G V L L I S
2661  CTCTGGAGTC CCCAGCCGCT TCTCTGGATC CAAAGATGCT TCGGCCAATG CAGGGGTTTT ACTCATCTCT

                                  VL
+1     G L R S E D E A D Y Y C M I W H S S A A V F G G·
2731  GGGCTCCGGT CTGAGGATGA GGCTGACTAT TACTGTATGA TTTGGCACAG CAGCGCTGCT GTGTTCGGAG

                       VL
+1    ·G G T Q L T V L S G I L E Q Q G
2801  CAGGCACCCA ACTGACCGTC CTCTCCGGAA TTCTAGAACA ACAGGGT
```

FIG. 2 CONT.

Nucleic Acid and Amino Acid sequences of MTBHSP70 (N) hinge anti-mesothelin scFv

```
                                          His-tag
 +1   M  A  H  H  H  H  H  H  H  H  H  H  G  A  L  E  V  L  F  Q  G  P  G  Y·
  1  ATGGCACATC ACCACCATCA TCACCATCAC CACCACGGTG CACTTGAAGT CCTCTTTCAG GGACCCGGGT
     TACCGTGTAG TGGTGGTAGT AGTGGTAGTG GTGGTGCCAC GTGAACTTCA GGAGAAAGTC CCTGGGCCCA

                  His-tag
                                                           VH
 +1  ·Y  Q  D  P  V  Q  V  D  A  A  A  S  Q  V  Q  L  Q  Q  S  G  P  G  L  V·
 71  ACCAGGATCC TGTACAAGTC GACGCGGCCG CAAGCCAGGT ACAGCTGCAG CAGTCAGGTC CAGGACTCGT
     TGGTCCTAGG ACATGTTCAG CTGCGCCGGC GTTCGGTCCA TGTCGACGTC GTCAGTCCAG GTCCTGAGCA

                                          VH
 +1  ·V  T  P  S  Q  T  L  S  L  T  C  A  I  S  G  D  S  V  S  S  N  S  A  T
141  GACGCCCTCG CAGACCCTCT CACTCACCTG TGCCATCTCC GGGGACAGTG TCTCTAGCAA CAGTGCTACT
     CTGCGGGAGC GTCTGGGAGA GTGAGTGGAC ACGGTAGAGG CCCCTGTCAC AGAGATCGTT GTCACGATGA

                                          VH
 +1   W  N  W  I  R  Q  S  P  S  R  G  L  E  W  L  G  R  T  Y  Y  R  S  K  W·
211  TGGAACTGGA TCAGGCAGTC CCCATCGAGA GGCCTTGAGT GGCTGGGAAG GACATACTAC AGGTCCAAGT
     ACCTTGACCT AGTCCGTCAG GGGTAGCTCT CCGGAACTCA CCGACCCTTC CTGTATGATG TCCAGGTTCA

                                          VH
 +1  ·W  Y  N  D  Y  A  V  S  V  K  S  R  M  S  I  N  P  D  T  S  K  N  Q  F·
281  GGTATAACGA CTATGCAGTA TCTGTGAAAA GTCGAATGAG CATCAACCCA GACACATCCA AGAACCAGTT
     CCATATTGCT GATACGTCAT AGACACTTTT CAGCTTACTC GTAGTTGGGT CTGTGTAGGT TCTTGGTCAA
```

FIG. 4

Nucleic Acid and Amino Acid sequences of MTBHSP70 (N) hinge anti-mesothelin scFv

VH
+1 ·F S L Q L N S V T P E D T A V Y Y C A R G M M T
351 CTCCCTGCAG CTGAACTCTG TGACTCCCGA GGACACGGCT GTGTATTACT GTGCAAGAGG AATGATGACT
GAGGGACGTC GACTTGAGAC ACTGAGGGCT CCTGTGCCGA CACATAATGA CACGTTCTCC TTACTACTGA

Linker
VH
+1 Y Y Y G M D V W G Q G T T V T V S S G I L G S G·
421 TACTATTACG GTATGGACGT CTGGGGCCAA GGGACCACGG TCACCGTCTC CTCAGGAATT CTAGGATCCG
ATGATAATGC CATACCTGCA GACCCCGGTT CCCTGGTGCC AGTGGCAGAG GAGTCCTTAA GATCCTAGGC VL
Linker
+1 ·G G G G S G G G G S G G G G S Q P V L T Q S S S·
491 GTGGCGGTGG CAGCGGCGGT GGTGGTTCCG GAGGCGGCGG TTCTCAGCCT GTGCTGACTC AGTCGTCTTC
CACCGCCACC GTCGCCGCCA CCACCAAGGC CTCCGCCGCC AAGAGTCGGA CACGACTGAG TCAGCAGAAG VL
+1 ·S L S A S P G A S A S L T C T L R S G I N V G P
561 CCTCTCTGCA TCTCCTGGAG CATCAGCCAG TCTCACCTGC ACCTTGCGCA GTGGCATCAA TGTTGGTCCC
GGAGAGACGT AGAGGACCTC GTAGTCGGTC AGAGTGGACG TGGAACGCGT CACCGTAGTT ACAACCAGGG VL
+1 Y R I Y W Y Q Q K P G S P P Q Y L L N Y K S D S·
631 TACAGGATAT ACTGGTACCA GCAGAAGCCA GGGAGTCCTC CCCAGTATCT CCTGAACTAC AAATCAGACT
ATGTCCTATA TGACCATGGT CGTCTTCGGT CCCTCAGGAG GGGTCATAGA GGACTTGATG TTTAGTCTGA

FIG. 4 CONT.

Nucleic Acid and Amino Acid sequences of MTBHSP70 (N) hinge anti-mesothelin scFv

```
                                  VL
+1  ·S D K Q Q G S G V P S R F S G S K D A S A N A G·
701  CAGATAAGCA GCAGGGCTCT GGAGTCCCCA GCCGCTTCTC TGGATCCAAA GATGCTTCGG CCAATGCAGG
     GTCTATTCGT CGTCCCGAGA CCTCAGGGGT CGGCGAAGAG ACCTAGGTTT CTACGAAGCC GGTTACGTCC

                                  VL
+1  ·G V L L I S G L R S E D E A D Y Y C M I W H S S·
771  GGTTTTACTC ATCTCTGGGC TCCGGTCTGA GGATGAGGCT GACTATTACT GTATGATTTG GCACAGCAGC
     CCAAAATGAG TAGAGACCCG AGGCCAGACT CCTACTCCGA CTGATAATGA CATACTAAAC CGTGTCGTCG

                                               Linker (hinge N. Scholler)
                             VL
+1  ·A A V F G G G T Q L T V L S G I L E Q Q G P S T·
841  GCTGCTGTGT TCGGAGGAGG CACCCAACTG ACCGTCCTCT CCGGAATTCT AGAACAACAG GGTCCATCAA
     CGACGACACA AGCCTCCTCC GTGGGTTGAC TGGCAGGAGA GGCCTTAAGA TCTTGTTGTC CCAGGTAGTT

                    Linker (hinge N. Scholler)
                                                              MTBHSP70sk
+1  ·T P P T P S P S T P P T P S P S G L N D I M A R·
911  CACCACCAAC TCCAAGTCCT TCTACTCCTC CTACACCTTC ACCATCAGGT TTGAATGATA TTATGGCTCG
     GTGGTGGTTG AGGTTCAGGA AGATGAGGAG GATGTGGAAG TGGTAGTCCA AACTTACTAT AATACCGAGC

                              MTBHSP70sk
+1  ·P A V G I D L G T T N S V V S V L E G G D P V V
981  TGCGGTCGGG ATCGACCTCG GGACCACCAA CTCCGTCGTC TCGGTTCTGG AAGGTGGCGA CCCGGTCGTC
     ACGCCAGCCC TAGCTGGAGC CCTGGTGGTT GAGGCAGCAG AGCCAAGACC TTCCACCGCT GGGCCAGCAG
```

FIG. 4 CONT.

Nucleic Acid and Amino Acid sequences of MTBHSP70 (N) hinge anti-mesothelin scFv

```
                                   MTBHSP70sk
  +1   V  A  M  S  E  G  S  R  T  T  P  S  I  V  A  E  A  R  N  G  E  Y  L V·
1051   GTCGCCAACT CCGAGGGCTC CAGGACCACC CCGTCAATTG TCGCGTTCGC CCGCAACGGT GAGGTGCTGG
       CAGCGGTTGA GGCTCCCGAG GTCCTGGTGG GGCAGTTAAC AGCGCAAGCG GGCGTTGCCA CTCCACGACC
                                   MTBHSP70sk
  +1  ·V  A  Q  P  A  K  N  Q  A  V  T  N  V  D  R  T  V  R  S  V  K  R  H M·
1121   TCGGCCAGCC CGCCAAGAAC CAGGCGGTGA CCAACGTCGA TCGCACCGTG CGCTCGGTCA AGCGACACAT
       AGCCGGTCGG GCGGTTCTTG GTCCGCCACT GGTTGCAGCT AGCGTGGCAC GCGAGCCAGT TCGCTGTGTA
                                   MTBHSP70sk
  +1  ·M  G  S  D  W  S  I  E  I  D  G  K  K  Y  T  A  P  E  I  S  A  R  I  L
1191   GGGCAGCGAC TGGTCCATAG AGATTGACGG CAAGAAATAC ACCGCGCCGG AGATCAGCGC CCGCATTCTG
       CCCGTCGCTG ACCAGGTATC TCTAACTGCC GTTCTTTATG TGGCGCGGCC TCTAGTCGCG GGCGTAAGAC
                                   MTBHSP70sk
  +1  ·M  K  L  K  R  Q  A  E  A  Y  L  G  E  D  I  T  D  A  V  I  T  T  P A·
1261   ATGAAGCTGA AGCGCGACGC CGAGGCCTAC CTCGGTGAGG ACATTACCGA CGCGGTTATC ACGACGCCCG
       TACTTCGACT TCGCGCTGCG GCTCCGGATG GAGCCACTCC TGTAATGGCT GCGCCAATAG TGCTGCGGGC
                                   MTBHSP70sk
  +1  ·A  Y  F  N  D  A  Q  R  Q  A  T  K  D  A  G  Q  I  A  G  L  N  V  L R·
1331   CCTACTTCAA TGACGCCCAG CGTCAGGCCA CCAAGGACGC CGGCCAGATC GCCGGCCTCA ACGTGCTGCG
       GGATGAAGTT ACTGCGGGTC GCAGTCCGGT GGTTCCTGCG GCCGGTCTAG CGGCCGGAGT TGCACGACGC
                                   MTBHSP70sk
  +1  ·R  I  V  N  E  P  T  A  A  A  L  A  Y  G  L  D  K  G  E  K  E  Q  R  I
1401   GATCGTCAAC GAGCCGACCG CTGCAGCGCT GGCCTACGGC CTCGACAAGG GCGAGAAGGA GCAGCGAATC
       GTAGCAGTTG CTCGGCTGGC GACGTCGCGA CCGGATGCCG GAGCTGTTCC CGCTCTTCCT CGTCGCTTAG
```

FIG. 4 CONT.

Nucleic Acid and Amino Acid sequences of MTBHSP70 (N) hinge anti-mesothelin scFv

```
                                   MTBHSP70sk
  +1   L  V  F  D  L  G  G  G  T  F  D  V  S  L  L  E  I  G  E  G  V  V  E  V·
1471  CTGGTCTTCG ACTTGGGTGG TGGCACTTTC GACGTTTCCC TGCTGGAGAT CGGCGAGGGT GTGGTTGAGG
      GACCAGAAGC TGAACCCACC ACCGTGAAAG CTGCAAAGGG ACGACCTCTA GCCGCTCCCA CACCAACTCC
                                   MTBHSP70sk
  +1  ·V  R  A  T  S  G  D  N  H  L  G  G  D  D  W  D  Q  R  V  V  D  W  L  V·
1541  TCCGTGCCAC TTCGGGTGAC AACCACCTCG GCGGCGACGA CTGGGACCAG CGGGTCGTCG ATTGGCTGGT
      AGGCACGGTG AAGCCCACTG TTGGTGGAGC CGCCGCTGCT GACCCTGGTC GCCCAGCAGC TAACCGACCA
                                   MTBHSP70sk
  +1 ·V  D  K  F  K  G  T  S  G  I  D  L  T  K  D  K  M  A  M  Q  R  L  R  E
1611  GGACAAGTTC AAGGGCACCA GCGGCATCGA TCTGACCAAG GACAAGATGG CGATGCAGCG GCTGCGGGAA
      CCTGTTCAAG TTCCCGTGGT CGCCGTAGCT AGACTGGTTC CTGTTCTACC GCTACGTCGC CGACGCCCTT
                                   MTBHSP70sk
  +1   A  A  E  K  A  K  I  E  L  S  S  S  Q  S  T  S  I  N  L  P  Y  I  T  V·
1681  GCCGCCGAGA AAGCAAAGAT CGAGCTGAGT TCGAGTCAGT CCACCTCGAT CAACCTGCCC TACATCACCG
      CGGCGGCTCT TTCGTTTCTA GCTCGACTCA AGCTCAGTCA GGTGGAGCTA GTTGGACGGG ATGTAGTGGC
                                   MTBHSP70sk
  +1  ·V  D  A  D  K  N  P  L  F  L  D  E  Q  L  T  R  A  E  F  Q  R  I  T  Q·
1751  TCGACGCCGA CAAGAACCCG TTGTTCTTAG ACGAGCAGCT GACCCGCGCG GAGTTCCAAC GGATCACTCA
      AGCTGCGGCT GTTCTTGGGC AACAAGAATC TGCTCGTCGA CTGGGCGCGC CTCAAGGTTG CCTAGTGAGT
                                   MTBHSP70sk
  +1 ·Q  D  L  L  D  R  T  A  K  P  F  Q  S  V  I  A  D  T  G  I  S  V  S  E
1821  GGACCTGCTG GACCGCACTC GCAAGCCGTT CCAGTCGGTG ATCGCTGACA CCGGCATTTC GGTGTCGGAG
      CCTGGACGAC CTGGCGTGAG CGTTCGGCAA GGTCAGCCAC TAGCGACTGT GGCCGTAAAG CCACAGCCTC
```

FIG. 4 CONT.

Nucleic Acid and Amino Acid sequences of MTBHSP70 (N) hinge anti-mesothelin scFv

MTBHSP70sk
+1 I D H V V L V G G S T R M P A V T D L V K E L T·
1891 ATCGATCACG TTGTGCTCGT GGGTGGTTCG ACCCGGATGC CCGCGGTGAC CGATCTGGTC AAGGAACTCA
TAGCTAGTGC AACACGAGCA CCCACCAAGC TGGGCCTACG GGCGCCACTG GCTAGACCAG TTCCTTGAGT

MTBHSP70sk
+1 ·T G G K E P N K G V N P D E V V A V G A A L Q A·
1961 CCGGCGGCAA GGAACCCAAC AAGGGCGTCA ACCCCGATGA GGTTGTCGCG GTGGGAGCCG CTCTGCAGGC
GGCCGCCGTT CCTTGGGTTG TTCCCGCAGT TGGGGCTACT CCAACAGCGC CACCCTCGGC GAGACGTCCG

MTBHSP70sk
+1 ·A G V L K G E V K D V L L L D V T P L S L G I E
2031 GGGCGTCCTC AAGGGCGAGG TGAAAGACGT TCTGCTGCTT GATGTTACCC CGCTGAGCCT GGGTATCGAG
GCCGCAGGAG TTCCCGCTCC ACTTTCTGCA AGACGACGAA CTACAATGGG GCGACTCGGA CCCATAGCTC

MTBHSP70sk
+1 T K G G V M T R L I E R N T T I P T K R S E S F·
2101 ACCAAGGGCG GGGTGATGAC CAGGCTCATC GAGCGCAACA CCACGATCCC CACCAAGCGG TCGGAGTCTT
TGGTTCCCGC CCCACTACTG GTCCGAGTAG CTCGCGTTGT GGTGCTAGGG GTGGTTCGCC AGCCTCAGAA

MTBHSP70sk
+1 ·F T T A D D N Q P S V Q I Q V Y Q G E R E I A A·
2171 TCACCACCGC CGACGACAAC CAACCGTCGG TGCAGATCCA GGTCTATCAG GGGGAGCGTG AGATCGCCGC
AGTGGTGGCG GCTGCTGTTG GTTGGCAGCC ACGTCTAGGT CCAGATAGTC CCCCTCGCAC TCTAGCGGCG

MTBHSP70sk
+1 ·A H N K L L G S F E L T G I P P A P R G I P Q I
2241 GCACAACAAG TTGCTCGGGT CCTTCGAGCT GACCGGCATC CCGCCGGCGC CGCGGGGGAT TCCGCAGATC
CGTGTTGTTC AACGAGCCCA GGAAGCTCGA CTGGCCGTAG GGCGGCCGCG GCGCCCCCTA AGGCGTCTAG

FIG. 4 CONT.

Nucleic Acid and Amino Acid sequences of MTBHSP70 (N) hinge anti-mesothelin scFv

```
                                     MTBHSP70sk
  +1   E  V  T  F  D  I  D  A  N  G  T  V  H  V  T  A  K  D  K  G  T  G  K E·
2311  GAGGTCACTT TCGACATCGA CGCCAACGGC ATTGTGCACG TCACCGCCAA GGACAAGGGC ACCGGCAAGG
      CTCCAGTGAA AGCTGTAGCT GCGGTTGCCG TAACACGTGC AGTGGCGGTT CCTGTTCCCG TGGCCGTTCC

                                     MTBHSP70sk
  +1  ·E N  T  I  R  I  Q  E  G  S  G  L  S  K  E  D  I  D  R  M  I  K  D A·
2381  AGAACACGAT CCGAATCCAG GAAGGCTCGG GCCTGTCCAA GGAAGACATT GACCGCATGA TCAAGGACGC
      TCTTGTGCTA GGCTTAGGTC CTTCCGAGCC CGGACAGGTT CCTTCTGTAA CTGGCGTACT AGTTCCTGCG

                                     MTBHSP70sk
  +1 ·A E  A  H  A  E  E  D  R  K  R  R  E  E  A  D  V  R  N  Q  A  E  T  L
2451  CGAAGCGCAC GCCGAGGAGG ATCGCAAGCG TCGCGAGGAG GCCGATGTTC GTAATCAAGC CGAGACATTG
      GCTTCGCGTG CGGCTCCTCC TAGCGTTCGC AGCGCTCCTC CGGCTACAAG CATTAGTTCG GCTCTGTAAC

                                     MTBHSP70sk
  +1   V  Y  Q  T  E  K  F  V  K  E  Q  R  E  A  E  G  G  S  K  V  P  E  D T·
2521  GTCTACCAGA CGGAGAAGTT CGTCAAAGAA CAGCGTGAGG CCGAGGGTGG TTCGAAGGTA CCTGAAGACA
      CAGATGGTCT GCCTCTTCAA GCAGTTTCTT GTCGCACTCC GGCTCCCACC AAGCTTCCAT GGACTTCTGT

                                     MTBHSP70sk
  +1  ·T L  N  K  V  D  A  A  V  A  E  A  K  A  A  L  G  G  S  D  I  S  A I·
2591  CGCTGAACAA GGTTGATGCC GCGGTGGCGG AAGCGAAGGC GGCACTTGGC GGATCGGATA TTTCGGCCAT
      GCGACTTGTT CCAACTACGG CGCCACCGCC TTCGCTTCCG CCGTGAACCG CCTAGCCTAT AAAGCCGGTA

                                     MTBHSP70sk
  +1 ·I K  S  A  M  E  K  L  G  Q  E  S  Q  A  L  G  Q  A  I  Y  E  A  A  Q
2661  CAAGTCGGCG ATGGAGAAGC TGGGCCAGGA GTCGCAGGCT CTGGGGCAAG CGATCTACGA AGCAGCTCAG
      GTTCAGCCGC TACCTCTTCG ACCCGGTCCT CAGCGTCCGA GACCCCGTTC GCTAGATGCT TCGTCGAGTC
```

FIG. 4 CONT.

Nucleic Acid and Amino Acid sequences of MTBHSP70 (N) hinge anti-mesothelin scFv

```
                                          MTBHSP70sk
  +1  A  A  S  Q  A  T  G  A  A  H  P  G  G  E  P  G  G  A  H  P  G  S  A D·
2731  GCTGCGTCAC AGGCCACTGG CGCTGCCCAC CCCGGCGGCG AGCCGGGCGG TGCCCACCCC GGCTCGGCTG
      CGACGCAGTG TCCGGTGACC GCGACGGGTG GGGCCGCCGC TCGGCCCGCC ACGGGTGGGG CCGAGCCCAC

                        MTBHSP70sk
  +1  ·D D  V  V  D  A  E  V  V  D  D  G  R  E  A  K
2801  ATGACGTTGT GGACGCGGAG GTGGTCGACG ACGGCCGGGA GGCCAAG
      TACTGCAACA CCTGCGCCTC CACCAGCTGC TGCCGGCCCT CCGGTTC
```

FIG. 4 CONT.

HuHSP70 (N) Hinge Anti-mesothelin scFv

1805bp

Nucleic Acid and Amino Acid sequences of HuHSP70 (C) hinge anti-mesothelin scFv

```
                               His-tag
+1   M  A  H  H  H  H  H  H  H  H  H  H  G  A  L  E  V  L  F  Q  G  P  G  Y·
1    ATGGCACATC ACCACCATCA TCACCATCAC CACCACGGTG CACTTGAAGT CCTCTTTCAG GGACCCGGGT

              His-tag
                                                    HuHSP70
+1  ·Y  Q  D  P  V  Q  V  D  A  A  A  M  A  K  A  A  A  I  G  I  D  L  G  T·
71   ACCAGGATCC TGTACAAGTC GACGCGGCCG CAATGGCCAA AGCGGCCGGG ATCGGCATCG AGCTCGCCAC

                               HuHSP70
+1  ·T  T  Y  S  C  V  G  V  F  Q  H  G  K  V  E  I  I  A  N  D  Q  G  N  R
141  CACCTACTCC TGCGTGGGGG TGTTCCAACA CGGCAAGGTG GAGATCATCG CCAACGACCA GGGCAACCGC

                               HuHSP70
+1   T  T  P  S  Y  V  A  F  T  D  T  E  R  L  I  G  D  A  A  K  N  Q  V  A·
211  ACCACCCCCA GCTACGTGGC CTTCACGGAC ACCGAGCGGC TCATCGGGGA TGCGGCCAAG AACCAGGTGG

                               HuHSP70
+1  ·A  L  N  P  Q  N  T  V  F  D  A  K  R  L  I  G  R  K  F  G  D  P  V  V·
281  CGCTGAACCC GCAGAACACC GTGTTTGACG CGAAGCGGCT GATCGGCCGC AAGTTCGGCG ACCCGGTGGT

                               HuHSP70
+1  ·V  Q  S  D  M  K  H  W  P  F  Q  V  I  N  D  G  D  K  P  K  V  Q  V  S
351  GCAGTCGGAC ATGAAGCACT GGCCTTTCCA GGTGATCAAC GACGGAGACA AGCCCAAGGT GCAGGTGAGC

                               HuHSP70
+1   Y  K  G  D  T  K  A  F  Y  P  E  E  I  S  S  M  V  L  T  K  M  K  E  I·
421  TACAAGGGGG ACACCAAGGC ATTCTACCCC GAGGAGATCT CGTCCATGGT GCTGACCAAG ATGAAGGAGA
```

FIG. 6

Nucleic Acid and Amino Acid sequences of HuHSP70 (C) hinge anti-mesothelin scFv

```
                                        HuHSP70
 +1  ·I  A  E  A  Y  L  G  Y  P  V  T  M  A  V  I  T  V  P  A  Y  F  N  D  S·
491   TCGCCGAGGC GTACCTGGGC TACCCGGTGA CCAACGCGGT GATCACCGTG CCGGCCTACT TCAACGACTC

                                        HuHSP70
 +1  ·S  Q  R  Q  A  T  K  D  A  G  V  I  A  G  L  N  V  L  R  I  I  N  E  P
561   GCAGCGCCAG GCCACCAAGG ATGCGGGTGT GATCGCGGGG CTCAACGTGC TGCGGATCAT CAACGAGCCC

                                        HuHSP70
 +1   T  A  A  A  I  A  Y  G  L  D  R  T  G  K  G  E  R  N  V  L  I  F  D  L·
631   ACGGCCGCCG CCATCGCCTA CGGCCTGGAC AGAACGGGCA AGGGGGAGCG CAACGTGCTC ATCTTTGACC

                                        HuHSP70
 +1  ·L  G  G  G  T  F  D  V  S  I  L  T  I  D  D  G  I  F  E  V  K  A  T  A·
701   TGGGCGGGGG CACCTTCGAC GTGTCCATCC TGACGATCGA CGACGGCATC TTCGAGGTGA AGGCCACGGC

                                        HuHSP70
 +1  ·A  G  D  T  H  L  G  G  E  D  F  D  N  R  L  V  N  H  F  V  E  E  F  K
771   CGGGGACACC CACCTGGGTG GGGAGGACTT TGACAACAGG CTGGTGAACC ACTTCGTGGA GGAGTTCAAG

                                        HuHSP70
 +1   R  K  H  K  K  D  I  S  Q  N  K  R  A  V  R  R  L  R  T  A  C  E  R  A·
841   AGAAAACACA AGAAGGACAT CAGCCAGAAC AAGCGAGCCG TGAGGCGGCT GCGCACCGCC TGCGAGAGGG

                                        HuHSP70
 +1  ·A  K  R  T  L  S  S  S  T  Q  A  S  L  E  I  D  S  L  F  E  G  I  D  F·
911   CCAAGAGGAC CCTGTCGTCC AGCACCCAGG CCAGCCTGGA GATCGACTCC CTGTTTGAGG GCATCGACTT
```

FIG. 6 CONT.

Nucleic Acid and Amino Acid sequences of HuHSP70 (C) hinge anti-mesothelin scFv

HuHSP70
+1 ·F Y T S I T R A R F E E L C S D L F R S T L E F
981 CTACACGTCC ATCACCAGGG CGAGGTTCGA GGAGCTGTGC TCCGACCTGT TCCGAAGCAC CCTGGAGCCC

HuHSP70
+1 V E K A L R D A K L D K A Q I H D L V L V G G S·
1051 GTGGAGAAGG CTCTGCGCGA CGCCAAGCTG GACAAGGCCC AGATTCACGA CCTGGTCCTG GTCGGGGGCT

HuHSP70
+1 ·S T R I P K V Q K L L Q D F F N G R D L N K S I·
1121 CCACCCGCAT CCCCAAGGTG CAGAAGCTGC TGCAGGACTT CTTCAACGGG CGCGACCTGA ACAAGAGCAT

HuHSP70
+1 ·L N P D E A V A Y G A A V Q A A I L M G D K S E
1191 CAACCCCGAC GAGGCTGTGG CCTACGGGGC GGCGGTGCAG GCGGCCATCC TGATGGGGGA CAAGTCCGAG

HuHSP70
+1 N V Q D L L L L D V A P L S L G L E T A G G V M·
1261 AACGTGCAGG ACCTGCTGCT GCTGGACGTG GCTCCCCTGT CGCTGGGGCT GGAGACGGCC GGAGGCGTGA

HuHSP70
+1 ·M T A L I K R N S T I P T K Q T Q I F T T Y S D·
1331 TGACTGCCCT GATCAAGCGC AACTCCACCA TCCCCACCAA GCAGACGCAG ATCTTCACCA CCTACTCCGA

HuHSP70
+1 ·D N Q P G V L I Q V Y E G E R A M T K D N N L L
1401 CAACCAACCC GGGGTGCTGA TCCAGGTGTA CGAGGGCGAG AGGGCCATGA CGAAAGACAA CAATCTGTTG

FIG. 6 CONT.

Nucleic Acid and Amino Acid sequences of HuHSP70 (C) hinge anti-mesothelin scFv

```
                                   HuHSP70
  +1   G  R  F  E  L  S  G  I  P  P  A  P  R  G  V  P  Q  I  E  V  T  F  DS·
1471  GGGCGCTTCG AGCTGAGCGG CATCCCTCCG GCCCCCAGGG GCGTGCCCCA GATCGAGGTG ACCTTCGACA
                                   HuHSP70
  +1  ·I D  A  N  G  I  L  N  V  T  A  T  D  K  S  T  G  K  A  N  K  I  T  I·
1541  TCGATGCCAA CGGCATCCTG AACGTCACGG CCACGGACAA GAGCACCGGC AAGGCCAACA AGATCACCAT
                                   HuHSP70
  +1  ·I T  N  D  K  G  R  L  S  K  E  E  I  E  R  M  V  Q  E  A  E  K  Y  K
1611  CACCAACGAC AAGGGCCGCC TGAGCAAGGA GGAGATCGAG CGCATGGTGC AGGAGGCGGA GAAGTACAAA
                                   HuHSP70
  +1   A  E  D  E  V  Q  R  E  R  V  S  A  K  N  A  L  E  S  Y  A  F  N  M K·
1681  GCGGAGGACG AGGTGCAGCG CGAGAGGGTG TCAGCCAAGA ACGCCCTGGA GTCCTACGCC TTCAACATGA
                                   HuHSP70
  +1  ·K S  A  V  E  D  E  G  L  K  G  K  I  S  E  A  D  K  K  K  V  L  D K·
1751  AGAGCGCCGT GGAGGATGAG GGGCTCAAGG GCAAGATCAG CGAGGCCGAC AAGAAGAAGG TGCTGGACAA
                                   HuHSP70
  +1 ·K C  Q  E  V  I  S  W  L  D  A  N  T  L  A  E  K  D  E  F  E  H  K  R
1821  GTGTCAAGAG GTCATCTCGT GGCTGGACGC CAACACCTTG GCCGAGAAGG ACGAGTTTGA GCACAAGAGG
                                   HuHSP70
  +1   K  E  L  E  Q  V  C  N  P  I  I  S  G  L  Y  Q  G  A  G  G  P  G  P G·
1891  AAGGAGCTGG AGCAGGTGTG TAACCCCATC ATCAGCGGAC TGTACCAGGG TGCCGGTGGT CCCGGGCCTG
```

FIG. 6 CONT.

Nucleic Acid and Amino Acid sequences of HuHSP70 (C) hinge anti-mesothelin scFv

```
                                                                Linker (hinge N. Scholler
                                          HuHSP70
  +1  ·G  G  F  G  A  Q  G  P  K  G  G  S  G  S  G  P  T  I  E  E  V  D  P  S·
1961  GGGGCTTCGG GGCTCAGGGT CCCAAGGGAG GGTCTGGGTC AGGCCCCACC ATTGAGGAGG TAGATCCATC

                          Linker (hinge N. Scholler
                                                                              VH
  +1  ·S T P  P  T  P  S  P  S  T  P  P  T  P  S  P  S  G  L  N  D  I  S  Q
2031  AACACCACCA ACTCCAAGTC CTTCTACTCC TCCTACACCT TCACCATCAG GTTTGAATGA TATTAGCCAG

                                     VH
  +1   V  Q  L  Q  Q  S  G  P  G  L  V  T  P  S  Q  T  L  S  L  T  C  A  I  S·
2101  GTACAGCTGC AGCAGTCAGG TCCAGGACTC GTGACGCCCT CGCAGACCCT CTCACTCACC TGTGCCATCT

                                     VH
  +1  ·S  G  D  S  V  S  S  N  S  A  T  W  N  W  I  R  Q  S  P  S  R  G  L  E·
2171  CCGGGGACAG TGTCTCTAGC AACAGTGCTA CTTGGAACTG GATCAGGCAG TCCCCATCGA GAGGCCTTGA

                                     VH
  +1  ·E W  L  G  R  T  Y  Y  R  S  K  W  Y  N  D  Y  A  V  S  V  K  S  R  M
2241  GTGGCTGGGA AGGACATACT ACAGGTCCAA GTGGTATAAC GACTATGCAG TATCTGTGAA AAGTCGAATG

                                     VH
  +1   S  I  N  P  D  T  S  K  N  Q  F  S  L  Q  L  N  S  V  T  P  E  D  T  A·
2311  AGCATCAACC CAGACACATC CAAGAACCAG TTCTCCCTGC AGCTGAACTC TGTGACTCCC GAGGACACGG

                                     VH
  +1  ·A  V  Y  Y  C  A  R  G  M  M  T  Y  Y  Y  G  M  D  V  W  G  Q  G  T  T·
2381  CTGTGTATTA CTGTGCAAGA GGAATGATGA CTTACTATTA CGGTATGGAC GTCTGGGGCC AAGGGACCAC
```

FIG. 6 CONT.

Nucleic Acid and Amino Acid sequences of HuHSP70 (C) hinge anti-mesothelin scFv

```
                                                   Linker
                 VH
+1    ·T V T  V  S  S  G  I  L  G  S  G  G  G  G  S  G  G  G  G  S  G  G  G
2451   GGTCACCGTC TCCTCAGGAA TTCTAGGATC CGGTGGCGGT GGCAGCGGCG GTGGTGGTTC CGGAGGCGGC

                                         VL
       Linker
+1     G  S  Q  P  V  L  T  Q  S  S  S  L  S  A  S  P  G  A  S  A  S  L  T C·
2521   GGTTCTCAGC CTGTGCTGAC TCAGTCGTCT TCCCTCTCTG CATCTCCTGG AGCATCAGCC AGTCTCACCT

                                       VL
+1    ·C  T  L  R  S  G  I  N  V  G  P  Y  R  I  Y  W  Y  Q  Q  K  P  G  S P·
2591   GCACCTTGCG CAGTGGCATC AATGTTGGTC CCTACAGGAT ATACTGGTAC CAGCAGAAGC CAGGGAGTCC

                                       VL
+1    ·P P  Q  Y  L  L  N  Y  K  S  D  S  D  K  Q  Q  G  S  G  V  P  S  R  F
2661   TCCCCAGTAT CTCCTGAACT ACAAATCAGA CTCAGATAAG CAGCAGGGCT CTGGAGTCCC CAGCCGCTTC

                                       VL
+1     S  G  S  K  D  A  S  A  N  A  G  V  L  L  I  S  G  L  R  S  E  D  E A·
2731   TCTGGATCCA AAGATGCTTC GGCCAATGCA GGGGTTTTAC TCATCTCTGG GCTCCGGTCT GAGGATGAGG

                                       VL
+1    ·A  D  Y  Y  C  M  I  W  H  S  S  A  A  V  F  G  G  G  T  Q  L  T  V L·
2801   GTGACTATTA CTGTATGATT TGGCACAGCA GCGCTGCTGT GTTCGGAGGA GGCACCCAAC TGACCGTCCT

                 VL
+1    ·L  S  G  I  L  E  Q  Q  G
2871   CTCCGGAATT CTAGAACAAC AGGGT
```

FIG. 6 CONT.

Nucleic Acid and Amino Acid sequences of HuHSP70 (N) hinge anti-mesothelin scFv

```
                         His-tag
+1   M  A  H  H  H  H  H  H  H  H  H  H  G  A  L  E  V  L  F  Q  G  P  G  Y·
1    ATGGCACATC ACCACCATCA TCACCATCAC CACCACGGTG CACTTGAAGT CCTCTTTCAG GGACCCGGGT

               His-tag
                                                        VH
+1  ·Y  Q  D  P  V  Q  V  D  A  A  A  S  Q  V  Q  L  Q  Q  S  G  P  G  L  V·
71   ACCAGGATCC TGTACAAGTC GACGCGGCCG CAAGCCAGGT ACAGCTGCAG CAGTCAGGTC CAGGACTCGT

                         VH
+1  ·V  T  P  S  Q  T  L  S  L  T  C  A  I  S  G  D  S  V  S  S  N  S  A  T
141  GACGCCCTCG CAGACCCTCT CACTCACCTG TGCCATCTCC GGGGACAGTG TCTCTAGCAA CAGTGCTACT

                         VH
+1   W  N  W  I  R  Q  S  P  S  R  G  L  E  W  L  G  R  T  Y  Y  R  S  K  W·
211  TGGAACTGGA TCAGGCAGTC CCCATCGAGA GGCCTTGAGT GGCTGGGAAG GACATACTAC AGGTCCAAGT

                         VH
+1  ·W  Y  N  D  Y  A  V  S  V  K  S  R  M  S  I  N  P  D  T  S  K  N  Q  F·
281  GGTATAACGA CTATGCAGTA TCTGTGAAAA GTCGAATGAG CATCAACCCA GACACATCCA AGAACCAGTT

                         VH
+1  ·F  S  L  Q  L  N  S  V  T  P  E  D  T  A  V  Y  Y  C  A  R  G  M  M  T
351  CTCCCTGCAG CTGAACTCTG TGACTCCCGA GGACACGGCT GTGTATTACT GTGCAAGAGG AATGATGACT

                                                                    Linker
                         VH
+1   Y  Y  Y  G  M  D  V  W  G  Q  G  T  T  V  T  V  S  S  G  I  L  G  S  G·
421  TACTATTACG GTATGGACGT CTGGGGCCAA GGGACCACGG TCACCGTCTC CTCAGGAATT CTAGGATCCG
```

FIG. 8

Nucleic Acid and Amino Acid sequences of HuHSP70 (N) hinge anti-mesothelin scFv

```
                    Linker                                          VL
+1   ·G G G G S G G G G S G G G G S Q P V L T Q S S S·
491  GTGGCGGTGG CAGCGGCGGT GGTGGTTCCG GAGGCGGCGG TTCTCAGCCT GTGCTGACTC AGTCGTCTTC

                                   VL
+1   ·S L S A S P G A S A S L T C T L R S G I N V G P
561  CCTCTCTGCA TCTCCTGGAG CATCAGCCAG TCTCACCTGC ACCTTGCGCA GTGGCATCAA TGTTGGTCCC

                                   VL
+1    Y R I Y W Y Q Q K P G S P P Q Y L L N Y K S D S·
631  TACAGGATAT ACTGGTACCA GCAGAAGCCA GGGAGTCCTC CCCAGTATCT CCTGAACTAC AAATCAGACT

                                   VL
+1   ·S D K Q Q G S G V P S R F S G S K D A S A N A G·
701  CAGATAAGCA GCAGGGCTCT GGAGTCCCCA GCCGCTTCTC TGGATCCAAA GATGCTTCGG CCAATGCAGG

                                   VL
+1   ·G V L L I S G L R S E D E A D Y Y C M I W H S S
771  GGTTTTACTC ATCTCTGGGC TCCGGTCTGA GGATGAGGCT GACTATTACT GTATGATTTG GCACAGCAGC

                                                       Linker(hinge N.Scholler)
                                 VL
+1    A A V F G G G T Q L T V L S G I L E Q Q G P S T·
841  GCTGCTGTGT TCGGAGGAGG CACCCAACTG ACCGTCCTCT CCGGAATTCT AGAACAACAG GGTCCATCAA

                        Linker(hinge N.Scholler)
                                                                      HuHSP70
+1   ·T P P T P S P S T P P T P S P S G L N D I M A K·
911  CACCACCAAC TCCAAGTCCT TCTACTCCTC CTACACCTTC ACCATCAGGT TTGAATGATA TTATGGCCAA
```

FIG. 8 CONT.

Nucleic Acid and Amino Acid sequences of HuHSP70 (N) hinge anti-mesothelin scFv

```
                              HuHSP70
  +1  ·K A  A  A  I  G  I  D  L  G  L  T  Y  S  C  V  G  V  F  Q  H  G  K  V
 981  AGCCGCGGCG ATCGGCATCG ACCTGGGCAC CACCTACTCC TGCGTGGGGG TGTTCCAACA CGGCAAGGTG

                              HuHSP70
  +1   E  I  I  A  N  D  Q  G  N  R  T  T  P  S  Y  V  A  F  T  D  T  E  R L·
1051  GAGATCATCG CCAACGACCA GGGCAACCGC ACCACCCCCA GCTACGTGGC CTTCACGGAC ACCGAGCGGC

                              HuHSP70
  +1  ·L I  G  D  A  A  K  N  Q  V  A  L  N  P  Q  N  T  V  F  D  A  K  R L·
1121  TCATCGGGGA TGCGGCCAAG AACCAGGTGG CGCTGAACCC GCAGAACACC GTGTTTGACG CGAAGCGGCT

                              HuHSP70
  +1  ·L I  G  R  K  F  G  D  P  V  V  Q  S  D  M  K  H  W  P  F  Q  V  I  N
1191  GATCGGCCGC AAGTTCGGCG ACCCGGTGGT GCAGTCGGAC ATGAAGCACT GGCCTTTCCA GGTGATCAAC

                              HuHSP70
  +1   D  G  D  K  P  K  V  Q  V  S  Y  K  G  D  T  K  A  E  Y  P  E  E  I S·
1261  GACGGAGACA AGCCCAAGGT GCAGGTGAGC TACAAGGGGG ACACCAAGGC ATTCTACCCC GAGGAGATCT

                              HuHSP70
  +1  ·S S  M  V  L  T  K  M  K  E  I  A  E  A  Y  L  G  Y  P  V  T  N  A V·
1331  CGTCCATGGT GCTGACCAAG ATGAAGGAGA TCGCCGAGGC GTACCTGGGC TACCCGGTGA CCAACGCGGT

                              HuHSP70
  +1  ·V I  T  V  P  A  Y  E  N  D  S  Q  R  Q  A  T  K  D  A  G  V  I  A  G
1401  GATCACCGTG CCGGCCTACT TCAACGACTC GCAGCGCCAG GCCACCAAGG ATGCGGGTGT GATCGCGGGG
```

FIG. 8 CONT.

Nucleic Acid and Amino Acid sequences of HuHSP70 (N) hinge anti-mesothelin scFv

```
                                 HuHSP70
  +1  L  N  V  L  R  I  I  N  E  P  T  A  A  A  I  A  Y  G  L  D  R  T  G K·
1471 CTCAACGTGC TGCGGATCAT CAACGAGCCC ACGGCCGCCG CCATCGCCTA CGGCCTGGAC AGAACGGGCA
                                 HuHSP70
  +1 ·K G  E  R  N  V  L  I  P  D  L  G  G  G  T  E  D  V  S  I  L  T  I D·
1541 AGGGGGAGCG CAACGTGCTC ATCTTTGACC TGGGCGGGGG CACCTTCGAC GTGTCCATCC TGACGATCGA
                                 HuHSP70
  +1 ·D D  G  I  F  E  V  K  A  T  A  G  D  T  H  L  G  G  E  D  F  D  N  R
1611 CGACGGCATC TTCGAGGTGA AGGCCACGGC CGGGGACACC CACCTGGGTG GGGAGGACTT TGACAACAGG
                                 HuHSP70
  +1  L  V  N  H  F  V  E  E  F  K  R  K  H  K  K  D  L  S  Q  N  K  R  A V·
1681 CTGGTGAACC ACTTCGTGGA GGAGTTCAAG AGAAAACACA AGAAGGACAT CAGCCAGAAC AAGCGAGCCG
                                 HuHSP70
  +1 ·V R  R  L  R  T  A  C  E  R  A  K  R  T  L  S  S  S  T  Q  A  S  L E·
1751 TGAGGCGGCT GCGCACCGCC TGCGAGAGGG CCAAGAGGAC CCTGTCGTCC AGCACCCAGG CCAGCCTGGA
                                 HuHSP70
  +1 ·E I  D  S  L  F  E  G  I  D  F  Y  T  S  I  T  R  A  R  F  E  E  L  C
1821 GATCGACTCC CTGTTTGAGG GCATCGACTT CTACACGTCC ATCACCAGGG CGAGGTTCGA GGAGCTGTGC
                                 HuHSP70
  +1  S  D  L  F  R  S  T  L  E  P  V  E  K  A  L  R  D  A  K  L  D  K  A Q·
1891 TCCGACCTGT TCCGAAGCAC CCTGGAGCCC GTGGAGAAGG CTCTGCGCGA CGCCAAGCTG GACAAGGCCC
```

FIG. 8 CONT.

Nucleic Acid and Amino Acid sequences of HuHSP70 (N) hinge anti-mesothelin scFv

```
                                    HuHSP70
  +1  Q  I  H  D  L  V  L  V  G  G  S  T  R  I  P  K  V  Q  K  L  L  Q  D  F·
1961  AGATTCACGA CCTGGTCCTG GTCGGGGGCT CCACCCGCAT CCCCAAGGTG CAGAAGCTGC TGCAGGACTT

                                    HuHSP70
  +1 ·F  F  N  G  R  D  L  N  K  S  I  N  P  D  E  A  V  A  Y  G  A  A  V  Q
2031  CTTCAACGGG CGCGACCTGA ACAAGAGCAT CAACCCCGAC GAGGCTGTGG CCTACGGGGC GGCGGTGCAG

                                    HuHSP70
  +1  A  A  I  L  M  G  D  K  S  E  N  V  Q  D  L  L  L  L  D  V  A  P  L  S·
2101  GCGGCCATCC TGATGGGGGA CAAGTCCGAG AACGTGCAGG ACCTGCTGCT GCTGGACGTG GCTCCCCTGT

                                    HuHSP70
  +1 ·S  L  G  L  E  T  A  G  G  V  M  T  A  L  I  K  R  N  S  T  I  P  T  K·
2171  CGCTGGGGCT GGAGACGGCC GGAGGCGTGA TGACTGCCCT GATCAAGCGC AACTCCACCA TCCCCACCAA

                                    HuHSP70
  +1 ·K  Q  T  Q  I  F  T  T  Y  S  D  N  Q  P  G  V  L  I  Q  V  Y  E  G  E
2241  GCAGACGCAG ATCTTCACCA CCTACTCCGA CAACCAACCC GGGGTGCTGA TCCAGGTGTA CGAGGGCGAG

                                    HuHSP70
  +1  R  A  M  T  K  D  N  N  L  L  G  R  F  E  L  S  G  I  P  P  A  P  R  G·
2311  AGGGCCATGA CGAAAGACAA CAATCTGTTG GGGCGCTTCG AGCTGAGCGG CATCCCTCCG GCCCCCAGGG

                                    HuHSP70
  +1 ·G  V  P  Q  I  E  V  T  F  D  I  D  A  N  G  I  L  N  V  T  A  T  D  K·
2381  GCGTGCCCCA GATCGAGGTG ACCTTCGACA TCGATGCCAA CGGCATCCTG AACGTCACGG CCACGGACAA
```

FIG. 8 CONT.

Nucleic Acid and Amino Acid sequences of HuHSP70 (N) hinge anti-mesothelin scFv

```
                                               HuHSP70
  +1 ·K S  T  G  K  A  N  K  I  T  I  T  N  D  K  G  R  L  S  K  E  E  I  E
2451 GAGCACCGGC AAGGCCAACA AGATCACCAT CACCAACGAC AAGGGCCGCC TGAGCAAGGA GGAGATCGAG

                                               HuHSP70
  +1  R  M  V  Q  E  A  E  K  Y  K  A  E  D  E  V  Q  R  E  R  V  S  A  K N·
2521 CGCATGGTGC AGGAGGCGGA GAAGTACAAA GCGGAGGACG AGGTGCAGCG CGAGAGGGTG TCAGCCAAGA

                                               HuHSP70
  +1 ·N  A  L  E  S  Y  A  F  N  M  K  S  A  V  E  D  E  G  L  K  G  K  I S·
2591 ACGCCCTGGA GTCCTACGCC TTCAACATGA AGAGCGCCGT GGAGGATGAG GGGCTCAAGG GCAAGATCAG

                                               HuHSP70
  +1 ·S E  A  D  K  K  K  V  L  D  K  C  Q  E  V  I  S  W  L  D  A  N  T  L
2661 CGAGGCCGAC AAGAAGAAGG TGCTGGACAA GTGTCAAGAG GTCATCTCGT GGCTGGACGC CAACACCTTG

                                               HuHSP70
  +1  A  E  K  D  E  F  E  H  K  R  K  E  L  E  Q  V  C  N  P  I  I  S  G L·
2731 GCCGAGAAGG ACGAGTTTGA GCACAAGAGG AAGGAGCTGG AGCAGGTGTG TAACCCCATC ATCAGCGGAC

                                               HuHSP70
  +1 ·L  Y  Q  G  A  G  G  P  G  P  G  G  F  G  A  Q  G  P  K  G  G  S  G S·
2801 TGTACCAGGG TGCCGGTGGT CCCGGGCCTG GGGGCTTCGG GGCTCAGGGT CCCAAGGGAG GGTCTGGGTC

                HuHSP70
  +1 ·S G  P  T  I  E  E  V  D
2871 AGGCCCCACC ATTGAGGAGG TAGAT
```

FIG. 8 CONT.

Nucleic Acid and Amino Acid sequences of MTBHSP70 (C) linker mesothelin peptide

```
                                        His-tag
+1   M  A  H  H  H  H  H  H  H  H  H  H  G  A  L  E  V  L  F  Q  G  P  G  Y·
1    ATGGCACATC ACCACCATCA TCACCATCAC CACCACGGTG CACTTGAAGT CCTCTTTCAG GGACCCGGGT

               His-tag
                                                      MTBHSP70sk
+1  ·Y  Q  D  P  V  Q  V  D  A  A  A  M  A  R  A  V  G  I  D  L  G  T  T  N·
71   ACCAGGATCC TGTACAAGTC GACGCGGCCG CAATGGCTCG TGCGGTCGGG ATCGACCTCG GGACCACCAA

                                   MTBHSP70sk
+1  ·N  S  V  V  S  V  L  E  G  G  D  P  V  V  V  A  N  S  E  G  S  R  T  T
141  CTCCGTCGTC TCGGTTCTGG AAGGTGGCGA CCCGGTCGTC GTCGCCAACT CCGAGGGCTC CAGGACCACC

                                   MTBHSP70sk
+1   P  S  I  V  A  F  A  R  N  G  E  V  L  V  G  Q  P  A  K  N  Q  A  V  T·
211  CCGTCAATTG TCGCGTTCGC CCGCAACGGT GAGGTGCTGG TCGGCCAGCC CGCCAAGAAC CAGGCGGTGA

                                   MTBHSP70sk
+1  ·T  N  V  D  R  T  V  R  S  V  K  R  H  M  G  S  D  W  S  I  E  I  D  G·
281  CCAACGTCGA TCGCACCGTG CGCTCGGTCA AGCGACACAT GGGCAGCGAC TGGTCCATAG AGATTGACGG

                                   MTBHSP70sk
+1  ·G  K  K  Y  T  A  P  E  I  S  A  R  I  L  M  K  L  K  R  D  A  R  A  Y
351  CAAGAAATAC ACCGCGCCGG AGATCAGCGC CCGCATTCTG ATGAAGCTGA AGCGCGACGC CGAGGCCTAC

                                   MTBHSP70sk
+1   L  G  E  D  I  T  D  A  V  I  T  T  P  A  Y  F  N  D  A  Q  R  Q  A  T·
421  CTCGGTGAGG ACATTACCGA CGCGGTTATC ACGACGCCCG CCTACTTCAA TGACGCCCAG CGTCAGGCCA
```

FIG. 10

Nucleic Acid and Amino Acid sequences of MTBHSP70 (C) linker mesothelin peptide

```
                          MTBHSP70sk
 +1  ·T K D A G Q I A G L N V L R I V N E P T A A A L·
491  CCAAGGACGC CGGCCAGATC GCCGGCCTCA ACGTGCTGCG GATCGTCAAC GAGCCGACCG CTGCAGCGCT

MTBHSP70sk
 +1  ·L A Y G L D K G E K E Q R I L V F D L G G G T F
561  GGCCTACGGC CTCGACAAGG GCGAGAAGGA GCAGCGAATC CTGGTCTTCG ACTTGGGTGG TGGCACTTTC

MTBHSP70sk
 +1   D V S L L E I G E G V V E V R A T S G D N H L G·
631  GACGTTTCCC TGCTGGAGAT CGGCGAGGGT GTGGTTGAGG TCCGTGCCAC TTCGGGTGAC AACCACCTCG

MTBHSP70sk
 +1  ·G G D D W D Q R V V D W L V D K F K G T S G I D·
701  GCGGCGACGA CTGGGACCAG CGGGTCGTCG ATTGGCTGGT GGACAAGTTC AAGGGCACCA GCGGCATCGA

MTBHSP70sk
 +1  ·D I T K D K M A M Q R L R E A A E K A K I E L S
771  TCTGACCAAG GACAAGATGG CGATGCAGCG GCTGCGGGAA GCCGCCGAGA AAGCAAAGAT CGAGCTGAGT

MTBHSP70sk
 +1   S S Q S T S I N L P Y I T V D A D K N P L F L D·
841  TCGAGTCAGT CCACCTCGAT CAACCTGCCC TACATCACCG TCGACGCCGA CAAGAACCCG TTGTTCTTAG

MTBHSP70sk
 +1  ·D E Q L T R A E F Q R I T Q D L L D R T R K P F·
911  ACGAGCAGCT GACCCGCGCG GAGTTCCAAC GGATCACTCA GGACCTGCTG GACCGCACTC GCAAGCCGTT
```

FIG. 10 CONT.

Nucleic Acid and Amino Acid sequences of MTBHSP70 (C) linker mesothelin peptide

```
                                MTBHSP70sk
  +1 ·F Q  S  V  I  A  D  T  G  I  S  V  S  E  I  D  H  V  V  L  V  G  G  S
 981 CCAGTCGGTG ATCGCTGACA CCGGCATTTC GGTGTCGGAG ATCGATCACG TTGTGCTCGT GGGTGGTTCG
                                MTBHSP70sk
  +1  T  R  M  P  A  V  T  D  L  V  K  E  L  T  G  G  K  E  P  N  K  G  V N·
1051 ACCCGGATGC CCGCGGTGAC CGATCTGGTC AAGGAACTCA CCGGCGGCAA GGAACCCAAC AAGGGCGTCA
                                MTBHSP70sk
  +1 ·N  P  D  E  V  V  A  V  G  A  A  L  Q  A  G  V  L  K  G  E  V  K  D V·
1121 ACCCCGATGA GGTTGTCGCG GTGGGAGCCG CTCTGCAGGC CGGCGTCCTC AAGGGCGAGG TGAAAGACGT
                                MTBHSP70sk
  +1 ·V L  L  L  D  V  T  P  L  S  L  G  I  E  T  K  G  G  V  M  T  R  L  I
1191 TCTGCTGCTT GATGTTACCC CGCTGAGCCT GGGTATCGAG ACCAAGGGCG GGGTGATGAC CAGGCTCATC
                                MTBHSP70sk
  +1  E  R  N  T  T  I  P  T  K  R  S  E  S  F  T  T  A  D  D  N  Q  P  S V·
1261 GAGCGCAACA CCACGATCCC CACCAAGCGG TCGGAGTCTT TCACCACCGC CGACGACAAC CAACCGTCGG
                                MTBHSP70sk
  +1 ·V  Q  I  Q  V  Y  Q  G  E  R  E  I  A  A  H  N  K  L  L  G  S  F  E L·
1331 TGCAGATCCA GGTCTATCAG GGGGAGCGTG AGATCGCCGC GCACAACAAG TTGCTCGGGT CCTTCGAGCT
                                MTBHSP70sk
  +1 ·L T  G  I  P  P  A  P  R  G  I  P  Q  I  E  V  T  F  D  I  D  A  N  G
1401 GACCGGCATC CCGCCGGCGC CGCGGGGGAT TCCGCAGATC GAGGTCACTT TCGACATCGA CGCCAACGGC
```

FIG. 10 CONT.

Nucleic Acid and Amino Acid sequences of MTBHSP70 (C) linker mesothelin peptide

```
                                         MTBHSP70sk
  +1  I  V  H  V  T  A  K  D  K  G  T  G  K  E  N  T  I  R  I  Q  E  G  S G·
1471  ATTGTGCACG TCACCGCCAA GGACAAGGGC ACCGGCAAGG AGAACACGAT CCGAATCCAG GAAGGCTCGG

                                         MTBHSP70sk
  +1 ·G L  S  K  E  D  I  D  R  M  I  K  D  A  E  A  H  A  E  E  D  R  K R·
1541  GCCTGTCCAA GGAAGACATT GACCGCATGA TCAAGGACGC CGAAGCGCAC GCCGAGGAGG ATCGCAAGCG

                                         MTBHSP70sk
  +1 ·R R  E  E  A  D  V  R  N  Q  A  E  T  I  V  Y  Q  T  E  K  F  V  K  E
1611  TCGCGAGGAG GCCGATGTTC GTAATCAAGC CGAGACATTG GTCTACCAGA CGGAGAAGTT CGTCAAAGAA

                                         MTBHSP70sk
  +1  Q  R  E  A  E  G  G  S  K  V  P  E  D  T  L  N  K  V  D  A  A  V  A E·
1681  CAGCGTGAGG CCGAGGGTGG TTCGAAGGTA CCTGAAGACA CGCTGAACAA GGTTGATGCC GCGGTGGCGG

                                         MTBHSP70sk
  +1 ·E  A  K  A  A  L  G  G  S  D  I  S  A  I  K  S  A  M  E  K  L  G  Q E·
1751  AAGCGAAGGC GGCACTTGGC GGATCGGATA TTTCGGCCAT CAAGTCGGCG ATGGAGAAGC TGGGCCAGGA

                                         MTBHSP70sk
  +1 ·E S  Q  A  L  G  Q  A  I  Y  E  A  A  Q  A  A  S  Q  A  T  G  A  A  H
1821  GTCGCAGGCT CTGGGGCAAG CGATCTACGA AGCAGCTCAG GCTGCGTCAC AGGCCACTGG CGCTGCCCAC

                                         MTBHSP70sk
  +1  P  G  G  E  P  G  G  A  H  P  G  S  A  D  D  V  V  D  A  E  V  V  D D·
1891  CCCGGCGGCG AGCCGGGCGG TGCCCACCCC GGCTCGGCTG ATGACGTTGT GGACGCGGAG GTGGTCGACG
```

FIG. 10 CONT.

Nucleic Acid and Amino Acid sequences of MTBHSP70 (C) linker mesothelin peptide

```
                                          Linker
          MTBHSP70sk                                                           Mesothelinpeptide
 +1   D G R E A K G G G G S G G G G S G G G G S K L L·
1961  ACGGCCGGGA GGCCAAGGGT GGCGGTGGCA GCGGCGGTGG TGGTTCCGGA GGCGGCGGTT CTAAACTTCT

          Mesothelinpeptide
 +1  ·L G P H V E G L
2031  GGGACCCCAC GTGGAGGGCC TG
```

FIG. 10 CONT.

Nucleic Acid and Amino Acid sequences of MTBHSP70 (N) linker mesothelin peptide

```
                                His-tag
+1   M  A  H  H  H  H  H  H  H  H  H  H  G  A  L  E  V  L  F  Q  G  P  G  Y·
1    ATGGCACATC ACCACCATCA TCACCATCAC CACCACGGTG CACTTGAAGT CCTCTTTCAG GGACCCGGGT

                                          Mesothelinpeptide
                    His-tag                                            Linker
+1   ·Y  Q  D  P  V  Q  V  D  A  A  A  K  L  L  G  P  H  V  E  G  L  G  G  G·
71   ACCAGGATCC TGTACAAGTC GACGCGGCCG CAAAACTTCT GGGACCCCAC GTGGAGGGCC TGGGTGGCGG

                     Linker
                                                  MTBHSP70sk
+1   ·G  G  S  G  G  G  G  S  G  G  G  G  S  M  A  R  A  V  G  I  D  L  G  T
141  TGGCAGCGGC GGTGGTGGTT CCGGAGGCGG CGGTTCTATG GCTCGTGCGG TCGGGATCGA CCTCGGGACC

                                MTBHSP70sk
+1   T  N  S  V  V  S  V  L  E  G  G  D  P  V  V  V  A  N  S  F  G  S  R  T·
211  ACCAACTCCG TCGTCTCGGT TCTGGAAGGT GGCGACCCGG TCGTCGTCGC CAACTCCGAG GGCTCCAGGA

                                MTBHSP70sk
+1   ·T  T  P  S  I  V  A  F  A  R  N  G  E  V  L  V  G  Q  P  A  K  N  Q  A·
281  CCACCCCGTC AATTGTCGCG TTCGCCCGCA ACGGTGAGGT GCTGGTCGGC CAGCCCGCCA AGAACCAGGC

                                MTBHSP70sk
+1   ·A  V  T  N  V  D  R  T  V  R  S  V  K  R  H  M  G  S  D  W  S  I  E  I
351  GGTGACCAAC GTCGATCGCA CCGTGCGCTC GGTCAAGCGA CACATGGGCA GCGACTGGTC CATAGAGATT

                                MTBHSP70sk
+1   D  G  K  K  Y  T  A  P  E  I  S  A  R  I  L  M  K  L  K  R  D  A  E  A·
421  GACGGCAAGA AATACACCGC GCCGGAGATC AGCGCCCGCA TTCTGATGAA GCTGAAGCGC GACGCCGAGG
```

FIG. 12

Nucleic Acid and Amino Acid sequences of MTBHSP70 (N) linker mesothelin peptide

```
                          MTBHSP70sk
 +1  ·A Y D G E D I T D A V I T T P A Y F N D A Q R Q·
491  CCTACCTCGG TGAGGACATT ACCGACGCGG TTATCACGAC GCCCGCCTAC TTCAATGACG CCCAGCGTCA

                          MTBHSP70sk
 +1  ·Q A T K D A G Q I A G L N V L R I V N E P T A A
561  GGCCACCAAG GACGCCGGCC AGATCGCCGG CCTCAACGTG CTGCGGATCG TCAACGAGCC GACCGCTGCA

                          MTBHSP70sk
 +1   A L A Y G L D K G E K E Q R I L V F D L G G G T·
631  GCGCTGGCCT ACGGCCTCGA CAAGGGCGAG AAGGAGCAGC GAATCCTGGT CTTCGACTTG GGTGGTGGCA

                          MTBHSP70sk
 +1  ·T F D V S L L E I G E G V V E V R A T S G D N H·
701  GTTTCGACGT TTCCCTGCTG GAGATCGGCG AGGGTGTGGT TGAGGTCCGT GCCACTTCGG GTGACAACCA

                          MTBHSP70sk
 +1  ·H L G G D D W D Q R V V D W L V D K F K G T S G
771  CCTCGGCGGC GACGACTGGG ACCAGCGGGT CGTCGATTGG CTGGTGGACA AGTTCAAGGG CACCAGCGGC

                          MTBHSP70sk
 +1   I D L T K D K M A M Q R L R E A A E K A K I E L·
841  ATCGATCTGA CCAAGGACAA GATGGCGATG CAGCGGCTGC GGGAAGCCGC CGAGAAAGCA AAGATCGAGC

                          MTBHSP70sk
 +1  ·L S S S Q S T S I N L P Y I T V D A D K N P L F·
911  TGAGTTCGAG TCAGTCCACC TCGATCAACC TGCCCTACAT CACCGTCGAC GCCGACAAGA ACCCGTTGTT
```

FIG. 12 CONT.

Nucleic Acid and Amino Acid sequences of MTBHSP70 (N) linker mesothelin peptide

MTBHSP70sk
+1 ·F L D E Q L T R A E F Q R I T Q D L L D R T R K
981 CTTAGACGAG CAGCTGACCC GCGCGGAGTT CCAACGGATC ACTCAGGACC TGCTGGACCG CACTCGCAAG

MTBHSP70sk
+1 P F Q S V I A D T G I S V S E I D H V V L V G G·
1051 CCGTTCCAGT CGGTGATCGC TGACACCGGC ATTTCGGTGT CGGAGATCGA TCACGTTGTG CTCGTGGGTG

MTBHSP70sk
+1 ·G S T R M P A V T D L V K E L T G G K E P N K G·
1121 GTTCGACCCG GATGCCCGCG GTGACCGATC TGGTCAAGGA ACTCACCGGC GGCAAGGAAC CCAACAAGGG

MTBHSP70sk
+1 ·G V N P D E V V A V G A A L Q A G V L K G E V K
1191 CGTCAACCCC GATGAGGTTG TCGCGGTGGG AGCCGCTCTG CAGGCCGGCG TCCTCAAGGG CGAGGTGAAA

MTBHSP70sk
+1 D V L L L D V T P L S L G I E T K G G V M T R L·
1261 GACGTTCTGC TGCTTGATGT TACCCCGCTG AGCCTGGGTA TCGAGACCAA GGGCGGGGTG ATGACCAGGC

MTBHSP70sk
+1 ·L I E R N T T I P T K R S E S F T T A D D N Q P·
1331 TCATCGAGCG CAACACCACG ATCCCCACCA AGCGGTCGGA GTCTTTCACC ACCGCCGACG ACAACCAACC

MTBHSP70sk
+1 ·P S V Q I Q V Y Q G E R E I A A H N K I L G S F
1401 GTCGGTGCAG ATCCAGGTCT ATCAGGGGGA GCGTGAGATC GCCGCGCACA ACAAGTTGCT CGGGTCCTTC

FIG. 12 CONT.

Nucleic Acid and Amino Acid sequences of MTBHSP70 (N) linker mesothelin peptide

```
                                      MTBHSP70sk
  +1   E  L  T  G  I  P  P  A  P  R  G  I  P  Q  I  E  V  T  F  D  I  D  A  N·
1471  GAGCTGACCG GCATCCCGCC GGCGCCGCGG GGGATTCCGC AGATCGAGGT CACTTTCGAC ATCGACGCCA

                                      MTBHSP70sk
  +1  ·N  G  I  V  H  V  T  A  K  D  K  G  T  G  K  E  H  T  I  R  I  Q  E  G·
1541  ACGGCATTGT GCACGTCACC GCCAAGGACA AGGGCACCGG CAAGGAGAAC ACGATCCCAA TCCAGGAAGG

                                      MTBHSP70sk
  +1  ·G  S  G  L  S  K  E  D  I  D  R  M  I  K  D  A  E  A  H  A  E  E  D  R
1611  CTCGGGCCTG TCCAAGGAAG ACATTGACCG CATGATCAAG GACGCCGAAG CGCACGCCGA GGAGGATCGC

                                      MTBHSP70sk
  +1   K  R  R  E  E  A  D  V  R  N  Q  A  E  T  L  V  Y  Q  T  E  K  F  V  K·
1681  AAGCGTCGCG AGGAGGCCGA TGTTCGTAAT CAAGCCGAGA CATTGGTCTA CCAGACGGAG AAGTTCGTCA

                                      MTBHSP70sk
  +1  ·K  E  Q  R  E  A  E  G  G  S  K  V  P  E  D  T  L  N  K  V  D  A  A  V·
1751  AAGAACAGCG TGAGGCCGAG GGTGGTTCGA AGGTACCTGA AGACACGCTG AACAAGGTTG ATGCCGCGGT

                                      MTBHSP70sk
  +1  ·V  A  E  A  K  A  A  L  G  G  S  D  I  S  A  I  K  S  A  M  E  K  L  G
1821  GGCGGAAGCG AAGGCGGCAC TTGGCGGATC GGATATTTCG GCCATCAAGT CGGCGATGGA GAAGCTGGGC

                                      MTBHSP70sk
  +1   Q  E  S  Q  A  L  G  Q  A  I  Y  E  A  A  Q  A  A  S  Q  A  T  G  A  A·
1891  CAGGAGTCGC AGGCTCTGGG GCAAGCGATC TACGAAGCAG CTCAGGCTGC GTCACAGGCC ACTGGCGCTG
```

FIG. 12 CONT.

Nucleic Acid and Amino Acid sequences of MTBHSP70 (N) linker mesothelin peptide

```
                                          MTBHSP70sk
  +1  A H  P   G   G   E   P   G   G   A   H   P   G   S   A   D   D   V   V   D   A   E   V  V•
1961  CCCACCCCGG CGGCGAGCCG GGCGGTGCCC ACCCCGGCTC GGCTGATGAC GTTGTGGACG CGGAGGTGGT

            MTBHSP70sk
  +1 ·V D  D   G   R   E   A   K
2031  CGACGACGGC CGGGAGGCCA AG
```

FIG. 12 CONT.

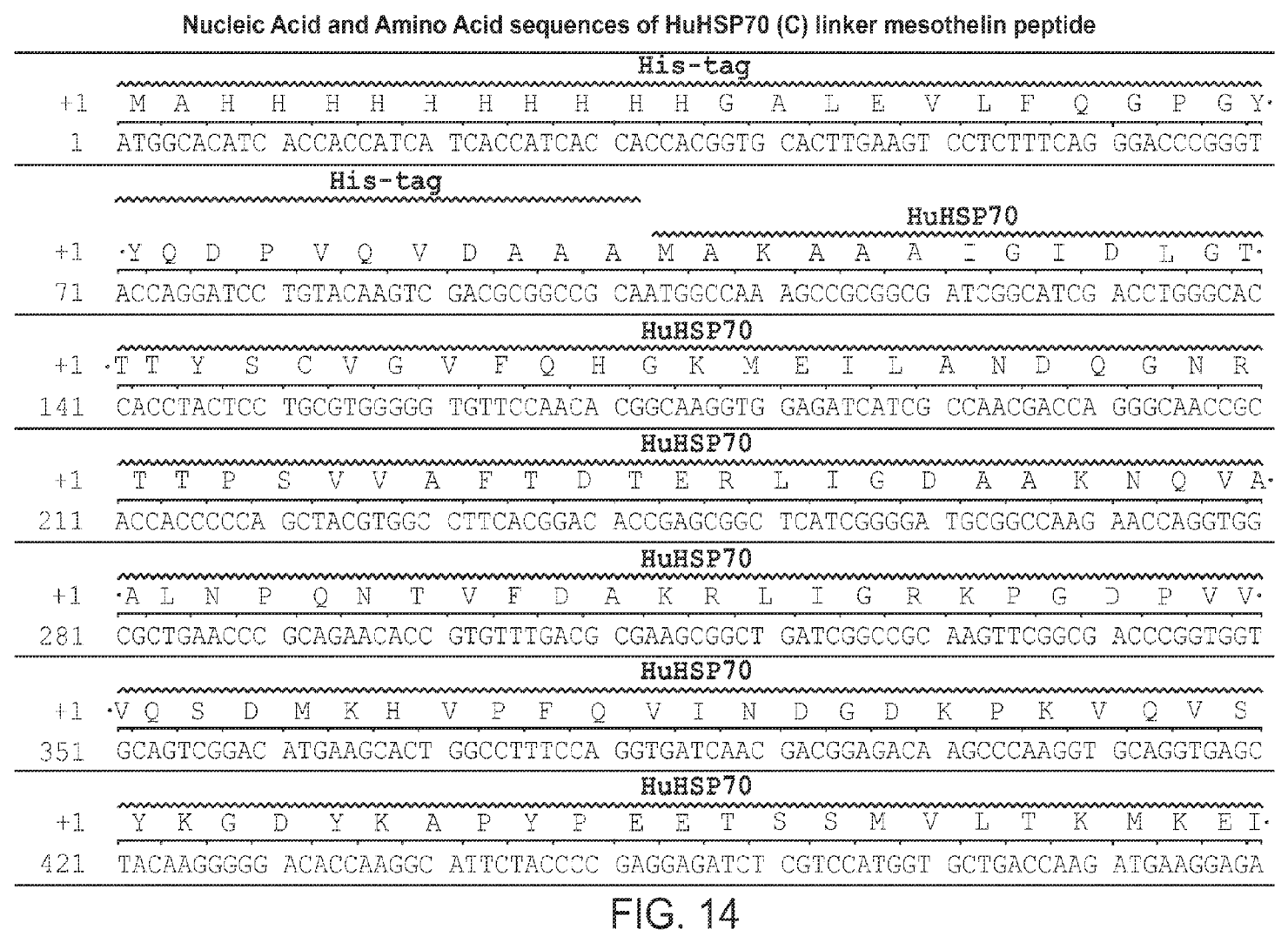

Nucleic Acid and Amino Acid sequences of HuHSP70 (C) linker mesothelin peptide

```
                                      His-tag
+1   M  A  H  H  H  H  H  H  H  H  H  H  G  A  L  E  V  L  F  Q  G  P  G  Y·
1    ATGGCACATC ACCACCATCA TCACCATCAC CACCACGGTG CACTTGAAGT CCTCTTTCAG GGACCCGGGT

                 His-tag
                                                      HuHSP70
+1  ·Y  Q  D  P  V  Q  V  D  A  A  A  M  A  K  A  A  A  I  G  I  D  L  G  T·
71   ACCAGGATCC TGTACAAGTC GACGCGGCCG CAATGGCCAA AGCCGCGGCG ATCGGCATCG ACCTGGGCAC

                                      HuHSP70
+1  ·T  T  Y  S  C  V  G  V  F  Q  H  G  K  M  E  I  L  A  N  D  Q  G  N  R
141  CACCTACTCC TGCGTGGGGG TGTTCCAACA CGGCAAGGTG GAGATCATCG CCAACGACCA GGGCAACCGC

                                      HuHSP70
+1   T  T  P  S  V  V  A  F  T  D  T  E  R  L  I  G  D  A  A  K  N  Q  V  A·
211  ACCACCCCCA GCTACGTGGC CTTCACGGAC ACCGAGCGGC TCATCGGGGA TGCGGCCAAG AACCAGGTGG

                                      HuHSP70
+1  ·A  L  N  P  Q  N  T  V  F  D  A  K  R  L  I  G  R  K  P  G  D  P  V  V·
281  CGCTGAACCC GCAGAACACC GTGTTTGACG CGAAGCGGCT GATCGGCCGC AAGTTCGGCG ACCCGGTGGT

                                      HuHSP70
+1  ·V  Q  S  D  M  K  H  V  P  F  Q  V  I  N  D  G  D  K  P  K  V  Q  V  S
351  GCAGTCGGAC ATGAAGCACT GGCCTTTCCA GGTGATCAAC GACGGAGACA AGCCCAAGGT GCAGGTGAGC

                                      HuHSP70
+1   Y  K  G  D  Y  K  A  P  Y  P  E  E  T  S  S  M  V  L  T  K  M  K  E  I·
421  TACAAGGGGG ACACCAAGGC ATTCTACCCC GAGGAGATCT CGTCCATGGT GCTGACCAAG ATGAAGGAGA
```

FIG. 14

Nucleic Acid and Amino Acid sequences of HuHSP70 (C) linker mesothelin peptide

```
                                      HuHSP70
 +1  ·I  A  E  A  Y  L  G  Y  P  V  T  N  A  V  I  T  V  P  A  Y  F  N  D  S·
491  TCGCCGAGGC GTACCTGGGC TACCCGGTGA CCAACGCGGT GATCACCGTG CCGGCCTACT TCAACGACTC
                                      HuHSP70
 +1  ·S  Q  R  Q  A  T  K  D  A  G  V  I  A  G  L  N  V  L  R  I  I  N  E  P
561  GCAGCGCCAG GCCACCAAGG ATGCGGGTGT GATCGCGGGG CTCAACGTGC TGCGGATCAT CAACGAGCCC
                                      HuHSP70
 +1   T  A  A  A  I  A  Y  G  L  D  R  T  G  K  G  E  R  N  V  L  I  F  D  L·
631  ACGGCCGCCG CCATCGCCTA CGGCCTGGAC AGAACGGGCA AGGGGGAGCG CAACGTGCTC ATCTTTGACC
                                      HuHSP70
 +1  ·L  G  G  G  T  F  D  V  S  I  L  T  I  D  D  G  I  F  E  V  K  A  T  A·
701  TGGGCGGGGG CACCTTCGAC GTGTCCATCC TGACGATCGA CGACGGCATC TTCGAGGTGA AGGCCACGGC
                                      HuHSP70
 +1  ·A  G  D  T  H  L  G  G  E  D  F  D  N  R  L  V  N  H  F  V  E  E  F  K
771  CGGGGACACC CACCTGGGTG GGGAGGACTT TGACAACAGG CTGGTGAACC ACTTCGTGGA GGAGTTCAAG
                                      HuHSP70
 +1   R  K  H  K  K  D  I  S  Q  M  K  R  A  V  R  R  L  R  T  A  C  E  R  A·
841  AGAAAACACA AGAAGGACAT CAGCCAGAAC AAGCGAGCCG TGAGGCGGCT GCGCACCGCC TGCGAGAGGG
                                      HuHSP70
 +1  ·A  K  R  T  L  S  S  S  T  Q  A  S  L  E  I  D  S  L  F  E  G  I  D  F·
911  CCAAGAGGAC CCTGTCGTCC AGCACCCAGG CCAGCCTGGA GATCGACTCC CTGTTTGAGG GCATCGACTT
```

FIG. 14 CONT.

Nucleic Acid and Amino Acid sequences of HuHSP70 (C) linker mesothelin peptide

```
                                          HuHSP70
  +1  ·F Y  T   S   I   T   R   A   R   F   E   E   L   C   S   D   L   F   R   S   T   L  E  P
 981  CTACACGTCC ATCACCAGGG CGAGGTTCGA GGAGCTGTGC TCCGACCTGT TCCGAAGCAC CCTGGAGCCC

                                          HuHSP70
  +1   V   E   K   A   L   R   D   A   K   L   D   K   A   Q   I   H   D   L   V   L   V   G   G  S·
1051  GTGGAGAAGG CTCTGCGCGA CGCCAAGCTG GACAAGGCCC AGATTCACGA CCTGGTCCTG GTCGGGGGCT

                                          HuHSP70
  +1  ·S   T   R   I   P   K   V   Q   K   L   L   Q   D   F   F   N   G   R   D   L   N   K   S  I·
1121  GCACCCGCAT CCCCAAGGTG CAGAAGCTGC TGCAGGACTT CTTCAACGGG CGCGACCTGA ACAAGAGCAT

                                          HuHSP70
  +1  ·I N   P   D   E   A   V   A   Y   G   A   A   V   Q   A   A   I   L   M   G   D   K   S   E
1191  CAACCCCGAC GAGGCTGTGG CCTACGGGGC GGCGGTGCAG GCGGCCATCC TGATGGGGGA CAAGTCCGAG

                                          HuHSP70
  +1   N   V   Q   D   L   L   L   L   D   V   A   P   L   S   L   G   L   E   T   A   G   G   V  M·
1261  AACGTGCAGG ACCTGCTGCT GCTGGACGTG GCTCCCCTGT CGCTGGGGCT GGAGACGGCC GGAGGCGTGA

                                          HuHSP70
  +1  ·M   T   A   L   I   K   R   N   S   T   I   P   T   K   Q   T   Q   I   F   T   T   Y   S  D·
1331  TGACTGCCCT GATCAAGCGC AACTCCACCA TCCCCACCAA GCAGACGCAG ATCTTCACCA CCTACTCCGA

                                          HuHSP70
  +1  ·D N   Q   P   G   V   L   I   Q   V   Y   E   G   E   R   A   M   T   K   D   N   N   L   L
1401  CAACCAACCC GGGGTGCTGA TCCAGGTGTA CGAGGGCGAG AGGGCCATGA CGAAAGACAA CAATCTGTTG
```

FIG. 14 CONT.

Nucleic Acid and Amino Acid sequences of HuHSP70 (C) linker mesothelin peptide

```
                                        HuHSP70
  +1  G R F E I S G I P P A P R G V P Q I E V T F D I·
1471  GGGCGCTTCG AGCTGAGCGG CATCCCTCCG GCCCCCAGGG GCGTGCCCCA GATCGAGGTG ACCTTCGACA

                                        HuHSP70
  +1  ·I D A N G I L N V T A T D K S T G K A N K I T I·
1541  TCGATGCCAA CGGCATCCTG AACGTCACGG CCACGGACAA GAGCACCGGC AAGGCCAACA AGATCACCAT

                                        HuHSP70
  +1  ·I T N D K G R L S K E E I E R M V Q E A E K Y K
1611  CACCAACGAC AAGGGCCGCC TGAGCAAGGA GGAGATCGAG CGCATGGTGC AGGAGGCGGA GAAGTACAAA

                                        HuHSP70
  +1  A E D E V Q R E R V S A K N A L E S Y A F N M K·
1681  GCGGAGGACG AGGTGCAGCG CGAGAGGGTG TCAGCCAAGA ACGCCCTGGA GTCCTACGCC TTCAACATGA

                                        HuHSP70
  +1  ·K S A V E D E G L K G K I S E A D K K K V L D K·
1751  AGAGCGCCGT GGAGGATGAG GGGCTCAAGG GCAAGATCAG CGAGGCCGAC AAGAAGAAGG TGCTGGACAA

                                        HuHSP70
  +1  ·K C Q E V I S W L D A N T L A E K D E F E H K R
1821  GTGTCAAGAG GTCATCTCGT GGCTGGACGC CAACACCTTG GCCGAGAAGG ACGAGTTTGA GCACAAGAGG

                                        HuHSP70
  +1  K E L E Q V G N P I I S G L Y Q G A G G P G P G·
1891  AAGGAGCTGG AGCAGGTGTG TAACCCCATC ATCAGCGGAC TGTACCAGGG TGCCGGTGGT CCCGGGCCTG
```

FIG. 14 CONT.

Nucleic Acid and Amino Acid sequences of HuHSP70 (C) linker mesothelin peptide

```
                                   HuHSP70                                        Linker
   +1  ·G  G  F  G  A  Q  G  P  K  G  G  S  G  S  G  P  T  I  E  E  V  D  G  G·
 1961  GGGGCTTCGG GGCTCAGGGT CCCAAGGGAG GGTCTGGGTC AGGCCCCACC ATTGAGGAGG TAGATGGTGG

                       Linker                              Mesothelin Peptide
   +1  ·G  G  G  S  G  G  G  G  S  G  G  G  G  S  K  L  L  G  P  H  V  E  G  L
 2031  CGGTGGCAGC GGCGGTGGTG GTTCCGGAGG CGGCGGTTCT AAACTTCTGG GACCCCACGT GGAGGGCCTG
```

FIG. 14 CONT.

Nucleic Acid and Amino Acid sequences of HuHSP70 (N) linker mesothelin peptide

```
                                        His-tag
 +1  M  A  H  H  H  H  H  H  H  H  H  H  G  A  L  E  V  L  F  Q  G  P  G  Y·
  1  ATGGCACATC ACCACCATCA TCACCATCAC CACCACGGTG CACTTGAAGT CCTCTTTCAG GGACCCGGGT

                                                      Mesothelin Peptide
                His-tag                                                  Linker
 +1 ·Y  Q  D  P  V  Q  V  D  A  A  A  K  L  L  G  P  H  V  E  G  L  G  G  G·
 71  ACCAGGATCC TGTACAAGTC GACGCGGCCG CAAAACTTCT GGGACCCCAC GTGGAGGGCC TGGGTGGCGG

                 Linker
                                                      HuHSP70
 +1 ·G  G  S  G  G  G  G  S  G  G  G  G  S  M  A  K  A  A  A  I  G  I  D  L
141  TGGCAGCGGC GGTGGTGGTT CCGGAGGCGG CGGTTCTATG GCCAAAGCCG CGGCGATCGG CATCGACCTG

                                        HuHSP70
 +1  G  T  T  Y  S  C  V  G  V  F  Q  H  G  K  V  E  I  I  A  N  D  Q  G  N·
211  GGCACCACCT ACTCCTGCGT GGGGGTGTTC CAACACGGCA AGGTGGAGAT CATCGCCAAC GACCAGGGCA

                                        HuHSP70
 +1 ·N  R  T  T  P  S  Y  V  A  F  T  D  T  E  R  L  I  G  D  A  A  K  M  Q·
281  ACCGCACCAC CCCCAGCTAC GTGGCCTTCA CGGACACCGA GCGGCTCATC GGGGATGCGG CCAAGAACCA

                                        HuHSP70
 +1 ·Q  V  A  L  N  P  Q  N  T  V  F  D  A  K  R  L  I  G  R  K  F  G  D  P
351  GGTGGCGCTG AACCCGCAGA ACACCGTGTT TGACGCGAAG CGGCTGATCG GCCGCAAGTT CGGCGACCCG

                                        HuHSP70
 +1  V  V  Q  S  D  M  K  H  W  P  F  Q  V  I  N  D  G  D  K  P  K  V  Q  V·
421  GTGGTGCAGT CGGACATGAA GCACTGGCCT TTCCAGGTGA TCAACGACGG AGACAAGCCC AAGGTGCAGG
```

FIG. 16

Nucleic Acid and Amino Acid sequences of HuHSP70 (N) linker mesothelin peptide

```
                         HuHSP70
 +1  ·V S  Y  K  G  D  T  K  A  F  Y  P  E  E  I  S  S  M  V  L  T  K  M  K·
491  TGAGCTACAA GGGGGACACC AAGGCATTCT ACCCCGAGGA GATCTCGTCC ATGGTGCTGA CCAAGATGAA

                         HuHSP70
 +1 ·K E  I  A  E  A  Y  L  G  Y  P  V  T  N  A  V  I  T  V  P  A  Y  F  N
561  GGAGATCGCC GAGGCGTACC TGGGCTACCC GGTGACCAAC GCGGTGATCA CCGTGCCGGC CTACTTCAAC

                         HuHSP70
 +1   D  S  Q  R  Q  A  T  K  D  A  G  V  I  A  G  L  N  V  L  R  I  I  N  E·
631  GACTCGCAGC GCCAGGCCAC CAAGGATGCG GGTGTGATCG CGGGGCTCAA CGTGCTGCGG ATCATCAACG

                         HuHSP70
 +1  ·E P  T  A  A  A  I  A  Y  G  L  D  R  T  G  K  G  E  R  N  V  L  I  F·
701  AGCCCACGGC CGCCGCCATC GCCTACGGCC TGGACAGAAC GGGCAAGGGG GAGCGCAACG TGCTCATCTT

                         HuHSP70
 +1 ·F D  L  G  G  G  T  F  D  V  S  I  L  T  I  D  D  G  I  F  E  V  K  A
771  TGACCTGGGC GGGGGCACCT TCGACGTGTC CATCCTGACG ATCGACGACG GCATCTTCGA GGTGAAGGCC

                         HuHSP70
 +1   T  A  G  D  T  H  L  G  G  E  D  F  D  N  R  L  V  N  H  F  V  E  E  F·
841  ACGGCCGGGG ACACCCACCT GGGTGGGGAG GACTTTGACA ACAGGCTGGT GAACCACTTC GTGGAGGAGT

                         HuHSP70
 +1  ·F K  R  K  H  K  K  D  T  S  Q  N  K  R  A  V  R  R  L  R  T  A  D  E·
911  TCAAGAGAAA ACACAAGAAG GACATCAGCC AGAACAAGCG AGCCGTGAGG CGGCTGCGCA CCGCCTGCGA
```

FIG. 16 CONT.

Nucleic Acid and Amino Acid sequences of HuHSP70 (N) linker mesothelin peptide

```
                      HuHSP70
  +1 ·E R A K R T L S S S T Q A S L E I D S L F E G I
 981  GAGGGCCAAG AGGACCCTGT CGTCCAGCAC CCAGGCCAGC CTGGAGATCG ACTCCCTGTT TGAGGGCATC
                      HuHSP70
  +1  D F Y T S I T R A R F E E L C S D L F R S T L E·
1051  GACTTCTACA CGTCCATCAC CAGGGCGAGG TTCGAGGAGC TGTGCTCCGA CCTGTTCCGA AGCACCCTGG
                      HuHSP70
  +1 ·E P V E K A L R D A K L D K A Q I H D L V L V G·
1121  AGCCCGTGGA GAAGGCTCTG CGCGACGCCA AGCTGGACAA GGCCCAGATT CACGACCTGG TCCTGGTCGG
                      HuHSP70
  +1 ·G G S T R I P K V Q K L L Q D F F N G P D L N E
1191  GGGCTCCACC CGCATCCCCA AGGTGCAGAA GCTGCTGCAG GACTTCTTCA ACGGGCGCGA CCTGAACAAG
                      HuHSP70
  +1  S I N P D E A V A V G A A V Q A A I L M G D K S·
1261  AGCATCAACC CCGACGAGGC TGTGGCCTAC GGGGCGGCGG TGCAGGCGGC CATCCTGATG GGGGACAAGT
                      HuHSP70
  +1 ·S E N V Q D L L L L D V A P L S L G L E T A G G·
1331  CCGAGAACGT GCAGCACCTG CTGCTGCTGG ACGTGGCTCC CCTGTCGCTG GGGCTGGAGA CGGCCGGAGG
                      HuHSP70
  +1 ·G V M T A L I K R N S T I P T K Q T Q I F T T Y
1401  CGTGATGACT GCCCTGATCA AGCGCAACTC CACCATCCCC ACCAAGCAGA CGCAGATCTT CACCACCTAC
```

FIG. 16 CONT.

Nucleic Acid and Amino Acid sequences of HuHSP70 (N) linker mesothelin peptide

```
                          HuHSP70
  +1   S  D  N  Q  P  G  V  I  I  Q  V  Y  E  G  E  R  A  M  T  K  D  N  N L·
1471  TCCGACAACC AACCCGGGGT GCTGATCCAG GTGTACGAGG GCGAGAGGGC CATGACGAAA GACAACAATC

                          HuHSP70
  +1  ·I  L  G  R  F  E  L  S  G  I  P  P  A  P  R  G  V  P  Q  I  E  V  T  F·
1541  TGTTGGGGCG CTTCGAGCTG AGCGGCATCC CTCCGGCCCC CAGGGGCGTG CCCCAGATCG AGGTGACCTT

                          HuHSP70
  +1  ·F D  I  D  A  N  G  I  L  N  V  T  A  T  D  K  S  T  G  K  A  N  K  I
1611  CGACATCGAT GCCAACGGCA TCCTGAACGT CACGGCCACG GACAAGAGCA CCGGCAAGGC CAACAAGATC

                          HuHSP70
  +1   T  I  T  N  D  K  G  R  L  S  K  E  E  I  E  R  M  V  Q  E  A  E  K Y·
1681  ACCATCACCA ACGACAAGGG CCGCCTGAGC AAGGAGGAGA TCGAGCGCAT GGTGCAGGAG GCGGAGAAGT

                          HuHSP70
  +1  ·Y  K  A  E  D  E  V  Q  R  E  R  V  S  A  K  N  A  L  E  S  Y  A  F N·
1751  ACAAAGCGGA GGACGAGGTG CAGCGCGAGA GGGTGTCAGC CAAGAACGCC CTGGAGTCCT ACGCCTTCAA

                          HuHSP70
  +1 ·N M  K  S  A  V  E  D  E  G  L  K  G  K  I  S  E  A  D  K  K  K  V  L
1821  CATGAAGAGC GCCGTGGAGG ATGAGGGGCT CAAGGGCAAG ATCAGCGAGG CCGACAAGAA GAAGGTGCTG

                          HuHSP70
  +1   D  K  C  Q  E  V  I  S  W  L  D  A  N  T  L  A  E  K  D  E  F  E  H K·
1891  GACAAGTGTC AAGAGGTCAT CTCGTGGCTG GACGCCAACA CCTTGGCCGA GAAGGACGAG TTTGAGCACA
```

FIG. 16 CONT.

Nucleic Acid and Amino Acid sequences of HuHSP70 (N) linker mesothelin peptide

```
                                        HuHSP70
  +1  ·K R  K   E   L   E   Q   V   C   N   P   I   I   S   G   L   Y   Q   G   A   G   G  P G·
1961  AGAGGAAGGA GCTGGAGCAG GTGTGTAACC CCATCATCAG CGGACTGTAC CAGGGTGCCG GTGGTCCCGG
                                        HuHSP70
  +1 ·G P   G   G   F   G   A   Q   G   P   K   G   G   S   G   S   G   P   T   I   E   E   V   D
2031  GCCTGGGGGC TTCGGGGCTC AGGGTCCCAA GGGAGGGTCT GGGTCAGGCC CCACCATTGA GGAGGTAGAT
```

FIG. 16 CONT.

wAvidin= native Avidin; mAvidin= monomeric Avidin

Chaperone protein dnaK (Heat shock protein 70) from *Mycobacterium tuberculosis*
(P0A5B9, GI:61222666)

```
1   maravgidlg ttnsvvsvle ggdpvvvans egsrttpsiv afarngevlv gqpaknqavt
61  nvdrtvrsvk rhmgsdwsie idgkkytape isarilmklk rdaeaylged itdavittpa
121 yfndaqrqat kdagqiagln vlrivnepta aalaygldkg ekeqrilvfd lgggtfdvsl
181 leigegvvev ratsgdnhlg gddwdqrvvd wlvdkfkgts gidltkdkma mqrlreaaek
241 akielsssqs tsinlpyitv dadknplfld eqltraefqr itqdlldrtr kpfqsviadt
301 gisvseidhv vlvggstrmp avtdlvkelt ggkepnkgvn pdevvavgaa lqagvlkgev
361 kdvllldvtp lslgietkgg vmtrliernt tiptkrsetf ttaddnqpsv qiqvyqgere
421 iaahnkllgs feltgippap rgipqievtf didangivhv takdkgtgke ntiriqegsg
481 lskedidrmi kdaeahaeed rkrreeadvr nqaetlvyqt ekfvkeqrea eggskvpedt
541 lnkvdaavae akaalggsdi saiksamekl gqesqalgqa iyeaaqaasq atgaahpgge
601 pggahpgsad dvvdaevvdd greak
```

FIG. 20A

Chaperone protein dnaK (Heat shock protein 70) from *Mycobacterium bovus*
(NP_854021.1 GI:31791528)

```
1   maravgidlg ttnsvvsvle ggdpvvvans egsrttpsiv afarngevlv gqpaknqavt
61  nvdrtvrsvk rhmgsdwsie idgkkytape isarilmklk rdaeaylged itdavittpa
121 yfndaqrqat kdagqiagln vlrivnepta aalaygldkg ekeqrilvfd lgggtfdvsl
181 leigegvvev ratsgdnhlg gddwdqrvvd wlvdkfkgts gidltkdkma mqrlreaaek
241 akielsssqs tsinlpyitv dadknplfld eqltraefqr itqdlldrtr kpfqsviadt
301 gisvseidhv vlvggstrmp avtdlvkelt ggkepnkgvn pdevvavgaa lqagvlkgev
361 kdvllldvtp lslgietkgg vmtrliernt tiptkrsetf ttaddnqpsv qiqvyqgere
421 iaahnkllgs feltgippap rgipqievtf didangivhv takdkgtgke ntiriqegsg
481 lskedidrmi kdaeahaeed rkrreeadvr nqaetlvyqt ekfvkeqrea eggskvpedt
541 lnkvdaavae akaalggsdi saiksamekl gqesqalgqa iyeaaqaasq atgaahpgge
601 pggahpgsad dvvdaevvdd greak
```

FIG. 20B

SEQUENCE LISTING

```
<160> NUMBER OF SEQ ID NOS: 30

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Ser Ser Arg Ser Ser
1               5


<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Ser Gly Gly Gly Gly Gly Gly Ser Gly Gly Gly Gly Gly
1               5                   10                  15

Gly Ser Gly Gly Gly Gly Gly Gly Ser Gly Gly Gly
            20                  25


<210> SEQ ID NO 3
<211> LENGTH: 15
<212> TYPE: PRT
<213> ORGANISM: Artificial Sequence
```

<220> FEATURE:
<223> OTHER INFORMATION: Description of Artificial Sequence: Synthetic
peptide

<400> SEQUENCE: 3

Gly Gly Gly Gly Ser Gly Gly Gly Gly Ser Gly Gly Gly Gly Ser
1 5 10 15

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 4

Lys Asp Glu Leu
1

<210> SEQ ID NO 5
<211> LENGTH: 35
<212> TYPE: PRT
<213> ORGANISM: Homo sapiens

<400> SEQUENCE: 5

Asp Phe Leu Pro Thr Thr Ala Gln Pro Thr Lys Lys Ser Thr Leu Lys
1 5 10 15

Lys Arg Val Cys Arg Leu Pro Arg Pro Glu Thr Gln Lys Gly Pro Leu
20 25 30

Cys Ser Pro
35

<210> SEQ ID NO 6
<211> LENGTH: 35
<212> TYPE: PRT
<213> ORGANISM: Cavia sp.

<400> SEQUENCE: 6

Asp Val Leu Pro Thr Thr Ala Gln Pro Thr Thr Lys Thr Thr Pro Lys
1 5 10 15

Lys Lys Lys Cys Gln Pro Pro Ser Pro Gly Pro Gln Lys Gly Leu His
20 25 30

Cys Ser Leu
35

<210> SEQ ID NO 7
<211> LENGTH: 37
<212> TYPE: PRT
<213> ORGANISM: Gallus sp.

<400> SEQUENCE: 7

Asp Val Leu Pro Pro Leu Pro Ser Met Ser Thr Leu Val Pro Leu Thr
1 5 10 15

Lys Lys Pro Met Arg Cys Lys Pro Lys Asn Lys Ala Ile Asn Lys Lys
20 25 30

Gly Ala Cys Thr Pro
35

<210> SEQ ID NO 8
<211> LENGTH: 42
<212> TYPE: PRT
<213> ORGANISM: Ambystoma mexicanum

```
<400> SEQUENCE: 8

Asp Ser Phe Pro Thr Thr Ala Ile Leu Thr Thr Ser Thr Pro Cys Val
1               5                   10                  15

Gly Cys Lys Glu His Glu Glu Thr Ser Lys Gly Ser Thr Lys Lys Lys
            20                  25                  30

Gly Ala Arg Ala Gly Val Ala Cys Ser Ser
        35                  40


<210> SEQ ID NO 9
<211> LENGTH: 35
<212> TYPE: PRT
<213> ORGANISM: Oncorhynchus mykiss

<400> SEQUENCE: 9

Glu Thr Arg Pro Thr Leu Thr Pro Val Thr Lys Pro Lys Pro Pro Gly
1               5                   10                  15

Ile Pro Thr Gly Arg Cys Thr Lys Arg Asn Tyr Gln Thr Pro Glu Gly
            20                  25                  30

Cys Gly Tyr
        35


<210> SEQ ID NO 10
<211> LENGTH: 35
<212> TYPE: PRT
<213> ORGANISM: Salmo trutta

<400> SEQUENCE: 10

Glu Thr Arg Pro Thr Leu Thr Pro Val Thr Lys Pro Lys Pro Pro Gly
1               5                   10                  15

Ile Pro Thr Gly Arg Cys Thr Lys Arg Asn Asp Gln Thr Pro Lys Gly
            20                  25                  30

Cys Gly Ser
        35


<210> SEQ ID NO 11
<211> LENGTH: 35
<212> TYPE: PRT
<213> ORGANISM: Unknown
<220> FEATURE:
<223> OTHER INFORMATION: Description of Unknown Sequence: Unknown salmon
      peptide

<400> SEQUENCE: 11

Glu Thr Arg Pro Thr Leu Thr Pro Val Thr Lys Pro Lys Pro Pro Arg
1               5                   10                  15

Ile Pro Thr Gly Arg Cys Thr Lys Arg Asn Asp Gln Thr Pro Lys Gly
            20                  25                  30

Cys Gly Ser
        35


<210> SEQ ID NO 12
<211> LENGTH: 2847
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(2847)
```

<400> SEQUENCE: 12

```
atg gca cat cac cac cat cat cac cat cac cac cac ggt gca ctt gaa       48
Met Ala His His His His His His His His His His Gly Ala Leu Glu
1               5                   10                  15

gtc ctc ttt cag gga ccc ggg tac cag gat cct gta caa gtc gac gcg       96
Val Leu Phe Gln Gly Pro Gly Tyr Gln Asp Pro Val Gln Val Asp Ala
            20                  25                  30

gcc gca atg gct cgt gcg gtc ggg atc gac ctc ggg acc acc aac tcc      144
Ala Ala Met Ala Arg Ala Val Gly Ile Asp Leu Gly Thr Thr Asn Ser
        35                  40                  45

gtc gtc tcg gtt ctg gaa ggt ggc gac ccg gtc gtc gtc gcc aac tcc      192
Val Val Ser Val Leu Glu Gly Gly Asp Pro Val Val Val Ala Asn Ser
    50                  55                  60

gag ggc tcc agg acc acc ccg tca att gtc gcg ttc gcc cgc aac ggt      240
Glu Gly Ser Arg Thr Thr Pro Ser Ile Val Ala Phe Ala Arg Asn Gly
65                  70                  75                  80

gag gtg ctg gtc ggc cag ccc gcc aag aac cag gcg gtg acc aac gtc      288
Glu Val Leu Val Gly Gln Pro Ala Lys Asn Gln Ala Val Thr Asn Val
                85                  90                  95

gat cgc acc gtg cgc tcg gtc aag cga cac atg ggc agc gac tgg tcc      336
Asp Arg Thr Val Arg Ser Val Lys Arg His Met Gly Ser Asp Trp Ser
            100                 105                 110

ata gag att gac ggc aag aaa tac acc gcg ccg gag atc agc gcc cgc      384
Ile Glu Ile Asp Gly Lys Lys Tyr Thr Ala Pro Glu Ile Ser Ala Arg
        115                 120                 125

att ctg atg aag ctg aag cgc gac gcc gag gcc tac ctc ggt gag gac      432
Ile Leu Met Lys Leu Lys Arg Asp Ala Glu Ala Tyr Leu Gly Glu Asp
    130                 135                 140

att acc gac gcg gtt atc acg acg ccc gcc tac ttc aat gac gcc cag      480
Ile Thr Asp Ala Val Ile Thr Thr Pro Ala Tyr Phe Asn Asp Ala Gln
145                 150                 155                 160

cgt cag gcc acc aag gac gcc ggc cag atc gcc ggc ctc aac gtg ctg      528
Arg Gln Ala Thr Lys Asp Ala Gly Gln Ile Ala Gly Leu Asn Val Leu
                165                 170                 175

cgg atc gtc aac gag ccg acc gct gca gcg ctg gcc tac ggc ctc gac      576
Arg Ile Val Asn Glu Pro Thr Ala Ala Ala Leu Ala Tyr Gly Leu Asp
            180                 185                 190

aag ggc gag aag gag cag cga atc ctg gtc ttc gac ttg ggt ggt ggc      624
Lys Gly Glu Lys Glu Gln Arg Ile Leu Val Phe Asp Leu Gly Gly Gly
        195                 200                 205

act ttc gac gtt tcc ctg ctg gag atc ggc gag ggt gtg gtt gag gtc      672
Thr Phe Asp Val Ser Leu Leu Glu Ile Gly Glu Gly Val Val Glu Val
    210                 215                 220

cgt gcc act tcg ggt gac aac cac ctc ggc ggc gac gac tgg gac cag      720
Arg Ala Thr Ser Gly Asp Asn His Leu Gly Gly Asp Asp Trp Asp Gln
225                 230                 235                 240

cgg gtc gtc gat tgg ctg gtg gac aag ttc aag ggc acc agc ggc atc      768
Arg Val Val Asp Trp Leu Val Asp Lys Phe Lys Gly Thr Ser Gly Ile
                245                 250                 255

gat ctg acc aag gac aag atg gcg atg cag cgg ctg cgg gaa gcc gcc      816
Asp Leu Thr Lys Asp Lys Met Ala Met Gln Arg Leu Arg Glu Ala Ala
            260                 265                 270

gag aaa gca aag atc gag ctg agt tcg agt cag tcc acc tcg atc aac      864
Glu Lys Ala Lys Ile Glu Leu Ser Ser Ser Gln Ser Thr Ser Ile Asn
        275                 280                 285

ctg ccc tac atc acc gtc gac gcc gac aag aac ccg ttg ttc tta gac      912
Leu Pro Tyr Ile Thr Val Asp Ala Asp Lys Asn Pro Leu Phe Leu Asp
    290                 295                 300

gag cag ctg acc cgc gcg gag ttc caa cgg atc act cag gac ctg ctg      960
Glu Gln Leu Thr Arg Ala Glu Phe Gln Arg Ile Thr Gln Asp Leu Leu
```

-continued

```
305                 310                 315                 320

gac cgc act cgc aag ccg ttc cag tcg gtg atc gct gac acc ggc att      1008
Asp Arg Thr Arg Lys Pro Phe Gln Ser Val Ile Ala Asp Thr Gly Ile
                325                 330                 335

tcg gtg tcg gag atc gat cac gtt gtg ctc gtg ggt ggt tcg acc cgg      1056
Ser Val Ser Glu Ile Asp His Val Val Leu Val Gly Gly Ser Thr Arg
            340                 345                 350

atg ccc gcg gtg acc gat ctg gtc aag gaa ctc acc ggc ggc aag gaa      1104
Met Pro Ala Val Thr Asp Leu Val Lys Glu Leu Thr Gly Gly Lys Glu
        355                 360                 365

ccc aac aag ggc gtc aac ccc gat gag gtt gtc gcg gtg gga gcc gct      1152
Pro Asn Lys Gly Val Asn Pro Asp Glu Val Val Ala Val Gly Ala Ala
    370                 375                 380

ctg cag gcc ggc gtc ctc aag ggc gag gtg aaa gac gtt ctg ctg ctt      1200
Leu Gln Ala Gly Val Leu Lys Gly Glu Val Lys Asp Val Leu Leu Leu
385                 390                 395                 400

gat gtt acc ccg ctg agc ctg ggt atc gag acc aag ggc ggg gtg atg      1248
Asp Val Thr Pro Leu Ser Leu Gly Ile Glu Thr Lys Gly Gly Val Met
                405                 410                 415

acc agg ctc atc gag cgc aac acc acg atc ccc acc aag cgg tcg gag      1296
Thr Arg Leu Ile Glu Arg Asn Thr Thr Ile Pro Thr Lys Arg Ser Glu
            420                 425                 430

tct ttc acc acc gcc gac gac aac caa ccg tcg gtg cag atc cag gtc      1344
Ser Phe Thr Thr Ala Asp Asp Asn Gln Pro Ser Val Gln Ile Gln Val
        435                 440                 445

tat cag ggg gag cgt gag atc gcc gcg cac aac aag ttg ctc ggg tcc      1392
Tyr Gln Gly Glu Arg Glu Ile Ala Ala His Asn Lys Leu Leu Gly Ser
    450                 455                 460

ttc gag ctg acc ggc atc ccg ccg gcg ccg cgg ggg att ccg cag atc      1440
Phe Glu Leu Thr Gly Ile Pro Pro Ala Pro Arg Gly Ile Pro Gln Ile
465                 470                 475                 480

gag gtc act ttc gac atc gac gcc aac ggc att gtg cac gtc acc gcc      1488
Glu Val Thr Phe Asp Ile Asp Ala Asn Gly Ile Val His Val Thr Ala
                485                 490                 495

aag gac aag ggc acc ggc aag gag aac acg atc cga atc cag gaa ggc      1536
Lys Asp Lys Gly Thr Gly Lys Glu Asn Thr Ile Arg Ile Gln Glu Gly
            500                 505                 510

tcg ggc ctg tcc aag gaa gac att gac cgc atg atc aag gac gcc gaa      1584
Ser Gly Leu Ser Lys Glu Asp Ile Asp Arg Met Ile Lys Asp Ala Glu
        515                 520                 525

gcg cac gcc gag gag gat cgc aag cgt cgc gag gag gcc gat gtt cgt      1632
Ala His Ala Glu Glu Asp Arg Lys Arg Arg Glu Glu Ala Asp Val Arg
    530                 535                 540

aat caa gcc gag aca ttg gtc tac cag acg gag aag ttc gtc aaa gaa      1680
Asn Gln Ala Glu Thr Leu Val Tyr Gln Thr Glu Lys Phe Val Lys Glu
545                 550                 555                 560

cag cgt gag gcc gag ggt ggt tcg aag gta cct gaa gac acg ctg aac      1728
Gln Arg Glu Ala Glu Gly Gly Ser Lys Val Pro Glu Asp Thr Leu Asn
                565                 570                 575

aag gtt gat gcc gcg gtg gcg gaa gcg aag gcg gca ctt ggc gga tcg      1776
Lys Val Asp Ala Ala Val Ala Glu Ala Lys Ala Ala Leu Gly Gly Ser
            580                 585                 590

gat att tcg gcc atc aag tcg gcg atg gag aag ctg ggc cag gag tcg      1824
Asp Ile Ser Ala Ile Lys Ser Ala Met Glu Lys Leu Gly Gln Glu Ser
        595                 600                 605

cag gct ctg ggg caa gcg atc tac gaa gca gct cag gct gcg tca cag      1872
Gln Ala Leu Gly Gln Ala Ile Tyr Glu Ala Ala Gln Ala Ala Ser Gln
    610                 615                 620

gcc act ggc gct gcc cac ccc ggc ggc gag ccg ggc ggt gcc cac ccc      1920
Ala Thr Gly Ala Ala His Pro Gly Gly Glu Pro Gly Gly Ala His Pro
```

-continued

```
625                 630                 635                 640

ggc tcg gct gat gac gtt gtg gac gcg gag gtg gtc gac gac ggc cgg     1968
Gly Ser Ala Asp Asp Val Val Asp Ala Glu Val Val Asp Asp Gly Arg
                645                 650                 655

gag gcc aag cca tca aca cca cca act cca agt cct tct act cct cct     2016
Glu Ala Lys Pro Ser Thr Pro Pro Thr Pro Ser Pro Ser Thr Pro Pro
            660                 665                 670

aca cct tca cca tca ggt ttg aat gat att agc cag gta cag ctg cag     2064
Thr Pro Ser Pro Ser Gly Leu Asn Asp Ile Ser Gln Val Gln Leu Gln
        675                 680                 685

cag tca ggt cca gga ctc gtg acg ccc tcg cag acc ctc tca ctc acc     2112
Gln Ser Gly Pro Gly Leu Val Thr Pro Ser Gln Thr Leu Ser Leu Thr
    690                 695                 700

tgt gcc atc tcc ggg gac agt gtc tct agc aac agt gct act tgg aac     2160
Cys Ala Ile Ser Gly Asp Ser Val Ser Ser Asn Ser Ala Thr Trp Asn
705                 710                 715                 720

tgg atc agg cag tcc cca tcg aga ggc ctt gag tgg ctg gga agg aca     2208
Trp Ile Arg Gln Ser Pro Ser Arg Gly Leu Glu Trp Leu Gly Arg Thr
                725                 730                 735

tac tac agg tcc aag tgg tat aac gac tat gca gta tct gtg aaa agt     2256
Tyr Tyr Arg Ser Lys Trp Tyr Asn Asp Tyr Ala Val Ser Val Lys Ser
            740                 745                 750

cga atg agc atc aac cca gac aca tcc aag aac cag ttc tcc ctg cag     2304
Arg Met Ser Ile Asn Pro Asp Thr Ser Lys Asn Gln Phe Ser Leu Gln
        755                 760                 765

ctg aac tct gtg act ccc gag gac acg gct gtg tat tac tgt gca aga     2352
Leu Asn Ser Val Thr Pro Glu Asp Thr Ala Val Tyr Tyr Cys Ala Arg
    770                 775                 780

gga atg atg act tac tat tac ggt atg gac gtc tgg ggc caa ggg acc     2400
Gly Met Met Thr Tyr Tyr Tyr Gly Met Asp Val Trp Gly Gln Gly Thr
785                 790                 795                 800

acg gtc acc gtc tcc tca gga att cta gga tcc ggt ggc ggt ggc agc     2448
Thr Val Thr Val Ser Ser Gly Ile Leu Gly Ser Gly Gly Gly Gly Ser
                805                 810                 815

ggc ggt ggt ggt tcc gga ggc ggc ggt tct cag cct gtg ctg act cag     2496
Gly Gly Gly Gly Ser Gly Gly Gly Gly Ser Gln Pro Val Leu Thr Gln
            820                 825                 830

tcg tct tcc ctc tct gca tct cct gga gca tca gcc agt ctc acc tgc     2544
Ser Ser Ser Leu Ser Ala Ser Pro Gly Ala Ser Ala Ser Leu Thr Cys
        835                 840                 845

acc ttg cgc agt ggc atc aat gtt ggt ccc tac agg ata tac tgg tac     2592
Thr Leu Arg Ser Gly Ile Asn Val Gly Pro Tyr Arg Ile Tyr Trp Tyr
    850                 855                 860

cag cag aag cca ggg agt cct ccc cag tat ctc ctg aac tac aaa tca     2640
Gln Gln Lys Pro Gly Ser Pro Pro Gln Tyr Leu Leu Asn Tyr Lys Ser
865                 870                 875                 880

gac tca gat aag cag cag ggc tct gga gtc ccc agc cgc ttc tct gga     2688
Asp Ser Asp Lys Gln Gln Gly Ser Gly Val Pro Ser Arg Phe Ser Gly
                885                 890                 895

tcc aaa gat gct tcg gcc aat gca ggg gtt tta ctc atc tct ggg ctc     2736
Ser Lys Asp Ala Ser Ala Asn Ala Gly Val Leu Leu Ile Ser Gly Leu
            900                 905                 910

cgg tct gag gat gag gct gac tat tac tgt atg att tgg cac agc agc     2784
Arg Ser Glu Asp Glu Ala Asp Tyr Tyr Cys Met Ile Trp His Ser Ser
        915                 920                 925

gct gct gtg ttc gga gga ggc acc caa ctg acc gtc ctc tcc gga att     2832
Ala Ala Val Phe Gly Gly Gly Thr Gln Leu Thr Val Leu Ser Gly Ile
    930                 935                 940

cta gaa caa cag ggt                                                 2847
Leu Glu Gln Gln Gly
```

945

<210> SEQ ID NO 13
<211> LENGTH: 949
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Met Ala His His His His His His His His His His Gly Ala Leu Glu
1 5 10 15

Val Leu Phe Gln Gly Pro Gly Tyr Gln Asp Pro Val Gln Val Asp Ala
20 25 30

Ala Ala Met Ala Arg Ala Val Gly Ile Asp Leu Gly Thr Thr Asn Ser
35 40 45

Val Val Ser Val Leu Glu Gly Gly Asp Pro Val Val Val Ala Asn Ser
50 55 60

Glu Gly Ser Arg Thr Thr Pro Ser Ile Val Ala Phe Ala Arg Asn Gly
65 70 75 80

Glu Val Leu Val Gly Gln Pro Ala Lys Asn Gln Ala Val Thr Asn Val
85 90 95

Asp Arg Thr Val Arg Ser Val Lys Arg His Met Gly Ser Asp Trp Ser
100 105 110

Ile Glu Ile Asp Gly Lys Lys Tyr Thr Ala Pro Glu Ile Ser Ala Arg
115 120 125

Ile Leu Met Lys Leu Lys Arg Asp Ala Glu Ala Tyr Leu Gly Glu Asp
130 135 140

Ile Thr Asp Ala Val Ile Thr Thr Pro Ala Tyr Phe Asn Asp Ala Gln
145 150 155 160

Arg Gln Ala Thr Lys Asp Ala Gly Gln Ile Ala Gly Leu Asn Val Leu
165 170 175

Arg Ile Val Asn Glu Pro Thr Ala Ala Ala Leu Ala Tyr Gly Leu Asp
180 185 190

Lys Gly Glu Lys Glu Gln Arg Ile Leu Val Phe Asp Leu Gly Gly Gly
195 200 205

Thr Phe Asp Val Ser Leu Leu Glu Ile Gly Glu Gly Val Val Glu Val
210 215 220

Arg Ala Thr Ser Gly Asp Asn His Leu Gly Gly Asp Asp Trp Asp Gln
225 230 235 240

Arg Val Val Asp Trp Leu Val Asp Lys Phe Lys Gly Thr Ser Gly Ile
245 250 255

Asp Leu Thr Lys Asp Lys Met Ala Met Gln Arg Leu Arg Glu Ala Ala
260 265 270

Glu Lys Ala Lys Ile Glu Leu Ser Ser Ser Gln Ser Thr Ser Ile Asn
275 280 285

Leu Pro Tyr Ile Thr Val Asp Ala Asp Lys Asn Pro Leu Phe Leu Asp
290 295 300

Glu Gln Leu Thr Arg Ala Glu Phe Gln Arg Ile Thr Gln Asp Leu Leu
305 310 315 320

Asp Arg Thr Arg Lys Pro Phe Gln Ser Val Ile Ala Asp Thr Gly Ile
325 330 335

Ser Val Ser Glu Ile Asp His Val Val Leu Val Gly Gly Ser Thr Arg
340 345 350

Met Pro Ala Val Thr Asp Leu Val Lys Glu Leu Thr Gly Gly Lys Glu

```
        355                 360                 365

Pro Asn Lys Gly Val Asn Pro Asp Glu Val Val Ala Val Gly Ala Ala
    370                 375                 380

Leu Gln Ala Gly Val Leu Lys Gly Glu Val Lys Asp Val Leu Leu Leu
385                 390                 395                 400

Asp Val Thr Pro Leu Ser Leu Gly Ile Glu Thr Lys Gly Gly Val Met
                405                 410                 415

Thr Arg Leu Ile Glu Arg Asn Thr Thr Ile Pro Thr Lys Arg Ser Glu
            420                 425                 430

Ser Phe Thr Thr Ala Asp Asp Asn Gln Pro Ser Val Gln Ile Gln Val
        435                 440                 445

Tyr Gln Gly Glu Arg Glu Ile Ala Ala His Asn Lys Leu Leu Gly Ser
    450                 455                 460

Phe Glu Leu Thr Gly Ile Pro Pro Ala Pro Arg Gly Ile Pro Gln Ile
465                 470                 475                 480

Glu Val Thr Phe Asp Ile Asp Ala Asn Gly Ile Val His Val Thr Ala
                485                 490                 495

Lys Asp Lys Gly Thr Gly Lys Glu Asn Thr Ile Arg Ile Gln Glu Gly
            500                 505                 510

Ser Gly Leu Ser Lys Glu Asp Ile Asp Arg Met Ile Lys Asp Ala Glu
        515                 520                 525

Ala His Ala Glu Glu Asp Arg Lys Arg Arg Glu Glu Ala Asp Val Arg
    530                 535                 540

Asn Gln Ala Glu Thr Leu Val Tyr Gln Thr Glu Lys Phe Val Lys Glu
545                 550                 555                 560

Gln Arg Glu Ala Glu Gly Gly Ser Lys Val Pro Glu Asp Thr Leu Asn
                565                 570                 575

Lys Val Asp Ala Ala Val Ala Glu Ala Lys Ala Ala Leu Gly Gly Ser
            580                 585                 590

Asp Ile Ser Ala Ile Lys Ser Ala Met Glu Lys Leu Gly Gln Glu Ser
        595                 600                 605

Gln Ala Leu Gly Gln Ala Ile Tyr Glu Ala Ala Gln Ala Ala Ser Gln
    610                 615                 620

Ala Thr Gly Ala Ala His Pro Gly Gly Glu Pro Gly Gly Ala His Pro
625                 630                 635                 640

Gly Ser Ala Asp Asp Val Val Asp Ala Glu Val Val Asp Asp Gly Arg
                645                 650                 655

Glu Ala Lys Pro Ser Thr Pro Pro Thr Pro Ser Pro Ser Thr Pro Pro
            660                 665                 670

Thr Pro Ser Pro Ser Gly Leu Asn Asp Ile Ser Gln Val Gln Leu Gln
        675                 680                 685

Gln Ser Gly Pro Gly Leu Val Thr Pro Ser Gln Thr Leu Ser Leu Thr
    690                 695                 700

Cys Ala Ile Ser Gly Asp Ser Val Ser Ser Asn Ser Ala Thr Trp Asn
705                 710                 715                 720

Trp Ile Arg Gln Ser Pro Ser Arg Gly Leu Glu Trp Leu Gly Arg Thr
                725                 730                 735

Tyr Tyr Arg Ser Lys Trp Tyr Asn Asp Tyr Ala Val Ser Val Lys Ser
            740                 745                 750

Arg Met Ser Ile Asn Pro Asp Thr Ser Lys Asn Gln Phe Ser Leu Gln
        755                 760                 765

Leu Asn Ser Val Thr Pro Glu Asp Thr Ala Val Tyr Tyr Cys Ala Arg
    770                 775                 780
```

```
Gly Met Met Thr Tyr Tyr Tyr Gly Met Asp Val Trp Gly Gln Gly Thr
785                 790                 795                 800

Thr Val Thr Val Ser Ser Gly Ile Leu Gly Ser Gly Gly Gly Gly Ser
                805                 810                 815

Gly Gly Gly Gly Ser Gly Gly Gly Gly Ser Gln Pro Val Leu Thr Gln
            820                 825                 830

Ser Ser Ser Leu Ser Ala Ser Pro Gly Ala Ser Ala Ser Leu Thr Cys
        835                 840                 845

Thr Leu Arg Ser Gly Ile Asn Val Gly Pro Tyr Arg Ile Tyr Trp Tyr
    850                 855                 860

Gln Gln Lys Pro Gly Ser Pro Pro Gln Tyr Leu Leu Asn Tyr Lys Ser
865                 870                 875                 880

Asp Ser Asp Lys Gln Gln Gly Ser Gly Val Pro Ser Arg Phe Ser Gly
                885                 890                 895

Ser Lys Asp Ala Ser Ala Asn Ala Gly Val Leu Leu Ile Ser Gly Leu
            900                 905                 910

Arg Ser Glu Asp Glu Ala Asp Tyr Tyr Cys Met Ile Trp His Ser Ser
        915                 920                 925

Ala Ala Val Phe Gly Gly Gly Thr Gln Leu Thr Val Leu Ser Gly Ile
    930                 935                 940

Leu Glu Gln Gln Gly
945


<210> SEQ ID NO 14
<211> LENGTH: 2847
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(2847)

<400> SEQUENCE: 14

atg gca cat cac cac cat cat cac cat cac cac cac ggt gca ctt gaa       48
Met Ala His His His His His His His His His His Gly Ala Leu Glu
1               5                   10                  15

gtc ctc ttt cag gga ccc ggg tac cag gat cct gta caa gtc gac gcg       96
Val Leu Phe Gln Gly Pro Gly Tyr Gln Asp Pro Val Gln Val Asp Ala
            20                  25                  30

gcc gca agc cag gta cag ctg cag cag tca ggt cca gga ctc gtg acg      144
Ala Ala Ser Gln Val Gln Leu Gln Gln Ser Gly Pro Gly Leu Val Thr
        35                  40                  45

ccc tcg cag acc ctc tca ctc acc tgt gcc atc tcc ggg gac agt gtc      192
Pro Ser Gln Thr Leu Ser Leu Thr Cys Ala Ile Ser Gly Asp Ser Val
    50                  55                  60

tct agc aac agt gct act tgg aac tgg atc agg cag tcc cca tcg aga      240
Ser Ser Asn Ser Ala Thr Trp Asn Trp Ile Arg Gln Ser Pro Ser Arg
65                  70                  75                  80

ggc ctt gag tgg ctg gga agg aca tac tac agg tcc aag tgg tat aac      288
Gly Leu Glu Trp Leu Gly Arg Thr Tyr Tyr Arg Ser Lys Trp Tyr Asn
                85                  90                  95

gac tat gca gta tct gtg aaa agt cga atg agc atc aac cca gac aca      336
Asp Tyr Ala Val Ser Val Lys Ser Arg Met Ser Ile Asn Pro Asp Thr
            100                 105                 110

tcc aag aac cag ttc tcc ctg cag ctg aac tct gtg act ccc gag gac      384
Ser Lys Asn Gln Phe Ser Leu Gln Leu Asn Ser Val Thr Pro Glu Asp
        115                 120                 125

acg gct gtg tat tac tgt gca aga gga atg atg act tac tat tac ggt      432
```

-continued

```
Thr Ala Val Tyr Tyr Cys Ala Arg Gly Met Met Thr Tyr Tyr Tyr Gly
    130                 135                 140

atg gac gtc tgg ggc caa ggg acc acg gtc acc gtc tcc tca gga att      480
Met Asp Val Trp Gly Gln Gly Thr Thr Val Thr Val Ser Ser Gly Ile
145                 150                 155                 160

cta gga tcc ggt ggc ggt ggc agc ggc ggt ggt ggt tcc gga ggc ggc      528
Leu Gly Ser Gly Gly Gly Gly Ser Gly Gly Gly Gly Ser Gly Gly Gly
                165                 170                 175

ggt tct cag cct gtg ctg act cag tcg tct tcc ctc tct gca tct cct      576
Gly Ser Gln Pro Val Leu Thr Gln Ser Ser Ser Leu Ser Ala Ser Pro
            180                 185                 190

gga gca tca gcc agt ctc acc tgc acc ttg cgc agt ggc atc aat gtt      624
Gly Ala Ser Ala Ser Leu Thr Cys Thr Leu Arg Ser Gly Ile Asn Val
        195                 200                 205

ggt ccc tac agg ata tac tgg tac cag cag aag cca ggg agt cct ccc      672
Gly Pro Tyr Arg Ile Tyr Trp Tyr Gln Gln Lys Pro Gly Ser Pro Pro
    210                 215                 220

cag tat ctc ctg aac tac aaa tca gac tca gat aag cag cag ggc tct      720
Gln Tyr Leu Leu Asn Tyr Lys Ser Asp Ser Asp Lys Gln Gln Gly Ser
225                 230                 235                 240

gga gtc ccc agc cgc ttc tct gga tcc aaa gat gct tcg gcc aat gca      768
Gly Val Pro Ser Arg Phe Ser Gly Ser Lys Asp Ala Ser Ala Asn Ala
                245                 250                 255

ggg gtt tta ctc atc tct ggg ctc cgg tct gag gat gag gct gac tat      816
Gly Val Leu Leu Ile Ser Gly Leu Arg Ser Glu Asp Glu Ala Asp Tyr
            260                 265                 270

tac tgt atg att tgg cac agc agc gct gct gtg ttc gga gga ggc acc      864
Tyr Cys Met Ile Trp His Ser Ser Ala Ala Val Phe Gly Gly Gly Thr
        275                 280                 285

caa ctg acc gtc ctc tcc gga att cta gaa caa cag ggt cca tca aca      912
Gln Leu Thr Val Leu Ser Gly Ile Leu Glu Gln Gln Gly Pro Ser Thr
    290                 295                 300

cca cca act cca agt cct tct act cct cct aca cct tca cca tca ggt      960
Pro Pro Thr Pro Ser Pro Ser Thr Pro Pro Thr Pro Ser Pro Ser Gly
305                 310                 315                 320

ttg aat gat att atg gct cgt gcg gtc ggg atc gac ctc ggg acc acc     1008
Leu Asn Asp Ile Met Ala Arg Ala Val Gly Ile Asp Leu Gly Thr Thr
                325                 330                 335

aac tcc gtc gtc tcg gtt ctg gaa ggt ggc gac ccg gtc gtc gtc gcc     1056
Asn Ser Val Val Ser Val Leu Glu Gly Gly Asp Pro Val Val Val Ala
            340                 345                 350

aac tcc gag ggc tcc agg acc acc ccg tca att gtc gcg ttc gcc cgc     1104
Asn Ser Glu Gly Ser Arg Thr Thr Pro Ser Ile Val Ala Phe Ala Arg
        355                 360                 365

aac ggt gag gtg ctg gtc ggc cag ccc gcc aag aac cag gcg gtg acc     1152
Asn Gly Glu Val Leu Val Gly Gln Pro Ala Lys Asn Gln Ala Val Thr
    370                 375                 380

aac gtc gat cgc acc gtg cgc tcg gtc aag cga cac atg ggc agc gac     1200
Asn Val Asp Arg Thr Val Arg Ser Val Lys Arg His Met Gly Ser Asp
385                 390                 395                 400

tgg tcc ata gag att gac ggc aag aaa tac acc gcg ccg gag atc agc     1248
Trp Ser Ile Glu Ile Asp Gly Lys Lys Tyr Thr Ala Pro Glu Ile Ser
                405                 410                 415

gcc cgc att ctg atg aag ctg aag cgc gac gcc gag gcc tac ctc ggt     1296
Ala Arg Ile Leu Met Lys Leu Lys Arg Asp Ala Glu Ala Tyr Leu Gly
            420                 425                 430

gag gac att acc gac gcg gtt atc acg acg ccc gcc tac ttc aat gac     1344
Glu Asp Ile Thr Asp Ala Val Ile Thr Thr Pro Ala Tyr Phe Asn Asp
        435                 440                 445

gcc cag cgt cag gcc acc aag gac gcc ggc cag atc gcc ggc ctc aac     1392
```

-continued

```
Ala Gln Arg Gln Ala Thr Lys Asp Ala Gly Gln Ile Ala Gly Leu Asn
    450                 455                 460

gtg ctg cgg atc gtc aac gag ccg acc gct gca gcg ctg gcc tac ggc      1440
Val Leu Arg Ile Val Asn Glu Pro Thr Ala Ala Ala Leu Ala Tyr Gly
465                 470                 475                 480

ctc gac aag ggc gag aag gag cag cga atc ctg gtc ttc gac ttg ggt      1488
Leu Asp Lys Gly Glu Lys Glu Gln Arg Ile Leu Val Phe Asp Leu Gly
                485                 490                 495

ggt ggc act ttc gac gtt tcc ctg ctg gag atc ggc gag ggt gtg gtt      1536
Gly Gly Thr Phe Asp Val Ser Leu Leu Glu Ile Gly Glu Gly Val Val
            500                 505                 510

gag gtc cgt gcc act tcg ggt gac aac cac ctc ggc ggc gac gac tgg      1584
Glu Val Arg Ala Thr Ser Gly Asp Asn His Leu Gly Gly Asp Asp Trp
        515                 520                 525

gac cag cgg gtc gtc gat tgg ctg gtg gac aag ttc aag ggc acc agc      1632
Asp Gln Arg Val Val Asp Trp Leu Val Asp Lys Phe Lys Gly Thr Ser
    530                 535                 540

ggc atc gat ctg acc aag gac aag atg gcg atg cag cgg ctg cgg gaa      1680
Gly Ile Asp Leu Thr Lys Asp Lys Met Ala Met Gln Arg Leu Arg Glu
545                 550                 555                 560

gcc gcc gag aaa gca aag atc gag ctg agt tcg agt cag tcc acc tcg      1728
Ala Ala Glu Lys Ala Lys Ile Glu Leu Ser Ser Ser Gln Ser Thr Ser
                565                 570                 575

atc aac ctg ccc tac atc acc gtc gac gcc gac aag aac ccg ttg ttc      1776
Ile Asn Leu Pro Tyr Ile Thr Val Asp Ala Asp Lys Asn Pro Leu Phe
            580                 585                 590

tta gac gag cag ctg acc cgc gcg gag ttc caa cgg atc act cag gac      1824
Leu Asp Glu Gln Leu Thr Arg Ala Glu Phe Gln Arg Ile Thr Gln Asp
        595                 600                 605

ctg ctg gac cgc act cgc aag ccg ttc cag tcg gtg atc gct gac acc      1872
Leu Leu Asp Arg Thr Arg Lys Pro Phe Gln Ser Val Ile Ala Asp Thr
    610                 615                 620

ggc att tcg gtg tcg gag atc gat cac gtt gtg ctc gtg ggt ggt tcg      1920
Gly Ile Ser Val Ser Glu Ile Asp His Val Val Leu Val Gly Gly Ser
625                 630                 635                 640

acc cgg atg ccc gcg gtg acc gat ctg gtc aag gaa ctc acc ggc ggc      1968
Thr Arg Met Pro Ala Val Thr Asp Leu Val Lys Glu Leu Thr Gly Gly
                645                 650                 655

aag gaa ccc aac aag ggc gtc aac ccc gat gag gtt gtc gcg gtg gga      2016
Lys Glu Pro Asn Lys Gly Val Asn Pro Asp Glu Val Val Ala Val Gly
            660                 665                 670

gcc gct ctg cag gcc ggc gtc ctc aag ggc gag gtg aaa gac gtt ctg      2064
Ala Ala Leu Gln Ala Gly Val Leu Lys Gly Glu Val Lys Asp Val Leu
        675                 680                 685

ctg ctt gat gtt acc ccg ctg agc ctg ggt atc gag acc aag ggc ggg      2112
Leu Leu Asp Val Thr Pro Leu Ser Leu Gly Ile Glu Thr Lys Gly Gly
    690                 695                 700

gtg atg acc agg ctc atc gag cgc aac acc acg atc ccc acc aag cgg      2160
Val Met Thr Arg Leu Ile Glu Arg Asn Thr Thr Ile Pro Thr Lys Arg
705                 710                 715                 720

tcg gag tct ttc acc acc gcc gac gac aac caa ccg tcg gtg cag atc      2208
Ser Glu Ser Phe Thr Thr Ala Asp Asp Asn Gln Pro Ser Val Gln Ile
                725                 730                 735

cag gtc tat cag ggg gag cgt gag atc gcc gcg cac aac aag ttg ctc      2256
Gln Val Tyr Gln Gly Glu Arg Glu Ile Ala Ala His Asn Lys Leu Leu
            740                 745                 750

ggg tcc ttc gag ctg acc ggc atc ccg ccg gcg ccg cgg ggg att ccg      2304
Gly Ser Phe Glu Leu Thr Gly Ile Pro Pro Ala Pro Arg Gly Ile Pro
        755                 760                 765

cag atc gag gtc act ttc gac atc gac gcc aac ggc att gtg cac gtc      2352
```

```
Gln Ile Glu Val Thr Phe Asp Ile Asp Ala Asn Gly Ile Val His Val
    770                 775                 780

acc gcc aag gac aag ggc acc ggc aag gag aac acg atc cga atc cag     2400
Thr Ala Lys Asp Lys Gly Thr Gly Lys Glu Asn Thr Ile Arg Ile Gln
785                 790                 795                 800

gaa ggc tcg ggc ctg tcc aag gaa gac att gac cgc atg atc aag gac     2448
Glu Gly Ser Gly Leu Ser Lys Glu Asp Ile Asp Arg Met Ile Lys Asp
            805                 810                 815

gcc gaa gcg cac gcc gag gag gat cgc aag cgt cgc gag gag gcc gat     2496
Ala Glu Ala His Ala Glu Glu Asp Arg Lys Arg Arg Glu Glu Ala Asp
            820                 825                 830

gtt cgt aat caa gcc gag aca ttg gtc tac cag acg gag aag ttc gtc     2544
Val Arg Asn Gln Ala Glu Thr Leu Val Tyr Gln Thr Glu Lys Phe Val
        835                 840                 845

aaa gaa cag cgt gag gcc gag ggt ggt tcg aag gta cct gaa gac acg     2592
Lys Glu Gln Arg Glu Ala Glu Gly Gly Ser Lys Val Pro Glu Asp Thr
    850                 855                 860

ctg aac aag gtt gat gcc gcg gtg gcg gaa gcg aag gcg gca ctt ggc     2640
Leu Asn Lys Val Asp Ala Ala Val Ala Glu Ala Lys Ala Ala Leu Gly
865                 870                 875                 880

gga tcg gat att tcg gcc atc aag tcg gcg atg gag aag ctg ggc cag     2688
Gly Ser Asp Ile Ser Ala Ile Lys Ser Ala Met Glu Lys Leu Gly Gln
            885                 890                 895

gag tcg cag gct ctg ggg caa gcg atc tac gaa gca gct cag gct gcg     2736
Glu Ser Gln Ala Leu Gly Gln Ala Ile Tyr Glu Ala Ala Gln Ala Ala
            900                 905                 910

tca cag gcc act ggc gct gcc cac ccc ggc ggc gag ccg ggc ggt gcc     2784
Ser Gln Ala Thr Gly Ala Ala His Pro Gly Gly Glu Pro Gly Gly Ala
        915                 920                 925

cac ccc ggc tcg gct gat gac gtt gtg gac gcg gag gtg gtc gac gac     2832
His Pro Gly Ser Ala Asp Asp Val Val Asp Ala Glu Val Val Asp Asp
    930                 935                 940

ggc cgg gag gcc aag                                                 2847
Gly Arg Glu Ala Lys
945


<210> SEQ ID NO 15
<211> LENGTH: 949
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Ala His His His His His His His His His His Gly Ala Leu Glu
1               5                   10                  15

Val Leu Phe Gln Gly Pro Gly Tyr Gln Asp Pro Val Gln Val Asp Ala
            20                  25                  30

Ala Ala Ser Gln Val Gln Leu Gln Gln Ser Gly Pro Gly Leu Val Thr
        35                  40                  45

Pro Ser Gln Thr Leu Ser Leu Thr Cys Ala Ile Ser Gly Asp Ser Val
    50                  55                  60

Ser Ser Asn Ser Ala Thr Trp Asn Trp Ile Arg Gln Ser Pro Ser Arg
65                  70                  75                  80

Gly Leu Glu Trp Leu Gly Arg Thr Tyr Tyr Arg Ser Lys Trp Tyr Asn
                85                  90                  95

Asp Tyr Ala Val Ser Val Lys Ser Arg Met Ser Ile Asn Pro Asp Thr
            100                 105                 110

Ser Lys Asn Gln Phe Ser Leu Gln Leu Asn Ser Val Thr Pro Glu Asp
```

-continued

```
        115                 120                 125

Thr Ala Val Tyr Tyr Cys Ala Arg Gly Met Met Thr Tyr Tyr Tyr Gly
    130                 135                 140

Met Asp Val Trp Gly Gln Gly Thr Thr Val Thr Val Ser Ser Gly Ile
145                 150                 155                 160

Leu Gly Ser Gly Gly Gly Gly Ser Gly Gly Gly Gly Ser Gly Gly Gly
                165                 170                 175

Gly Ser Gln Pro Val Leu Thr Gln Ser Ser Ser Leu Ser Ala Ser Pro
            180                 185                 190

Gly Ala Ser Ala Ser Leu Thr Cys Thr Leu Arg Ser Gly Ile Asn Val
        195                 200                 205

Gly Pro Tyr Arg Ile Tyr Trp Tyr Gln Gln Lys Pro Gly Ser Pro Pro
    210                 215                 220

Gln Tyr Leu Leu Asn Tyr Lys Ser Asp Ser Asp Lys Gln Gln Gly Ser
225                 230                 235                 240

Gly Val Pro Ser Arg Phe Ser Gly Ser Lys Asp Ala Ser Ala Asn Ala
                245                 250                 255

Gly Val Leu Leu Ile Ser Gly Leu Arg Ser Glu Asp Glu Ala Asp Tyr
            260                 265                 270

Tyr Cys Met Ile Trp His Ser Ser Ala Ala Val Phe Gly Gly Gly Thr
        275                 280                 285

Gln Leu Thr Val Leu Ser Gly Ile Leu Glu Gln Gln Gly Pro Ser Thr
    290                 295                 300

Pro Pro Thr Pro Ser Pro Ser Thr Pro Pro Thr Pro Ser Pro Ser Gly
305                 310                 315                 320

Leu Asn Asp Ile Met Ala Arg Ala Val Gly Ile Asp Leu Gly Thr Thr
                325                 330                 335

Asn Ser Val Val Ser Val Leu Glu Gly Gly Asp Pro Val Val Val Ala
            340                 345                 350

Asn Ser Glu Gly Ser Arg Thr Thr Pro Ser Ile Val Ala Phe Ala Arg
        355                 360                 365

Asn Gly Glu Val Leu Val Gly Gln Pro Ala Lys Asn Gln Ala Val Thr
    370                 375                 380

Asn Val Asp Arg Thr Val Arg Ser Val Lys Arg His Met Gly Ser Asp
385                 390                 395                 400

Trp Ser Ile Glu Ile Asp Gly Lys Lys Tyr Thr Ala Pro Glu Ile Ser
                405                 410                 415

Ala Arg Ile Leu Met Lys Leu Lys Arg Asp Ala Glu Ala Tyr Leu Gly
            420                 425                 430

Glu Asp Ile Thr Asp Ala Val Ile Thr Thr Pro Ala Tyr Phe Asn Asp
        435                 440                 445

Ala Gln Arg Gln Ala Thr Lys Asp Ala Gly Gln Ile Ala Gly Leu Asn
    450                 455                 460

Val Leu Arg Ile Val Asn Glu Pro Thr Ala Ala Ala Leu Ala Tyr Gly
465                 470                 475                 480

Leu Asp Lys Gly Glu Lys Glu Gln Arg Ile Leu Val Phe Asp Leu Gly
                485                 490                 495

Gly Gly Thr Phe Asp Val Ser Leu Leu Glu Ile Gly Glu Gly Val Val
            500                 505                 510

Glu Val Arg Ala Thr Ser Gly Asp Asn His Leu Gly Gly Asp Asp Trp
        515                 520                 525

Asp Gln Arg Val Val Asp Trp Leu Val Asp Lys Phe Lys Gly Thr Ser
    530                 535                 540
```

-continued

Gly Ile Asp Leu Thr Lys Asp Lys Met Ala Met Gln Arg Leu Arg Glu
545 550 555 560

Ala Ala Glu Lys Ala Lys Ile Glu Leu Ser Ser Ser Gln Ser Thr Ser
565 570 575

Ile Asn Leu Pro Tyr Ile Thr Val Asp Ala Asp Lys Asn Pro Leu Phe
580 585 590

Leu Asp Glu Gln Leu Thr Arg Ala Glu Phe Gln Arg Ile Thr Gln Asp
595 600 605

Leu Leu Asp Arg Thr Arg Lys Pro Phe Gln Ser Val Ile Ala Asp Thr
610 615 620

Gly Ile Ser Val Ser Glu Ile Asp His Val Val Leu Val Gly Gly Ser
625 630 635 640

Thr Arg Met Pro Ala Val Thr Asp Leu Val Lys Glu Leu Thr Gly Gly
645 650 655

Lys Glu Pro Asn Lys Gly Val Asn Pro Asp Glu Val Val Ala Val Gly
660 665 670

Ala Ala Leu Gln Ala Gly Val Leu Lys Gly Glu Val Lys Asp Val Leu
675 680 685

Leu Leu Asp Val Thr Pro Leu Ser Leu Gly Ile Glu Thr Lys Gly Gly
690 695 700

Val Met Thr Arg Leu Ile Glu Arg Asn Thr Thr Ile Pro Thr Lys Arg
705 710 715 720

Ser Glu Ser Phe Thr Thr Ala Asp Asp Asn Gln Pro Ser Val Gln Ile
725 730 735

Gln Val Tyr Gln Gly Glu Arg Glu Ile Ala Ala His Asn Lys Leu Leu
740 745 750

Gly Ser Phe Glu Leu Thr Gly Ile Pro Pro Ala Pro Arg Gly Ile Pro
755 760 765

Gln Ile Glu Val Thr Phe Asp Ile Asp Ala Asn Gly Ile Val His Val
770 775 780

Thr Ala Lys Asp Lys Gly Thr Gly Lys Glu Asn Thr Ile Arg Ile Gln
785 790 795 800

Glu Gly Ser Gly Leu Ser Lys Glu Asp Ile Asp Arg Met Ile Lys Asp
805 810 815

Ala Glu Ala His Ala Glu Glu Asp Arg Lys Arg Arg Glu Glu Ala Asp
820 825 830

Val Arg Asn Gln Ala Glu Thr Leu Val Tyr Gln Thr Glu Lys Phe Val
835 840 845

Lys Glu Gln Arg Glu Ala Glu Gly Gly Ser Lys Val Pro Glu Asp Thr
850 855 860

Leu Asn Lys Val Asp Ala Ala Val Ala Glu Ala Lys Ala Ala Leu Gly
865 870 875 880

Gly Ser Asp Ile Ser Ala Ile Lys Ser Ala Met Glu Lys Leu Gly Gln
885 890 895

Glu Ser Gln Ala Leu Gly Gln Ala Ile Tyr Glu Ala Ala Gln Ala Ala
900 905 910

Ser Gln Ala Thr Gly Ala Ala His Pro Gly Gly Glu Pro Gly Gly Ala
915 920 925

His Pro Gly Ser Ala Asp Asp Val Val Asp Ala Glu Val Val Asp Asp
930 935 940

Gly Arg Glu Ala Lys
945

<210> SEQ ID NO 16

```
<211> LENGTH: 2895
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(2895)

<400> SEQUENCE: 16

atg gca cat cac cac cat cat cac cat cac cac cac ggt gca ctt gaa       48
Met Ala His His His His His His His His His His Gly Ala Leu Glu
1               5                   10                  15

gtc ctc ttt cag gga ccc ggg tac cag gat cct gta caa gtc gac gcg       96
Val Leu Phe Gln Gly Pro Gly Tyr Gln Asp Pro Val Gln Val Asp Ala
            20                  25                  30

gcc gca atg gcc aaa gcc gcg gcg atc ggc atc gac ctg ggc acc acc      144
Ala Ala Met Ala Lys Ala Ala Ala Ile Gly Ile Asp Leu Gly Thr Thr
        35                  40                  45

tac tcc tgc gtg ggg gtg ttc caa cac ggc aag gtg gag atc atc gcc      192
Tyr Ser Cys Val Gly Val Phe Gln His Gly Lys Val Glu Ile Ile Ala
    50                  55                  60

aac gac cag ggc aac cgc acc acc ccc agc tac gtg gcc ttc acg gac      240
Asn Asp Gln Gly Asn Arg Thr Thr Pro Ser Tyr Val Ala Phe Thr Asp
65                  70                  75                  80

acc gag cgg ctc atc ggg gat gcg gcc aag aac cag gtg gcg ctg aac      288
Thr Glu Arg Leu Ile Gly Asp Ala Ala Lys Asn Gln Val Ala Leu Asn
                85                  90                  95

ccg cag aac acc gtg ttt gac gcg aag cgg ctg atc ggc cgc aag ttc      336
Pro Gln Asn Thr Val Phe Asp Ala Lys Arg Leu Ile Gly Arg Lys Phe
            100                 105                 110

ggc gac ccg gtg gtg cag tcg gac atg aag cac tgg cct ttc cag gtg      384
Gly Asp Pro Val Val Gln Ser Asp Met Lys His Trp Pro Phe Gln Val
        115                 120                 125

atc aac gac gga gac aag ccc aag gtg cag gtg agc tac aag ggg gac      432
Ile Asn Asp Gly Asp Lys Pro Lys Val Gln Val Ser Tyr Lys Gly Asp
    130                 135                 140

acc aag gca ttc tac ccc gag gag atc tcg tcc atg gtg ctg acc aag      480
Thr Lys Ala Phe Tyr Pro Glu Glu Ile Ser Ser Met Val Leu Thr Lys
145                 150                 155                 160

atg aag gag atc gcc gag gcg tac ctg ggc tac ccg gtg acc aac gcg      528
Met Lys Glu Ile Ala Glu Ala Tyr Leu Gly Tyr Pro Val Thr Asn Ala
                165                 170                 175

gtg atc acc gtg ccg gcc tac ttc aac gac tcg cag cgc cag gcc acc      576
Val Ile Thr Val Pro Ala Tyr Phe Asn Asp Ser Gln Arg Gln Ala Thr
            180                 185                 190

aag gat gcg ggt gtg atc gcg ggg ctc aac gtg ctg cgg atc atc aac      624
Lys Asp Ala Gly Val Ile Ala Gly Leu Asn Val Leu Arg Ile Ile Asn
        195                 200                 205

gag ccc acg gcc gcc gcc atc gcc tac ggc ctg gac aga acg ggc aag      672
Glu Pro Thr Ala Ala Ala Ile Ala Tyr Gly Leu Asp Arg Thr Gly Lys
    210                 215                 220

ggg gag cgc aac gtg ctc atc ttt gac ctg ggc ggg ggc acc ttc gac      720
Gly Glu Arg Asn Val Leu Ile Phe Asp Leu Gly Gly Gly Thr Phe Asp
225                 230                 235                 240

gtg tcc atc ctg acg atc gac gac ggc atc ttc gag gtg aag gcc acg      768
Val Ser Ile Leu Thr Ile Asp Asp Gly Ile Phe Glu Val Lys Ala Thr
                245                 250                 255

gcc ggg gac acc cac ctg ggt ggg gag gac ttt gac aac agg ctg gtg      816
Ala Gly Asp Thr His Leu Gly Gly Glu Asp Phe Asp Asn Arg Leu Val
            260                 265                 270
```

-continued

```
aac cac ttc gtg gag gag ttc aag aga aaa cac aag aag gac atc agc      864
Asn His Phe Val Glu Glu Phe Lys Arg Lys His Lys Lys Asp Ile Ser
        275                 280                 285

cag aac aag cga gcc gtg agg cgg ctg cgc acc gcc tgc gag agg gcc      912
Gln Asn Lys Arg Ala Val Arg Arg Leu Arg Thr Ala Cys Glu Arg Ala
    290                 295                 300

aag agg acc ctg tcg tcc agc acc cag gcc agc ctg gag atc gac tcc      960
Lys Arg Thr Leu Ser Ser Ser Thr Gln Ala Ser Leu Glu Ile Asp Ser
305                 310                 315                 320

ctg ttt gag ggc atc gac ttc tac acg tcc atc acc agg gcg agg ttc     1008
Leu Phe Glu Gly Ile Asp Phe Tyr Thr Ser Ile Thr Arg Ala Arg Phe
                325                 330                 335

gag gag ctg tgc tcc gac ctg ttc cga agc acc ctg gag ccc gtg gag     1056
Glu Glu Leu Cys Ser Asp Leu Phe Arg Ser Thr Leu Glu Pro Val Glu
            340                 345                 350

aag gct ctg cgc gac gcc aag ctg gac aag gcc cag att cac gac ctg     1104
Lys Ala Leu Arg Asp Ala Lys Leu Asp Lys Ala Gln Ile His Asp Leu
        355                 360                 365

gtc ctg gtc ggg ggc tcc acc cgc atc ccc aag gtg cag aag ctg ctg     1152
Val Leu Val Gly Gly Ser Thr Arg Ile Pro Lys Val Gln Lys Leu Leu
    370                 375                 380

cag gac ttc ttc aac ggg cgc gac ctg aac aag agc atc aac ccc gac     1200
Gln Asp Phe Phe Asn Gly Arg Asp Leu Asn Lys Ser Ile Asn Pro Asp
385                 390                 395                 400

gag gct gtg gcc tac ggg gcg gcg gtg cag gcg gcc atc ctg atg ggg     1248
Glu Ala Val Ala Tyr Gly Ala Ala Val Gln Ala Ala Ile Leu Met Gly
                405                 410                 415

gac aag tcc gag aac gtg cag gac ctg ctg ctg ctg gac gtg gct ccc     1296
Asp Lys Ser Glu Asn Val Gln Asp Leu Leu Leu Leu Asp Val Ala Pro
            420                 425                 430

ctg tcg ctg ggg ctg gag acg gcc gga ggc gtg atg act gcc ctg atc     1344
Leu Ser Leu Gly Leu Glu Thr Ala Gly Gly Val Met Thr Ala Leu Ile
        435                 440                 445

aag cgc aac tcc acc atc ccc acc aag cag acg cag atc ttc acc acc     1392
Lys Arg Asn Ser Thr Ile Pro Thr Lys Gln Thr Gln Ile Phe Thr Thr
    450                 455                 460

tac tcc gac aac caa ccc ggg gtg ctg atc cag gtg tac gag ggc gag     1440
Tyr Ser Asp Asn Gln Pro Gly Val Leu Ile Gln Val Tyr Glu Gly Glu
465                 470                 475                 480

agg gcc atg acg aaa gac aac aat ctg ttg ggg cgc ttc gag ctg agc     1488
Arg Ala Met Thr Lys Asp Asn Asn Leu Leu Gly Arg Phe Glu Leu Ser
                485                 490                 495

ggc atc cct ccg gcc ccc agg ggc gtg ccc cag atc gag gtg acc ttc     1536
Gly Ile Pro Pro Ala Pro Arg Gly Val Pro Gln Ile Glu Val Thr Phe
            500                 505                 510

gac atc gat gcc aac ggc atc ctg aac gtc acg gcc acg gac aag agc     1584
Asp Ile Asp Ala Asn Gly Ile Leu Asn Val Thr Ala Thr Asp Lys Ser
        515                 520                 525

acc ggc aag gcc aac aag atc acc atc acc aac gac aag ggc cgc ctg     1632
Thr Gly Lys Ala Asn Lys Ile Thr Ile Thr Asn Asp Lys Gly Arg Leu
    530                 535                 540

agc aag gag gag atc gag cgc atg gtg cag gag gcg gag aag tac aaa     1680
Ser Lys Glu Glu Ile Glu Arg Met Val Gln Glu Ala Glu Lys Tyr Lys
545                 550                 555                 560

gcg gag gac gag gtg cag cgc gag agg gtg tca gcc aag aac gcc ctg     1728
Ala Glu Asp Glu Val Gln Arg Glu Arg Val Ser Ala Lys Asn Ala Leu
                565                 570                 575

gag tcc tac gcc ttc aac atg aag agc gcc gtg gag gat gag ggg ctc     1776
Glu Ser Tyr Ala Phe Asn Met Lys Ser Ala Val Glu Asp Glu Gly Leu
            580                 585                 590
```

-continued

```
aag ggc aag atc agc gag gcc gac aag aag aag gtg ctg gac aag tgt      1824
Lys Gly Lys Ile Ser Glu Ala Asp Lys Lys Lys Val Leu Asp Lys Cys
        595                 600                 605

caa gag gtc atc tcg tgg ctg gac gcc aac acc ttg gcc gag aag gac      1872
Gln Glu Val Ile Ser Trp Leu Asp Ala Asn Thr Leu Ala Glu Lys Asp
    610                 615                 620

gag ttt gag cac aag agg aag gag ctg gag cag gtg tgt aac ccc atc      1920
Glu Phe Glu His Lys Arg Lys Glu Leu Glu Gln Val Cys Asn Pro Ile
625                 630                 635                 640

atc agc gga ctg tac cag ggt gcc ggt ggt ccc ggg cct ggg ggc ttc      1968
Ile Ser Gly Leu Tyr Gln Gly Ala Gly Gly Pro Gly Pro Gly Gly Phe
                645                 650                 655

ggg gct cag ggt ccc aag gga ggg tct ggg tca ggc ccc acc att gag      2016
Gly Ala Gln Gly Pro Lys Gly Gly Ser Gly Ser Gly Pro Thr Ile Glu
            660                 665                 670

gag gta gat cca tca aca cca cca act cca agt cct tct act cct cct      2064
Glu Val Asp Pro Ser Thr Pro Pro Thr Pro Ser Pro Ser Thr Pro Pro
        675                 680                 685

aca cct tca cca tca ggt ttg aat gat att agc cag gta cag ctg cag      2112
Thr Pro Ser Pro Ser Gly Leu Asn Asp Ile Ser Gln Val Gln Leu Gln
    690                 695                 700

cag tca ggt cca gga ctc gtg acg ccc tcg cag acc ctc tca ctc acc      2160
Gln Ser Gly Pro Gly Leu Val Thr Pro Ser Gln Thr Leu Ser Leu Thr
705                 710                 715                 720

tgt gcc atc tcc ggg gac agt gtc tct agc aac agt gct act tgg aac      2208
Cys Ala Ile Ser Gly Asp Ser Val Ser Ser Asn Ser Ala Thr Trp Asn
                725                 730                 735

tgg atc agg cag tcc cca tcg aga ggc ctt gag tgg ctg gga agg aca      2256
Trp Ile Arg Gln Ser Pro Ser Arg Gly Leu Glu Trp Leu Gly Arg Thr
            740                 745                 750

tac tac agg tcc aag tgg tat aac gac tat gca gta tct gtg aaa agt      2304
Tyr Tyr Arg Ser Lys Trp Tyr Asn Asp Tyr Ala Val Ser Val Lys Ser
        755                 760                 765

cga atg agc atc aac cca gac aca tcc aag aac cag ttc tcc ctg cag      2352
Arg Met Ser Ile Asn Pro Asp Thr Ser Lys Asn Gln Phe Ser Leu Gln
    770                 775                 780

ctg aac tct gtg act ccc gag gac acg gct gtg tat tac tgt gca aga      2400
Leu Asn Ser Val Thr Pro Glu Asp Thr Ala Val Tyr Tyr Cys Ala Arg
785                 790                 795                 800

gga atg atg act tac tat tac ggt atg gac gtc tgg ggc caa ggg acc      2448
Gly Met Met Thr Tyr Tyr Tyr Gly Met Asp Val Trp Gly Gln Gly Thr
                805                 810                 815

acg gtc acc gtc tcc tca gga att cta gga tcc ggt ggc ggt ggc agc      2496
Thr Val Thr Val Ser Ser Gly Ile Leu Gly Ser Gly Gly Gly Gly Ser
            820                 825                 830

ggc ggt ggt ggt tcc gga ggc ggc ggt tct cag cct gtg ctg act cag      2544
Gly Gly Gly Gly Ser Gly Gly Gly Gly Ser Gln Pro Val Leu Thr Gln
        835                 840                 845

tcg tct tcc ctc tct gca tct cct gga gca tca gcc agt ctc acc tgc      2592
Ser Ser Ser Leu Ser Ala Ser Pro Gly Ala Ser Ala Ser Leu Thr Cys
    850                 855                 860

acc ttg cgc agt ggc atc aat gtt ggt ccc tac agg ata tac tgg tac      2640
Thr Leu Arg Ser Gly Ile Asn Val Gly Pro Tyr Arg Ile Tyr Trp Tyr
865                 870                 875                 880

cag cag aag cca ggg agt cct ccc cag tat ctc ctg aac tac aaa tca      2688
Gln Gln Lys Pro Gly Ser Pro Pro Gln Tyr Leu Leu Asn Tyr Lys Ser
                885                 890                 895

gac tca gat aag cag cag ggc tct gga gtc ccc agc cgc ttc tct gga      2736
Asp Ser Asp Lys Gln Gln Gly Ser Gly Val Pro Ser Arg Phe Ser Gly
            900                 905                 910
```

```
tcc aaa gat gct tcg gcc aat gca ggg gtt tta ctc atc tct ggg ctc     2784
Ser Lys Asp Ala Ser Ala Asn Ala Gly Val Leu Leu Ile Ser Gly Leu
        915                 920                 925

cgg tct gag gat gag gct gac tat tac tgt atg att tgg cac agc agc     2832
Arg Ser Glu Asp Glu Ala Asp Tyr Tyr Cys Met Ile Trp His Ser Ser
    930                 935                 940

gct gct gtg ttc gga gga ggc acc caa ctg acc gtc ctc tcc gga att     2880
Ala Ala Val Phe Gly Gly Gly Thr Gln Leu Thr Val Leu Ser Gly Ile
945                 950                 955                 960

cta gaa caa cag ggt                                                 2895
Leu Glu Gln Gln Gly
                965


<210> SEQ ID NO 17
<211> LENGTH: 965
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala His His His His His His His His His His Gly Ala Leu Glu
1               5                   10                  15

Val Leu Phe Gln Gly Pro Gly Tyr Gln Asp Pro Val Gln Val Asp Ala
            20                  25                  30

Ala Ala Met Ala Lys Ala Ala Ala Ile Gly Ile Asp Leu Gly Thr Thr
        35                  40                  45

Tyr Ser Cys Val Gly Val Phe Gln His Gly Lys Val Glu Ile Ile Ala
    50                  55                  60

Asn Asp Gln Gly Asn Arg Thr Thr Pro Ser Tyr Val Ala Phe Thr Asp
65                  70                  75                  80

Thr Glu Arg Leu Ile Gly Asp Ala Ala Lys Asn Gln Val Ala Leu Asn
                85                  90                  95

Pro Gln Asn Thr Val Phe Asp Ala Lys Arg Leu Ile Gly Arg Lys Phe
            100                 105                 110

Gly Asp Pro Val Val Gln Ser Asp Met Lys His Trp Pro Phe Gln Val
        115                 120                 125

Ile Asn Asp Gly Asp Lys Pro Lys Val Gln Val Ser Tyr Lys Gly Asp
    130                 135                 140

Thr Lys Ala Phe Tyr Pro Glu Glu Ile Ser Ser Met Val Leu Thr Lys
145                 150                 155                 160

Met Lys Glu Ile Ala Glu Ala Tyr Leu Gly Tyr Pro Val Thr Asn Ala
                165                 170                 175

Val Ile Thr Val Pro Ala Tyr Phe Asn Asp Ser Gln Arg Gln Ala Thr
            180                 185                 190

Lys Asp Ala Gly Val Ile Ala Gly Leu Asn Val Leu Arg Ile Ile Asn
        195                 200                 205

Glu Pro Thr Ala Ala Ala Ile Ala Tyr Gly Leu Asp Arg Thr Gly Lys
    210                 215                 220

Gly Glu Arg Asn Val Leu Ile Phe Asp Leu Gly Gly Gly Thr Phe Asp
225                 230                 235                 240

Val Ser Ile Leu Thr Ile Asp Asp Gly Ile Phe Glu Val Lys Ala Thr
                245                 250                 255

Ala Gly Asp Thr His Leu Gly Gly Glu Asp Phe Asp Asn Arg Leu Val
            260                 265                 270

Asn His Phe Val Glu Glu Phe Lys Arg Lys His Lys Lys Asp Ile Ser
        275                 280                 285
```

-continued

```
Gln Asn Lys Arg Ala Val Arg Arg Leu Arg Thr Ala Cys Glu Arg Ala
    290                 295                 300

Lys Arg Thr Leu Ser Ser Ser Thr Gln Ala Ser Leu Glu Ile Asp Ser
305                 310                 315                 320

Leu Phe Glu Gly Ile Asp Phe Tyr Thr Ser Ile Thr Arg Ala Arg Phe
                325                 330                 335

Glu Glu Leu Cys Ser Asp Leu Phe Arg Ser Thr Leu Glu Pro Val Glu
            340                 345                 350

Lys Ala Leu Arg Asp Ala Lys Leu Asp Lys Ala Gln Ile His Asp Leu
        355                 360                 365

Val Leu Val Gly Gly Ser Thr Arg Ile Pro Lys Val Gln Lys Leu Leu
    370                 375                 380

Gln Asp Phe Phe Asn Gly Arg Asp Leu Asn Lys Ser Ile Asn Pro Asp
385                 390                 395                 400

Glu Ala Val Ala Tyr Gly Ala Ala Val Gln Ala Ala Ile Leu Met Gly
                405                 410                 415

Asp Lys Ser Glu Asn Val Gln Asp Leu Leu Leu Leu Asp Val Ala Pro
            420                 425                 430

Leu Ser Leu Gly Leu Glu Thr Ala Gly Gly Val Met Thr Ala Leu Ile
        435                 440                 445

Lys Arg Asn Ser Thr Ile Pro Thr Lys Gln Thr Gln Ile Phe Thr Thr
    450                 455                 460

Tyr Ser Asp Asn Gln Pro Gly Val Leu Ile Gln Val Tyr Glu Gly Glu
465                 470                 475                 480

Arg Ala Met Thr Lys Asp Asn Asn Leu Leu Gly Arg Phe Glu Leu Ser
                485                 490                 495

Gly Ile Pro Pro Ala Pro Arg Gly Val Pro Gln Ile Glu Val Thr Phe
            500                 505                 510

Asp Ile Asp Ala Asn Gly Ile Leu Asn Val Thr Ala Thr Asp Lys Ser
        515                 520                 525

Thr Gly Lys Ala Asn Lys Ile Thr Ile Thr Asn Asp Lys Gly Arg Leu
    530                 535                 540

Ser Lys Glu Glu Ile Glu Arg Met Val Gln Glu Ala Glu Lys Tyr Lys
545                 550                 555                 560

Ala Glu Asp Glu Val Gln Arg Glu Arg Val Ser Ala Lys Asn Ala Leu
                565                 570                 575

Glu Ser Tyr Ala Phe Asn Met Lys Ser Ala Val Glu Asp Glu Gly Leu
            580                 585                 590

Lys Gly Lys Ile Ser Glu Ala Asp Lys Lys Lys Val Leu Asp Lys Cys
        595                 600                 605

Gln Glu Val Ile Ser Trp Leu Asp Ala Asn Thr Leu Ala Glu Lys Asp
    610                 615                 620

Glu Phe Glu His Lys Arg Lys Glu Leu Glu Gln Val Cys Asn Pro Ile
625                 630                 635                 640

Ile Ser Gly Leu Tyr Gln Gly Ala Gly Gly Pro Gly Pro Gly Gly Phe
                645                 650                 655

Gly Ala Gln Gly Pro Lys Gly Gly Ser Gly Ser Gly Pro Thr Ile Glu
            660                 665                 670

Glu Val Asp Pro Ser Thr Pro Pro Thr Pro Ser Pro Ser Thr Pro Pro
        675                 680                 685

Thr Pro Ser Pro Ser Gly Leu Asn Asp Ile Ser Gln Val Gln Leu Gln
    690                 695                 700

Gln Ser Gly Pro Gly Leu Val Thr Pro Ser Gln Thr Leu Ser Leu Thr
```

```
705                 710                 715                 720

Cys Ala Ile Ser Gly Asp Ser Val Ser Ser Asn Ser Ala Thr Trp Asn
                725                 730                 735

Trp Ile Arg Gln Ser Pro Ser Arg Gly Leu Glu Trp Leu Gly Arg Thr
            740                 745                 750

Tyr Tyr Arg Ser Lys Trp Tyr Asn Asp Tyr Ala Val Ser Val Lys Ser
        755                 760                 765

Arg Met Ser Ile Asn Pro Asp Thr Ser Lys Asn Gln Phe Ser Leu Gln
    770                 775                 780

Leu Asn Ser Val Thr Pro Glu Asp Thr Ala Val Tyr Tyr Cys Ala Arg
785                 790                 795                 800

Gly Met Met Thr Tyr Tyr Tyr Gly Met Asp Val Trp Gly Gln Gly Thr
                805                 810                 815

Thr Val Thr Val Ser Ser Gly Ile Leu Gly Ser Gly Gly Gly Gly Ser
            820                 825                 830

Gly Gly Gly Gly Ser Gly Gly Gly Gly Ser Gln Pro Val Leu Thr Gln
        835                 840                 845

Ser Ser Ser Leu Ser Ala Ser Pro Gly Ala Ser Ala Ser Leu Thr Cys
    850                 855                 860

Thr Leu Arg Ser Gly Ile Asn Val Gly Pro Tyr Arg Ile Tyr Trp Tyr
865                 870                 875                 880

Gln Gln Lys Pro Gly Ser Pro Pro Gln Tyr Leu Leu Asn Tyr Lys Ser
                885                 890                 895

Asp Ser Asp Lys Gln Gln Gly Ser Gly Val Pro Ser Arg Phe Ser Gly
            900                 905                 910

Ser Lys Asp Ala Ser Ala Asn Ala Gly Val Leu Leu Ile Ser Gly Leu
        915                 920                 925

Arg Ser Glu Asp Glu Ala Asp Tyr Tyr Cys Met Ile Trp His Ser Ser
    930                 935                 940

Ala Ala Val Phe Gly Gly Gly Thr Gln Leu Thr Val Leu Ser Gly Ile
945                 950                 955                 960

Leu Glu Gln Gln Gly
                965


<210> SEQ ID NO 18
<211> LENGTH: 2895
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(2895)

<400> SEQUENCE: 18

atg gca cat cac cac cat cat cac cat cac cac cac ggt gca ctt gaa       48
Met Ala His His His His His His His His His His Gly Ala Leu Glu
1               5                   10                  15

gtc ctc ttt cag gga ccc ggg tac cag gat cct gta caa gtc gac gcg       96
Val Leu Phe Gln Gly Pro Gly Tyr Gln Asp Pro Val Gln Val Asp Ala
            20                  25                  30

gcc gca agc cag gta cag ctg cag cag tca ggt cca gga ctc gtg acg      144
Ala Ala Ser Gln Val Gln Leu Gln Gln Ser Gly Pro Gly Leu Val Thr
        35                  40                  45

ccc tcg cag acc ctc tca ctc acc tgt gcc atc tcc ggg gac agt gtc      192
Pro Ser Gln Thr Leu Ser Leu Thr Cys Ala Ile Ser Gly Asp Ser Val
    50                  55                  60
```

-continued

```
tct agc aac agt gct act tgg aac tgg atc agg cag tcc cca tcg aga       240
Ser Ser Asn Ser Ala Thr Trp Asn Trp Ile Arg Gln Ser Pro Ser Arg
65                  70                  75                  80

ggc ctt gag tgg ctg gga agg aca tac tac agg tcc aag tgg tat aac       288
Gly Leu Glu Trp Leu Gly Arg Thr Tyr Tyr Arg Ser Lys Trp Tyr Asn
                85                  90                  95

gac tat gca gta tct gtg aaa agt cga atg agc atc aac cca gac aca       336
Asp Tyr Ala Val Ser Val Lys Ser Arg Met Ser Ile Asn Pro Asp Thr
            100                 105                 110

tcc aag aac cag ttc tcc ctg cag ctg aac tct gtg act ccc gag gac       384
Ser Lys Asn Gln Phe Ser Leu Gln Leu Asn Ser Val Thr Pro Glu Asp
        115                 120                 125

acg gct gtg tat tac tgt gca aga gga atg atg act tac tat tac ggt       432
Thr Ala Val Tyr Tyr Cys Ala Arg Gly Met Met Thr Tyr Tyr Tyr Gly
    130                 135                 140

atg gac gtc tgg ggc caa ggg acc acg gtc acc gtc tcc tca gga att       480
Met Asp Val Trp Gly Gln Gly Thr Thr Val Thr Val Ser Ser Gly Ile
145                 150                 155                 160

cta gga tcc ggt ggc ggt ggc agc ggc ggt ggt ggt tcc gga ggc ggc       528
Leu Gly Ser Gly Gly Gly Gly Ser Gly Gly Gly Gly Ser Gly Gly Gly
                165                 170                 175

ggt tct cag cct gtg ctg act cag tcg tct tcc ctc tct gca tct cct       576
Gly Ser Gln Pro Val Leu Thr Gln Ser Ser Ser Leu Ser Ala Ser Pro
            180                 185                 190

gga gca tca gcc agt ctc acc tgc acc ttg cgc agt ggc atc aat gtt       624
Gly Ala Ser Ala Ser Leu Thr Cys Thr Leu Arg Ser Gly Ile Asn Val
        195                 200                 205

ggt ccc tac agg ata tac tgg tac cag cag aag cca ggg agt cct ccc       672
Gly Pro Tyr Arg Ile Tyr Trp Tyr Gln Gln Lys Pro Gly Ser Pro Pro
    210                 215                 220

cag tat ctc ctg aac tac aaa tca gac tca gat aag cag cag ggc tct       720
Gln Tyr Leu Leu Asn Tyr Lys Ser Asp Ser Asp Lys Gln Gln Gly Ser
225                 230                 235                 240

gga gtc ccc agc cgc ttc tct gga tcc aaa gat gct tcg gcc aat gca       768
Gly Val Pro Ser Arg Phe Ser Gly Ser Lys Asp Ala Ser Ala Asn Ala
                245                 250                 255

ggg gtt tta ctc atc tct ggg ctc cgg tct gag gat gag gct gac tat       816
Gly Val Leu Leu Ile Ser Gly Leu Arg Ser Glu Asp Glu Ala Asp Tyr
            260                 265                 270

tac tgt atg att tgg cac agc agc gct gct gtg ttc gga gga ggc acc       864
Tyr Cys Met Ile Trp His Ser Ser Ala Ala Val Phe Gly Gly Gly Thr
        275                 280                 285

caa ctg acc gtc ctc tcc gga att cta gaa caa cag ggt cca tca aca       912
Gln Leu Thr Val Leu Ser Gly Ile Leu Glu Gln Gln Gly Pro Ser Thr
    290                 295                 300

cca cca act cca agt cct tct act cct cct aca cct tca cca tca ggt       960
Pro Pro Thr Pro Ser Pro Ser Thr Pro Pro Thr Pro Ser Pro Ser Gly
305                 310                 315                 320

ttg aat gat att atg gcc aaa gcc gcg gcg atc ggc atc gac ctg ggc      1008
Leu Asn Asp Ile Met Ala Lys Ala Ala Ala Ile Gly Ile Asp Leu Gly
                325                 330                 335

acc acc tac tcc tgc gtg ggg gtg ttc caa cac ggc aag gtg gag atc      1056
Thr Thr Tyr Ser Cys Val Gly Val Phe Gln His Gly Lys Val Glu Ile
            340                 345                 350

atc gcc aac gac cag ggc aac cgc acc acc ccc agc tac gtg gcc ttc      1104
Ile Ala Asn Asp Gln Gly Asn Arg Thr Thr Pro Ser Tyr Val Ala Phe
        355                 360                 365

acg gac acc gag cgg ctc atc ggg gat gcg gcc aag aac cag gtg gcg      1152
Thr Asp Thr Glu Arg Leu Ile Gly Asp Ala Ala Lys Asn Gln Val Ala
    370                 375                 380
```

-continued

```
ctg aac ccg cag aac acc gtg ttt gac gcg aag cgg ctg atc ggc cgc      1200
Leu Asn Pro Gln Asn Thr Val Phe Asp Ala Lys Arg Leu Ile Gly Arg
385                 390                 395                 400

aag ttc ggc gac ccg gtg gtg cag tcg gac atg aag cac tgg cct ttc      1248
Lys Phe Gly Asp Pro Val Val Gln Ser Asp Met Lys His Trp Pro Phe
                405                 410                 415

cag gtg atc aac gac gga gac aag ccc aag gtg cag gtg agc tac aag      1296
Gln Val Ile Asn Asp Gly Asp Lys Pro Lys Val Gln Val Ser Tyr Lys
            420                 425                 430

ggg gac acc aag gca ttc tac ccc gag gag atc tcg tcc atg gtg ctg      1344
Gly Asp Thr Lys Ala Phe Tyr Pro Glu Glu Ile Ser Ser Met Val Leu
        435                 440                 445

acc aag atg aag gag atc gcc gag gcg tac ctg ggc tac ccg gtg acc      1392
Thr Lys Met Lys Glu Ile Ala Glu Ala Tyr Leu Gly Tyr Pro Val Thr
    450                 455                 460

aac gcg gtg atc acc gtg ccg gcc tac ttc aac gac tcg cag cgc cag      1440
Asn Ala Val Ile Thr Val Pro Ala Tyr Phe Asn Asp Ser Gln Arg Gln
465                 470                 475                 480

gcc acc aag gat gcg ggt gtg atc gcg ggg ctc aac gtg ctg cgg atc      1488
Ala Thr Lys Asp Ala Gly Val Ile Ala Gly Leu Asn Val Leu Arg Ile
                485                 490                 495

atc aac gag ccc acg gcc gcc gcc atc gcc tac ggc ctg gac aga acg      1536
Ile Asn Glu Pro Thr Ala Ala Ala Ile Ala Tyr Gly Leu Asp Arg Thr
            500                 505                 510

ggc aag ggg gag cgc aac gtg ctc atc ttt gac ctg ggc ggg ggc acc      1584
Gly Lys Gly Glu Arg Asn Val Leu Ile Phe Asp Leu Gly Gly Gly Thr
        515                 520                 525

ttc gac gtg tcc atc ctg acg atc gac gac ggc atc ttc gag gtg aag      1632
Phe Asp Val Ser Ile Leu Thr Ile Asp Asp Gly Ile Phe Glu Val Lys
    530                 535                 540

gcc acg gcc ggg gac acc cac ctg ggt ggg gag gac ttt gac aac agg      1680
Ala Thr Ala Gly Asp Thr His Leu Gly Gly Glu Asp Phe Asp Asn Arg
545                 550                 555                 560

ctg gtg aac cac ttc gtg gag gag ttc aag aga aaa cac aag aag gac      1728
Leu Val Asn His Phe Val Glu Glu Phe Lys Arg Lys His Lys Lys Asp
                565                 570                 575

atc agc cag aac aag cga gcc gtg agg cgg ctg cgc acc gcc tgc gag      1776
Ile Ser Gln Asn Lys Arg Ala Val Arg Arg Leu Arg Thr Ala Cys Glu
            580                 585                 590

agg gcc aag agg acc ctg tcg tcc agc acc cag gcc agc ctg gag atc      1824
Arg Ala Lys Arg Thr Leu Ser Ser Ser Thr Gln Ala Ser Leu Glu Ile
        595                 600                 605

gac tcc ctg ttt gag ggc atc gac ttc tac acg tcc atc acc agg gcg      1872
Asp Ser Leu Phe Glu Gly Ile Asp Phe Tyr Thr Ser Ile Thr Arg Ala
    610                 615                 620

agg ttc gag gag ctg tgc tcc gac ctg ttc cga agc acc ctg gag ccc      1920
Arg Phe Glu Glu Leu Cys Ser Asp Leu Phe Arg Ser Thr Leu Glu Pro
625                 630                 635                 640

gtg gag aag gct ctg cgc gac gcc aag ctg gac aag gcc cag att cac      1968
Val Glu Lys Ala Leu Arg Asp Ala Lys Leu Asp Lys Ala Gln Ile His
                645                 650                 655

gac ctg gtc ctg gtc ggg ggc tcc acc cgc atc ccc aag gtg cag aag      2016
Asp Leu Val Leu Val Gly Gly Ser Thr Arg Ile Pro Lys Val Gln Lys
            660                 665                 670

ctg ctg cag gac ttc ttc aac ggg cgc gac ctg aac aag agc atc aac      2064
Leu Leu Gln Asp Phe Phe Asn Gly Arg Asp Leu Asn Lys Ser Ile Asn
        675                 680                 685

ccc gac gag gct gtg gcc tac ggg gcg gcg gtg cag gcg gcc atc ctg      2112
Pro Asp Glu Ala Val Ala Tyr Gly Ala Ala Val Gln Ala Ala Ile Leu
    690                 695                 700
```

```
atg ggg gac aag tcc gag aac gtg cag gac ctg ctg ctg ctg gac gtg     2160
Met Gly Asp Lys Ser Glu Asn Val Gln Asp Leu Leu Leu Leu Asp Val
705                 710                 715                 720

gct ccc ctg tcg ctg ggg ctg gag acg gcc gga ggc gtg atg act gcc     2208
Ala Pro Leu Ser Leu Gly Leu Glu Thr Ala Gly Gly Val Met Thr Ala
                725                 730                 735

ctg atc aag cgc aac tcc acc atc ccc acc aag cag acg cag atc ttc     2256
Leu Ile Lys Arg Asn Ser Thr Ile Pro Thr Lys Gln Thr Gln Ile Phe
            740                 745                 750

acc acc tac tcc gac aac caa ccc ggg gtg ctg atc cag gtg tac gag     2304
Thr Thr Tyr Ser Asp Asn Gln Pro Gly Val Leu Ile Gln Val Tyr Glu
        755                 760                 765

ggc gag agg gcc atg acg aaa gac aac aat ctg ttg ggg cgc ttc gag     2352
Gly Glu Arg Ala Met Thr Lys Asp Asn Asn Leu Leu Gly Arg Phe Glu
    770                 775                 780

ctg agc ggc atc cct ccg gcc ccc agg ggc gtg ccc cag atc gag gtg     2400
Leu Ser Gly Ile Pro Pro Ala Pro Arg Gly Val Pro Gln Ile Glu Val
785                 790                 795                 800

acc ttc gac atc gat gcc aac ggc atc ctg aac gtc acg gcc acg gac     2448
Thr Phe Asp Ile Asp Ala Asn Gly Ile Leu Asn Val Thr Ala Thr Asp
                805                 810                 815

aag agc acc ggc aag gcc aac aag atc acc atc acc aac gac aag ggc     2496
Lys Ser Thr Gly Lys Ala Asn Lys Ile Thr Ile Thr Asn Asp Lys Gly
            820                 825                 830

cgc ctg agc aag gag gag atc gag cgc atg gtg cag gag gcg gag aag     2544
Arg Leu Ser Lys Glu Glu Ile Glu Arg Met Val Gln Glu Ala Glu Lys
        835                 840                 845

tac aaa gcg gag gac gag gtg cag cgc gag agg gtg tca gcc aag aac     2592
Tyr Lys Ala Glu Asp Glu Val Gln Arg Glu Arg Val Ser Ala Lys Asn
    850                 855                 860

gcc ctg gag tcc tac gcc ttc aac atg aag agc gcc gtg gag gat gag     2640
Ala Leu Glu Ser Tyr Ala Phe Asn Met Lys Ser Ala Val Glu Asp Glu
865                 870                 875                 880

ggg ctc aag ggc aag atc agc gag gcc gac aag aag aag gtg ctg gac     2688
Gly Leu Lys Gly Lys Ile Ser Glu Ala Asp Lys Lys Lys Val Leu Asp
                885                 890                 895

aag tgt caa gag gtc atc tcg tgg ctg gac gcc aac acc ttg gcc gag     2736
Lys Cys Gln Glu Val Ile Ser Trp Leu Asp Ala Asn Thr Leu Ala Glu
            900                 905                 910

aag gac gag ttt gag cac aag agg aag gag ctg gag cag gtg tgt aac     2784
Lys Asp Glu Phe Glu His Lys Arg Lys Glu Leu Glu Gln Val Cys Asn
        915                 920                 925

ccc atc atc agc gga ctg tac cag ggt gcc ggt ggt ccc ggg cct ggg     2832
Pro Ile Ile Ser Gly Leu Tyr Gln Gly Ala Gly Gly Pro Gly Pro Gly
    930                 935                 940

ggc ttc ggg gct cag ggt ccc aag gga ggg tct ggg tca ggc ccc acc     2880
Gly Phe Gly Ala Gln Gly Pro Lys Gly Gly Ser Gly Ser Gly Pro Thr
945                 950                 955                 960

att gag gag gta gat                                                 2895
Ile Glu Glu Val Asp
                965
```

<210> SEQ ID NO 19
<211> LENGTH: 965
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Met Ala His His His His His His His His His His Gly Ala Leu Glu
```

-continued

```
1               5                   10                  15

Val Leu Phe Gln Gly Pro Gly Tyr Gln Asp Pro Val Gln Val Asp Ala
            20                  25                  30

Ala Ala Ser Gln Val Gln Leu Gln Gln Ser Gly Pro Gly Leu Val Thr
        35                  40                  45

Pro Ser Gln Thr Leu Ser Leu Thr Cys Ala Ile Ser Gly Asp Ser Val
    50                  55                  60

Ser Ser Asn Ser Ala Thr Trp Asn Trp Ile Arg Gln Ser Pro Ser Arg
65                  70                  75                  80

Gly Leu Glu Trp Leu Gly Arg Thr Tyr Tyr Arg Ser Lys Trp Tyr Asn
                85                  90                  95

Asp Tyr Ala Val Ser Val Lys Ser Arg Met Ser Ile Asn Pro Asp Thr
            100                 105                 110

Ser Lys Asn Gln Phe Ser Leu Gln Leu Asn Ser Val Thr Pro Glu Asp
        115                 120                 125

Thr Ala Val Tyr Tyr Cys Ala Arg Gly Met Met Thr Tyr Tyr Tyr Gly
    130                 135                 140

Met Asp Val Trp Gly Gln Gly Thr Thr Val Thr Val Ser Ser Gly Ile
145                 150                 155                 160

Leu Gly Ser Gly Gly Gly Gly Ser Gly Gly Gly Gly Ser Gly Gly Gly
                165                 170                 175

Gly Ser Gln Pro Val Leu Thr Gln Ser Ser Ser Leu Ser Ala Ser Pro
            180                 185                 190

Gly Ala Ser Ala Ser Leu Thr Cys Thr Leu Arg Ser Gly Ile Asn Val
        195                 200                 205

Gly Pro Tyr Arg Ile Tyr Trp Tyr Gln Gln Lys Pro Gly Ser Pro Pro
    210                 215                 220

Gln Tyr Leu Leu Asn Tyr Lys Ser Asp Ser Asp Lys Gln Gln Gly Ser
225                 230                 235                 240

Gly Val Pro Ser Arg Phe Ser Gly Ser Lys Asp Ala Ser Ala Asn Ala
                245                 250                 255

Gly Val Leu Leu Ile Ser Gly Leu Arg Ser Glu Asp Glu Ala Asp Tyr
            260                 265                 270

Tyr Cys Met Ile Trp His Ser Ser Ala Ala Val Phe Gly Gly Gly Thr
        275                 280                 285

Gln Leu Thr Val Leu Ser Gly Ile Leu Glu Gln Gln Gly Pro Ser Thr
    290                 295                 300

Pro Pro Thr Pro Ser Pro Ser Thr Pro Pro Thr Pro Ser Pro Ser Gly
305                 310                 315                 320

Leu Asn Asp Ile Met Ala Lys Ala Ala Ala Ile Gly Ile Asp Leu Gly
                325                 330                 335

Thr Thr Tyr Ser Cys Val Gly Val Phe Gln His Gly Lys Val Glu Ile
            340                 345                 350

Ile Ala Asn Asp Gln Gly Asn Arg Thr Thr Pro Ser Tyr Val Ala Phe
        355                 360                 365

Thr Asp Thr Glu Arg Leu Ile Gly Asp Ala Ala Lys Asn Gln Val Ala
    370                 375                 380

Leu Asn Pro Gln Asn Thr Val Phe Asp Ala Lys Arg Leu Ile Gly Arg
385                 390                 395                 400

Lys Phe Gly Asp Pro Val Val Gln Ser Asp Met Lys His Trp Pro Phe
                405                 410                 415

Gln Val Ile Asn Asp Gly Asp Lys Pro Lys Val Gln Val Ser Tyr Lys
            420                 425                 430
```

-continued

```
Gly Asp Thr Lys Ala Phe Tyr Pro Glu Glu Ile Ser Ser Met Val Leu
        435                 440                 445

Thr Lys Met Lys Glu Ile Ala Glu Ala Tyr Leu Gly Tyr Pro Val Thr
    450                 455                 460

Asn Ala Val Ile Thr Val Pro Ala Tyr Phe Asn Asp Ser Gln Arg Gln
465                 470                 475                 480

Ala Thr Lys Asp Ala Gly Val Ile Ala Gly Leu Asn Val Leu Arg Ile
                485                 490                 495

Ile Asn Glu Pro Thr Ala Ala Ala Ile Ala Tyr Gly Leu Asp Arg Thr
            500                 505                 510

Gly Lys Gly Glu Arg Asn Val Leu Ile Phe Asp Leu Gly Gly Gly Thr
        515                 520                 525

Phe Asp Val Ser Ile Leu Thr Ile Asp Asp Gly Ile Phe Glu Val Lys
    530                 535                 540

Ala Thr Ala Gly Asp Thr His Leu Gly Gly Glu Asp Phe Asp Asn Arg
545                 550                 555                 560

Leu Val Asn His Phe Val Glu Glu Phe Lys Arg Lys His Lys Lys Asp
                565                 570                 575

Ile Ser Gln Asn Lys Arg Ala Val Arg Arg Leu Arg Thr Ala Cys Glu
            580                 585                 590

Arg Ala Lys Arg Thr Leu Ser Ser Ser Thr Gln Ala Ser Leu Glu Ile
        595                 600                 605

Asp Ser Leu Phe Glu Gly Ile Asp Phe Tyr Thr Ser Ile Thr Arg Ala
    610                 615                 620

Arg Phe Glu Glu Leu Cys Ser Asp Leu Phe Arg Ser Thr Leu Glu Pro
625                 630                 635                 640

Val Glu Lys Ala Leu Arg Asp Ala Lys Leu Asp Lys Ala Gln Ile His
                645                 650                 655

Asp Leu Val Leu Val Gly Gly Ser Thr Arg Ile Pro Lys Val Gln Lys
            660                 665                 670

Leu Leu Gln Asp Phe Phe Asn Gly Arg Asp Leu Asn Lys Ser Ile Asn
        675                 680                 685

Pro Asp Glu Ala Val Ala Tyr Gly Ala Ala Val Gln Ala Ala Ile Leu
    690                 695                 700

Met Gly Asp Lys Ser Glu Asn Val Gln Asp Leu Leu Leu Leu Asp Val
705                 710                 715                 720

Ala Pro Leu Ser Leu Gly Leu Glu Thr Ala Gly Gly Val Met Thr Ala
                725                 730                 735

Leu Ile Lys Arg Asn Ser Thr Ile Pro Thr Lys Gln Thr Gln Ile Phe
            740                 745                 750

Thr Thr Tyr Ser Asp Asn Gln Pro Gly Val Leu Ile Gln Val Tyr Glu
        755                 760                 765

Gly Glu Arg Ala Met Thr Lys Asp Asn Asn Leu Leu Gly Arg Phe Glu
    770                 775                 780

Leu Ser Gly Ile Pro Pro Ala Pro Arg Gly Val Pro Gln Ile Glu Val
785                 790                 795                 800

Thr Phe Asp Ile Asp Ala Asn Gly Ile Leu Asn Val Thr Ala Thr Asp
                805                 810                 815

Lys Ser Thr Gly Lys Ala Asn Lys Ile Thr Ile Thr Asn Asp Lys Gly
            820                 825                 830

Arg Leu Ser Lys Glu Glu Ile Glu Arg Met Val Gln Glu Ala Glu Lys
        835                 840                 845

Tyr Lys Ala Glu Asp Glu Val Gln Arg Glu Arg Val Ser Ala Lys Asn
    850                 855                 860
```

```
Ala Leu Glu Ser Tyr Ala Phe Asn Met Lys Ser Ala Val Glu Asp Glu
865                 870                 875                 880

Gly Leu Lys Gly Lys Ile Ser Glu Ala Asp Lys Lys Lys Val Leu Asp
                885                 890                 895

Lys Cys Gln Glu Val Ile Ser Trp Leu Asp Ala Asn Thr Leu Ala Glu
            900                 905                 910

Lys Asp Glu Phe Glu His Lys Arg Lys Glu Leu Glu Gln Val Cys Asn
        915                 920                 925

Pro Ile Ile Ser Gly Leu Tyr Gln Gly Ala Gly Gly Pro Gly Pro Gly
    930                 935                 940

Gly Phe Gly Ala Gln Gly Pro Lys Gly Gly Ser Gly Ser Gly Pro Thr
945                 950                 955                 960

Ile Glu Glu Val Asp
                965


<210> SEQ ID NO 20
<211> LENGTH: 2052
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(2052)

<400> SEQUENCE: 20

atg gca cat cac cac cat cat cac cat cac cac cac ggt gca ctt gaa       48
Met Ala His His His His His His His His His His Gly Ala Leu Glu
1               5                   10                  15

gtc ctc ttt cag gga ccc ggg tac cag gat cct gta caa gtc gac gcg       96
Val Leu Phe Gln Gly Pro Gly Tyr Gln Asp Pro Val Gln Val Asp Ala
            20                  25                  30

gcc gca atg gct cgt gcg gtc ggg atc gac ctc ggg acc acc aac tcc      144
Ala Ala Met Ala Arg Ala Val Gly Ile Asp Leu Gly Thr Thr Asn Ser
        35                  40                  45

gtc gtc tcg gtt ctg gaa ggt ggc gac ccg gtc gtc gtc gcc aac tcc      192
Val Val Ser Val Leu Glu Gly Gly Asp Pro Val Val Val Ala Asn Ser
    50                  55                  60

gag ggc tcc agg acc acc ccg tca att gtc gcg ttc gcc cgc aac ggt      240
Glu Gly Ser Arg Thr Thr Pro Ser Ile Val Ala Phe Ala Arg Asn Gly
65                  70                  75                  80

gag gtg ctg gtc ggc cag ccc gcc aag aac cag gcg gtg acc aac gtc      288
Glu Val Leu Val Gly Gln Pro Ala Lys Asn Gln Ala Val Thr Asn Val
                85                  90                  95

gat cgc acc gtg cgc tcg gtc aag cga cac atg ggc agc gac tgg tcc      336
Asp Arg Thr Val Arg Ser Val Lys Arg His Met Gly Ser Asp Trp Ser
            100                 105                 110

ata gag att gac ggc aag aaa tac acc gcg ccg gag atc agc gcc cgc      384
Ile Glu Ile Asp Gly Lys Lys Tyr Thr Ala Pro Glu Ile Ser Ala Arg
        115                 120                 125

att ctg atg aag ctg aag cgc gac gcc gag gcc tac ctc ggt gag gac      432
Ile Leu Met Lys Leu Lys Arg Asp Ala Glu Ala Tyr Leu Gly Glu Asp
    130                 135                 140

att acc gac gcg gtt atc acg acg ccc gcc tac ttc aat gac gcc cag      480
Ile Thr Asp Ala Val Ile Thr Thr Pro Ala Tyr Phe Asn Asp Ala Gln
145                 150                 155                 160

cgt cag gcc acc aag gac gcc ggc cag atc gcc ggc ctc aac gtg ctg      528
Arg Gln Ala Thr Lys Asp Ala Gly Gln Ile Ala Gly Leu Asn Val Leu
                165                 170                 175
```

-continued

```
cgg atc gtc aac gag ccg acc gct gca gcg ctg gcc tac ggc ctc gac       576
Arg Ile Val Asn Glu Pro Thr Ala Ala Ala Leu Ala Tyr Gly Leu Asp
            180                 185                 190

aag ggc gag aag gag cag cga atc ctg gtc ttc gac ttg ggt ggt ggc       624
Lys Gly Glu Lys Glu Gln Arg Ile Leu Val Phe Asp Leu Gly Gly Gly
        195                 200                 205

act ttc gac gtt tcc ctg ctg gag atc ggc gag ggt gtg gtt gag gtc       672
Thr Phe Asp Val Ser Leu Leu Glu Ile Gly Glu Gly Val Val Glu Val
    210                 215                 220

cgt gcc act tcg ggt gac aac cac ctc ggc ggc gac gac tgg gac cag       720
Arg Ala Thr Ser Gly Asp Asn His Leu Gly Gly Asp Asp Trp Asp Gln
225                 230                 235                 240

cgg gtc gtc gat tgg ctg gtg gac aag ttc aag ggc acc agc ggc atc       768
Arg Val Val Asp Trp Leu Val Asp Lys Phe Lys Gly Thr Ser Gly Ile
                245                 250                 255

gat ctg acc aag gac aag atg gcg atg cag cgg ctg cgg gaa gcc gcc       816
Asp Leu Thr Lys Asp Lys Met Ala Met Gln Arg Leu Arg Glu Ala Ala
            260                 265                 270

gag aaa gca aag atc gag ctg agt tcg agt cag tcc acc tcg atc aac       864
Glu Lys Ala Lys Ile Glu Leu Ser Ser Ser Gln Ser Thr Ser Ile Asn
        275                 280                 285

ctg ccc tac atc acc gtc gac gcc gac aag aac ccg ttg ttc tta gac       912
Leu Pro Tyr Ile Thr Val Asp Ala Asp Lys Asn Pro Leu Phe Leu Asp
    290                 295                 300

gag cag ctg acc cgc gcg gag ttc caa cgg atc act cag gac ctg ctg       960
Glu Gln Leu Thr Arg Ala Glu Phe Gln Arg Ile Thr Gln Asp Leu Leu
305                 310                 315                 320

gac cgc act cgc aag ccg ttc cag tcg gtg atc gct gac acc ggc att      1008
Asp Arg Thr Arg Lys Pro Phe Gln Ser Val Ile Ala Asp Thr Gly Ile
                325                 330                 335

tcg gtg tcg gag atc gat cac gtt gtg ctc gtg ggt ggt tcg acc cgg      1056
Ser Val Ser Glu Ile Asp His Val Val Leu Val Gly Gly Ser Thr Arg
            340                 345                 350

atg ccc gcg gtg acc gat ctg gtc aag gaa ctc acc ggc ggc aag gaa      1104
Met Pro Ala Val Thr Asp Leu Val Lys Glu Leu Thr Gly Gly Lys Glu
        355                 360                 365

ccc aac aag ggc gtc aac ccc gat gag gtt gtc gcg gtg gga gcc gct      1152
Pro Asn Lys Gly Val Asn Pro Asp Glu Val Val Ala Val Gly Ala Ala
    370                 375                 380

ctg cag gcc ggc gtc ctc aag ggc gag gtg aaa gac gtt ctg ctg ctt      1200
Leu Gln Ala Gly Val Leu Lys Gly Glu Val Lys Asp Val Leu Leu Leu
385                 390                 395                 400

gat gtt acc ccg ctg agc ctg ggt atc gag acc aag ggc ggg gtg atg      1248
Asp Val Thr Pro Leu Ser Leu Gly Ile Glu Thr Lys Gly Gly Val Met
                405                 410                 415

acc agg ctc atc gag cgc aac acc acg atc ccc acc aag cgg tcg gag      1296
Thr Arg Leu Ile Glu Arg Asn Thr Thr Ile Pro Thr Lys Arg Ser Glu
            420                 425                 430

tct ttc acc acc gcc gac gac aac caa ccg tcg gtg cag atc cag gtc      1344
Ser Phe Thr Thr Ala Asp Asp Asn Gln Pro Ser Val Gln Ile Gln Val
        435                 440                 445

tat cag ggg gag cgt gag atc gcc gcg cac aac aag ttg ctc ggg tcc      1392
Tyr Gln Gly Glu Arg Glu Ile Ala Ala His Asn Lys Leu Leu Gly Ser
    450                 455                 460

ttc gag ctg acc ggc atc ccg ccg gcg ccg cgg ggg att ccg cag atc      1440
Phe Glu Leu Thr Gly Ile Pro Pro Ala Pro Arg Gly Ile Pro Gln Ile
465                 470                 475                 480

gag gtc act ttc gac atc gac gcc aac ggc att gtg cac gtc acc gcc      1488
Glu Val Thr Phe Asp Ile Asp Ala Asn Gly Ile Val His Val Thr Ala
                485                 490                 495
```

-continued

```
aag gac aag ggc acc ggc aag gag aac acg atc cga atc cag gaa ggc     1536
Lys Asp Lys Gly Thr Gly Lys Glu Asn Thr Ile Arg Ile Gln Glu Gly
            500                 505                 510

tcg ggc ctg tcc aag gaa gac att gac cgc atg atc aag gac gcc gaa     1584
Ser Gly Leu Ser Lys Glu Asp Ile Asp Arg Met Ile Lys Asp Ala Glu
        515                 520                 525

gcg cac gcc gag gag gat cgc aag cgt cgc gag gag gcc gat gtt cgt     1632
Ala His Ala Glu Glu Asp Arg Lys Arg Arg Glu Glu Ala Asp Val Arg
    530                 535                 540

aat caa gcc gag aca ttg gtc tac cag acg gag aag ttc gtc aaa gaa     1680
Asn Gln Ala Glu Thr Leu Val Tyr Gln Thr Glu Lys Phe Val Lys Glu
545                 550                 555                 560

cag cgt gag gcc gag ggt ggt tcg aag gta cct gaa gac acg ctg aac     1728
Gln Arg Glu Ala Glu Gly Gly Ser Lys Val Pro Glu Asp Thr Leu Asn
                565                 570                 575

aag gtt gat gcc gcg gtg gcg gaa gcg aag gcg gca ctt ggc gga tcg     1776
Lys Val Asp Ala Ala Val Ala Glu Ala Lys Ala Ala Leu Gly Gly Ser
            580                 585                 590

gat att tcg gcc atc aag tcg gcg atg gag aag ctg ggc cag gag tcg     1824
Asp Ile Ser Ala Ile Lys Ser Ala Met Glu Lys Leu Gly Gln Glu Ser
        595                 600                 605

cag gct ctg ggg caa gcg atc tac gaa gca gct cag gct gcg tca cag     1872
Gln Ala Leu Gly Gln Ala Ile Tyr Glu Ala Ala Gln Ala Ala Ser Gln
    610                 615                 620

gcc act ggc gct gcc cac ccc ggc ggc gag ccg ggc ggt gcc cac ccc     1920
Ala Thr Gly Ala Ala His Pro Gly Gly Glu Pro Gly Gly Ala His Pro
625                 630                 635                 640

ggc tcg gct gat gac gtt gtg gac gcg gag gtg gtc gac gac ggc cgg     1968
Gly Ser Ala Asp Asp Val Val Asp Ala Glu Val Val Asp Asp Gly Arg
                645                 650                 655

gag gcc aag ggt ggc ggt ggc agc ggc ggt ggt ggt tcc gga ggc ggc     2016
Glu Ala Lys Gly Gly Gly Gly Ser Gly Gly Gly Gly Ser Gly Gly Gly
            660                 665                 670

ggt tct aaa ctt ctg gga ccc cac gtg gag ggc ctg                     2052
Gly Ser Lys Leu Leu Gly Pro His Val Glu Gly Leu
        675                 680
```

```
<210> SEQ ID NO 21
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Ala His His His His His His His His His His Gly Ala Leu Glu
1               5                   10                  15

Val Leu Phe Gln Gly Pro Gly Tyr Gln Asp Pro Val Gln Val Asp Ala
            20                  25                  30

Ala Ala Met Ala Arg Ala Val Gly Ile Asp Leu Gly Thr Thr Asn Ser
        35                  40                  45

Val Val Ser Val Leu Glu Gly Gly Asp Pro Val Val Val Ala Asn Ser
    50                  55                  60

Glu Gly Ser Arg Thr Thr Pro Ser Ile Val Ala Phe Ala Arg Asn Gly
65                  70                  75                  80

Glu Val Leu Val Gly Gln Pro Ala Lys Asn Gln Ala Val Thr Asn Val
                85                  90                  95

Asp Arg Thr Val Arg Ser Val Lys Arg His Met Gly Ser Asp Trp Ser
            100                 105                 110
```

-continued

```
Ile Glu Ile Asp Gly Lys Lys Tyr Thr Ala Pro Glu Ile Ser Ala Arg
        115                 120                 125

Ile Leu Met Lys Leu Lys Arg Asp Ala Glu Ala Tyr Leu Gly Glu Asp
    130                 135                 140

Ile Thr Asp Ala Val Ile Thr Thr Pro Ala Tyr Phe Asn Asp Ala Gln
145                 150                 155                 160

Arg Gln Ala Thr Lys Asp Ala Gly Gln Ile Ala Gly Leu Asn Val Leu
                165                 170                 175

Arg Ile Val Asn Glu Pro Thr Ala Ala Ala Leu Ala Tyr Gly Leu Asp
            180                 185                 190

Lys Gly Glu Lys Glu Gln Arg Ile Leu Val Phe Asp Leu Gly Gly Gly
        195                 200                 205

Thr Phe Asp Val Ser Leu Leu Glu Ile Gly Glu Gly Val Val Glu Val
    210                 215                 220

Arg Ala Thr Ser Gly Asp Asn His Leu Gly Gly Asp Asp Trp Asp Gln
225                 230                 235                 240

Arg Val Val Asp Trp Leu Val Asp Lys Phe Lys Gly Thr Ser Gly Ile
                245                 250                 255

Asp Leu Thr Lys Asp Lys Met Ala Met Gln Arg Leu Arg Glu Ala Ala
            260                 265                 270

Glu Lys Ala Lys Ile Glu Leu Ser Ser Ser Gln Ser Thr Ser Ile Asn
        275                 280                 285

Leu Pro Tyr Ile Thr Val Asp Ala Asp Lys Asn Pro Leu Phe Leu Asp
    290                 295                 300

Glu Gln Leu Thr Arg Ala Glu Phe Gln Arg Ile Thr Gln Asp Leu Leu
305                 310                 315                 320

Asp Arg Thr Arg Lys Pro Phe Gln Ser Val Ile Ala Asp Thr Gly Ile
                325                 330                 335

Ser Val Ser Glu Ile Asp His Val Val Leu Val Gly Gly Ser Thr Arg
            340                 345                 350

Met Pro Ala Val Thr Asp Leu Val Lys Glu Leu Thr Gly Gly Lys Glu
        355                 360                 365

Pro Asn Lys Gly Val Asn Pro Asp Glu Val Val Ala Val Gly Ala Ala
    370                 375                 380

Leu Gln Ala Gly Val Leu Lys Gly Glu Val Lys Asp Val Leu Leu Leu
385                 390                 395                 400

Asp Val Thr Pro Leu Ser Leu Gly Ile Glu Thr Lys Gly Gly Val Met
                405                 410                 415

Thr Arg Leu Ile Glu Arg Asn Thr Thr Ile Pro Thr Lys Arg Ser Glu
            420                 425                 430

Ser Phe Thr Thr Ala Asp Asp Asn Gln Pro Ser Val Gln Ile Gln Val
        435                 440                 445

Tyr Gln Gly Glu Arg Glu Ile Ala Ala His Asn Lys Leu Leu Gly Ser
    450                 455                 460

Phe Glu Leu Thr Gly Ile Pro Pro Ala Pro Arg Gly Ile Pro Gln Ile
465                 470                 475                 480

Glu Val Thr Phe Asp Ile Asp Ala Asn Gly Ile Val His Val Thr Ala
                485                 490                 495

Lys Asp Lys Gly Thr Gly Lys Glu Asn Thr Ile Arg Ile Gln Glu Gly
            500                 505                 510

Ser Gly Leu Ser Lys Glu Asp Ile Asp Arg Met Ile Lys Asp Ala Glu
        515                 520                 525

Ala His Ala Glu Glu Asp Arg Lys Arg Arg Glu Glu Ala Asp Val Arg
    530                 535                 540
```

```
Asn Gln Ala Glu Thr Leu Val Tyr Gln Thr Glu Lys Phe Val Lys Glu
545                 550                 555                 560

Gln Arg Glu Ala Glu Gly Gly Ser Lys Val Pro Glu Asp Thr Leu Asn
                565                 570                 575

Lys Val Asp Ala Ala Val Ala Glu Ala Lys Ala Ala Leu Gly Gly Ser
            580                 585                 590

Asp Ile Ser Ala Ile Lys Ser Ala Met Glu Lys Leu Gly Gln Glu Ser
        595                 600                 605

Gln Ala Leu Gly Gln Ala Ile Tyr Glu Ala Ala Gln Ala Ala Ser Gln
    610                 615                 620

Ala Thr Gly Ala Ala His Pro Gly Gly Glu Pro Gly Gly Ala His Pro
625                 630                 635                 640

Gly Ser Ala Asp Asp Val Val Asp Ala Glu Val Val Asp Asp Gly Arg
                645                 650                 655

Glu Ala Lys Gly Gly Gly Gly Ser Gly Gly Gly Gly Ser Gly Gly Gly
            660                 665                 670

Gly Ser Lys Leu Leu Gly Pro His Val Glu Gly Leu
        675                 680


<210> SEQ ID NO 22
<211> LENGTH: 2052
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(2052)

<400> SEQUENCE: 22

atg gca cat cac cac cat cat cac cat cac cac cac ggt gca ctt gaa       48
Met Ala His His His His His His His His His His Gly Ala Leu Glu
1               5                   10                  15

gtc ctc ttt cag gga ccc ggg tac cag gat cct gta caa gtc gac gcg       96
Val Leu Phe Gln Gly Pro Gly Tyr Gln Asp Pro Val Gln Val Asp Ala
            20                  25                  30

gcc gca aaa ctt ctg gga ccc cac gtg gag ggc ctg ggt ggc ggt ggc      144
Ala Ala Lys Leu Leu Gly Pro His Val Glu Gly Leu Gly Gly Gly Gly
        35                  40                  45

agc ggc ggt ggt ggt tcc gga ggc ggc ggt tct atg gct cgt gcg gtc      192
Ser Gly Gly Gly Gly Ser Gly Gly Gly Gly Ser Met Ala Arg Ala Val
    50                  55                  60

ggg atc gac ctc ggg acc acc aac tcc gtc gtc tcg gtt ctg gaa ggt      240
Gly Ile Asp Leu Gly Thr Thr Asn Ser Val Val Ser Val Leu Glu Gly
65                  70                  75                  80

ggc gac ccg gtc gtc gtc gcc aac tcc gag ggc tcc agg acc acc ccg      288
Gly Asp Pro Val Val Val Ala Asn Ser Glu Gly Ser Arg Thr Thr Pro
                85                  90                  95

tca att gtc gcg ttc gcc cgc aac ggt gag gtg ctg gtc ggc cag ccc      336
Ser Ile Val Ala Phe Ala Arg Asn Gly Glu Val Leu Val Gly Gln Pro
            100                 105                 110

gcc aag aac cag gcg gtg acc aac gtc gat cgc acc gtg cgc tcg gtc      384
Ala Lys Asn Gln Ala Val Thr Asn Val Asp Arg Thr Val Arg Ser Val
        115                 120                 125

aag cga cac atg ggc agc gac tgg tcc ata gag att gac ggc aag aaa      432
Lys Arg His Met Gly Ser Asp Trp Ser Ile Glu Ile Asp Gly Lys Lys
    130                 135                 140

tac acc gcg ccg gag atc agc gcc cgc att ctg atg aag ctg aag cgc      480
Tyr Thr Ala Pro Glu Ile Ser Ala Arg Ile Leu Met Lys Leu Lys Arg
```

-continued

```
145                 150                 155                 160

gac gcc gag gcc tac ctc ggt gag gac att acc gac gcg gtt atc acg      528
Asp Ala Glu Ala Tyr Leu Gly Glu Asp Ile Thr Asp Ala Val Ile Thr
            165                 170                 175

acg ccc gcc tac ttc aat gac gcc cag cgt cag gcc acc aag gac gcc      576
Thr Pro Ala Tyr Phe Asn Asp Ala Gln Arg Gln Ala Thr Lys Asp Ala
            180                 185                 190

ggc cag atc gcc ggc ctc aac gtg ctg cgg atc gtc aac gag ccg acc      624
Gly Gln Ile Ala Gly Leu Asn Val Leu Arg Ile Val Asn Glu Pro Thr
        195                 200                 205

gct gca gcg ctg gcc tac ggc ctc gac aag ggc gag aag gag cag cga      672
Ala Ala Ala Leu Ala Tyr Gly Leu Asp Lys Gly Glu Lys Glu Gln Arg
    210                 215                 220

atc ctg gtc ttc gac ttg ggt ggt ggc act ttc gac gtt tcc ctg ctg      720
Ile Leu Val Phe Asp Leu Gly Gly Gly Thr Phe Asp Val Ser Leu Leu
225                 230                 235                 240

gag atc ggc gag ggt gtg gtt gag gtc cgt gcc act tcg ggt gac aac      768
Glu Ile Gly Glu Gly Val Val Glu Val Arg Ala Thr Ser Gly Asp Asn
            245                 250                 255

cac ctc ggc ggc gac gac tgg gac cag cgg gtc gtc gat tgg ctg gtg      816
His Leu Gly Gly Asp Asp Trp Asp Gln Arg Val Val Asp Trp Leu Val
            260                 265                 270

gac aag ttc aag ggc acc agc ggc atc gat ctg acc aag gac aag atg      864
Asp Lys Phe Lys Gly Thr Ser Gly Ile Asp Leu Thr Lys Asp Lys Met
        275                 280                 285

gcg atg cag cgg ctg cgg gaa gcc gcc gag aaa gca aag atc gag ctg      912
Ala Met Gln Arg Leu Arg Glu Ala Ala Glu Lys Ala Lys Ile Glu Leu
    290                 295                 300

agt tcg agt cag tcc acc tcg atc aac ctg ccc tac atc acc gtc gac      960
Ser Ser Ser Gln Ser Thr Ser Ile Asn Leu Pro Tyr Ile Thr Val Asp
305                 310                 315                 320

gcc gac aag aac ccg ttg ttc tta gac gag cag ctg acc cgc gcg gag     1008
Ala Asp Lys Asn Pro Leu Phe Leu Asp Glu Gln Leu Thr Arg Ala Glu
            325                 330                 335

ttc caa cgg atc act cag gac ctg ctg gac cgc act cgc aag ccg ttc     1056
Phe Gln Arg Ile Thr Gln Asp Leu Leu Asp Arg Thr Arg Lys Pro Phe
            340                 345                 350

cag tcg gtg atc gct gac acc ggc att tcg gtg tcg gag atc gat cac     1104
Gln Ser Val Ile Ala Asp Thr Gly Ile Ser Val Ser Glu Ile Asp His
        355                 360                 365

gtt gtg ctc gtg ggt ggt tcg acc cgg atg ccc gcg gtg acc gat ctg     1152
Val Val Leu Val Gly Gly Ser Thr Arg Met Pro Ala Val Thr Asp Leu
    370                 375                 380

gtc aag gaa ctc acc ggc ggc aag gaa ccc aac aag ggc gtc aac ccc     1200
Val Lys Glu Leu Thr Gly Gly Lys Glu Pro Asn Lys Gly Val Asn Pro
385                 390                 395                 400

gat gag gtt gtc gcg gtg gga gcc gct ctg cag gcc ggc gtc ctc aag     1248
Asp Glu Val Val Ala Val Gly Ala Ala Leu Gln Ala Gly Val Leu Lys
            405                 410                 415

ggc gag gtg aaa gac gtt ctg ctg ctt gat gtt acc ccg ctg agc ctg     1296
Gly Glu Val Lys Asp Val Leu Leu Leu Asp Val Thr Pro Leu Ser Leu
            420                 425                 430

ggt atc gag acc aag ggc ggg gtg atg acc agg ctc atc gag cgc aac     1344
Gly Ile Glu Thr Lys Gly Gly Val Met Thr Arg Leu Ile Glu Arg Asn
        435                 440                 445

acc acg atc ccc acc aag cgg tcg gag tct ttc acc acc gcc gac gac     1392
Thr Thr Ile Pro Thr Lys Arg Ser Glu Ser Phe Thr Thr Ala Asp Asp
    450                 455                 460

aac caa ccg tcg gtg cag atc cag gtc tat cag ggg gag cgt gag atc     1440
Asn Gln Pro Ser Val Gln Ile Gln Val Tyr Gln Gly Glu Arg Glu Ile
```

```
465                 470                 475                 480

gcc gcg cac aac aag ttg ctc ggg tcc ttc gag ctg acc ggc atc ccg      1488
Ala Ala His Asn Lys Leu Leu Gly Ser Phe Glu Leu Thr Gly Ile Pro
                485                 490                 495

ccg gcg ccg cgg ggg att ccg cag atc gag gtc act ttc gac atc gac      1536
Pro Ala Pro Arg Gly Ile Pro Gln Ile Glu Val Thr Phe Asp Ile Asp
            500                 505                 510

gcc aac ggc att gtg cac gtc acc gcc aag gac aag ggc acc ggc aag      1584
Ala Asn Gly Ile Val His Val Thr Ala Lys Asp Lys Gly Thr Gly Lys
        515                 520                 525

gag aac acg atc cga atc cag gaa ggc tcg ggc ctg tcc aag gaa gac      1632
Glu Asn Thr Ile Arg Ile Gln Glu Gly Ser Gly Leu Ser Lys Glu Asp
    530                 535                 540

att gac cgc atg atc aag gac gcc gaa gcg cac gcc gag gag gat cgc      1680
Ile Asp Arg Met Ile Lys Asp Ala Glu Ala His Ala Glu Glu Asp Arg
545                 550                 555                 560

aag cgt cgc gag gag gcc gat gtt cgt aat caa gcc gag aca ttg gtc      1728
Lys Arg Arg Glu Glu Ala Asp Val Arg Asn Gln Ala Glu Thr Leu Val
                565                 570                 575

tac cag acg gag aag ttc gtc aaa gaa cag cgt gag gcc gag ggt ggt      1776
Tyr Gln Thr Glu Lys Phe Val Lys Glu Gln Arg Glu Ala Glu Gly Gly
            580                 585                 590

tcg aag gta cct gaa gac acg ctg aac aag gtt gat gcc gcg gtg gcg      1824
Ser Lys Val Pro Glu Asp Thr Leu Asn Lys Val Asp Ala Ala Val Ala
        595                 600                 605

gaa gcg aag gcg gca ctt ggc gga tcg gat att tcg gcc atc aag tcg      1872
Glu Ala Lys Ala Ala Leu Gly Gly Ser Asp Ile Ser Ala Ile Lys Ser
    610                 615                 620

gcg atg gag aag ctg ggc cag gag tcg cag gct ctg ggg caa gcg atc      1920
Ala Met Glu Lys Leu Gly Gln Glu Ser Gln Ala Leu Gly Gln Ala Ile
625                 630                 635                 640

tac gaa gca gct cag gct gcg tca cag gcc act ggc gct gcc cac ccc      1968
Tyr Glu Ala Ala Gln Ala Ala Ser Gln Ala Thr Gly Ala Ala His Pro
                645                 650                 655

ggc ggc gag ccg ggc ggt gcc cac ccc ggc tcg gct gat gac gtt gtg      2016
Gly Gly Glu Pro Gly Gly Ala His Pro Gly Ser Ala Asp Asp Val Val
            660                 665                 670

gac gcg gag gtg gtc gac gac ggc cgg gag gcc aag                      2052
Asp Ala Glu Val Val Asp Asp Gly Arg Glu Ala Lys
        675                 680


<210> SEQ ID NO 23
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ala His His His His His His His His His His Gly Ala Leu Glu
1               5                   10                  15

Val Leu Phe Gln Gly Pro Gly Tyr Gln Asp Pro Val Gln Val Asp Ala
            20                  25                  30

Ala Ala Lys Leu Leu Gly Pro His Val Glu Gly Leu Gly Gly Gly Gly
        35                  40                  45

Ser Gly Gly Gly Gly Ser Gly Gly Gly Gly Ser Met Ala Arg Ala Val
    50                  55                  60

Gly Ile Asp Leu Gly Thr Thr Asn Ser Val Val Ser Val Leu Glu Gly
65                  70                  75                  80
```

-continued

```
Gly Asp Pro Val Val Val Ala Asn Ser Glu Gly Ser Arg Thr Thr Pro
                85                  90                  95

Ser Ile Val Ala Phe Ala Arg Asn Gly Glu Val Leu Val Gly Gln Pro
            100                 105                 110

Ala Lys Asn Gln Ala Val Thr Asn Val Asp Arg Thr Val Arg Ser Val
        115                 120                 125

Lys Arg His Met Gly Ser Asp Trp Ser Ile Glu Ile Asp Gly Lys Lys
    130                 135                 140

Tyr Thr Ala Pro Glu Ile Ser Ala Arg Ile Leu Met Lys Leu Lys Arg
145                 150                 155                 160

Asp Ala Glu Ala Tyr Leu Gly Glu Asp Ile Thr Asp Ala Val Ile Thr
                165                 170                 175

Thr Pro Ala Tyr Phe Asn Asp Ala Gln Arg Gln Ala Thr Lys Asp Ala
            180                 185                 190

Gly Gln Ile Ala Gly Leu Asn Val Leu Arg Ile Val Asn Glu Pro Thr
        195                 200                 205

Ala Ala Ala Leu Ala Tyr Gly Leu Asp Lys Gly Glu Lys Glu Gln Arg
    210                 215                 220

Ile Leu Val Phe Asp Leu Gly Gly Gly Thr Phe Asp Val Ser Leu Leu
225                 230                 235                 240

Glu Ile Gly Glu Gly Val Val Glu Val Arg Ala Thr Ser Gly Asp Asn
                245                 250                 255

His Leu Gly Gly Asp Asp Trp Asp Gln Arg Val Val Asp Trp Leu Val
            260                 265                 270

Asp Lys Phe Lys Gly Thr Ser Gly Ile Asp Leu Thr Lys Asp Lys Met
        275                 280                 285

Ala Met Gln Arg Leu Arg Glu Ala Ala Glu Lys Ala Lys Ile Glu Leu
    290                 295                 300

Ser Ser Ser Gln Ser Thr Ser Ile Asn Leu Pro Tyr Ile Thr Val Asp
305                 310                 315                 320

Ala Asp Lys Asn Pro Leu Phe Leu Asp Glu Gln Leu Thr Arg Ala Glu
                325                 330                 335

Phe Gln Arg Ile Thr Gln Asp Leu Leu Asp Arg Thr Arg Lys Pro Phe
            340                 345                 350

Gln Ser Val Ile Ala Asp Thr Gly Ile Ser Val Ser Glu Ile Asp His
        355                 360                 365

Val Val Leu Val Gly Gly Ser Thr Arg Met Pro Ala Val Thr Asp Leu
    370                 375                 380

Val Lys Glu Leu Thr Gly Gly Lys Glu Pro Asn Lys Gly Val Asn Pro
385                 390                 395                 400

Asp Glu Val Val Ala Val Gly Ala Ala Leu Gln Ala Gly Val Leu Lys
                405                 410                 415

Gly Glu Val Lys Asp Val Leu Leu Leu Asp Val Thr Pro Leu Ser Leu
            420                 425                 430

Gly Ile Glu Thr Lys Gly Gly Val Met Thr Arg Leu Ile Glu Arg Asn
        435                 440                 445

Thr Thr Ile Pro Thr Lys Arg Ser Glu Ser Phe Thr Thr Ala Asp Asp
    450                 455                 460

Asn Gln Pro Ser Val Gln Ile Gln Val Tyr Gln Gly Glu Arg Glu Ile
465                 470                 475                 480

Ala Ala His Asn Lys Leu Leu Gly Ser Phe Glu Leu Thr Gly Ile Pro
                485                 490                 495

Pro Ala Pro Arg Gly Ile Pro Gln Ile Glu Val Thr Phe Asp Ile Asp
            500                 505                 510
```

Ala Asn Gly Ile Val His Val Thr Ala Lys Asp Lys Gly Thr Gly Lys
515 520 525

Glu Asn Thr Ile Arg Ile Gln Glu Gly Ser Gly Leu Ser Lys Glu Asp
530 535 540

Ile Asp Arg Met Ile Lys Asp Ala Glu Ala His Ala Glu Glu Asp Arg
545 550 555 560

Lys Arg Arg Glu Glu Ala Asp Val Arg Asn Gln Ala Glu Thr Leu Val
565 570 575

Tyr Gln Thr Glu Lys Phe Val Lys Glu Gln Arg Glu Ala Glu Gly Gly
580 585 590

Ser Lys Val Pro Glu Asp Thr Leu Asn Lys Val Asp Ala Ala Val Ala
595 600 605

Glu Ala Lys Ala Ala Leu Gly Gly Ser Asp Ile Ser Ala Ile Lys Ser
610 615 620

Ala Met Glu Lys Leu Gly Gln Glu Ser Gln Ala Leu Gly Gln Ala Ile
625 630 635 640

Tyr Glu Ala Ala Gln Ala Ala Ser Gln Ala Thr Gly Ala Ala His Pro
645 650 655

Gly Gly Glu Pro Gly Gly Ala His Pro Gly Ser Ala Asp Asp Val Val
660 665 670

Asp Ala Glu Val Val Asp Asp Gly Arg Glu Ala Lys
675 680

<210> SEQ ID NO 24
<211> LENGTH: 2100
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(2100)

<400> SEQUENCE: 24 atg gca cat cac cac cat cat cac cat cac cac cac ggt gca ctt gaa 48
Met Ala His His His His His His His His His His Gly Ala Leu Glu
1 5 10 15 gtc ctc ttt cag gga ccc ggg tac cag gat cct gta caa gtc gac gcg 96
Val Leu Phe Gln Gly Pro Gly Tyr Gln Asp Pro Val Gln Val Asp Ala
20 25 30 gcc gca atg gcc aaa gcc gcg gcg atc ggc atc gac ctg ggc acc acc 144
Ala Ala Met Ala Lys Ala Ala Ala Ile Gly Ile Asp Leu Gly Thr Thr
35 40 45 tac tcc tgc gtg ggg gtg ttc caa cac ggc aag gtg gag atc atc gcc 192
Tyr Ser Cys Val Gly Val Phe Gln His Gly Lys Val Glu Ile Ile Ala
50 55 60 aac gac cag ggc aac cgc acc acc ccc agc tac gtg gcc ttc acg gac 240
Asn Asp Gln Gly Asn Arg Thr Thr Pro Ser Tyr Val Ala Phe Thr Asp
65 70 75 80 acc gag cgg ctc atc ggg gat gcg gcc aag aac cag gtg gcg ctg aac 288
Thr Glu Arg Leu Ile Gly Asp Ala Ala Lys Asn Gln Val Ala Leu Asn
85 90 95 ccg cag aac acc gtg ttt gac gcg aag cgg ctg atc ggc cgc aag ttc 336
Pro Gln Asn Thr Val Phe Asp Ala Lys Arg Leu Ile Gly Arg Lys Phe
100 105 110 ggc gac ccg gtg gtg cag tcg gac atg aag cac tgg cct ttc cag gtg 384
Gly Asp Pro Val Val Gln Ser Asp Met Lys His Trp Pro Phe Gln Val
115 120 125

-continued

```
atc aac gac gga gac aag ccc aag gtg cag gtg agc tac aag ggg gac      432
Ile Asn Asp Gly Asp Lys Pro Lys Val Gln Val Ser Tyr Lys Gly Asp
    130                 135                 140

acc aag gca ttc tac ccc gag gag atc tcg tcc atg gtg ctg acc aag      480
Thr Lys Ala Phe Tyr Pro Glu Glu Ile Ser Ser Met Val Leu Thr Lys
145                 150                 155                 160

atg aag gag atc gcc gag gcg tac ctg ggc tac ccg gtg acc aac gcg      528
Met Lys Glu Ile Ala Glu Ala Tyr Leu Gly Tyr Pro Val Thr Asn Ala
                165                 170                 175

gtg atc acc gtg ccg gcc tac ttc aac gac tcg cag cgc cag gcc acc      576
Val Ile Thr Val Pro Ala Tyr Phe Asn Asp Ser Gln Arg Gln Ala Thr
            180                 185                 190

aag gat gcg ggt gtg atc gcg ggg ctc aac gtg ctg cgg atc atc aac      624
Lys Asp Ala Gly Val Ile Ala Gly Leu Asn Val Leu Arg Ile Ile Asn
        195                 200                 205

gag ccc acg gcc gcc gcc atc gcc tac ggc ctg gac aga acg ggc aag      672
Glu Pro Thr Ala Ala Ala Ile Ala Tyr Gly Leu Asp Arg Thr Gly Lys
    210                 215                 220

ggg gag cgc aac gtg ctc atc ttt gac ctg ggc ggg ggc acc ttc gac      720
Gly Glu Arg Asn Val Leu Ile Phe Asp Leu Gly Gly Gly Thr Phe Asp
225                 230                 235                 240

gtg tcc atc ctg acg atc gac gac ggc atc ttc gag gtg aag gcc acg      768
Val Ser Ile Leu Thr Ile Asp Asp Gly Ile Phe Glu Val Lys Ala Thr
                245                 250                 255

gcc ggg gac acc cac ctg ggt ggg gag gac ttt gac aac agg ctg gtg      816
Ala Gly Asp Thr His Leu Gly Gly Glu Asp Phe Asp Asn Arg Leu Val
            260                 265                 270

aac cac ttc gtg gag gag ttc aag aga aaa cac aag aag gac atc agc      864
Asn His Phe Val Glu Glu Phe Lys Arg Lys His Lys Lys Asp Ile Ser
        275                 280                 285

cag aac aag cga gcc gtg agg cgg ctg cgc acc gcc tgc gag agg gcc      912
Gln Asn Lys Arg Ala Val Arg Arg Leu Arg Thr Ala Cys Glu Arg Ala
    290                 295                 300

aag agg acc ctg tcg tcc agc acc cag gcc agc ctg gag atc gac tcc      960
Lys Arg Thr Leu Ser Ser Ser Thr Gln Ala Ser Leu Glu Ile Asp Ser
305                 310                 315                 320

ctg ttt gag ggc atc gac ttc tac acg tcc atc acc agg gcg agg ttc     1008
Leu Phe Glu Gly Ile Asp Phe Tyr Thr Ser Ile Thr Arg Ala Arg Phe
                325                 330                 335

gag gag ctg tgc tcc gac ctg ttc cga agc acc ctg gag ccc gtg gag     1056
Glu Glu Leu Cys Ser Asp Leu Phe Arg Ser Thr Leu Glu Pro Val Glu
            340                 345                 350

aag gct ctg cgc gac gcc aag ctg gac aag gcc cag att cac gac ctg     1104
Lys Ala Leu Arg Asp Ala Lys Leu Asp Lys Ala Gln Ile His Asp Leu
        355                 360                 365

gtc ctg gtc ggg ggc tcc acc cgc atc ccc aag gtg cag aag ctg ctg     1152
Val Leu Val Gly Gly Ser Thr Arg Ile Pro Lys Val Gln Lys Leu Leu
    370                 375                 380

cag gac ttc ttc aac ggg cgc gac ctg aac aag agc atc aac ccc gac     1200
Gln Asp Phe Phe Asn Gly Arg Asp Leu Asn Lys Ser Ile Asn Pro Asp
385                 390                 395                 400

gag gct gtg gcc tac ggg gcg gcg gtg cag gcg gcc atc ctg atg ggg     1248
Glu Ala Val Ala Tyr Gly Ala Ala Val Gln Ala Ala Ile Leu Met Gly
                405                 410                 415

gac aag tcc gag aac gtg cag gac ctg ctg ctg ctg gac gtg gct ccc     1296
Asp Lys Ser Glu Asn Val Gln Asp Leu Leu Leu Leu Asp Val Ala Pro
            420                 425                 430

ctg tcg ctg ggg ctg gag acg gcc gga ggc gtg atg act gcc ctg atc     1344
Leu Ser Leu Gly Leu Glu Thr Ala Gly Gly Val Met Thr Ala Leu Ile
        435                 440                 445
```

-continued

```
aag cgc aac tcc acc atc ccc acc aag cag acg cag atc ttc acc acc     1392
Lys Arg Asn Ser Thr Ile Pro Thr Lys Gln Thr Gln Ile Phe Thr Thr
    450                 455                 460

tac tcc gac aac caa ccc ggg gtg ctg atc cag gtg tac gag ggc gag     1440
Tyr Ser Asp Asn Gln Pro Gly Val Leu Ile Gln Val Tyr Glu Gly Glu
465                 470                 475                 480

agg gcc atg acg aaa gac aac aat ctg ttg ggg cgc ttc gag ctg agc     1488
Arg Ala Met Thr Lys Asp Asn Asn Leu Leu Gly Arg Phe Glu Leu Ser
                485                 490                 495

ggc atc cct ccg gcc ccc agg ggc gtg ccc cag atc gag gtg acc ttc     1536
Gly Ile Pro Pro Ala Pro Arg Gly Val Pro Gln Ile Glu Val Thr Phe
            500                 505                 510

gac atc gat gcc aac ggc atc ctg aac gtc acg gcc acg gac aag agc     1584
Asp Ile Asp Ala Asn Gly Ile Leu Asn Val Thr Ala Thr Asp Lys Ser
        515                 520                 525

acc ggc aag gcc aac aag atc acc atc acc aac gac aag ggc cgc ctg     1632
Thr Gly Lys Ala Asn Lys Ile Thr Ile Thr Asn Asp Lys Gly Arg Leu
    530                 535                 540

agc aag gag gag atc gag cgc atg gtg cag gag gcg gag aag tac aaa     1680
Ser Lys Glu Glu Ile Glu Arg Met Val Gln Glu Ala Glu Lys Tyr Lys
545                 550                 555                 560

gcg gag gac gag gtg cag cgc gag agg gtg tca gcc aag aac gcc ctg     1728
Ala Glu Asp Glu Val Gln Arg Glu Arg Val Ser Ala Lys Asn Ala Leu
                565                 570                 575

gag tcc tac gcc ttc aac atg aag agc gcc gtg gag gat gag ggg ctc     1776
Glu Ser Tyr Ala Phe Asn Met Lys Ser Ala Val Glu Asp Glu Gly Leu
            580                 585                 590

aag ggc aag atc agc gag gcc gac aag aag aag gtg ctg gac aag tgt     1824
Lys Gly Lys Ile Ser Glu Ala Asp Lys Lys Lys Val Leu Asp Lys Cys
        595                 600                 605

caa gag gtc atc tcg tgg ctg gac gcc aac acc ttg gcc gag aag gac     1872
Gln Glu Val Ile Ser Trp Leu Asp Ala Asn Thr Leu Ala Glu Lys Asp
    610                 615                 620

gag ttt gag cac aag agg aag gag ctg gag cag gtg tgt aac ccc atc     1920
Glu Phe Glu His Lys Arg Lys Glu Leu Glu Gln Val Cys Asn Pro Ile
625                 630                 635                 640

atc agc gga ctg tac cag ggt gcc ggt ggt ccc ggg cct ggg ggc ttc     1968
Ile Ser Gly Leu Tyr Gln Gly Ala Gly Gly Pro Gly Pro Gly Gly Phe
                645                 650                 655

ggg gct cag ggt ccc aag gga ggg tct ggg tca ggc ccc acc att gag     2016
Gly Ala Gln Gly Pro Lys Gly Gly Ser Gly Ser Gly Pro Thr Ile Glu
            660                 665                 670

gag gta gat ggt ggc ggt ggc agc ggc ggt ggt ggt tcc gga ggc ggc     2064
Glu Val Asp Gly Gly Gly Gly Ser Gly Gly Gly Gly Ser Gly Gly Gly
        675                 680                 685

ggt tct aaa ctt ctg gga ccc cac gtg gag ggc ctg                     2100
Gly Ser Lys Leu Leu Gly Pro His Val Glu Gly Leu
    690                 695                 700


<210> SEQ ID NO 25
<211> LENGTH: 700
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Ala His His His His His His His His His His Gly Ala Leu Glu
1               5                   10                  15

Val Leu Phe Gln Gly Pro Gly Tyr Gln Asp Pro Val Gln Val Asp Ala
            20                  25                  30
```

```
Ala Ala Met Ala Lys Ala Ala Ala Ile Gly Ile Asp Leu Gly Thr Thr
        35                  40                  45

Tyr Ser Cys Val Gly Val Phe Gln His Gly Lys Val Glu Ile Ile Ala
    50                  55                  60

Asn Asp Gln Gly Asn Arg Thr Thr Pro Ser Tyr Val Ala Phe Thr Asp
65                  70                  75                  80

Thr Glu Arg Leu Ile Gly Asp Ala Ala Lys Asn Gln Val Ala Leu Asn
                85                  90                  95

Pro Gln Asn Thr Val Phe Asp Ala Lys Arg Leu Ile Gly Arg Lys Phe
            100                 105                 110

Gly Asp Pro Val Val Gln Ser Asp Met Lys His Trp Pro Phe Gln Val
        115                 120                 125

Ile Asn Asp Gly Asp Lys Pro Lys Val Gln Val Ser Tyr Lys Gly Asp
    130                 135                 140

Thr Lys Ala Phe Tyr Pro Glu Glu Ile Ser Ser Met Val Leu Thr Lys
145                 150                 155                 160

Met Lys Glu Ile Ala Glu Ala Tyr Leu Gly Tyr Pro Val Thr Asn Ala
                165                 170                 175

Val Ile Thr Val Pro Ala Tyr Phe Asn Asp Ser Gln Arg Gln Ala Thr
            180                 185                 190

Lys Asp Ala Gly Val Ile Ala Gly Leu Asn Val Leu Arg Ile Ile Asn
        195                 200                 205

Glu Pro Thr Ala Ala Ala Ile Ala Tyr Gly Leu Asp Arg Thr Gly Lys
    210                 215                 220

Gly Glu Arg Asn Val Leu Ile Phe Asp Leu Gly Gly Gly Thr Phe Asp
225                 230                 235                 240

Val Ser Ile Leu Thr Ile Asp Asp Gly Ile Phe Glu Val Lys Ala Thr
                245                 250                 255

Ala Gly Asp Thr His Leu Gly Gly Glu Asp Phe Asp Asn Arg Leu Val
            260                 265                 270

Asn His Phe Val Glu Glu Phe Lys Arg Lys His Lys Lys Asp Ile Ser
        275                 280                 285

Gln Asn Lys Arg Ala Val Arg Arg Leu Arg Thr Ala Cys Glu Arg Ala
    290                 295                 300

Lys Arg Thr Leu Ser Ser Ser Thr Gln Ala Ser Leu Glu Ile Asp Ser
305                 310                 315                 320

Leu Phe Glu Gly Ile Asp Phe Tyr Thr Ser Ile Thr Arg Ala Arg Phe
                325                 330                 335

Glu Glu Leu Cys Ser Asp Leu Phe Arg Ser Thr Leu Glu Pro Val Glu
            340                 345                 350

Lys Ala Leu Arg Asp Ala Lys Leu Asp Lys Ala Gln Ile His Asp Leu
        355                 360                 365

Val Leu Val Gly Gly Ser Thr Arg Ile Pro Lys Val Gln Lys Leu Leu
    370                 375                 380

Gln Asp Phe Phe Asn Gly Arg Asp Leu Asn Lys Ser Ile Asn Pro Asp
385                 390                 395                 400

Glu Ala Val Ala Tyr Gly Ala Ala Val Gln Ala Ala Ile Leu Met Gly
                405                 410                 415

Asp Lys Ser Glu Asn Val Gln Asp Leu Leu Leu Leu Asp Val Ala Pro
            420                 425                 430

Leu Ser Leu Gly Leu Glu Thr Ala Gly Gly Val Met Thr Ala Leu Ile
        435                 440                 445

Lys Arg Asn Ser Thr Ile Pro Thr Lys Gln Thr Gln Ile Phe Thr Thr
```

```
    450                 455                 460

Tyr Ser Asp Asn Gln Pro Gly Val Leu Ile Gln Val Tyr Glu Gly Glu
465                 470                 475                 480

Arg Ala Met Thr Lys Asp Asn Asn Leu Leu Gly Arg Phe Glu Leu Ser
                485                 490                 495

Gly Ile Pro Pro Ala Pro Arg Gly Val Pro Gln Ile Glu Val Thr Phe
            500                 505                 510

Asp Ile Asp Ala Asn Gly Ile Leu Asn Val Thr Ala Thr Asp Lys Ser
        515                 520                 525

Thr Gly Lys Ala Asn Lys Ile Thr Ile Thr Asn Asp Lys Gly Arg Leu
    530                 535                 540

Ser Lys Glu Glu Ile Glu Arg Met Val Gln Glu Ala Glu Lys Tyr Lys
545                 550                 555                 560

Ala Glu Asp Glu Val Gln Arg Glu Arg Val Ser Ala Lys Asn Ala Leu
                565                 570                 575

Glu Ser Tyr Ala Phe Asn Met Lys Ser Ala Val Glu Asp Glu Gly Leu
            580                 585                 590

Lys Gly Lys Ile Ser Glu Ala Asp Lys Lys Lys Val Leu Asp Lys Cys
        595                 600                 605

Gln Glu Val Ile Ser Trp Leu Asp Ala Asn Thr Leu Ala Glu Lys Asp
    610                 615                 620

Glu Phe Glu His Lys Arg Lys Glu Leu Glu Gln Val Cys Asn Pro Ile
625                 630                 635                 640

Ile Ser Gly Leu Tyr Gln Gly Ala Gly Gly Pro Gly Pro Gly Gly Phe
                645                 650                 655

Gly Ala Gln Gly Pro Lys Gly Gly Ser Gly Ser Gly Pro Thr Ile Glu
            660                 665                 670

Glu Val Asp Gly Gly Gly Gly Ser Gly Gly Gly Gly Ser Gly Gly Gly
        675                 680                 685

Gly Ser Lys Leu Leu Gly Pro His Val Glu Gly Leu
    690                 695                 700
```

<210> SEQ ID NO 26
<211> LENGTH: 2100
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(2100)

<400> SEQUENCE: 26

```
atg gca cat cac cac cat cat cac cat cac cac cac ggt gca ctt gaa       48
Met Ala His His His His His His His His His His Gly Ala Leu Glu
1               5                   10                  15

gtc ctc ttt cag gga ccc ggg tac cag gat cct gta caa gtc gac gcg       96
Val Leu Phe Gln Gly Pro Gly Tyr Gln Asp Pro Val Gln Val Asp Ala
            20                  25                  30

gcc gca aaa ctt ctg gga ccc cac gtg gag ggc ctg ggt ggc ggt ggc      144
Ala Ala Lys Leu Leu Gly Pro His Val Glu Gly Leu Gly Gly Gly Gly
        35                  40                  45

agc ggc ggt ggt ggt tcc gga ggc ggc ggt tct atg gcc aaa gcc gcg      192
Ser Gly Gly Gly Gly Ser Gly Gly Gly Gly Ser Met Ala Lys Ala Ala
    50                  55                  60

gcg atc ggc atc gac ctg ggc acc acc tac tcc tgc gtg ggg gtg ttc      240
Ala Ile Gly Ile Asp Leu Gly Thr Thr Tyr Ser Cys Val Gly Val Phe
65                  70                  75                  80
```

```
caa cac ggc aag gtg gag atc atc gcc aac gac cag ggc aac cgc acc      288
Gln His Gly Lys Val Glu Ile Ile Ala Asn Asp Gln Gly Asn Arg Thr
                85                  90                  95

acc ccc agc tac gtg gcc ttc acg gac acc gag cgg ctc atc ggg gat      336
Thr Pro Ser Tyr Val Ala Phe Thr Asp Thr Glu Arg Leu Ile Gly Asp
            100                 105                 110

gcg gcc aag aac cag gtg gcg ctg aac ccg cag aac acc gtg ttt gac      384
Ala Ala Lys Asn Gln Val Ala Leu Asn Pro Gln Asn Thr Val Phe Asp
        115                 120                 125

gcg aag cgg ctg atc ggc cgc aag ttc ggc gac ccg gtg gtg cag tcg      432
Ala Lys Arg Leu Ile Gly Arg Lys Phe Gly Asp Pro Val Val Gln Ser
    130                 135                 140

gac atg aag cac tgg cct ttc cag gtg atc aac gac gga gac aag ccc      480
Asp Met Lys His Trp Pro Phe Gln Val Ile Asn Asp Gly Asp Lys Pro
145                 150                 155                 160

aag gtg cag gtg agc tac aag ggg gac acc aag gca ttc tac ccc gag      528
Lys Val Gln Val Ser Tyr Lys Gly Asp Thr Lys Ala Phe Tyr Pro Glu
                165                 170                 175

gag atc tcg tcc atg gtg ctg acc aag atg aag gag atc gcc gag gcg      576
Glu Ile Ser Ser Met Val Leu Thr Lys Met Lys Glu Ile Ala Glu Ala
            180                 185                 190

tac ctg ggc tac ccg gtg acc aac gcg gtg atc acc gtg ccg gcc tac      624
Tyr Leu Gly Tyr Pro Val Thr Asn Ala Val Ile Thr Val Pro Ala Tyr
        195                 200                 205

ttc aac gac tcg cag cgc cag gcc acc aag gat gcg ggt gtg atc gcg      672
Phe Asn Asp Ser Gln Arg Gln Ala Thr Lys Asp Ala Gly Val Ile Ala
    210                 215                 220

ggg ctc aac gtg ctg cgg atc atc aac gag ccc acg gcc gcc gcc atc      720
Gly Leu Asn Val Leu Arg Ile Ile Asn Glu Pro Thr Ala Ala Ala Ile
225                 230                 235                 240

gcc tac ggc ctg gac aga acg ggc aag ggg gag cgc aac gtg ctc atc      768
Ala Tyr Gly Leu Asp Arg Thr Gly Lys Gly Glu Arg Asn Val Leu Ile
                245                 250                 255

ttt gac ctg ggc ggg ggc acc ttc gac gtg tcc atc ctg acg atc gac      816
Phe Asp Leu Gly Gly Gly Thr Phe Asp Val Ser Ile Leu Thr Ile Asp
            260                 265                 270

gac ggc atc ttc gag gtg aag gcc acg gcc ggg gac acc cac ctg ggt      864
Asp Gly Ile Phe Glu Val Lys Ala Thr Ala Gly Asp Thr His Leu Gly
        275                 280                 285

ggg gag gac ttt gac aac agg ctg gtg aac cac ttc gtg gag gag ttc      912
Gly Glu Asp Phe Asp Asn Arg Leu Val Asn His Phe Val Glu Glu Phe
    290                 295                 300

aag aga aaa cac aag aag gac atc agc cag aac aag cga gcc gtg agg      960
Lys Arg Lys His Lys Lys Asp Ile Ser Gln Asn Lys Arg Ala Val Arg
305                 310                 315                 320

cgg ctg cgc acc gcc tgc gag agg gcc aag agg acc ctg tcg tcc agc     1008
Arg Leu Arg Thr Ala Cys Glu Arg Ala Lys Arg Thr Leu Ser Ser Ser
                325                 330                 335

acc cag gcc agc ctg gag atc gac tcc ctg ttt gag ggc atc gac ttc     1056
Thr Gln Ala Ser Leu Glu Ile Asp Ser Leu Phe Glu Gly Ile Asp Phe
            340                 345                 350

tac acg tcc atc acc agg gcg agg ttc gag gag ctg tgc tcc gac ctg     1104
Tyr Thr Ser Ile Thr Arg Ala Arg Phe Glu Glu Leu Cys Ser Asp Leu
        355                 360                 365

ttc cga agc acc ctg gag ccc gtg gag aag gct ctg cgc gac gcc aag     1152
Phe Arg Ser Thr Leu Glu Pro Val Glu Lys Ala Leu Arg Asp Ala Lys
    370                 375                 380

ctg gac aag gcc cag att cac gac ctg gtc ctg gtc ggg ggc tcc acc     1200
Leu Asp Lys Ala Gln Ile His Asp Leu Val Leu Val Gly Gly Ser Thr
385                 390                 395                 400
```

```
cgc atc ccc aag gtg cag aag ctg ctg cag gac ttc ttc aac ggg cgc      1248
Arg Ile Pro Lys Val Gln Lys Leu Leu Gln Asp Phe Phe Asn Gly Arg
                405                 410                 415

gac ctg aac aag agc atc aac ccc gac gag gct gtg gcc tac ggg gcg      1296
Asp Leu Asn Lys Ser Ile Asn Pro Asp Glu Ala Val Ala Tyr Gly Ala
            420                 425                 430

gcg gtg cag gcg gcc atc ctg atg ggg gac aag tcc gag aac gtg cag      1344
Ala Val Gln Ala Ala Ile Leu Met Gly Asp Lys Ser Glu Asn Val Gln
        435                 440                 445

gac ctg ctg ctg ctg gac gtg gct ccc ctg tcg ctg ggg ctg gag acg      1392
Asp Leu Leu Leu Leu Asp Val Ala Pro Leu Ser Leu Gly Leu Glu Thr
    450                 455                 460

gcc gga ggc gtg atg act gcc ctg atc aag cgc aac tcc acc atc ccc      1440
Ala Gly Gly Val Met Thr Ala Leu Ile Lys Arg Asn Ser Thr Ile Pro
465                 470                 475                 480

acc aag cag acg cag atc ttc acc acc tac tcc gac aac caa ccc ggg      1488
Thr Lys Gln Thr Gln Ile Phe Thr Thr Tyr Ser Asp Asn Gln Pro Gly
                485                 490                 495

gtg ctg atc cag gtg tac gag ggc gag agg gcc atg acg aaa gac aac      1536
Val Leu Ile Gln Val Tyr Glu Gly Glu Arg Ala Met Thr Lys Asp Asn
            500                 505                 510

aat ctg ttg ggg cgc ttc gag ctg agc ggc atc cct ccg gcc ccc agg      1584
Asn Leu Leu Gly Arg Phe Glu Leu Ser Gly Ile Pro Pro Ala Pro Arg
        515                 520                 525

ggc gtg ccc cag atc gag gtg acc ttc gac atc gat gcc aac ggc atc      1632
Gly Val Pro Gln Ile Glu Val Thr Phe Asp Ile Asp Ala Asn Gly Ile
    530                 535                 540

ctg aac gtc acg gcc acg gac aag agc acc ggc aag gcc aac aag atc      1680
Leu Asn Val Thr Ala Thr Asp Lys Ser Thr Gly Lys Ala Asn Lys Ile
545                 550                 555                 560

acc atc acc aac gac aag ggc cgc ctg agc aag gag gag atc gag cgc      1728
Thr Ile Thr Asn Asp Lys Gly Arg Leu Ser Lys Glu Glu Ile Glu Arg
                565                 570                 575

atg gtg cag gag gcg gag aag tac aaa gcg gag gac gag gtg cag cgc      1776
Met Val Gln Glu Ala Glu Lys Tyr Lys Ala Glu Asp Glu Val Gln Arg
            580                 585                 590

gag agg gtg tca gcc aag aac gcc ctg gag tcc tac gcc ttc aac atg      1824
Glu Arg Val Ser Ala Lys Asn Ala Leu Glu Ser Tyr Ala Phe Asn Met
        595                 600                 605

aag agc gcc gtg gag gat gag ggg ctc aag ggc aag atc agc gag gcc      1872
Lys Ser Ala Val Glu Asp Glu Gly Leu Lys Gly Lys Ile Ser Glu Ala
    610                 615                 620

gac aag aag aag gtg ctg gac aag tgt caa gag gtc atc tcg tgg ctg      1920
Asp Lys Lys Lys Val Leu Asp Lys Cys Gln Glu Val Ile Ser Trp Leu
625                 630                 635                 640

gac gcc aac acc ttg gcc gag aag gac gag ttt gag cac aag agg aag      1968
Asp Ala Asn Thr Leu Ala Glu Lys Asp Glu Phe Glu His Lys Arg Lys
                645                 650                 655

gag ctg gag cag gtg tgt aac ccc atc atc agc gga ctg tac cag ggt      2016
Glu Leu Glu Gln Val Cys Asn Pro Ile Ile Ser Gly Leu Tyr Gln Gly
            660                 665                 670

gcc ggt ggt ccc ggg cct ggg ggc ttc ggg gct cag ggt ccc aag gga      2064
Ala Gly Gly Pro Gly Pro Gly Gly Phe Gly Ala Gln Gly Pro Lys Gly
        675                 680                 685

ggg tct ggg tca ggc ccc acc att gag gag gta gat                      2100
Gly Ser Gly Ser Gly Pro Thr Ile Glu Glu Val Asp
    690                 695                 700
```

<210> SEQ ID NO 27
<211> LENGTH: 700

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 27

```
Met Ala His His His His His His His His His His Gly Ala Leu Glu
1               5                   10                  15

Val Leu Phe Gln Gly Pro Gly Tyr Gln Asp Pro Val Gln Val Asp Ala
            20                  25                  30

Ala Ala Lys Leu Leu Gly Pro His Val Glu Gly Leu Gly Gly Gly Gly
        35                  40                  45

Ser Gly Gly Gly Gly Ser Gly Gly Gly Gly Ser Met Ala Lys Ala Ala
    50                  55                  60

Ala Ile Gly Ile Asp Leu Gly Thr Thr Tyr Ser Cys Val Gly Val Phe
65                  70                  75                  80

Gln His Gly Lys Val Glu Ile Ile Ala Asn Asp Gln Gly Asn Arg Thr
                85                  90                  95

Thr Pro Ser Tyr Val Ala Phe Thr Asp Thr Glu Arg Leu Ile Gly Asp
            100                 105                 110

Ala Ala Lys Asn Gln Val Ala Leu Asn Pro Gln Asn Thr Val Phe Asp
        115                 120                 125

Ala Lys Arg Leu Ile Gly Arg Lys Phe Gly Asp Pro Val Val Gln Ser
    130                 135                 140

Asp Met Lys His Trp Pro Phe Gln Val Ile Asn Asp Gly Asp Lys Pro
145                 150                 155                 160

Lys Val Gln Val Ser Tyr Lys Gly Asp Thr Lys Ala Phe Tyr Pro Glu
                165                 170                 175

Glu Ile Ser Ser Met Val Leu Thr Lys Met Lys Glu Ile Ala Glu Ala
            180                 185                 190

Tyr Leu Gly Tyr Pro Val Thr Asn Ala Val Ile Thr Val Pro Ala Tyr
        195                 200                 205

Phe Asn Asp Ser Gln Arg Gln Ala Thr Lys Asp Ala Gly Val Ile Ala
    210                 215                 220

Gly Leu Asn Val Leu Arg Ile Ile Asn Glu Pro Thr Ala Ala Ala Ile
225                 230                 235                 240

Ala Tyr Gly Leu Asp Arg Thr Gly Lys Gly Glu Arg Asn Val Leu Ile
                245                 250                 255

Phe Asp Leu Gly Gly Gly Thr Phe Asp Val Ser Ile Leu Thr Ile Asp
            260                 265                 270

Asp Gly Ile Phe Glu Val Lys Ala Thr Ala Gly Asp Thr His Leu Gly
        275                 280                 285

Gly Glu Asp Phe Asp Asn Arg Leu Val Asn His Phe Val Glu Glu Phe
    290                 295                 300

Lys Arg Lys His Lys Lys Asp Ile Ser Gln Asn Lys Arg Ala Val Arg
305                 310                 315                 320

Arg Leu Arg Thr Ala Cys Glu Arg Ala Lys Arg Thr Leu Ser Ser Ser
                325                 330                 335

Thr Gln Ala Ser Leu Glu Ile Asp Ser Leu Phe Glu Gly Ile Asp Phe
            340                 345                 350

Tyr Thr Ser Ile Thr Arg Ala Arg Phe Glu Glu Leu Cys Ser Asp Leu
        355                 360                 365

Phe Arg Ser Thr Leu Glu Pro Val Glu Lys Ala Leu Arg Asp Ala Lys
    370                 375                 380
```

Leu Asp Lys Ala Gln Ile His Asp Leu Val Leu Val Gly Gly Ser Thr
385 390 395 400

Arg Ile Pro Lys Val Gln Lys Leu Leu Gln Asp Phe Phe Asn Gly Arg
405 410 415

Asp Leu Asn Lys Ser Ile Asn Pro Asp Glu Ala Val Ala Tyr Gly Ala
420 425 430

Ala Val Gln Ala Ala Ile Leu Met Gly Asp Lys Ser Glu Asn Val Gln
435 440 445

Asp Leu Leu Leu Leu Asp Val Ala Pro Leu Ser Leu Gly Leu Glu Thr
450 455 460

Ala Gly Gly Val Met Thr Ala Leu Ile Lys Arg Asn Ser Thr Ile Pro
465 470 475 480

Thr Lys Gln Thr Gln Ile Phe Thr Thr Tyr Ser Asp Asn Gln Pro Gly
485 490 495

Val Leu Ile Gln Val Tyr Glu Gly Glu Arg Ala Met Thr Lys Asp Asn
500 505 510

Asn Leu Leu Gly Arg Phe Glu Leu Ser Gly Ile Pro Pro Ala Pro Arg
515 520 525

Gly Val Pro Gln Ile Glu Val Thr Phe Asp Ile Asp Ala Asn Gly Ile
530 535 540

Leu Asn Val Thr Ala Thr Asp Lys Ser Thr Gly Lys Ala Asn Lys Ile
545 550 555 560

Thr Ile Thr Asn Asp Lys Gly Arg Leu Ser Lys Glu Glu Ile Glu Arg
565 570 575

Met Val Gln Glu Ala Glu Lys Tyr Lys Ala Glu Asp Glu Val Gln Arg
580 585 590

Glu Arg Val Ser Ala Lys Asn Ala Leu Glu Ser Tyr Ala Phe Asn Met
595 600 605

Lys Ser Ala Val Glu Asp Glu Gly Leu Lys Gly Lys Ile Ser Glu Ala
610 615 620

Asp Lys Lys Lys Val Leu Asp Lys Cys Gln Glu Val Ile Ser Trp Leu
625 630 635 640

Asp Ala Asn Thr Leu Ala Glu Lys Asp Glu Phe Glu His Lys Arg Lys
645 650 655

Glu Leu Glu Gln Val Cys Asn Pro Ile Ile Ser Gly Leu Tyr Gln Gly
660 665 670

Ala Gly Gly Pro Gly Pro Gly Gly Phe Gly Ala Gln Gly Pro Lys Gly
675 680 685

Gly Ser Gly Ser Gly Pro Thr Ile Glu Glu Val Asp
690 695 700

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 28

His His His His His His
1 5

<210> SEQ ID NO 29
<211> LENGTH: 625
<212> TYPE: PRT
<213> ORGANISM: Mycobacterium tuberculosis -continued

<400> SEQUENCE: 29

```
Met Ala Arg Ala Val Gly Ile Asp Leu Gly Thr Thr Asn Ser Val Val
1               5                   10                  15

Ser Val Leu Glu Gly Gly Asp Pro Val Val Val Ala Asn Ser Glu Gly
            20                  25                  30

Ser Arg Thr Thr Pro Ser Ile Val Ala Phe Ala Arg Asn Gly Glu Val
        35                  40                  45

Leu Val Gly Gln Pro Ala Lys Asn Gln Ala Val Thr Asn Val Asp Arg
    50                  55                  60

Thr Val Arg Ser Val Lys Arg His Met Gly Ser Asp Trp Ser Ile Glu
65                  70                  75                  80

Ile Asp Gly Lys Lys Tyr Thr Ala Pro Glu Ile Ser Ala Arg Ile Leu
                85                  90                  95

Met Lys Leu Lys Arg Asp Ala Glu Ala Tyr Leu Gly Glu Asp Ile Thr
            100                 105                 110

Asp Ala Val Ile Thr Thr Pro Ala Tyr Phe Asn Asp Ala Gln Arg Gln
        115                 120                 125

Ala Thr Lys Asp Ala Gly Gln Ile Ala Gly Leu Asn Val Leu Arg Ile
    130                 135                 140

Val Asn Glu Pro Thr Ala Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
        195                 200                 205

Val Asp Trp Leu Val Asp Lys Phe Lys Gly Thr Ser Gly Ile Asp Leu
    210                 215                 220

Thr Lys Asp Lys Met Ala Met Gln Arg Leu Arg Glu Ala Ala Glu Lys
225                 230                 235                 240

Ala Lys Ile Glu Leu Ser Ser Ser Gln Ser Thr Ser Ile Asn Leu Pro
                245                 250                 255

Tyr Ile Thr Val Asp Ala Asp Lys Asn Pro Leu Phe Leu Asp Glu Gln
            260                 265                 270

Leu Thr Arg Ala Glu Phe Gln Arg Ile Thr Gln Asp Leu Leu Asp Arg
        275                 280                 285

Thr Arg Lys Pro Phe Gln Ser Val Ile Ala Asp Thr Gly Ile Ser Val
    290                 295                 300

Ser Glu Ile Asp His Val Val Leu Val Gly Gly Ser Thr Arg Met Pro
305                 310                 315                 320

Ala Val Thr Asp Leu Val Lys Glu Leu Thr Gly Gly Lys Glu Pro Asn
                325                 330                 335

Lys Gly Val Asn Pro Asp Glu Val Val Ala Val Gly Ala Ala Leu Gln
            340                 345                 350

Ala Gly Val Leu Lys Gly Glu Val Lys Asp Val Leu Leu Leu Asp Val
        355                 360                 365

Thr Pro Leu Ser Leu Gly Ile Glu Thr Lys Gly Gly Val Met Thr Arg
    370                 375                 380

Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
                405                 410                 415
```

```
Gly Glu Arg Glu Ile Ala Ala His Asn Lys Leu Leu Gly Ser Phe Glu
            420                 425                 430

Leu Thr Gly Ile Pro Pro Ala Pro Arg Gly Ile Pro Gln Ile Glu Val
        435                 440                 445

Thr Phe Asp Ile Asp Ala Asn Gly Ile Val His Val Thr Ala Lys Asp
    450                 455                 460

Lys Gly Thr Gly Lys Glu Asn Thr Ile Arg Ile Gln Glu Gly Ser Gly
465                 470                 475                 480

Leu Ser Lys Glu Asp Ile Asp Arg Met Ile Lys Asp Ala Glu Ala His
                485                 490                 495

Ala Glu Glu Asp Arg Lys Arg Arg Glu Glu Ala Asp Val Arg Asn Gln
            500                 505                 510

Ala Glu Thr Leu Val Tyr Gln Thr Glu Lys Phe Val Lys Glu Gln Arg
        515                 520                 525

Glu Ala Glu Gly Gly Ser Lys Val Pro Glu Asp Thr Leu Asn Lys Val
    530                 535                 540

Asp Ala Ala Val Ala Glu Ala Lys Ala Ala Leu Gly Gly Ser Asp Ile
545                 550                 555                 560

Ser Ala Ile Lys Ser Ala Met Glu Lys Leu Gly Gln Glu Ser Gln Ala
                565                 570                 575

Leu Gly Gln Ala Ile Tyr Glu Ala Ala Gln Ala Ala Ser Gln Ala Thr
            580                 585                 590

Gly Ala Ala His Pro Gly Gly Glu Pro Gly Gly Ala His Pro Gly Ser
        595                 600                 605

Ala Asp Asp Val Val Asp Ala Glu Val Val Asp Asp Gly Arg Glu Ala
    610                 615                 620

Lys
625
```

<210> SEQ ID NO 30
<211> LENGTH: 625
<212> TYPE: PRT
<213> ORGANISM: Mycobacterium bovus

<400> SEQUENCE: 30

```
Met Ala Arg Ala Val Gly Ile Asp Leu Gly Thr Thr Asn Ser Val Val
1               5                   10                  15

Ser Val Leu Glu Gly Gly Asp Pro Val Val Val Ala Asn Ser Glu Gly
            20                  25                  30

Ser Arg Thr Thr Pro Ser Ile Val Ala Phe Ala Arg Asn Gly Glu Val
        35                  40                  45

Leu Val Gly Gln Pro Ala Lys Asn Gln Ala Val Thr Asn Val Asp Arg
    50                  55                  60

Thr Val Arg Ser Val Lys Arg His Met Gly Ser Asp Trp Ser Ile Glu
65                  70                  75                  80

Ile Asp Gly Lys Lys Tyr Thr Ala Pro Glu Ile Ser Ala Arg Ile Leu
                85                  90                  95

Met Lys Leu Lys Arg Asp Ala Glu Ala Tyr Leu Gly Glu Asp Ile Thr
            100                 105                 110

Asp Ala Val Ile Thr Thr Pro Ala Tyr Phe Asn Asp Ala Gln Arg Gln
        115                 120                 125

Ala Thr Lys Asp Ala Gly Gln Ile Ala Gly Leu Asn Val Leu Arg Ile
    130                 135                 140

Val Asn Glu Pro Thr Ala Ala Ala Leu Ala Tyr Gly Leu Asp Lys Gly
145                 150                 155                 160
```

-continued

```
Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
        195                 200                 205

Val Asp Trp Leu Val Asp Lys Phe Lys Gly Thr Ser Gly Ile Asp Leu
    210                 215                 220

Thr Lys Asp Lys Met Ala Met Gln Arg Leu Arg Glu Ala Ala Glu Lys
225                 230                 235                 240

Ala Lys Ile Glu Leu Ser Ser Ser Gln Ser Thr Ser Ile Asn Leu Pro
                245                 250                 255

Tyr Ile Thr Val Asp Ala Asp Lys Asn Pro Leu Phe Leu Asp Glu Gln
            260                 265                 270

Leu Thr Arg Ala Glu Phe Gln Arg Ile Thr Gln Asp Leu Leu Asp Arg
        275                 280                 285

Thr Arg Lys Pro Phe Gln Ser Val Ile Ala Asp Thr Gly Ile Ser Val
    290                 295                 300

Ser Glu Ile Asp His Val Val Leu Val Gly Gly Ser Thr Arg Met Pro
305                 310                 315                 320

Ala Val Thr Asp Leu Val Lys Glu Leu Thr Gly Gly Lys Glu Pro Asn
                325                 330                 335

Lys Gly Val Asn Pro Asp Glu Val Val Ala Val Gly Ala Ala Leu Gln
            340                 345                 350

Ala Gly Val Leu Lys Gly Glu Val Lys Asp Val Leu Leu Leu Asp Val
        355                 360                 365

Thr Pro Leu Ser Leu Gly Ile Glu Thr Lys Gly Gly Val Met Thr Arg
    370                 375                 380

Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
                405                 410                 415

Gly Glu Arg Glu Ile Ala Ala His Asn Lys Leu Leu Gly Ser Phe Glu
            420                 425                 430

Leu Thr Gly Ile Pro Pro Ala Pro Arg Gly Ile Pro Gln Ile Glu Val
        435                 440                 445

Thr Phe Asp Ile Asp Ala Asn Gly Ile Val His Val Thr Ala Lys Asp
    450                 455                 460

Lys Gly Thr Gly Lys Glu Asn Thr Ile Arg Ile Gln Glu Gly Ser Gly
465                 470                 475                 480

Leu Ser Lys Glu Asp Ile Asp Arg Met Ile Lys Asp Ala Glu Ala His
                485                 490                 495

Ala Glu Glu Asp Arg Lys Arg Arg Glu Glu Ala Asp Val Arg Asn Gln
            500                 505                 510

Ala Glu Thr Leu Val Tyr Gln Thr Glu Lys Phe Val Lys Glu Gln Arg
        515                 520                 525

Glu Ala Glu Gly Gly Ser Lys Val Pro Glu Asp Thr Leu Asn Lys Val
    530                 535                 540

Asp Ala Ala Val Ala Glu Ala Lys Ala Ala Leu Gly Gly Ser Asp Ile
545                 550                 555                 560

Ser Ala Ile Lys Ser Ala Met Glu Lys Leu Gly Gln Glu Ser Gln Ala
                565                 570                 575

Leu Gly Gln Ala Ile Tyr Glu Ala Ala Gln Ala Ala Ser Gln Ala Thr
            580                 585                 590
```

-continued

```
Gly Ala Ala His Pro Gly Gly Glu Pro Gly Gly Ala His Pro Gly Ser
        595                 600                 605

Ala Asp Asp Val Val Asp Ala Glu Val Val Asp Asp Gly Arg Glu Ala
    610                 615                 620

Lys
625
```

MESOTHELIN ANTIBODY PROTEIN FUSIONS AND METHODS OF USE

RELATED APPLICATIONS/PATENTS & INCORPORATION BY REFERENCE

This application is a continuation of U.S. application Ser. No. 12/291,104, filed on Nov. 6, 2008, issued as U.S. Pat. No. 7,943,133 on May 17, 2011. The entire teachings of the above application is incorporated herein by reference.

BACKGROUND OF THE INVENTION

Mesothelin is a differentiation antigen whose expression in normal human tissues is limited to mesothelial cells lining the pleura, pericardium and peritoneum. However, mesothelin is highly expressed in several human cancers, including mesotheliomas, pancreatic adenocarcinomas, ovarian cancers and lung adenocarcinomas. Mesothelin is an appropriate target for methods of disease prevention or treatment and antibodies specific for mesothelin, and vaccines comprising mesothelin are useful for prophylactic and therapeutic methods.

Classical monoclonal antibodies are currently produced in mammalian cells. Drawbacks of this method of production include the difficulty of producing and selecting appropriate clones, and the expense of culturing mammalian cells. The "next generation" of monoclonal antibodies are being engineered in *E. coli*. Recently, microbial expression of $V_H$ and $V_L$ domains tethered together by polypeptide linkers has created the capability of generating engineered "mini-antibodies." These mini-bodies can be generated in *E. coli* in a virtually combinatorial fashion. These artificially created Fab or single chain Fv (scFv) can be linked together to form multimers, e.g., diabodies, triabodies and tetrabodies. Although they are capable of binding to antigens with almost antibody-like efficiency, these engineered, Fc deficient mini-antibodies lack the ability to interact with antigen presenting cells and are poorly immunogenic. Existing solutions to the lack of immunogenicity of engineered antibodies involve directing one of the antigen binding sites to bind directly with immune cells. This brings them in apposition, but does not result in the same MHC class I priming as would be observed for a monoclonal antibody.

Immunization with vaccines remains a cornerstone of protection against threat of disease and infection. The key difficulty in vaccine development is rapidly matching a vaccine, or antitoxin, to a specific threat. Current vaccine development strategies rely on the identification and characterization of antigens that can be targeted to successfully eradicate infection or disease. Current vaccine development strategies are time- and labor-intensive and can only commence once a threat emerges. Such strategies are also impractical for generating personalized vaccines to combat disease for which target antigens varies among individuals. Current vaccine development strategies are therefore insufficient if a new and serious threat were to emerge, for which sufficient time were not available to identify and characterize target antigens before such a threat could be contained. Current vaccine development strategies are also insufficient for generating personalized vaccines for the general population.

BRIEF DESCRIPTION OF THE DRAWINGS

FIG. 2 presents the nucleic (SEQ ID NO: 12) and amino acid (SEQ ID NO: 13) sequence of an MTBHSP70 (C) Hinge anti-mesothelin scFv fusion protein.

FIG. 4 presents the nucleic (SEQ ID NO: 14) and amino acid (SEQ ID NO: 15) sequence of an MTBHSP70 (N) hinge anti-mesothelin scFv fusion protein.

FIG. 6 presents the nucleic (SEQ ID NO: 16) and amino acid (SEQ ID NO: 17) sequence of HuHSP70(C) hinge anti-mesothelin scFv.

FIG. 8 presents the nucleic (SEQ ID NO: 18) and amino acid (SEQ ID NO: 19) sequence of HuHSP70 (N) hinge anti-mesothelin scFv.

FIG. 10 presents the nucleic (SEQ ID NO: 20) and amino acid (SEQ ID NO: 21) sequence of MTBHSP70 (C) linker mesothelin peptide fusion protein.

FIG. 12 presents the nucleic (SEQ ID NO: 22) and amino acid (SEQ ID NO: 23) sequence of MTBHSP70 (N) linker mesothelin peptide.

FIG. 14 presents the nucleic (SEQ ID NO: 24) and amino acid (SEQ ID NO: 25) sequence of HuHSP70 (C) linker mesothelin peptide fusion protein.

FIG. 16 presents the nucleic (SEQ ID NO: 26) and amino acid (SEQ ID NO: 27) sequence of HuHSP70 (N) linker mesothelin peptide.

FIG. 17 A-E presents fusion proteins according to the invention.

FIG. 19 B presents a diagram of an hsp70-avidin protein.

FIGS. 20A and B depict the full-length polypeptide sequences of HSP70 from *Mycobacterium tuberculosis* (SEQ ID NO: 29) HSP70 and *Mycobacterium bovis* (SEQ ID NO: 30) HSP70, respectively.

SUMMARY OF THE INVENTION

Figure 1:
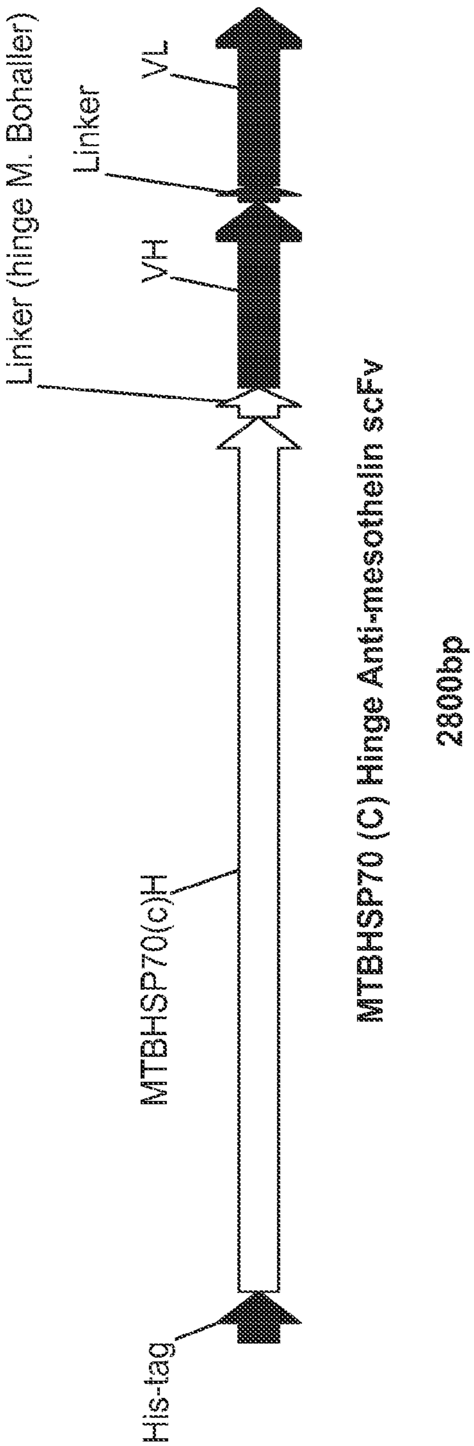
FIG. 1 presents a diagram of an MTBHSP70(C) Hinge Anti-mesothelin scFv fusion protein.
Figure 3:
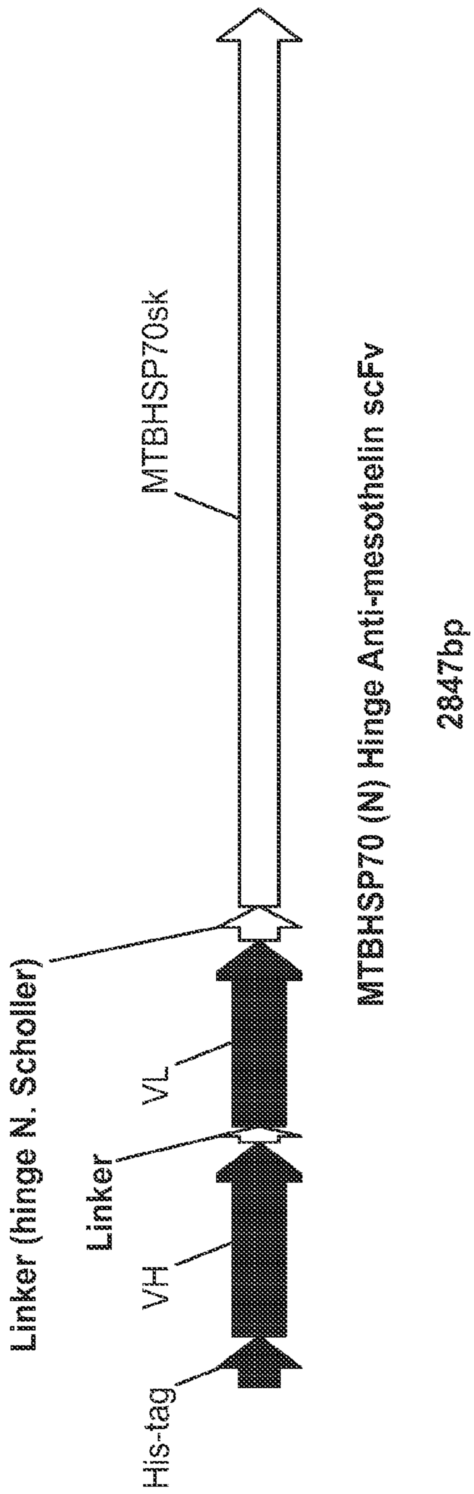
FIG. 3 presents a diagram of an MTBHSP70(N) Hinge Anti-mesothelin scFv fusion protein.
Figure 5:
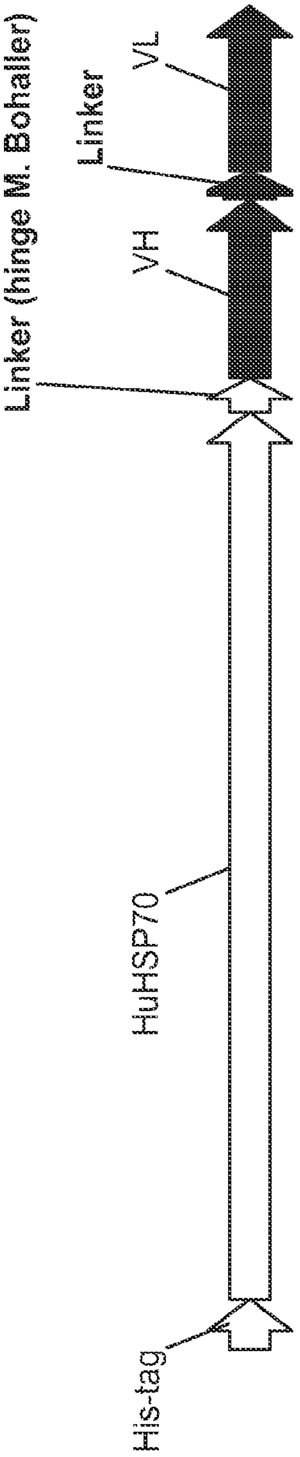
FIG. 5 presents a diagram of an HuHSP70(C) Hinge Anti-mesothelin scFv fusion protein.
Figure 7:
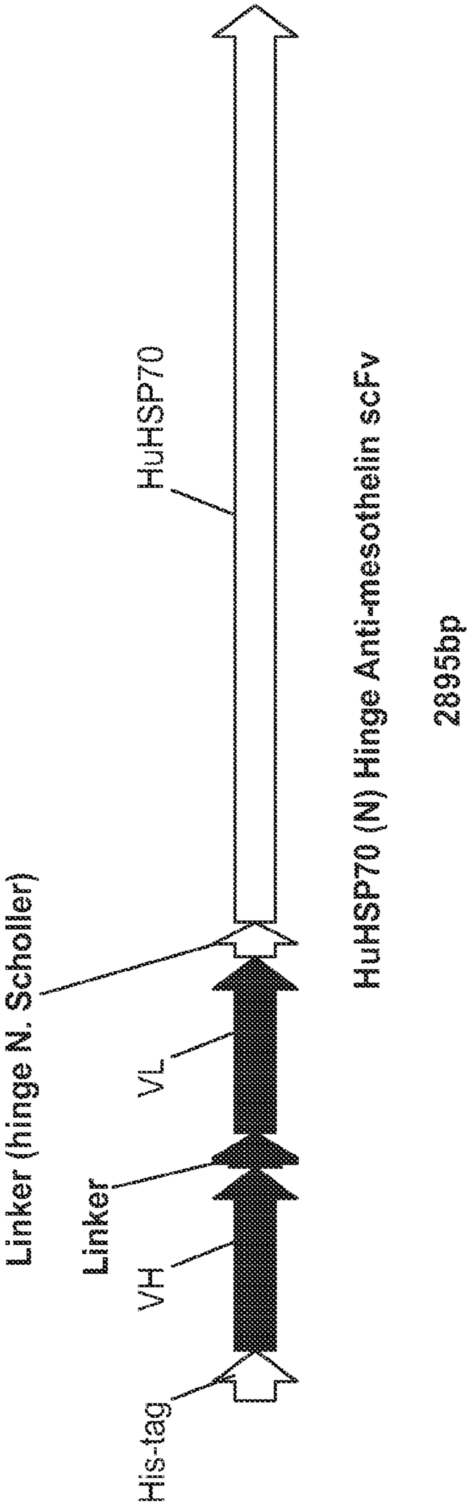
FIG. 7 presents the diagram of an HuHSP70 (N) Hinge Anti-mesothelin scFv fusion protein.
Figure 9:
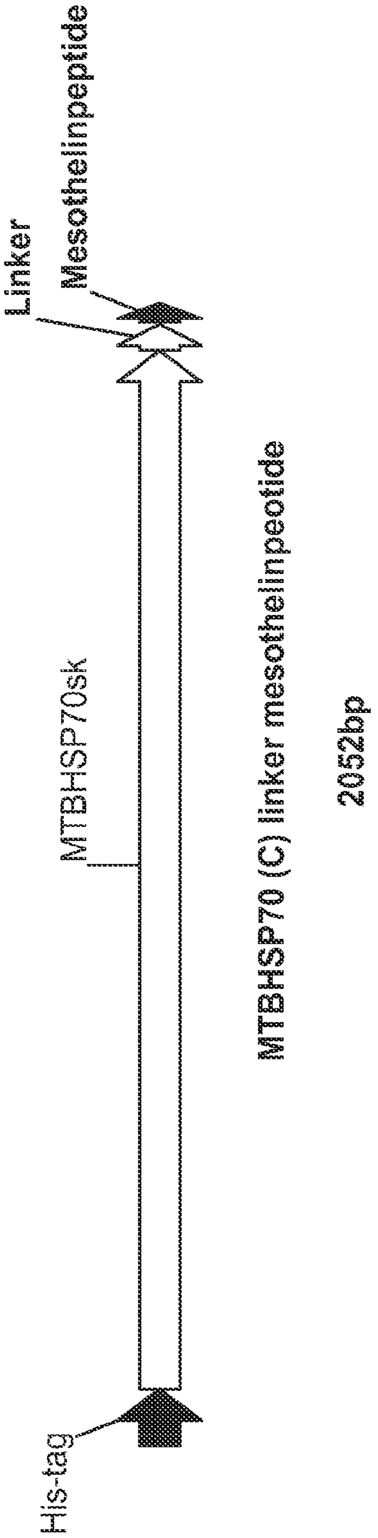
FIG. 9 presents a diagram of an MTBHSP70 (C) linker mesothelin peptide fusion protein.
Figure 11:
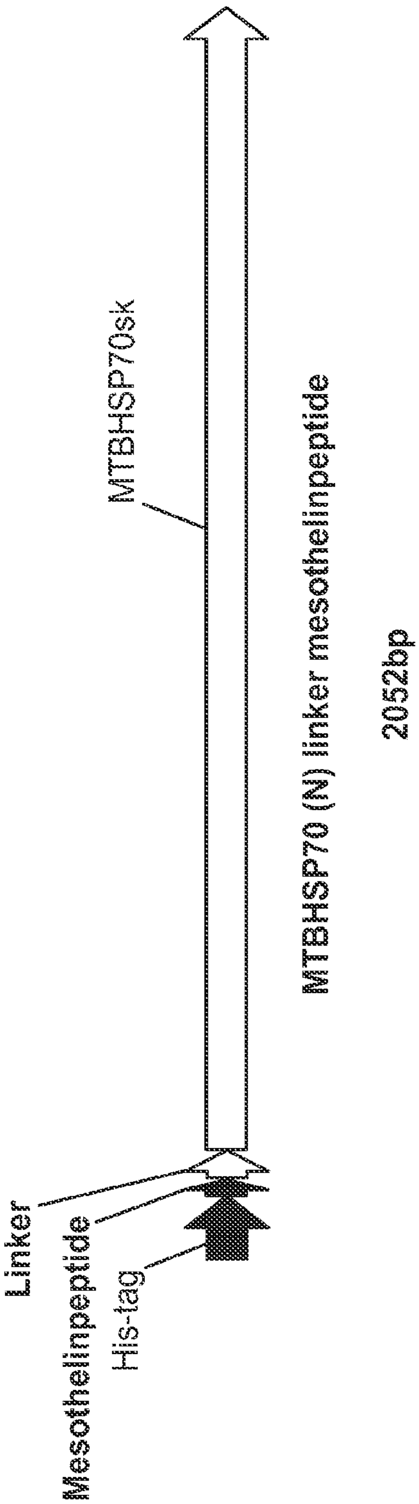
FIG. 11 presents a diagram of an MTBHSP70 (N) linker mesothelin peptide fusion protein.
Figure 13:
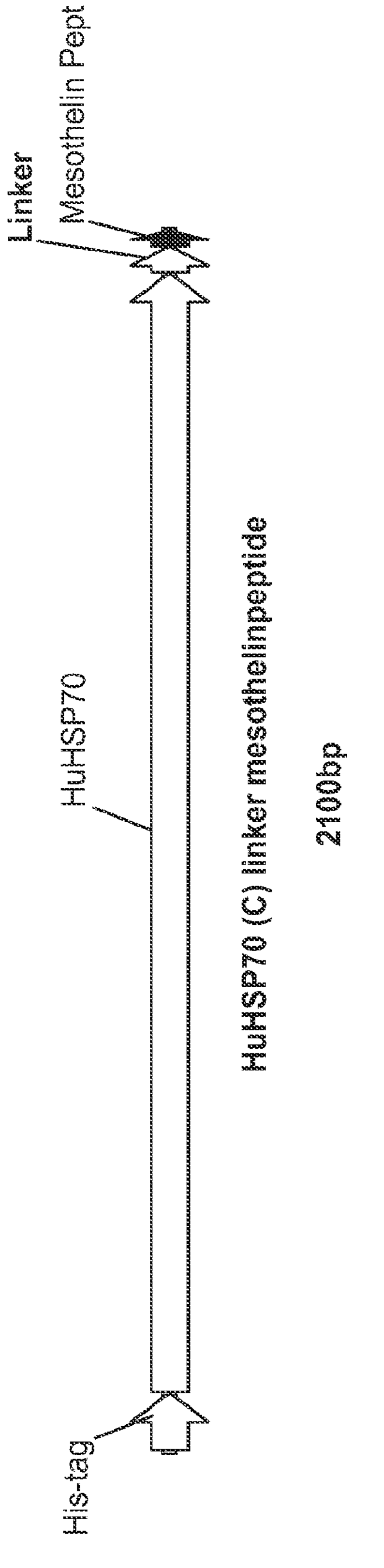
FIG. 13 presents a diagram of an HuHSP70 (C) linker mesothelin peptide.
Figure 15:
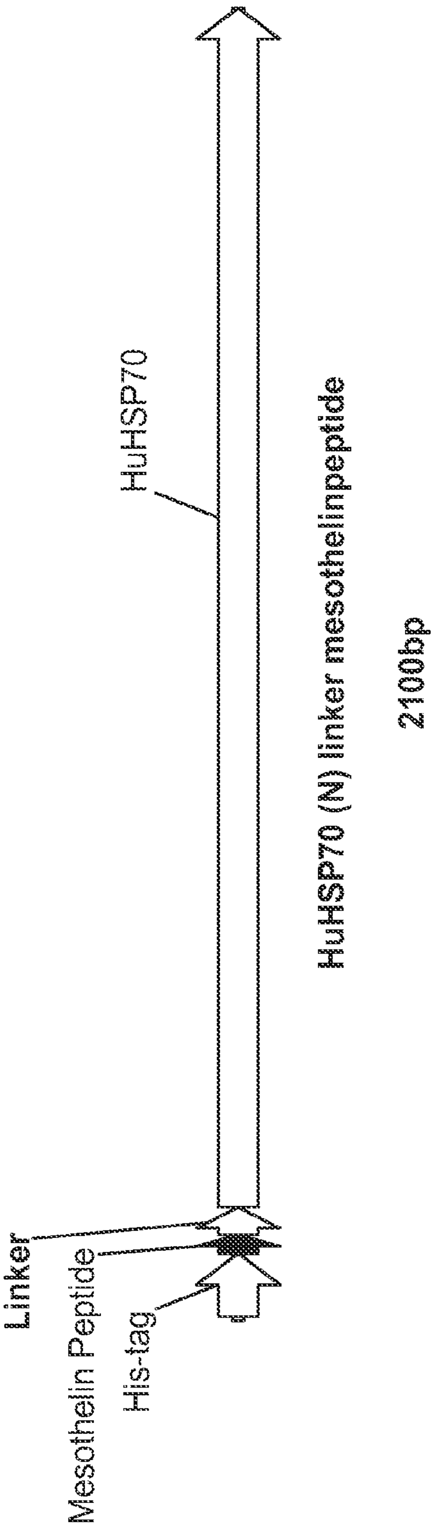
FIG. 15 presents a diagram of an HuHSP70 (N) linker mesothelin peptide.
Figure 17A:
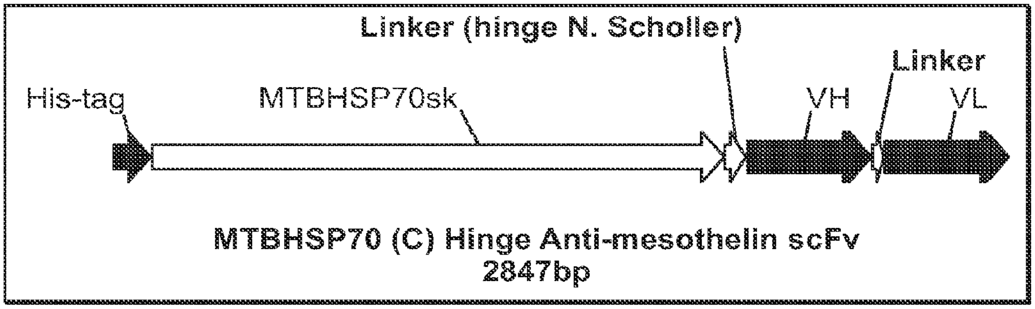
FIG. 17 A-E presents fusion proteins according to the invention (6×His disclosed as SEQ ID NO: 28).
Figure 17B:
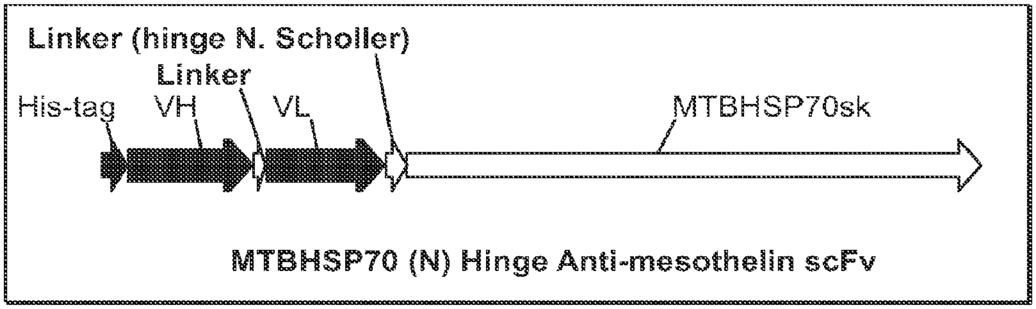
Figure 17C:
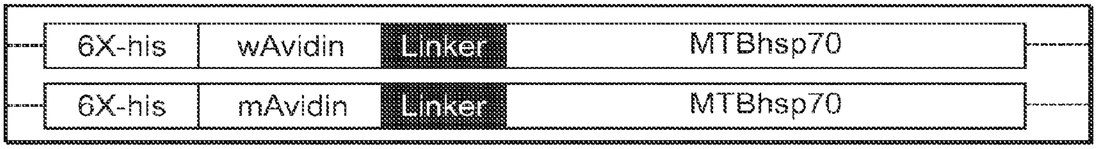
Figure 17D:
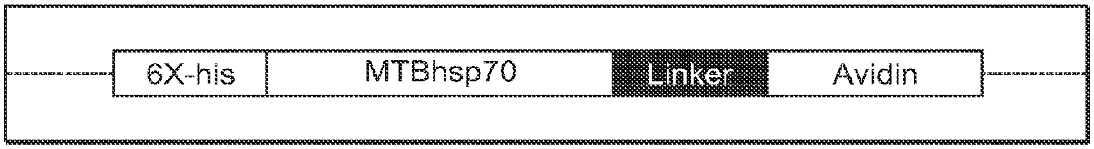
Figure 17E:
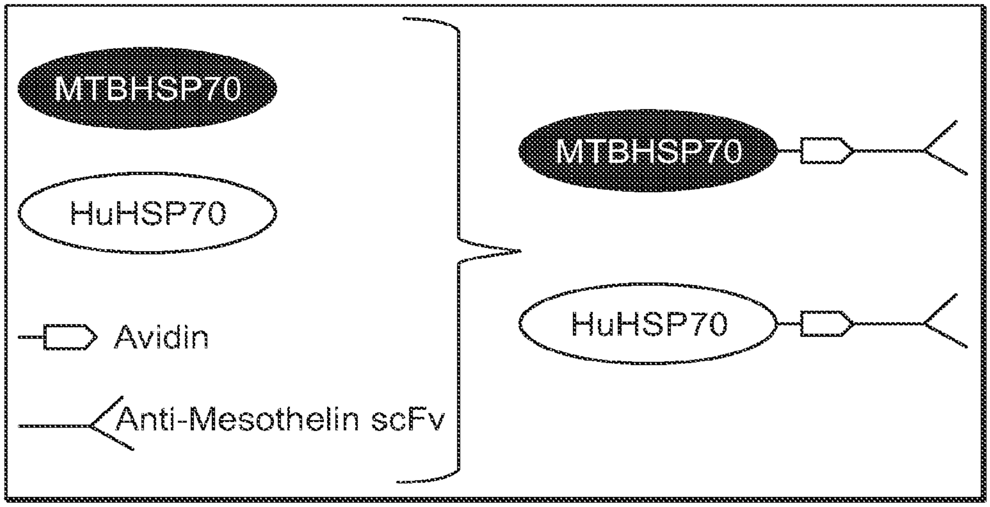

The invention provides a fusion protein comprising a stress protein fused in frame with an engineered antibody or fragment thereof, that binds specifically to mesothelin.

The invention also provides a fusion protein comprising a stress protein fused in frame with a biotin-binding protein in combination with a biotinylated engineered antibody or fragment thereof, that binds specifically to mesothelin.

The invention also provides a fusion protein comprising a stress protein fused in frame with an antibody binding protein in combination with an engineered antibody or fragment thereof, that binds specifically to mesothelin.

The invention also provides a fusion protein comprising an engineered antibody or fragment thereof, that binds specifically to mesothelin fused in frame with a biotin binding protein.

The invention also provides a fusion protein comprising an engineered antibody or fragment thereof, that binds specifically to mesothelin fused in frame with an antibody binding protein.

In one embodiment the biotin-binding protein is selected from the group consisting of: avidin, streptavidin, and neutravidin.

In another embodiment the biotin-binding protein is non-covalently bound to a biotinylated component.

In another embodiment the biotin binding protein is non-covalently bound to four biotinylated components, and further wherein at least two of the four biotinylated components are not identical.

In another embodiment, at least one of the four biotinylated components is a costimulatory molecule.

In another embodiment, the antibody binding protein is selected from the group consisting of: protein A, protein G, protein A/G and protein L.

In another embodiment the fusion protein further comprises a linker.

In another embodiment, the linker comprises an amino acid sequence selected from the group consisting of: GGSSRSS (SEQ ID NO: 1), (GGGSGGG)×4 (SEQ ID NO: 2) or GGGGSGGGGSGGGGS (SEQ ID NO: 3).

The invention also provides for an isolated nucleic acid encoding the fusion protein of the invention.

The invention also provides for an expression vector comprising a nucleic acid encoding the fusion protein of the invention.

The invention also provides for a cell comprising an expression vector comprising a nucleic acid encoding the fusion protein of the invention.

The invention also provides for a pharmaceutical composition comprising an effective amount of a fusion protein of the invention, and a pharmaceutically acceptable carrier.

The invention also provides for an immunogenic composition or vaccine comprising a fusion protein of the invention.

The invention also provides for a kit comprising a composition or vaccine comprising a fusion protein of the invention, and packaging means thereof.

In one embodiment, the kit further comprises instructions for performing any of the methods of the claimed invention, including a method for inducing an immune response to mesothelin, and a method of treating a disease.

The invention also provides for a method for inducing an immune response to mesothelin in a subject comprising administering to the subject a fusion protein comprising a stress protein fused in frame with an engineered antibody or fragment thereof, that binds specifically to mesothelin to induce an immune response.

The invention also provides for a method of treating a disease in a subject, comprising administering to the subject a fusion protein comprising a stress protein fused in frame with an engineered antibody or fragment thereof, that binds specifically to mesothelin to treat a disease.

The invention also provides for a method for inducing an immune response in a subject, comprising administering to said subject a fusion protein comprising a stress protein fused in frame with a biotin-binding protein in combination with a biotinylated engineered antibody or fragment thereof, that binds specifically to mesothelin, to induce an immune response.

The invention also provides for a method of treating a disease in a subject, comprising administering to said subject a fusion protein comprising a stress protein fused in frame with a biotin-binding protein in combination with a biotinylated engineered antibody or fragment thereof, that binds specifically to mesothelin, to treat a disease.

The invention also provides for a method for inducing an immune response in a subject, comprising administering to said subject a fusion protein comprising an engineered antibody or fragment thereof, that binds specifically to mesothelin, fused in frame with a biotin binding protein to induce an immune response.

The invention also provides for a method of treating a disease in a subject, comprising administering to said subject a fusion protein comprising an engineered antibody or fragment thereof, that binds specifically to mesothelin fused in frame with a biotin binding protein to treat a disease.

In one embodiment, the claimed methods are performed with a biotin-binding protein selected from the group consisting of avidin, streptavidin, and neuravidin.

In another embodiment the biotin-binding protein is non-covalently bound to a biotinylated component.

In another embodiment, the biotin binding protein is non-covalently bound to four biotinylated components, and further wherein at least two of the four biotinylated components are not identical.

In another embodiment, at least one of the four biotinylated components is a costimulatory molecule.

In another embodiment, the fusion protein further comprises a linker.

In another embodiment, the linker comprises an amino acid sequence selected from the group consisting of: GGSSRSS (SEQ ID NO: 1), (GGGSGGG)×4 (SEQ ID NO: 2) or GGGGSGGGGSGGGGS (SEQ ID NO: 3).

The invention also provides for a method for inducing an immune response in a subject, comprising administering to said subject a fusion protein comprising a stress protein fused in frame with an antibody binding protein in combination with an engineered antibody or fragment thereof, that binds specifically to mesothelin, to induce an immune response.

The invention also provides for a method of treating a disease in a subject, comprising administering to said subject a fusion protein comprising a stress protein fused in frame with an antibody binding protein in combination with an engineered antibody or fragment thereof, that binds specifically to mesothelin, to treat a disease.

The invention also provides for a method for inducing an immune response in a subject, comprising administering to said subject a fusion protein comprising an engineered antibody or fragment thereof, that binds specifically to mesothelin fused in frame with an antibody binding protein to induce an immune response.

The invention also provides for a method of treating a disease in a subject, comprising administering to said subject a fusion protein comprising an engineered antibody or fragment thereof, that binds specifically to mesothelin fused in frame with an antibody binding protein to treat a disease.

In one embodiment, the claimed methods are performed with an antibody binding protein selected from the group consisting of: protein A, protein G, protein A/G and protein L.

In another embodiment, the fusion protein comprises a linker.

In another embodiment, the linker comprises an amino acid sequence selected from the group consisting of: GGSSRSS (SEQ ID NO: 1), (GGGSGGG)×4 (SEQ ID NO: 2) or GGGGSGGGGSGGGGS (SEQ ID NO: 3).

DETAILED DESCRIPTION OF THE INVENTION

The invention relates to novel proteins that illicit an immune response to mesothelin and their methods of use.

Definitions

The singular forms “a”, “an”, and “the” include plural references unless the context clearly dictates otherwise.

As used herein “mesothelin” refers to a differentiation antigen whose expression in normal human tissues is limited to mesothelial cells lining the pleura, pericardium and peritoneum. However, mesothelin is highly expressed in several human cancers, including mesotheliomas, pancreatic adenocarcinomas, ovarian cancers and lung adenocarcinomas. The mesothelin gene encodes a precursor protein of 71 kDa that is processed to a 31 kDa shed protein called megakaryocyte potentiating factor (MPF) and a 40 kDa fragment, mesothelin, that is attached to the cell membrane by a glycosylphosphatidylinositol (GPI) anchor.

There are three (3) variants of mesothelin: soluble mesothelin-1, a unique mesothelin-2 transcript, and a mesothelin-3 variant with an extended C-terminus Mesothelin-1 is found in pleura, pericardium and peritoneum and on surface epithelium of the ovaries, tonsils, and fallopian tubes (Ordonez, 2003). Mesothelin is also overexpressed in mesotheliomas, pancreatic adenocarcinomas, and squamous cell carcinomas of the head, neck, lung, esophagus, cervix, and vulva (Chang and Pastan 1992, 1996; Frierson et al. 2003).

The term “administering” includes any method of delivery of a compound of the present invention, including but not limited to, a pharmaceutical composition or therapeutic agent, into a subject’s system or to a particular region in or on a subject, including systemic or localized administration. The phrases “systemic administration,” “administered systemically,” “peripheral administration” and “administered peripherally” as used herein mean the administration of a compound, drug or other material other than directly into the central nervous system, such that it enters the patient’s system and, thus, is subject to metabolism and other like processes, for example, subcutaneous administration. “Parenteral administration” and “administered parenterally” means modes of administration other than enteral and topical administration, usually by injection, and includes, without limitation, intravenous, intramuscular, intralesional, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection, oral, epidural, intranasal and infusion.

The term “amino acid” is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

The term “antibody” refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, IgE and IgY. In exemplary embodiments, antibodies used with the methods and compositions described herein are derivatives of the IgG class. The term “antibody” also includes an antibody fragment as defined herein.

The term “antibody fragment” refers to any derivative of an antibody which is less than full-length. In exemplary embodiments, the antibody fragment retains at least a significant portion of the full-length antibody’s specific binding ability. Examples of antibody fragments include, but are not limited to, Fab, Fab', $F(ab')_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term “Fab fragment” refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term “F(ab')2 fragment” refers to a fragment of an antibody containing two antigen-binding sites, generated by cleavage of the antibody molecule with the enzyme pepsin which cuts at the hinge region C-terminally to the inter-H-chain disulfide bond.

The term “Fc fragment” refers to the fragment of an antibody comprising the constant domain of its heavy chain.

The term “Fv fragment” refers to the fragment of an antibody comprising the variable domains of its heavy chain and light chain.

The term “engineered antibody” refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY). Examples of engineered antibodies include enhanced single chain monoclonal antibodies and enhanced monoclonal antibodies. Examples of engineered antibodies are further described in PCT/US2007/061554, the entire contents of which are incorporated herein by reference. An “engineered antibody” includes an engineered antibody fragment, according to the method of the invention, and as defined herein.

The term “single chain variable fragment or scFv” refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

The term “multivalent antibody” refers to an antibody or engineered antibody comprising more than one antigen recognition site. For example, a “bivalent” antibody has two antigen recognition sites, whereas a “tetravalent” antibody has four antigen recognition sites. The terms “monospecific”, “bispecific”, “trispecific”, “tetraspecific”, etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

An "antigen" refers to a target of an immune response induced by a composition described herein. An antigen may be a protein antigen and is understood to include an entire protein, fragment of the protein exhibited on the surface of a virus or an infected, foreign, or tumor cell of a subject, as well as a peptide displayed by an infected, foreign, or tumor cell as a result of processing and presentation of the protein, for example, through the typical MHC class I or II pathways. Examples of such foreign cells include bacteria, fungi, and protozoa. Examples of bacterial antigens include Protein A (PrA), Protein G (PrG), and Protein L (PrL).

The term "antigen binding site" refers to a region of an antibody or fragment thereof, that specifically binds an epitope on an antigen.

The term "biotin-binding protein" refers to a protein, which non-covalently binds to biotin. A biotin-binding protein may be a monomer, dimer, or tetramer, capable of forming monovalent, divalent, or tetravalent pharmaceutical compositions, respectively, as described herein. Non-limiting examples include anti-biotin antibodies, avidin, streptavidin, and neutravidin. The avidin may comprise mature avidin, or a sequence that is at least 50%, 60%, 70%, 80%, 85%, 90%, 95%, or 99% identical to the sequence identified by NCBI Accession No. NP__990651. The streptavidin may comprise, for example, a sequence that is at least 50%, 60%, 70%, 80%, 85%, 90%, 95%, or 99% identical to the sequence identified by of NCBI Accession No. AAU48617. The term "biotin-binding protein" is intended to encompass wild-type and derivatives of avidin, streptavidin, and neutravidin, which form monomers, dimers or tetramers. Examples of such derivatives are set forth below and also described in Laitinen, O. H. (2007), "Brave New (Strept)avidins in Biotechnology," *Trends in Biotechnology* 25 (6): 269-277 and Nordlund, H. R. (2003), "Introduction of histidine residues into avidin subunit interfaces allows pH-dependent regulation of quaternary structure and biotin binding," *FEBS Letters* 555: 449-454, the contents of both of which are expressly incorporated herein by reference.

The term "costimulatory molecule" as used herein includes any molecule which is able to either enhance the stimulating effect of an antigen-specific primary T cell stimulant or to raise its activity beyond the threshold level required for cellular activation, resulting in activation of naive T cells. Such a costimulatory molecule can be a membrane-resident receptor protein.

In this disclosure, "comprises," "comprising," "containing" and "having" and the like have the open-ended meaning ascribed to them in U.S. Patent law and mean "includes," "including," and the like.

The term "effective amount" refers to that amount of a compound, material, or composition which is sufficient to effect a desired result. An effective amount of a compound can be administered in one or more administrations.

A "fusion protein" or "fusion polypeptide" refers to a hybrid polypeptide which comprises polypeptide portions from at least two different polypeptides. A "fusion protein" as defined herein, is a fusion of a first amino acid sequence (protein) comprising, for example a stress protein of the invention, joined to a second amino acid sequence comprising an antibody or fragment thereof that binds specifically to mesothelin or a biotin-binding protein. A fusion protein also includes a fusion protein comprising a first amino acid sequence comprising a stress protein, and a second amino sequence comprising a biotin binding protein. A fusion protein also includes a fusion protein comprising a first amino acid sequence comprising a stress protein and second amino acid sequence comprising an antibody binding protein. A fusion protein also includes a fusion protein comprising a first amino acid sequence comprising an antibody or fragment thereof that binds specifically to mesothelin and a second amino acid sequence comprising a biotin binding protein or an antibody binding protein.

The portions may be from proteins of the same organism, in which case the fusion protein is said to be "interspecies", "intergenic", etc. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. A first polypeptide may be fused to the N-terminus, the C-terminus, or the N- and C-terminus of a second polypeptide. Furthermore, a first polypeptide may be inserted within the sequence of a second polypeptide.

The term "linker" is art-recognized and refers to a molecule (including but not limited to unmodified or modified nucleic acids or amino acids) or group of molecules (for example, 2 or more, e.g., 2, 3, 4, 5, 6, 7, 8, 9, 10, 15, 20, 25, 30, 35, 40, 45, 50, 55, 60, 65, 70, 75, 80, 85, 90, 95, 100 or more) connecting two compounds, such as two polypeptides. The linker may be comprised of a single linking molecule or may comprise a linking molecule and at least one spacer molecule, intended to separate the linking molecule and a compound by a specific distance.

A "spacer molecule" includes any amino acid segment that is not related to the two protein segments it separates. For example, in a fusion consisting of a stress protein and a biotin protein, a spacer molecule would consist of a stretch of amino acids that is unrelated to the proteins comprising the fusion protein. A "spacer molecule useful according to the invention includes neutral amino acids such as glycine, leucine, valine, alanine, rather than acidic or basic amino acids like aspartate, or arginine respectively.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

"Host cell" refers to a cell that may be transduced with a specified transfer vector. The cell is optionally selected from in vitro cells such as those derived from cell culture, ex vivo cells, such as those derived from an organism, and in vivo cells, such as those in an organism. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "including" is used herein to mean "including but not limited to". "Including" and "including but not limited to" are used interchangeably.

The term "immunogenic" refers to the ability of a substance to elicit an immune response. An "immunogenic composition" or "immunogenic substance" is a composition or substance which elicits an immune response. An "immune response" refers to the reaction of a subject to the presence of an antigen, which may include at least one of the following: antibody production, inflammation, developing immunity, developing hypersensitivity to an antigen, the response of antigen specific lymphocytes to antigen, tolerance, and transplant or graft rejection.

As used herein, "an immune response to mesothelin" means, for example, a humoral or cellular response to mesothelin.

If a patient is mounting a humoral immune response to mesothelin, anti-mesothelin antibody titer is measured. A typical immunoassay consists of coating the wells of an immunoassay plate with mesothelin (for example by adding recombinant mesothelin or using a capture anti-mesothelin antibody) and then adding serial dilutions of patient serum to the wells. After washing away the sera, human immunoglobulins are detected with a conjugated anti-human immunoglobulin.

A cellular immune response is measured by using a cell-killing assay. Patients peripheral blood lymphocytes (PBL) are isolated and added at different ratios to a CHO cell line expressing mesothelin (non-transfected CHO cells or CHO cells transfected with a non-mesothelin construct are used as negative control). The mesothelin expressing CHO cells are transfected with a mesothelin construct and selected to express mesothelin on their surface. Killing is measured using radioactivity or release of a specific dye.

As used herein, "treating a disease" means reducing the amount of soluble mesothelin in the plasma of patients. Treating a disease also refers to reducing the tumor burden as measured by clinical means (for example by ecography or other methods known in the art. Treating a disease also refers to reducing tumor size/mass and/or prevention of metastases.

The enhanced mesothelin antibody as described herein, will reduce (eliminate) the tumor burden in patients diagnosed with ovarian cancer, meningiomas, gliomas and metastases to the leptomininges, mesotheliomas, adenocarcinoma of the uterus, malignant mesothelioma, pancreatic cancer and lung adenocarcinoma.

The term "isolated polypeptide" or "isolated protein" refers to a polypeptide, which may be prepared from recombinant DNA or RNA, or be of synthetic origin, some combination thereof, or which may be a naturally-occurring polypeptide, which (1) is not associated with proteins with which it is normally associated in nature, (2) is isolated from the cell in which it normally occurs, (3) is essentially free of other proteins from the same cellular source, (4) is expressed by a cell from a different species, or (5) does not occur in nature.

"Isolating" a polypeptide or protein refers to the process of removing a polypeptide from a tissue, cell or any mixture of polypeptides which are not polypeptides or proteins of interest. An isolated polypeptide or protein will be generally free from contamination by other polypeptides or proteins. An isolated polypeptide or protein can exist in the presence of a small fraction of other polypeptides or proteins which do not interfere with the utilization of the polypeptide or protein of interest. Isolated polypeptides or proteins will generally be at least 30%, 35%, 40%, 45%, 50%, 55%, 60%, 65%, 70%, 75%, 80%, 85%, 90%, 95%, 96%, 97%, 98%, 99% or 100% pure. In one embodiment, isolated polypeptides or proteins according to the invention will be at least 98% or 99% pure.

The term "isolated nucleic acid" refers to a polynucleotide of genomic, cDNA, synthetic, or natural origin or some combination thereof, which (1) is not associated with the cell in which the "isolated nucleic acid" is found in nature, or (2) is operably linked to a polynucleotide to which it is not linked in nature.

"Isolating" a nucleic acid refers to the process of removing a nucleic acid from a tissue, cell or any mixture of nucleic acids which are not nucleic acids of interest. An isolated nucleic acid will be generally free from contamination by other nucleic acids. An isolated nucleic acid can exist in the presence of a small fraction of other nucleic acids which do not interfere with the utilization of the nucleic acid of interest. Isolated nucleic acids will generally be at least 30%, 35%, 40%, 45%, 50%, 55%, 60%, 65%, 70%, 75%, 80%, 85%, 90%, 95%, 96%, 97%, 98%, 99% or 100% pure. In one embodiment, isolated polypeptides or proteins according to the invention will be at least 98% or 99% pure.

When referring to "polypeptide" herein, a person of skill in the art will recognize that a protein can be used instead, unless the context clearly indicates otherwise. A "protein" may also refer to an association of one or more polypeptides The term "nucleic acid" refers to a polymeric form of nucleotides, either ribonucleotides or deoxynucleotides, a combination of ribo and deoxyribonucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

Unless the context clearly indicates otherwise, "protein," "polypeptide," and "peptide" are used interchangeably herein when referring to a gene expression product, e.g., an amino acid sequence as encoded by a coding sequence. A "protein" may also refer to an association of one or more proteins, such as an antibody. A "protein" may also refer to a protein fragment. A protein may be a post-translationally modified protein such as a glycosylated protein.

A "protein" according to the invention includes a protein wherein one or more (for example, 1, 2, 3, 4, 5, 6, 7, 8, 9, 10, 20, 30, 40, 50, 60, 70, 80, 90, 100 or more) amino acids are not identical to the amino acids of the corresponding wild type protein. A "protein" according to the invention includes a protein wherein one or more (for example, 1, 2, 3, 4, 5, 6, 7, 8, 9, 10, 20, 30, 40, 50, 60, 70, 80, 90, 100 or more) amino acids have been deleted as compared to the corresponding wild type protein. A "protein" according to the invention includes a protein wherein one or more (for example, 1, 2, 3, 4, 5, 6, 7, 8, 9, 10 or more) amino acids have been added as compared the corresponding wild type protein.

By "gene expression product" is meant a molecule that is produced as a result of transcription of an entire gene or a portion of a gene. Gene products include RNA molecules transcribed from a gene, as well as proteins translated from such transcripts. Proteins may be naturally occurring isolated proteins or may be the product of recombinant or chemical synthesis. The term "protein fragment" refers to a protein in which amino acid residues are deleted as compared to the reference protein itself, but where the remaining amino acid sequence is usually identical to or substantially identical (for example, 100%, 99%, 95%, 90%, 85%, 80%, 75%, 70%, 65%, or 60% identical) to that of the reference protein. Such deletions may occur at the amino-terminus or carboxy-terminus of the reference protein, or alternatively both. Deletions may also occur internally.

Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. Fragments may be obtained using proteinases to fragment a larger protein, or by recombinant methods, such as the expression of only part of a protein-encoding nucleotide sequence (either alone or fused with another protein-encoding nucleic acid sequence). In various embodiments, a fragment may comprise an enzymatic activity and/or an interaction site of the reference protein to, e.g., a cell receptor. In another embodiment, a fragment may have immunogenic properties. The proteins may include mutations introduced at particular loci by a variety of known techniques, which do not adversely effect, but may enhance, their use in the methods provided herein. A fragment can retain one or more of the biological activities of the reference protein.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical or substantially identical as defined herein above, to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

A "patient" or "subject" or "host" refers to either a human or non-human animal.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

A "pharmaceutically-acceptable salt" refers to the relatively non-toxic, inorganic and organic acid addition salts of compounds.

The term "self-assembling" as used herein refers to the ability of a heat shock protein fused to a biotin-binding protein to form a non-covalent complex with biotinylated component(s) as described herein. Such ability is conferred by the non-covalent association of biotin with a biotin-binding protein.

The term "self-assembling" as used herein refers to the ability of a heat shock protein fused to an antibody binding protein to form a non-covalent complex with an antibody or fragment thereof that binds specifically to mesothelin, as described herein. Such ability is conferred by the non-covalent association of an antibody or fragment thereof with a biotin-binding protein.

As used herein, a "stress protein," also known as a "heat shock protein" or "Hsp," is a protein that is encoded by a stress gene, and is therefore typically produced in significantly greater amounts upon the contact or exposure of the stressor to the organism. The term "stress protein" as used herein is intended to include such portions and peptides of a stress protein. A "stress gene," also known as "heat shock gene", as used herein, refers to a gene that is activated or otherwise detectably upregulated due to the contact or exposure of an organism (containing the gene) to a stressor, such as heat shock, hypoxia, glucose deprivation, heavy metal salts, inhibitors of energy metabolism and electron transport, and protein denaturants, or to certain benzoquinone ansamycins. Nover, L., Heat Shock Response, CRC Press, Inc., Boca Raton, Fla. (1991). "Stress gene" also includes homologous genes within known stress gene families, such as certain genes within the Hsp70 and Hsp90 stress gene families, even though such homologous genes are not themselves induced by a stressor. Each of the terms stress gene and stress protein as used in the present specification may be inclusive of the other, unless the context indicates otherwise.

"Treating" a disease in a subject or "treating" a subject having a disease refers to subjecting the subject to a pharmaceutical treatment, e.g., the administration of a drug, such that the extent of the disease is decreased or prevented. Treatment includes (but is not limited to) administration of a composition, such as a pharmaceutical composition, and may be performed either prophylactically, or subsequent to the initiation of a pathologic event.

The term "vaccine" refers to a substance that elicits an immune response and also confers protective immunity upon a subject.

"Vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops, which, in their vector form are not bound to the chromosome. In the present specification, "plasmid" and "vector" are used interchangeably as the plasmid is the most commonly used form of vector. However, as will be appreciated by those skilled in the art, the invention is intended to include such other forms of expression vectors which serve equivalent functions and which become subsequently known in the art.

As used herein, "Specifically binds" means via covalent or hydrogen bonding or electrostatic attraction.

As used herein, "antibody binding protein" means any protein that can be cloned and expressed and that has affinity for any component of an antibody. For example some proteins bind to the Fc portion of the antibody while others have high affinity for the light chain (e.g. protein L). Proteins such as Protein A, Protein G, Protein A/G, Protein L. Similarly other molecules showing affinity for antibodies could be used for this purpose.

As used herein, an "immune response" or a "detectable response" includes a detectable level of a response that occurs in a subject that has been exposed to a fusion protein of the invention, as described herein, but not in a subject that has not been exposed to a fusion protein of the invention. A "response" that is detected includes but is not limited to an increase in an immune response or an increase in immunogenicity.

A "detectable response" means a response that is at least 0.01%, 0.5%, 1% or more than the response of a subject that has not been exposed to a fusion protein of the invention. A "detectable response" also means a response that is at least 0.5, 1, 2, 3, 4, 5, 10, 20, 30, 40, 50, 60, 70, 80, 90, 100, 1000-fold or more greater than the response of a subject that has not been exposed to a fusion protein of the invention.

As used herein, "immunogenicity" refers to the ability, for example the ability of a fusion protein of the invention to induce humoral and/or cell-mediated immune responses.

As used herein, "immune response" refers to a response made by the immune system of an organism to a substance, which includes but is not limited to foreign or self proteins. There are three general types of "immune response" including, but not limited to mucosal, humoral and cellular "immune responses." A "mucosal immune response" results from the production of secretory IgA (sIgA) antibodies in secretions that bathe all mucosal surfaces of the respiratory tract, gastrointestinal tract and the genitourinary tract and in secretions from all secretory glands (McGhee, J. R. et al., 1983, *Annals NY Acad. Sci.* 409). These sIgA antibodies act to prevent colonization of pathogens on a mucosal surface (Williams, R. C. et al., *Science* 177, 697 (1972); McNabb, P. C. et al., *Ann. Rev. Microbiol.* 35, 477 (1981)) and thus act as a first line of defense to prevent colonization or invasion through a mucosal surface. The production of sIgA can be stimulated either by local immunization of the secretory gland or tissue or by presentation of an antigen to either the gut-associated lymphoid tissue (GALT or Peyer's patches) or the bronchial-associated lymphoid tissue (BALT; Cebra, J. J. et al., *Cold Spring Harbor Symp. Quant. Biol.* 41, 210 (1976); Bienenstock, J. M., *Adv. Exp. Med. Biol.* 107, 53 (1978); Weisz-Carrington, P. et al., *J. Immunol.* 123, 1705 (1979); McCaughan, G. et al., *Internal Rev. Physiol* 28, 131 (1983)). Membranous microfold cells, otherwise known as M cells, cover the surface of the GALT and BALT and may be associated with other secretory mucosal surfaces. M cells act to sample antigens from the luminal space adjacent to the mucosal surface and transfer such antigens to antigen-presenting cells (dendritic cells and macrophages), which in turn present the antigen to a T lymphocyte (in the case of T-dependent antigens), which process the antigen for presentation to a committed B cell. B cells are then stimulated to proliferate, migrate and ultimately be transformed into an antibody-secreting plasma cell producing IgA against the presented antigen. When the antigen is taken up by M cells overlying the GALT and BALT, a generalized mucosal immunity results with sIgA against the antigen being produced by all secretory tissues in the body (Cebra et al., supra; Bienenstock et al., supra; Weinz-Carrington et al., supra; McCaughan et al., supra). Oral immunization is therefore an important route to stimulate a generalized mucosal immune response and, in addition, leads to local stimulation of a secretory immune response in the oral cavity and in the gastrointestinal tract.

An "immune response" may be measured using techniques known to those of skill in the art. For example, serum, blood or other secretions may be obtained from an organism for which an "immune response" is suspected to be present, and assayed for the presence of the above mentioned immunoglobulins using an enzyme-linked immuno-absorbant assay (ELISA; U.S. Pat. No. 5,951,988; Ausubel et al., *Short Protocols in Molecular Biology* 3$^{rd}$ Ed. John Wiley & Sons, Inc. 1995). A statistical test known in the art may be used to determine the difference in measured immunoglobulin levels including, but not limited to ANOVA, Student's T-test, and the like, wherein the P value is at least <0.1, <0.05, <0.01, <0.005, <0.001, and even <0.0001.

An "immune response" may be measured using other techniques such as immunohistochemistry using labeled antibodies which are specific for portions of the immunoglobulins raised during the "immune response". Microscopic data obtained by immunohistochemistry may be quantitated by scanning the immunohistochemically stained tissue sample and quantitating the level of staining using a computer software program known to those of skill in the art including, but not limited to NIH Image (National Institutes of Health, Bethesda, Md.). According to the present invention, a fusion protein of the present invention can be said to stimulate an "immune response" if the quantitative measure of immunohistochemical staining in a subject treated with a fusion protein is statistically different from the measure of immunohistochemical staining detected in a subject not treated with a fusion protein. A statistical test known in the art may be used to determine the difference in measured immunohistochemical staining levels including, but not limited to ANOVA, Student's T-test, and the like, wherein the P value is at least <0.1, <0.05, <0.01, <0.005, <0.001, and even <0.0001.

1. Engineered Fusion Proteins

Provided are fusion proteins comprising: a stress protein fused to an engineered antibody or fragment thereof, that binds specifically to mesothelin; a stress protein fused to a biotin-binding protein, a stress protein fused to an antibody binding protein, an engineered antibody that binds specifically to mesothelin fused to a biotin binding protein and an engineered antibody that binds specifically to mesothelin fused to an antibody binding protein (see FIGS. 1-19).

The engineered mesothelin antibody may comprise for example, at least one scFv, at least one Fab fragment, at least one Fv fragment, etc. It may be monovalent or it may be multivalent. In embodiments wherein the engineered antibody is multivalent, it may be bivalent, trivalent, tetravalent, etc. The multivalent antibodies may be monospecific or multispecific, e.g., bispecific, trispecific, tetraspecific, etc. The multivalent antibodies may be in any form, such as a diabody, triabody, tetrabody, etc. In certain embodiments, the engineered antibody is a Tandab. The stress protein may comprise any stress protein. In certain embodiments, the stress protein comprises HSP70, for example, *Mycobacterium tuberculosis* HSP70 or *Mycobacterium bovis* HSP70. The full-length polypeptide sequences of *Mycobacterium tuberculosis* HSP70 and *Mycobacterium bovis* HSP70 are depicted in FIGS. 20A and 20B, respectively.

Further detail about engineered antibodies, stress proteins, biotin-binding proteins and antibody binding proteins which may be incorporated into the subject fusion polypeptides is provided below.

A. Engineered Antibodies

Natural antibodies are themselves dimers, and thus, bivalent. If two hybridoma cells producing different antibodies are artificially fused, some of the antibodies produced by the hybrid hybridoma are composed of two monomers with different specificities. Such bispecific antibodies can also be produced by chemically conjugating two antibodies. Natural antibodies and their bispecific derivatives are relatively large and expensive to produce. The constant domains of mouse antibodies are also a major cause of the human anti-mouse antibody (HAMA) response, which prevents their extensive use as therapeutic agents. They can also give rise to unwanted effects due to their binding of Fc-receptors. For these reasons, molecular immunologists have been concentrating on the production of the much smaller Fab- and Fv-fragments in microorganisms. These smaller fragments are not only much easier to produce, they are also less immunogenic, have no effector functions, and, because of their relatively small size, they are better able to penetrate tissues and tumors. In the case of the Fab-fragments, the constant domains adjacent to the variable domains play a major role in stabilizing the heavy and light chain dimer. Accordingly, while full-length or nearly full length engineered antibodies may comprise the subject fusion polypeptides, smaller, single domain engineered antibodies (that may be multivalent and multispecific) are preferred for use in the fusion polypeptides.

The Fv-fragment is much less stable, and a peptide linker may therefore be introduced between the heavy and light chain variable domains to increase stability. This construct is known as a single chain Fv(scFv)-fragment. A disulfide bond is sometimes introduced between the two domains for extra stability. Thus far, tetravalent scFv-based antibodies have been produced by fusion to extra polymerizing domains such as the streptavidin monomer that forms tetramers, and to amphipathic alpha helices. However, these extra domains can increase the immunogenicity of the tetravalent molecule.

Bivalent and bispecific antibodies can be constructed using only antibody variable domains. A fairly efficient and relatively simple method is to make the linker sequence between the $V_H$ and $V_L$ domains so short that they cannot fold over and bind one another. Reduction of the linker length to 3-12 residues prevents the monomeric configuration of the scFv molecule and favors intermolecular $V_H$-$V_L$ pairings with formation of a 60 kDa non-covalent scFv dimer "diabody" (Holliger et al., 1993, *Proc. Natl. Acad. Sci. USA* 90, 6444-6448). The diabody format can also be used for generation of recombinant bispecific antibodies, which are obtained by the non-covalent association of two single-chain fusion products, consisting of the $V_H$ domain from one antibody connected by a short linker to the $V_L$ domain of another antibody. Reducing the linker length still further below three residues can result in the formation of trimers ("triabody", about 90 kDa) or tetramers ("tetrabody", about 120 kDa) (Le Gall et al., 1999, *FEBS Letters* 453, 164-168). For a review of engineered antibodies, particularly single domain fragments, see Holliger and Hudson, 2005, *Nature Biotechnology,* 23:1126-1136. All of such engineered antibodies may be used in the fusion polypeptides provided herein.

Other multivalent engineered antibodies that may comprise the subject fusion polypeptides are described in Lu, et al., 2003, *J. Immunol. Meth.* 279:219-232 (di-diabodies or tetravalent bispecific antibodies); US Published Application 20050079170 (multimeric Fv molecules or "flexibodies"), and WO99/57150 and Kipriyanov, et al., 1999, J. Mol. Biol. 293:41-56 (tandem diabodies, or "Tandabs").

Any of the above-described multivalent engineered antibodies may be developed by one of skill in the art using routine recombinant DNA techniques, for example as described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988)*Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; Beidler et al. (1988) *J. Immunol.* 141:4053-4060; and Winter and Milstein, *Nature,* 349, pp. 293-99 (1991)). Preferably non-human antibodies are "humanized" by linking the non-human antigen binding domain with a human constant domain (e.g. Cabilly et al., U.S. Pat. No. 4,816,567; Morrison et al., Proc. Natl. Acad. Sci. U.S.A., 81, pp. 6851-55 (1984)).

The antigen recognition sites or entire variable regions of the engineered antibodies may be derived from one or more parental antibodies directed against mesothelin. The parental antibodies can include naturally occurring antibodies or antibody fragments, antibodies or antibody fragments adapted from naturally occurring antibodies, antibodies constructed de novo using sequences of antibodies or antibody fragments known to be specific for an antigen of interest. Sequences that may be derived from parental antibodies include heavy and/or light chain variable regions and/or CDRs, framework regions or other portions thereof.

Multivalent, multispecific antibodies may contain a heavy chain comprising two or more variable regions and/or a light chain comprising one or more variable regions wherein at least two of the variable regions recognize different epitopes on the same antigen.

Candidate engineered antibodies for inclusion in the fusion polypeptides, or the fusion polypeptides themselves, may be screened for activity using a variety of known assays. For example, screening assays to determine binding specificity are well known and routinely practiced in the art. For a comprehensive discussion of such assays, see Harlow et al. (Eds.), Antibodies: A Laboratory Manual; Cold Spring Harbor Laboratory; Cold Spring Harbor, N.Y., 1988, Chapter 6.

B. Stress Proteins

Any suitable stress protein (heat shock protein (hsp)) can be used in the fusion polypeptides of the present invention.

A "heat shock protein" is encoded by a "heat shock gene" or a stress gene, refers to the protein product of a gene that is activated or otherwise detectably upregulated due to the contact or exposure of an organism (containing the gene) to a stressor, such as heat shock, hypoxia, glucose deprivation, heavy metal salts, inhibitors of energy metabolism and electron transport, and protein denaturants, or to certain benzoquinone ansamycins. Nover, L., Heat Shock Response, CRC Press, Inc., Boca Raton, Fla. (1991). "Heat shock protein" also includes homologous proteins encoded by genes within known stress gene families, even though such homologous genes are not themselves induced by a stressor. A "heat shock protein fusion" refers to a heat shock protein or portion thereof, linked to at least one of an engineered mesothelin antibody, a biotin binding protein or an antibody binding protein.

Cells respond to a stressor (typically heat shock treatment) by increasing the expression of a group of genes commonly referred to as stress, or heat shock genes. Heat shock treatment involves exposure of cells or organisms to temperatures that are one to several degrees Celsius above the temperature to which the cells are adapted. In coordination with the induction of such genes, the levels of corresponding stress proteins increase in stressed cells.

For example, a heat shock protein may be C- or N-terminally joined to a biotin-binding protein, an antibody binding protein or a mesothelin antibody to generate a heat shock protein fusion. When administered in conjunction with a biotinylated component provided herein, a heat shock protein fusion comprising a heat shock protein and a biotin binding protein is capable of stimulating humoral and/or cellular immune responses, including CD8 cytotoxic T cell (CTL) responses, to an antigen of interest.

For example, but not by way of limitation, heat shock proteins which may be used according to the invention include BiP (also referred to as grp78), Hsp10, Hsp20-30, Hsp60 hsp70, hsc70, gp96 (grp94), hsp60, hsp40, and Hsp100-200, Hsp100, Hsp90, and members of the families thereof. Especially preferred heat shock proteins are BiP, gp96, and hsp70, as exemplified below. A particular group of heat shock proteins includes Hsp90, Hsp70, Hsp60, Hsp20-30, further preferably Hsp70 and Hsp60. Most preferred is a member of the hsp70 family.

In bacteria, the predominant stress proteins are proteins with molecular sizes of about 70 and 60 kDa, respectively, that are commonly referred to as Hsp70 and Hsp60, respectively. These and other specific stress proteins and the genes encoding them are discussed further below. In bacteria, Hsp70 and Hsp60 typically represent about 1-3% of cell protein based on the staining pattern using sodium dodecyl sulfate polyacrylamide gel electrophoresis and the stain Coomassie blue, but accumulate to levels as high as 25% under stressful conditions. Stress proteins appear to participate in important cellular processes such as protein synthesis, intracellular trafficking, and assembly and disassembly of protein complexes. It appears that the increased amounts of stress proteins synthesized during stress serve primarily to minimize the consequences of induced protein unfolding. Indeed, the preexposure of cells to mildly stressful conditions that induce the synthesis of stress proteins affords protection to the cells from the deleterious effects of a subsequent more extreme stress.

The major stress proteins appear to be expressed in every organism and tissue type examined so far. Also, it appears that stress proteins represent the most highly conserved group of proteins identified to date. For example, when stress proteins in widely diverse organisms are compared, Hsp90 and Hsp70 exhibit 50% or higher identity at the amino acid level and share many similarities at non-identical positions. It is noted that similar or higher levels of homology exist between different members of a particular stress protein family within species.

The stress proteins, particularly Hsp70, Hsp60, Hsp20-30 and Hsp 10, are among the major determinants recognized by the host immune system in the immune response to infection by *Mycobacterium tuberculosis* and *Mycobacterium leprae*. Young, R. A. and Elliott. T. J., Stress Proteins, Infection, And Immune Surveillance, *Cell* 50:5-8 (1989). Further, some rat arthritogenic T cells recognize Hsp60 epitopes. Van Eden, W. et al., *Nature* 331:171-173 (1988). However, individuals, including healthy individuals, with no history of mycobacterial infection or autoimmune disease also carry T cells that recognize both bacterial and human Hsp60 epitopes; a considerable fraction of T cells in healthy individuals that are characterized by expression of the gamma-delta T cell receptor recognize both self and foreign stress proteins. O'Brien, R. et al., *Cell* 57:664-674 (1989). Thus, individuals, even healthy individuals, possess T-cell populations that recognize both foreign and self stress protein epitopes.

This system recognizing stress protein epitopes presumably constitutes an "early defense system" against invading organisms. Murray, P. J. and Young, R. A., *J. Bacteriol* 174: 4193-6 (1992). The system may be maintained by frequent stimulation by bacteria and viruses. As discussed before, healthy individuals have T cell populations recognizing self stress proteins. Thus, the presence of autoreactive T cells is compatible with normal health and does not cause autoimmune disease; this demonstrates the safety of stress proteins within an individual. The safety of stress proteins is additionally demonstrated by the success and relative safety of BCG (Bacille Calmette Guerin, a strain of *Mycobacterium bovis*) vaccinations, which induce an immune response against stress proteins that is also protective against *Mycobacterium tuberculosis*.

Families of stress genes and proteins for use in the fusion polypeptides are those well known in the art and include, for example, Hsp 100-200, Hsp100, Hsp90, Lon, Hsp70, Hsp60, TF55, Hsp40, FKBPs, cyclophilins, Hsp20-30, ClpP, GrpE, Hsp10, ubiquitin, calnexin, and protein disulfide isomerases. Macario, A. J. L., Cold Spring Harbor Laboratory Res. 25:59-70, 1995; Parsell, D. A. & Lindquist, S. *Ann. Rev. Genet.* 27:437-496 (1993); U.S. Pat. No. 5,232,833 (Sanders et al.). A particular group of stress proteins includes Hsp90, Hsp70. Hsp60, Hsp20-30, further preferably Hsp70 and Hsp60.

Hsp100 examples include mammalian Hsp110, yeast Hsp104, ClpA, ClpB, ClpC, ClpX and ClpY. Yeast Hsp104 and *E. coli* ClpA, form hexameric and *E. coli* ClpB, tetrameric particles whose assembly appears to require adenine nucleotide binding. Clp protease provides a 750 kDa heterooligomer composed of ClpP (a proteolytic subunit) and of ClpA. ClpB-Y are structurally related to ClpA, although unlike ClpA they do not appear to complex with ClpP.

Hsp90 examples include HtpG in *E. coli*, Hsp83 and Hsc83 yeast, and Hsp90alpha, Hsp90beta and Grp94 in humans. Hsp90 binds groups of proteins, which proteins are typically cellular regulatory molecules such as steroid hormone receptors (e.g., glucocorticoid, estrogen, progesterone, and testosterone receptors), transcription factors and protein kinases that play a role in signal transduction mechanisms. Hsp90 proteins also participate in the formation of large, abundant protein complexes that include other stress proteins.

Lon is a tetrameric protein functioning as an ATP-dependent protease degrading non-native proteins in *E. coli*.

Hsp70 examples include Hsp72 and Hsc73 from mammalian cells, DnaK from bacteria, particularly mycobacteria such as *Mycobacterium leprae, Mycobacterium tuberculosis*, and *Mycobacterium bovis* (such as Bacille-Calmette Guerin: referred to herein as Hsp71), DnaK from *Escherichia coli*, yeast, and other prokaryotes, and BiP and Grp78. Hsp70 is capable of specifically binding ATP as well as unfolded polypeptides and peptides, thereby participating in protein folding and unfolding as well as in the assembly and disassembly of protein complexes.

Hsp60 examples include Hsp65 from mycobacteria. Bacterial Hsp60 is also commonly known as GroEL, such as the GroEL from *E. coli*. Hsp60 forms large homooligomeric complexes, and appears to play a key role in protein folding. Hsp60 homologues are present in eukaryotic mitochondria and chloroplasts.

TF55 examples include Tcpl, TRiC and thermosome. The proteins typically occur in the cytoplasm of eukaryotes and some archaebacteria, and form multi-membered rings, promoting protein folding. They are also weakly homologous to Hsp60.

Hsp40 examples include DnaJ from prokaryotes such as *E. coli* and mycobacteria and HSJ1, HDJ1 and Hsp40. Hsp40 plays a role as a molecular chaperone in protein folding, thermotolerance and DNA replication, among other cellular activities.

FKBPs examples include FKBP12, FKBP13, FKBP25, and FKBP59, Fprl and Nepl. The proteins typically have peptidyl-prolyl isomerase activity and interact with immunosuppressants such as FK506 and rapamycin. The proteins are typically found in the cytoplasm and the endoplasmic reticululum.

Cyclophilin examples include cyclophilins A, B and C. The proteins have peptidyl-prolyl isomerase activity and interact with the immunosuppressant cyclosporin A. The protein cyclosporin A binds calcineurin (a protein phosphatase).

Hsp20-30 is also referred to as small Hsp. Hsp20-30 is typically found in large homooligomeric complexes or, possibly, also heterooligomeric complexes where an organism or cell type expresses several different types of small Hsps. Hsp20-30 interacts with cytoskeletal structures, and may play a regulatory role in the polymerization/depolymerization of actin. Hsp20-30 is rapidly phosphorylated upon stress or exposure of resting cells to growth factors. Hsp20-30 homologues include alpha-crystallin.

ClpP is an *E. coli* protease involved in degradation of abnormal proteins. Homologues of ClpP are found in chloroplasts. ClpP forms a heterooligomeric complex with ClpA.

GrpE is an *E. coli* protein of about 20 kDa that is involved in both the rescue of stress-damaged proteins as well as the degradation of damaged proteins. GrpE plays a role in the regulation of stress gene expression in *E. coli*.

Hsp10 examples include GroES and Cpn10. Hsp10 is typically found in *E. coli* and in mitochondria and chloroplasts of eukaryotic cells. Hsp10 forms a seven-membered ring that associates with Hsp60 oligomers. Hsp10 is also involved in protein folding.

Ubiquitin has been found to bind proteins in coordination with the proteolytic removal of the proteins by ATP-dependent cytosolic proteases.

In particular embodiments, the stress proteins of the present invention are obtained from enterobacteria, mycobacteria (particularly *M leprae, M. tuberculosis, M. vaccae, M. smegmatis* and *M. bovis*), *E. coli*, yeast, *Drosophila*, vertebrates, avians, chickens, mammals, rats, mice, primates, or humans.

Naturally occurring or recombinantly derived mutants of heat shock proteins may be used according to the invention. For example, but not by way of limitation, the present invention provides for the use of heat shock proteins mutated so as to facilitate their secretion from the cell (for example having mutation or deletion of an element which facilitates endoplasmic reticulum recapture, such as KDEL (SEQ ID NO: 4) or its homologues; such mutants are described in PCT Application No. PCT/US96/13233 (WO 97/06685), which is incorporated herein by reference.

In particular embodiments, e.g., in cases involving chemical conjugates between a stress protein and an engineered mesothelin antibody, the stress proteins used are isolated stress proteins, which means that the stress proteins have been selected and separated from the host cell in which they were produced. Such isolation can be carried out as described herein and using routine methods of protein isolation known in the art.

The stress proteins may be in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance the increased biological activity of the stress protein. Due to code degeneracy, for example, there may be considerable variation in nucleotide sequences encoding the same amino acid sequence. Portions of stress proteins or peptides obtained from stress proteins may be used in the fusion polypeptides, provided such portions or peptides include the epitopes involved with enhancing the immune response. Portions of stress proteins may be obtained by fragmentation using proteinases, or by recombinant methods, such as the expression of only part of a stress protein-encoding nucleotide sequence (either alone or fused with another protein-encoding nucleic acid sequence). Peptides may also be produced by such methods, or by chemical synthesis. The stress proteins may include mutations introduced at particular loci by a variety of known techniques. See, e.g., Sambrook et al., Molecular Cloning: A Laboratory Manual. 2d Ed., Cold Spring Harbor Laboratory Press (1989); Drinkwater and Klinedinst *Proc. Natl. Acad. Sci*. USA 83:3402-3406 (1986); Liao and Wise, *Gene* 88:107-111 (1990): Horwitz et al., *Genome* 3:112-117 (1989).

The pharmaceutical compositions provided herein may have individual amino acid residues that are modified by oxidation or reduction. Furthermore, various substitutions, deletions, or additions may be made to the amino acid or nucleic acid sequences, the net effect of which is to retain or further enhance the increased biological activity of the heat shock protein. Due to codon degeneracy, for example, there may be considerable variation in nucleotide sequences encoding the same amino acid sequence.

The term "heat shock protein" is intended to encompass fragments of heat shock proteins obtained from heat shock proteins, provided such fragments include the epitopes involved with enhancing the immune response to mesothelin. Fragments of heat shock proteins may be obtained using proteinases, or by recombinant methods, such as the expression of only part of a stress protein-encoding nucleotide sequence (either alone or fused with another protein-encoding nucleic acid sequence). The heat shock proteins may include mutations introduced at particular loci by a variety of known techniques to enhance its effect on the immune system. See, e.g., Sambrook et al., Molecular Cloning: A Laboratory Manual, 2d Ed., Cold Spring Harbor Laboratory Press (1989); Drinkwater and Klinedinst Proc. Natl. Acad. Sci.

USA 83:3402-3406 (1986); Liao and Wise, Gene 88:107-111 (1990); Horwitz et al., Genome 3:112-117 (1989).

In particular embodiments, the heat shock proteins used in the present invention are isolated heat shock proteins, which means that the heat shock proteins have been selected and separated from the host cell in which they were produced. Such isolation can be carried out as described herein and using routine methods of protein isolation known in the art. Maniatis et al., Molecular Cloning, A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press (1989); Deutscher, M., Guide to Protein Purification Methods Enzymology, vol. 182, Academic Press, Inc., San Diego, Calif. (1990).

C. Biotin Binding Proteins

The invention provides for biotin binding proteins including but not limited to avidin, streptavidin, or neutravidin. Any naturally occurring or engineered biotin binding protein known in the art is useful according to the invention.

A pH-sensitive mutant of avidin, streptavidin, or neutravidin, for example, may be employed to control the noncovalent interaction of avidin-, streptavidin-, or neutravidin-to biotin, and thereby achieve the desired stoichiometry of heat shock protein fusion with the various permutations and combinations of biotinylated component, as described herein. The choice of wild-type or a particular mutant form of biotin-binding protein such as avidin may be employed to control the desired valency of the pharmaceutical composition (e.g., monomeric, dimeric, or tetrameric form of avidin). Monovalent or divalent vaccines may be similarly produced by employing heat shock fusion proteins comprising other avidin, streptavidin, or neutravidin mutant proteins that bind biotin but in a monovalent or divalent fashion. An example of an avidin mutant is monomeric avidin.

An example of a pH-sensitive point mutant of Avidin which confers pH-adjustable biotin binding is Y33H. Another mutant has substitutions of histidine for Met96, Val115, and Ile117, optionally with histidine replacement at Trp110. Such approaches for controlling biotin-streptavidin binding are described in Laitinen, O. H. (2007), "Brave (Strept)avidins in Biotechnology," *Trends in Biotechnology* 25 (6): 269-277 and Nordlund, H. R. (2003), "Introduction of histidine residues into avidin subunit interfaces allows pH-dependent regulation of quaternary structure and biotin binding," *FEBS Letters* 555: 449-454, the contents of both of which are incorporated herein by reference.

D. Antibody Binding Proteins

An antibody binding protein useful according to the invention includes but is not limited to Protein A, Protein G, Protein A/G, and Protein L. Protein A binds the heavy chain Fc portion of immunoglobulins. An antibody binding protein binds with high affinity to human IgG1 and IgG2 as well as mouse IgG2a and IgG2b. Protein G, like Protein A binds immunoglobulins through the Fc portion of the heavy chain. Native Protein G naturally binds serum albumin. Recombinant Protein G has been engineered not to bind serum albumin. Protein L binds immunoglobulins through the kappa light chain. It binds a broader range of antibodies since it does not rely on the Fc portion of the heavy chain. However, protein L binds human VκI, VκIII and VκIV subtypes but does not bind the VκII subtype. In mouse, it only binds antibodies having the VκI light chain.

E. Biotinylated Components

The term "biotinylated component" as used herein, refers to a biotinylated protein. Non-limiting examples of biotinylated proteins include biotinylated antigens, antibodies, and costimulatory molecules. The biotinylated component is to be administered to a subject in conjunction with a heat shock protein fusion as described herein. For example, in one embodiment a fusion protein comprising a stress protein fused to a biotin-binding protein is used in combination with a biotinylated antibody that binds specifically to mesothelin.

In one embodiment, an antibody or fragment thereof, that binds specifically to mesothelin may be biotinylated and administered in conjunction with a heat shock protein fusion comprising a heat shock fusion fused with a biotin binding protein, as described herein.

2. Methods of Making the Fusion Proteins

Provided also are compositions and methods for making fusion proteins according to the invention. Any of the fusion proteins described herein can be produced by recombinant means. For example, a nucleic acid encoding a stress protein can be joined to either end of a nucleic acid sequence encoding an engineered mesothelin antibody or fragment thereof, the antibody binding protein or the biotin binding protein, or combinations thereof, such that the protein-coding sequences are sharing a common translational reading frame and can be expressed as a fusion protein including, for example, the engineered mesothelin antibody or fragment thereof, and the stress protein.

The combined sequence is inserted into a suitable vector chosen based on the expression features desired and the nature of the host cell. In the examples provided hereinafter, the nucleic acid sequences are assembled in a vector suitable for protein expression in the bacterium *E. coli*. Following expression in the chosen host cell, fusion protein can be purified by routine biochemical separation techniques or by immunoaffinity methods using an antibody to one of the components of the fusion protein. Alternatively, the selected vector can add a tag to the fusion protein sequence, e.g., an oligohistidine tag, permitting expression of a tagged fusion protein that can be purified by affinity methods using an antibody or other material having an appropriately high affinity for the tag. Sambrook et al., Molecular Cloning: A Laboratory Manual, 2d Ed., Cold Spring Harbor Laboratory Press (1989); Deutscher, M. Guide to Protein Purification Methods Enzymology, vol. 182. Academic Press, Inc. San Diego, Calif. (1990). If a vector suitable for expression in mammalian cells is used. e.g., one of the vectors discussed below, the fusion protein can be expressed and purified from mammalian cells. Alternatively, the mammalian expression vector (including fusion protein-coding sequences) can be administered to a subject to direct expression of a fusion protein according to the method of the invention in the subject's cells. A nucleic acid encoding fusion protein of the invention can also be produced chemically and then inserted into a suitable vector for fusion protein production and purification or administration to a subject. Finally, a fusion protein can also be prepared chemically.

Techniques for making fusion genes are well known in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed to generate a chimeric gene sequence (see, for example, *Current Protocols in Molecular Biology*, eds. Ausubel et al., John Wiley & Sons: 1992). Accordingly, provided is an isolated nucleic acid comprising a fusion gene of a gene encoding at least one engineered antibody and a gene encoding at least one stress protein.

The nucleic acid may be provided in a vector comprising a nucleotide sequence encoding an engineered fusion protein according to the invention, and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered. Such vectors may be administered in any biologically effective carrier, e.g., any formulation or composition capable of effectively transfecting cells either ex vivo or in vivo with genetic material encoding a chimeric polypeptide. Approaches include insertion of the nucleic acid into viral vectors including recombinant retroviruses, adenoviruses, adeno-associated viruses, human immunodeficiency viruses, and herpes simplex viruses-1, or recombinant bacterial or eukaryotic plasmids. Viral vectors may be used to transfect cells directly; plasmid DNA may be delivered alone with the help of, for example, cationic liposomes (lipofectin) or derivatized (e.g., antibody conjugated), polylysine conjugates, gramicidin S, artificial viral envelopes or other such intracellular carriers. Nucleic acids may also be directly injected. Alternatively, calcium phosphate precipitation may be carried out to facilitate entry of a nucleic acid into a cell.

The subject nucleic acids may be used to cause expression and over-expression of a fusion protein of the invention in cells propagated in culture, e.g. to produce fusion proteins or polypeptides.

Provided also is a host cell transfected with a recombinant gene in order to express an engineered mesothelin antibody fusion protein. The host cell may be any prokaryotic or eukaryotic cell. For example, a stress protein fusion may be expressed in bacterial cells, such as *E. coli*, insect cells (baculovirus), yeast, insect, plant, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Other methods suitable for maximizing expression of the fusion polypeptide will be known to those in the art.

A cell culture includes host cells, media and other byproducts. Suitable media for cell culture are well known in the art. A fusion polypeptide may be secreted and isolated from a mixture of cells and medium comprising the polypeptide. Alternatively, a fusion polypeptide may be retained cytoplasmically and the cells harvested, lysed and the protein isolated. A fusion polypeptide may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of a fusion.

Thus, a nucleotide sequence encoding all or part of a fusion protein of the invention may be used to produce a recombinant form of a protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant fusion polypeptides by microbial means or tissue-culture technology in accord with the subject invention.

Expression vehicles for production of a recombinant protein include plasmids and other vectors. For instance, suitable vectors for the expression of a fusion polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli.*

In another embodiment, the nucleic acid is a fusion protein operably linked to a bacterial promoter, e.g., the anaerobic *E. coli*, NirB promoter or the *E. coli* lipoprotein IIp promoter, described, e.g., in Inouye et al. (1985) *Nucl. Acids Res.* 13:3101; *Salmonella* pagC promoter (Miller et al., supra), *Shigella ent* promoter (Schmitt and Payne, *J. Bacteriol.* 173: 816 (1991)), the tet promoter on Tn10 (Miller et al., supra), or the ctx promoter of *Vibrio cholera*. Any other promoter can be used. The bacterial promoter can be a constitutive promoter or an inducible promoter. An exemplary inducible promoter is a promoter which is inducible by iron or in iron-limiting conditions. In fact, some bacteria, e.g., intracellular organisms, are believed to encounter iron-limiting conditions in the host cytoplasm. Examples of iron-regulated promoters of FepA and TonB are known in the art and are described, e.g., in the following references: Headley, V. et al. (1997) *Infection & Immunity* 65:818; Ochsner, U. A. et al. (1995) *Journal of Bacteriology* 177:7194; Hunt, M. D. et al. (1994) *Journal of Bacteriology* 176:3944; Svinarich, D. M. and S. Palchaudhuri. (1992) *Journal of Diarrhoeal Diseases Research* 10:139; Prince, R. W. et al. (1991) *Molecular Microbiology* 5:2823; Goldberg, M. B. et al. (1990) *Journal of Bacteriology* 172:6863; de Lorenzo, V. et al. (1987) *Journal of Bacteriology* 169:2624; and Hantke, K. (1981) *Molecular & General Genetics* 182:288.

A plasmid preferably comprises sequences required for appropriate transcription of the nucleic acid in bacteria, e.g., a transcription termination signal. The vector can further comprise sequences encoding factors allowing for the selection of bacteria comprising the nucleic acid of interest, e.g., gene encoding a protein providing resistance to an antibiotic, sequences required for the amplification of the nucleic acid, e.g., a bacterial origin of replication.

In another embodiment, a signal peptide sequence is added to the construct, such that the fusion protein/polypeptide is secreted from cells. Such signal peptides are well known in the art.

In one embodiment, the powerful phage T5 promoter, that is recognized by *E. coli* RNA polymerase is used together with a lac operator repression module to provide tightly regulated, high level expression or recombinant proteins in *E. coli*. In this system, protein expression is blocked in the presence of high levels of lac repressor. In one embodiment, the DNA is operably linked to a first promoter and the bacterium further comprises a second DNA encoding a first polymerase which is capable of mediating transcription from the first promoter, wherein the DNA encoding the first polymerase is operably linked to a second promoter. In a preferred embodiment, the second promoter is a bacterial promoter, such as those delineated above. In an even more preferred embodiment, the polymerase is a bacteriophage polymerase, e.g., SP6, T3, or T7 polymerase and the first promoter is a bacteriophage promoter, e.g., an SP6, T3, or T7 promoter, respectively. Plasmids comprising bacteriophage promoters and plasmids encoding bacteriophage polymerases can be obtained commercially, e.g., from Promega Corp. (Madison, Wis.) and InVitrogen (San Diego, Calif.), or can be obtained directly from the bacteriophage using standard recombinant DNA techniques (J. Sambrook, E. Fritsch, T. Maniatis, *Molecular Cloning: A Laboratory Manual*, Cold Spring Laboratory Press, 1989). Bacteriophage polymerases and promoters are further described, e.g., in the following references: Sagawa, H. et al. (1996) Gene 168:37; Cheng, X. et al. (1994) *PNAS USA* 91:4034; Dubendorff, J. W. and F. W. Studier (1991) *Journal of Molecular Biology* 219:45; Bujarski, J. J. and P. Kaesberg (1987) *Nucleic Acids Research* 15:1337; and Studier, F. W. et al. (1990) *Methods in Enzymology* 185:60). Such plasmids can be modified further according to the specific embodiment of the fusion polypeptide to be expressed.

In another embodiment, the bacterium further comprises a DNA encoding a second polymerase which is capable of mediating transcription from the second promoter, wherein the DNA encoding the second polymerase is operably linked to a third promoter. The third promoter may be a bacterial promoter. However, more than two different polymerases and promoters could be introduced in a bacterium to obtain high levels of transcription. The use of one or more polymerases for mediating transcription in the bacterium can provide a significant increase in the amount of polypeptide in the bacterium relative to a bacterium in which the DNA is directly under the control of a bacterial promoter. The selection of the system to adopt will vary depending on the specific use, e.g., on the amount of protein that one desires to produce.

Generally, a nucleic acid encoding a fusion protein of the invention is introduced into a host cell, such as by transfection, and the host cell is cultured under conditions allowing expression of the fusion polypeptide. Methods of introducing nucleic acids into prokaryotic and eukaryotic cells are well known in the art. Suitable media for mammalian and prokaryotic host cell culture are well known in the art. Generally, the nucleic acid encoding the subject fusion polypeptide is under the control of an inducible promoter, which is induced once the host cells comprising the nucleic acid have divided a certain number of times. For example, where a nucleic acid is under the control of a beta-galactose operator and repressor, isopropyl beta-D-thiogalactopyranoside (IPTG) is added to the culture when the bacterial host cells have attained a density of about $OD_{600}$ 0.45-0.60. The culture is then grown for some more time to give the host cell the time to synthesize the polypeptide. Cultures are then typically frozen and may be stored frozen for some time, prior to isolation and purification of the polypeptide.

When using a prokaryotic host cell, the host cell may include a plasmid which expresses an internal T7 lysozyme, e.g., expressed from plasmid pLysSL (see Examples). Lysis of such host cells liberates the lysozyme which then degrades the bacterial membrane.

Other sequences that may be included in a vector for expression in bacterial or other prokaryotic cells include a synthetic ribosomal binding site; strong transcriptional terminators, e.g., $t_0$ from phage lambda and $t_4$ from the rrnB operon in *E. coli*, to prevent read through transcription and ensure stability of the expressed polypeptide; an origin of replication, e.g., ColE1; and beta-lactamase gene, conferring ampicillin resistance.

Other host cells include prokaryotic host cells. Even more preferred host cells are bacteria, e.g., *E. coli*. Other bacteria that can be used include *Shigella* spp., *Salmonella* spp., *Listeria* spp., *Rickettsia* spp., *Yersinia* spp., *Escherichia* spp., *Klebsiella* spp., *Bordetella* spp., *Neisseria* spp., *Aeromonas* spp., *Francisella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., and *Erysipelothrix* spp. Most of these bacteria can be obtained from the American Type Culture Collection (ATCC; 10801 University Blvd., Manassas, Va. 20110-2209).

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al., (1983) in *Experimental Manipulation of Gene Expression*, ed. M. Inouye Academic Press, p. 83). These vectors may replicate in *E. coli* due to the presence of the pBR322 ori, and in *S. cerevisiae* due to the replication determinant of the yeast 2 micron plasmid. In addition, drug resistance markers such as ampicillin may be used.

In certain embodiments, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal comprising pBlueBac III).

In another variation, protein production may be achieved using in vitro translation systems. In vitro translation systems are, generally, a translation system which is a cell-free extract comprising at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. An RNA nucleotide for in vitro translation may be produced using methods known in the art. In vitro transcription and translation may be coupled in a one-pot reaction to produce proteins from one or more isolated DNAs.

When expression of a carboxy terminal fragment of a polypeptide is desired, i.e. a truncation mutant, it may be necessary to add a start codon (ATG) to the oligonucleotide fragment comprising the desired sequence to be expressed. It is well known in the art that a methionine at the N-terminal position may be enzymatically cleaved by the use of the enzyme methionine aminopeptidase (MAP). MAP has been cloned from *E. coli* (Ben-Bassat et al., (1987) *J. Bacteriol.* 169:751-757) and *Salmonella typhimurium* and its in vitro activity has been demonstrated on recombinant proteins (Miller et al., (1987) *PNAS USA* 84:2718-1722). Therefore, removal of an N-terminal methionine, if desired, may be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

In cases where plant expression vectors are used, the expression of a fusion protein may be driven by any of a number of promoters. For example, viral promoters such as the 35S RNA and 19S RNA promoters of CaMV (Brisson et al., 1984, Nature, 310:511-514), or the coat protein promoter of TMV (Takamatsu et al., 1987, EMBO J., 6:307-311) may be used; alternatively, plant promoters such as the small subunit of RUBISCO (Coruzzi et al., 1994, EMBO J., 3:1671-1680; Broglie et al., 1984, Science, 224:838-843); or heat shock promoters, e.g., soybean hsp 17.5-E or hsp 17.3-B (Gurley et al., 1986, Mol. Cell. Biol., 6:559-565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, New York, Section VIII, pp. 421-463; and Grierson & Corey, 1988, Plant Molecular Biology, 2d Ed., Blackie, London, Ch. 7-9.

An alternative expression system which can be used to express a polypeptide tag or fusion protein comprising a polypeptide tag is an insect system. In one such system, *Autographa californica* nuclear polyhedrosis virus (AcNPV) is used as a vector to express foreign genes. The virus grows in *Spodoptera frugiperda* cells. The PGHS-2 sequence may be cloned into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Virol., 46:584, Smith, U.S. Pat. No. 4,215,051).

In a specific embodiment of an insect system, the DNA encoding fusion protein is cloned into the pBlueBacIII recombinant transfer vector (Invitrogen, San Diego, Calif.) downstream of the polyhedrin promoter and transfected into Sf9 insect cells (derived from *Spodoptera frugiperda* ovarian cells, available from Invitrogen, San Diego, Calif.) to generate recombinant virus. After plaque purification of the recombinant virus high-titer viral stocks are prepared that in turn would be used to infect Sf9 or High Five™ (BTI-TN-5B1-4 cells derived from *Trichoplusia ni* egg cell homogenates; available from Invitrogen, San Diego, Calif.) insect cells, to produce large quantities of appropriately post-translationally modified subject polypeptide.

In other embodiments, the components of any the fusion proteins of the invention are produced separately and then linked, e.g. covalently linked, to each other.

For example, an engineered mesothelin antibody or fragment thereof, and stress protein are produced separately in vitro, purified, and mixed together under conditions under which a tag, for example, a biotin or antibody binding protein, will be able to be linked to the polypeptide of interest. For example, the stress protein and/or the engineered mesothelin antibody or fragment thereof, can be obtained (isolated) from a source in which they are known to occur, can be produced and harvested from cell cultures, can be produced by cloning and expressing a gene encoding the desired stress protein or engineered mesothelin antibody, or can be synthesized chemically. Furthermore, a nucleic acid sequence encoding the desired stress protein or engineered mesothelin antibody or fragment thereof, or any component of the fusion proteins of the invention, can be synthesized chemically. Such mixtures of conjugated proteins may have properties different from single fusion proteins.

Linkers (also known as "linker molecules" or "cross-linkers") may be used to conjugate the components of an fusion protein according to the invention. Linkers include chemicals able to react with a defined chemical group of several, usually two, molecules and thus conjugate them. The majority of known cross-linkers react with amine, carboxyl, and sulfhydryl groups. The choice of target chemical group is crucial if the group may be involved in the biological activity of the polypeptides to be conjugated. For example, maleimides, which react with sulfhydryl groups, may inactivate Cys-comprising peptides or proteins that require the Cys to bind to a target. Linkers may be homofunctional (comprising reactive groups of the same type), heterofunctional (comprising different reactive groups), or photoreactive (comprising groups that become reactive on illumination.

Linker molecules may be responsible for different properties of the conjugated compositions. The length of the linker should be considered in light of molecular flexibility during the conjugation step, and the availability of the conjugated molecule for its target (cell surface molecules and the like.) Longer linkers may thus improve the biological activity of the compositions of the present invention, as well as the ease of preparation of them. The geometry of the linker may be used to orient a molecule for optimal reaction with a target. A linker with flexible geometry may allow the cross-linked polypeptides to conformationally adapt as they bind other polypeptides. The nature of the linker may be altered for other various purposes. For example, the aryl-structure of MBuS was found to be less immunogenic than the aromatic spacer of MBS. Furthermore, the hydrophobicity and functionality of the linker molecules may be controlled by the physical properties of component molecules. For example, the hydrophobicity of a polymeric linker may be controlled by the order of monomeric units along the polymer, e.g. a block polymer in which there is a block of hydrophobic monomers interspersed with a block of hydrophilic monomers.

A linker or cross-linker that is useful according to the invention can facilitate proper folding of the fusion protein, improve the biological activity of the fusion proteins of the invention, can facilitate preparation of the fusion proteins of the invention etc. . . .

A linker can also function to provide for proper folding of the heavy and light chain segments of the scFv. A "linker" according to the invention may also contribute to target recognition.

Any suitable amino acid linker that does not interfere with proper protein folding and function is useful according to the invention.

In one embodiment, a linker is a combination of nucleic acids that yields a series of neutral or slightly polar amino acids that facilitates proper folding of the fusion protein If an amino acid side chain cannot be ionized it is considered polar but neutral. For example, aspartate is polar and acidic because the carboxylic side chain can be ionized. Tyrosine is polar. The hydroxyl group on the phenyl ring is not easily ionized thus it is considered polar but neutral.

In one embodiment, a linker consists of nucleic acids encoding the following amino acid sequence: GGSSRSS (SEQ ID NO: 1). In another embodiment, the linker consists of nucleic acids encoding the following amino acid sequence: (GGGSGGG)×4 (SEQ ID NO: 2).

In another embodiment the linker sequence comprises the sequence (Gly4Ser)3 (SEQ ID NO: 3); GGGGSGGGGSGGGGS (SEQ ID NO: 3). It is preferable to include glycine in the linker sequence because it has an H-side chain whereas all other amino acids have bulkier side chains. Linkers include chemicals able to react with a defined chemical group of several, usually two, molecules and thus conjugate them. The majority of known cross-linkers react with amine, carboxyl, and sulfhydryl groups. The choice of target chemical group is crucial if the group may be involved in the biological activity of the proteins to be conjugated. For example, maleimides, which react with sulfhydryl groups, may inactivate Cys-comprising proteins that require the Cys to bind to a target. Linkers may be homofunctional (comprising reactive groups of the same type), heterofunctional (comprising different reactive groups), or photoreactive (comprising groups that become reactive on illumination).

Linker molecules may be responsible for different properties of the conjugated compositions. The length of the linker should be considered in light of molecular flexibility during the conjugation step, and the availability of the conjugated molecule for its target (cell surface molecules and the like.) Longer linkers may thus improve the biological activity of the compositions of the present invention, as well as the ease of preparation of them. The geometry of the linker may be used to orient a molecule for optimal reaction with a target. A linker with flexible geometry may allow the cross-linked proteins to conformationally adapt as they bind other proteins. The nature of the linker may be altered for other various purposes. For example, the aryl-structure of MBuS was found less immunogenic than the aromatic spacer of MBS. Furthermore, the hydrophobicity and functionality of the linker molecules may be controlled by the physical properties of component molecules. For example, the hydrophobicity of a polymeric linker may be controlled by the order of monomeric units along the polymer, e.g. a block polymer in which there is a block of hydrophobic monomers interspersed with a block of hydrophilic monomers.

The chemistry of preparing and utilizing a wide variety of molecular linkers is well-known in the art and many pre-made linkers for use in conjugating molecules are commercially available from vendors such as Pierce Chemical Co., Roche Molecular Biochemicals, United States Biological, and the like.

The prepared and/or isolated heat shock protein fused to a biotin-binding protein is to be administered to a subject in conjunction with the desired biotinylated components, sufficient to form a non-covalent association of the biotin moiety with the biotin-binding protein. The heat shock protein fusion and the biotinylated component or components may be administered simultaneously or sequentially. If administered simultaneously, the heat shock protein fusion and the biotinylated component or components may be administered as a mixture or as a noncovalent complex. If administered as a noncovalent complex, a heat shock protein fused to a biotin-binding protein may be noncovalently bound to the desired biotinylated components either in vitro or in vivo once prepared and/or isolated.

The chemistry of preparing and utilizing a wide variety of molecular linkers is well-known in the art and many pre-made linkers for use in conjugating molecules are commercially available from vendors such as Pierce Chemical Co., Roche Molecular Biochemicals, United States Biological, and the like.

3. Methods of Using the Fusion Proteins

The fusion proteins described herein can be administered to a subject to enhance that subject's immune response, particularly a cell-mediated cytolytic response, against a cell expressing mesothelin. The fusion protein may simply enhance the immune response (thus serving as an immunogenic composition), or confer protective immunity (thus serving as a vaccine).

Thus, the protein fusion polypeptides produced as described above may be purified to a suitable purity for use as a pharmaceutical composition. Generally, a purified composition will have one species that comprises more than about 85 percent of all species present in the composition, more than about 85%, 86%, 875, 88%, 89%, 90%, 91%, 92%, 93%, 94%, 95%, 96%, 97%, 98%, 99% or more of all species present. The object species may be purified to essential homogeneity (contaminant species cannot be detected in the composition by conventional detection methods) wherein the composition consists essentially of a single species. A skilled artisan may purify a fusion protein using standard techniques for protein purification, for example, immunoaffinity chromotography, size exclusion chromatography, etc. in light of the teachings herein. Purity of a polypeptide may be determined by a number of methods known to those of skill in the art, including for example, amino-terminal amino acid sequence analysis, gel electrophoresis and mass-spectrometry analysis.

Accordingly, provided are pharmaceutical compositions comprising the above-described fusion proteins. In one aspect, provided are pharmaceutically acceptable compositions which comprise a therapeutically-effective amount of one or more of the compounds described above and below, formulated together with one or more pharmaceutically acceptable carriers (additives) and/or diluents. In another aspect, in certain embodiments, the compounds may be administered as such or in admixtures with pharmaceutically acceptable carriers and may also be administered in conjunction with other agents. Conjunctive (combination) therapy thus includes sequential, simultaneous and separate, or co-administration of the active compound in a way that the therapeutic effects of the first administered one has not entirely disappeared when the subsequent is administered.

The fusion proteins described herein can be administered to a subject in a variety of ways. The routes of administration include intradermal, transdermal (e.g., slow release polymers), intramuscular, intraperitoneal, intravenous, subcutaneous, oral, epidural and intranasal routes. Any other convenient route of administration can be used, for example, infusion or bolus injection, or absorption through epithelial or mucocutaneous linings. In addition, the compositions described herein can contain and be administered together with other pharmacologically acceptable components such as biologically active agents (e.g., adjuvants such as alum), surfactants (e.g., glycerides), excipients (e.g., lactose), carriers, diluents and vehicles. Furthermore, the compositions can be used ex vivo as a means of stimulating white blood cells obtained from a subject to elicit, expand and propagate antigen-specific immune cells in vitro that are subsequently reintroduced into the subject.

Further, a fusion protein can be administered by in vivo expression of a nucleic acid encoding such protein sequences into a human subject. Expression of such a nucleic acid can also be achieved ex vivo as a means of stimulating white blood cells obtained from a subject to elicit, expand and propagate mesothelin-specific immune cells in vitro that are subsequently reintroduced into the subject. Expression vectors suitable for directing the expression of a fusion protein of interest can be selected from the large variety of vectors currently used in the field. Preferred will be vectors that are capable of producing high levels of expression as well as are effective in transducing a gene of interest. For example, recombinant adenovirus vector pJM17 (All et al., *Gene Therapy* 1:367-84 (1994); Berkner K. L., *Biotechniques* 6:616-24 1988), second generation adenovirus vectors DE1/DE4 (Wang and Finer, *Nature Medicine* 2:714-6 (1996)), or adeno-associated viral vector AAV/Neo (Muro-Cacho et al., *J. Immunotherapy* 11:231-7 (1992)) can be used. Furthermore, recombinant retroviral vectors MFG (Jaffee et al., *Cancer Res.* 53:2221-6 (1993)) or LN, LNSX, LNCX, LXSN (Miller and Rosman, *Biotechniques* 7:980-9 (1989)) can be employed. Herpes simplex virus-based vectors such as pHSV1 (Geller et al., *Proc. Nat'l Acad. Sci.* 87:8950-4 (1990) or vaccinia viral vectors such as MVA (Sutter and Moss. *Proc. Nat'l Acad. Sci.* 89:10847-51 (1992)) can serve as alternatives.

Frequently used specific expression units including promoter and 3' sequences are those found in plasmid CDNA3 (Invitrogen), plasmid AH5, pRC/CMV (Invitrogen), pCMU II (Paabo et al., EMBO J. 5:1921-1927 (1986)), pZip-Neo SV (Cepko et al., Cell 37:1053-1062 (1984)) and pSRa (DNAX, Palo Alto, Calif.). The introduction of genes into expression units and/or vectors can be accomplished using genetic engineering techniques, as described in manuals like Molecular Cloning and Current Protocols in Molecular Biology (Sambrook, J., et al., Molecular Cloning, Cold Spring Harbor Press (1989); Ausubel, F. M. et al., Current Protocols in Molecular Biology, Greene Publishing Associates and Wiley-Interscience (1989)). A resulting expressible nucleic acid can be introduced into cells of a human subject by any method capable of placing the nucleic acid into cells in an expressible form, for example as part of a viral vector such as described above, as naked plasmid or other DNA, or encapsulated in targeted liposomes or in erythrocyte ghosts (Friedman, T., *Science,* 244:1275-1281 (1989); Rabinovich, N. R. et al., *Science.* 265:1401-1404 (1994)). Methods of transduction include direct injection into tissues and tumors, liposomal transfection (Fraley et al., *Nature* 370:111-117 (1980)), receptor-mediated endocytosis (Zatloukal et al., *Ann. N.Y. Acad. Sci.* 660:136-153 (1992)), and particle bombardment-mediated gene transfer (Eisenbraun et al., *DNA & Cell. Biol.* 12:791-797 (1993)).

The amount of fusion polypeptide (fused, conjugated or noncovalently joined as discussed before) in the compositions of the present invention is an amount which produces an effective immunostimulatory response in a subject as determined by the methods described herein. An effective amount is an amount such that when administered, it induces an immune response. In addition, the amount of fusion protein administered to the subject will vary depending on a variety of factors, including the engineered antibody and stress protein employed, the size, age, body weight, general health, sex, and diet of the subject as well as on the subject's general immunological responsiveness. Adjustment and manipulation of established dose ranges are well within the ability of those skilled in the art. For example, the amount of engineered fusion protein according to the invention, for example, mesothelin antibody-stress protein fusion protein, can be from about 1 microgram to about 1 gram, preferably from about 100 microgram to about 1 gram, and from about 1 milligram to about 1 gram. An effective amount of a composition comprising an expression vector is an amount such that when administered, it induces an immune response against mesothelin against which the engineered antibody or fragment thereof, is directed. Furthermore, the amount of expression vector administered to the subject will vary depending on a variety of factors, including the engineered mesothelin antibody and stress protein expressed, the size, age, body weight, general health, sex, and diet of the subject, as well as on the subject's general immunological responsiveness. Additional factors that need to be considered are the route of application and the type of vector used. For example, when prophylactic or therapeutic treatment is carried out with a viral vector containing a nucleic acid encoding an engineered fusion protein according to the invention, the effective amount will be in the range of $10^4$ to $10^{12}$ helper-free, replication-defective virus per kg body weight, preferably in the range of $10^5$ to $10^{11}$ virus per kg body weight and most preferably in the range of $10^6$ to $10^{10}$ virus per kg body weight.

Fusion proteins of the invention can also be administered in combination with another factor. For example, a fusion protein comprising a stress protein fused to a biotin binding protein is administered with a biotinylated antibody or fragment thereof that binds specifically to mesothelin, to form a non-covalent interaction. In another embodiment, a fusion protein comprising a stress protein fused to an antibody binding protein is administered with an antibody or fragment thereof that binds specifically to mesothelin, to form a non-covalent interaction.

In one embodiment the ratio of stress protein-biotin binding protein fusion to biotinylated antibody or the ratio of stress protein-antibody binding protein to antibody is 1:1. The methods of the invention also include ratios of stress protein-biotin binding protein fusion to biotinylated antibody or the ratio of stress protein-antibody binding protein to antibody wherein the ratio is 1:1.1, 1:1.2, 1:1.3, 1:1.4, 1:1.5, 1:1.6, 1:1.7, 1:1.8, 1:1.9, 1:2, 1:2.5, 1:3, 1:3.5, 1:4, 1:5 or more.

4. Self-Assembling Vaccines

Multiple components may be administered in conjunction with a heat shock protein fusion as further described. For example, a fusion protein comprising a stress protein fused to either a biotin binding protein or an antibody binding protein can be administered in conjunction with a biotinylated antibody or fragment thereof that binds specifically to mesothelin or an antibody or fragment thereof that binds specifically to mesothelin, respectively. In this way, multivalent pharmaceutical compositions may be generated and administered to a subject. The generation of multivalent pharmaceutical compositions allow for the production of "supercharged," or more potent vaccines and therapeutics. When the biotinylated component comprises an antibody, such vaccine exhibits activity improvement for marketed antibodies. Alternatively, an antibody that binds specifically to mesothelin can be used in combination with a stress protein fused to an antibody binding protein to produce a vaccine that exhibits increased activity.

Wherein the pharmaceutical composition is multivalent, the biotinylated components to be administered may be any combination of biotinylated components described herein. For example, biotinylated components of the same or different identities may be administered in conjunction with a heat shock protein fusion as provided herein, provided that the biotin-binding protein, and in turn the heat shock protein fusion, is multivalent, or capable of binding multiple biotinylated components. As an example, the wild-type biotin-binding protein avidin has four biotin-binding sites and is therefore capable of binding four biotinylated components. In this example, the four sites are to be bound by four biotinylated components, and the biotin-binding components may be mixed and matched based on identity in any possible permutation of one, two, three, or four identical biotinylated components described herein. Four identical biotinylated components may be bound to the four biotin-binding sites.

Therefore, an effective amount of a biotinylated component with a first identity may be may be administered to a subject in conjunction with a heat shock protein fused to a biotin-binding protein, sufficient to form a pharmaceutical composition comprising four parts biotinylated component of a first identity and one part heat shock protein fused to a biotin-binding protein. Alternatively, an effective amount of biotinylated components with a first and second identity may be may be administered to a subject in conjunction with a heat shock protein fused to a biotin-binding protein, sufficient to form a pharmaceutical composition comprising three parts biotinylated component of a first identity, one part biotinylated component of a second identity, and one part heat shock protein fusion. In another embodiment, an effective amount of biotinylated components with a first and second identity may be administered to a subject in conjunction with a heat shock protein fused to a biotin-binding protein, sufficient to form a pharmaceutical composition comprising two parts biotinylated component of a first identity, two parts biotinylated component of a second identity, and one part heat shock protein fusion.

Wherein the self-assembling pharmaceutical composition is divalent, an effective amount of biotinylated component of a first identity may be administered to a subject in conjunction with a heat shock protein fused to a biotin-binding protein, sufficient to form a pharmaceutical composition comprising two parts biotinylated component of a first identity and one part heat shock protein fusion. Alternatively, an effective amount of biotinylated components with a first and second identity may be administered to a subject in conjunction with a heat shock protein fused to a biotin-binding protein, sufficient to form a pharmaceutical composition comprising one part biotinylated component of a first identity, one part biotinylated component of a second identity, and one part heat shock protein fusion.

A biotinylated component of a multivalent pharmaceutical composition may include a costimulatory molecule, or a blocking group (i.e., biotin alone or biotin conjugated to a non-functional molecule). Examples of costimulatory molecules that may be administered in conjunction with the present invention include B7 molecules, including B7-1 (CD80) and B7-2 (CD86), CD28, CD58, LFA-3, CD40, B7-H3, CD137 (4-1BB), and interleukins (e.g., IL-1, IL-2, or IL-12). As an example, one part biotinylated component comprising a costimulatory molecule may be administered in conjunction with i) three parts of another biotinylated component comprising a protein, cell or virus; and ii) one part heat shock protein fused to a biotin-binding protein. In another example, two parts biotinylated component comprising a costimulatory molecule may be administered in conjunction with i) two parts of another biotinylated component comprising a protein, cell, or virus; and ii) one part heat shock protein fused to a biotin-binding protein. In another example, three parts biotinylated component comprising a costimulatory molecule may be administered in conjunction with i) one part of another biotinylated component comprising a protein, cell, or virus; and ii) one part heat shock protein fused to a biotin-binding protein.

A pH-sensitive mutant of avidin, streptavidin, or neutravidin, for example, may be employed to control the noncovalent interaction of avidin-, streptavidin-, or neutravidin-to biotin, and thereby achieve the desired stoichiometry of heat shock protein fusion with the various permutations and combinations of biotinylated component, as described herein. The choice of wild-type or a particular mutant form of biotin-binding protein such as avidin may be employed to control the desired valency of the pharmaceutical composition (e.g., monomeric, dimeric, or tetrameric form of avidin). Monovalent or divalent vaccines may be similarly produced by employing heat shock fusion proteins comprising other avidin, streptavidin, or neutravidin mutant proteins that bind biotin but in a monovalent or divalent fashion. An example of a pH-sensitive point mutant of Avidin which confers pH-adjustable biotin binding is Y33H. Another mutant has substitutions of histidine for Met96, Val115, and Ile117, optionally with histidine replacement at Trp110. Such approaches for controlling biotin-streptavidin binding are described in Laitinen, O. H. (2007), "Brave New (Strept)avidins in Biotechnology," *Trends in Biotechnology* 25 (6): 269-277 and Nordlund, H. R. (2003), "Introduction of histidine residues into avidin subunit interfaces allows pH-dependent regulation of quaternary structure and biotin binding," *FEBS Letters* 555: 449-454, the contents of both of which are incorporated herein by reference.

5. Methods of Producing the Self-Assembling Pharmaceutical Compositions

In one embodiment of the present invention, compositions are comprised of two moieties: a heat shock protein fused to a biotin-binding protein in combination with a biotinylated component which targets the immune response to the antigen to which the immune response is desired, for example, mesothelin. The present invention provides for fast, easy production of large amounts pharmaceutical composition (e.g., vaccine) because the production of biotinylated antigens or antibodies is well known and rapid, which, in turn, allows for an increased capacity for vaccine production. Because a heat shock protein fusion of a single identity may be administered in conjunction with any of a number of various biotinylated components as described herein, the heat shock fusion protein need not be synthesized de novo each time a new target antigen of interest is identified. Therefore, such methods of production are particularly rapid once the heat shock protein fusion to be administered is established and has been produced.

Methods for making the heat shock protein fused to a biotin-binding protein or antibody binding protein are described in detail hereinabove.

The heat shock protein may be prepared, using standard techniques, from natural sources, for example as described in Flynn et al., Science 245:385-390 (1989), or using recombinant techniques such as expression of a heat shock encoding gene construct in a suitable host cell such as a bacterial, yeast or mammalian cell. A fusion protein including the heat shock protein and biotin-binding protein can be produced by recombinant means. For example, a nucleic acid encoding the heat shock protein can be joined to either end of a nucleic acid sequence encoding the biotin-binding protein such that the two protein-coding sequences are sharing a common translational reading frame and can be expressed as a fusion protein including the biotin-binding protein and the heat shock protein. The combined sequence is inserted into a suitable vector chosen based on the expression features desired and the nature of the host cell. In the examples provided hereinafter, the nucleic acid sequences are assembled in a vector suitable for protein expression in the bacterium *E. coli*. Following expression in the chosen host cell, the fusion protein can be purified by routine biochemical separation techniques or by immunoaffinity methods using an antibody to one or the other part of the fusion protein. Alternatively, the selected vector can add a tag to the fusion protein sequence, e.g., an oligohistidine tag as described in the examples presented hereinafter, permitting expression of a tagged fusion protein that can be purified by affinity methods using an antibody or other material having an appropriately high affinity for the tag. Sambrook et al., Molecular Cloning: A Laboratory Manual, 2d Ed., Cold Spring Harbor Laboratory Press (1989); Deutscher, M. Guide to Protein Purification Methods Enzymology, vol. 182. Academic Press, Inc. San Diego, Calif. (1990). If a vector suitable for expression in mammalian cells is used. e.g., one of the vectors discussed below, the heat shock protein fusion can be expressed and purified from mammalian cells. Alternatively, the mammalian expression vector (including fusion protein-coding sequences) can be administered to a subject to direct expression of heat shock protein fusion protein in the subject's cells. A nucleic acid encoding a heat shock protein can also be produced chemically and then inserted into a suitable vector for fusion protein production and purification or administration to a subject. Finally, a fusion protein can also be prepared chemically.

Linkers (also known as "linker molecules" or "cross-linkers") may be used to conjugate the components of any fusion protein according to the invention.

The invention also provides for linkers or cross-linkers that can be used to conjugate the two or more components of a fusion protein of the invention. Cross-linkers include chemicals able to react with a defined chemical group of several, usually two, molecules and thus conjugate them. The majority of known cross-linkers react with amine, carboxyl, and sulfhydryl groups. The choice of target chemical group is crucial if the group may be involved in the biological activity of the polypeptides to be conjugated. For example, maleimides, which react with sulfhydryl groups, may inactivate Cys-comprising peptides or proteins that require the Cys to bind to a target. Linkers may be homofunctional (comprising reactive groups of the same type), heterofunctional (comprising different reactive groups), or photoreactive (comprising groups that become reactive on illumination).

The prepared and/or isolated heat shock protein fused to a biotin-binding protein is to be administered to a subject in conjunction with the desired biotinylated components, sufficient to form a non-covalent association of the biotin moiety with the biotin-binding protein. The heat shock protein fusion and the biotinylated component or components may be administered simultaneously or sequentially. If administered simultaneously, the heat shock protein fusion and the biotinylated component or components may be administered as a mixture or as a noncovalent complex. If administered as a noncovalent complex, a heat shock protein fused to a biotin-binding protein may be noncovalently bound to the desired biotinylated components either in vitro or in vivo once prepared and/or isolated.

The noncovalent complex may be produced by contacting the heat shock protein fused to a biotin-binding protein with the biotinylated components, under conditions sufficient to promote the binding of the biotin-binding protein with biotin, which conditions are known in the art.

Genes for various heat shock proteins have been cloned and sequenced, and which may be used to obtain a heat shock protein fusion, including, but not limited to, gp96 (human: Genebank Accession No. X15187; Maki et al., Proc. Natl. Acad. Sci. U.S.A. 87:5658-5562 (1990); mouse: Genebank Accession No. M16370; Srivastava et al., Proc. Natl. Acad. Sci. U.S.A. 84:3807-3811 (1987)), BiP (mouse: Genebank Accession No. U16277; Haas et al., Proc. Natl. Acad. Sci. U.S.A. 85:2250-2254 (1988); human: Genebank Accession No. M19645; Ting et al., DNA 7:275-286 (1988)), hsp70 (mouse: Genebank Accession No. M35021; Hunt et al., Gene 87:199-204 (1990); human: Genebank Accession No. M24743; Hunt et al, Proc. Natl. Acad. Sci. U.S.A. 82:6455-6489 (1995)), and hsp40 (human: Genebank Accession No. D49547; Ohtsuka K., Biochem. Biophys. Res. Commun. 197:235-240 (1993)).

The heat shock protein fused to a biotin-binding protein may be non-covalently bound to the biotinylated component.

The component to be administered in conjunction with the heat shock protein comprising the protein, cell, or virus may be conjugated to biotin by means such as is known in the art. Prior to conjugation to biotin, the protein, cell, or virus may be produced and/or isolated using methods known in the art. Recombinant techniques may be employed in much the same way as described herein for the heat shock protein fusion. Once the component is produced and/or isolated, a biotin molecule or molecules may be conjugated directly to a protein, cell, or virus. Biotin may also be conjugated indirectly through a linker to said protein, cell, or virus. Biotin is to be conjugated to a region that sterically allows for the interaction of biotin with the biotin-binding protein. Biotinylation kits and reagents may be purchased from Pierce (Rockford, Ill.) and used to generate the biotinylated components described herein.

The sequences of many different antigens can be cloned and characterized by DNA sequence analysis and included in the compositions provided herein. Bacterial vectors containing complete or partial cellular or viral genomes or antigens may be obtained from various sources including, for example, the American Tissue Culture Collection (ATCC). Additional antigens which may be used can be isolated and typed by the methods previously established for this purpose, which methods are well known in the art.

6. Methods of Using the Heat Shock Protein Fusion and Biotinylated Components

The heat shock protein fusion and biotinylated components described herein can be administered to a subject to induce or enhance that subject's immune response, particularly a cell-mediated cytolytic response, against a cell expressing an antigen against which the biotinylated components are directed. The fusion protein may simply enhance the immune response (thus serving as an immunogenic composition), or confer protective immunity (thus serving as a vaccine).

Thus, the heat shock protein fusion and biotinylated components produced as described above may be purified to a suitable purity for use as a pharmaceutical composition. Generally, purified compositions will have one species that comprises more than about 85 percent of all species present in the composition, more than about 85%, 90%, 95%, 99% or more of all species present. The object species may be purified to essential homogeneity (contaminant species cannot be detected in the composition by conventional detection methods) wherein the composition consists essentially of a single species. A skilled artisan may purify a heat shock protein fusion and biotinylated components, or a non-covalent complex of the same, using standard techniques for purification, for example, immunoaffinity chromotography, size exclusion chromatography, etc. in light of the teachings herein. Purity of a protein may be determined by a number of methods known to those of skill in the art, including for example, amino-terminal amino acid sequence analysis, gel electrophoresis and mass-spectrometry analysis.

Accordingly, provided are pharmaceutical compositions comprising the above-described heat shock protein fusion and biotinylated components, or a non-covalent complex of the same. In one aspect, provided are pharmaceutically acceptable compositions which comprise a therapeutically-effective amount of one or more of the pharmaceutical compositions described herein, formulated together with one or more pharmaceutically acceptable carriers (additives) and/or diluents. In another aspect, in certain embodiments, the pharmaceutical compositions may be administered as such or in admixtures with pharmaceutically acceptable carriers and may also be administered in conjunction with other agents. Conjunctive (combination) therapy thus includes sequential, simultaneous and separate, or co-administration in a way that the therapeutic effects of the first administered one has not entirely disappeared when the subsequent is administered.

The heat shock protein fusion and biotinylated components, or components bound to an antibody-binding protein, or a non-covalent complex of the same, as described herein can be administered to a subject in a variety of ways. The routes of administration include systemic, peripheral, parenteral, enteral, topical, and transdermal (e.g., slow release polymers). Any other convenient route of administration can be used, for example, infusion or bolus injection, or absorption through epithelial or mucocutaneous linings. In addition, the compositions described herein can contain and be administered together with or without other pharmacologically acceptable components such as biologically active agents (e.g., adjuvants such as alum), surfactants (e.g., glycerides), excipients (e.g., lactose), carriers, diluents and vehicles. Furthermore, the compositions can be used ex vivo as a means of stimulating white blood cells obtained from a subject to elicit, expand and propagate antigen-specific immune cells in vitro that are subsequently reintroduced into the subject.

Further, a heat shock protein fusion protein can be administered by in vivo expression of a nucleic acid encoding such protein sequences into a human subject. Expression of such a nucleic acid and contact with biotinylated components can also be achieved ex vivo as a means of stimulating white blood cells obtained from a subject to elicit, expand and propagate antigen-specific immune cells in vitro that are subsequently reintroduced into the subject. Expression vectors suitable for directing the expression of heat shock protein fusion proteins can be selected from the large variety of vectors currently used in the field. Preferred will be vectors that are capable of producing high levels of expression as well as are effective in transducing a gene of interest. For example, recombinant adenovirus vector pJM17 (All et al., *Gene Therapy* 1:367-84 (1994); Berkner K. L., *Biotechniques* 6:616-24 1988), second generation adenovirus vectors DE1/DE4 (Wang and Finer, *Nature Medicine* 2:714-6 (1996)), or adeno-associated viral vector AAV/Neo (Muro-Cacho et al., *J. Immunotherapy* 11:231-7 (1992)) can be used. Furthermore, recombinant retroviral vectors MFG (Jaffee et al., *Cancer Res.* 53:2221-6 (1993)) or LN, LNSX, LNCX, LXSN (Miller and Rosman, *Biotechniques* 7:980-9 (1989)) can be employed. Herpes simplex virus-based vectors such as pHSV1 (Geller et al., *Proc. Nat'l Acad. Sci.* 87:8950-4 (1990) or vaccinia viral vectors such as MVA (Sutter and Moss. *Proc. Nat'l Acad. Sci.* 89:10847-51 (1992)) can serve as alternatives.

Frequently used specific expression units including promoter and 3' sequences are those found in plasmid CDNA3 (Invitrogen), plasmid AH5, pRC/CMV (Invitrogen), pCMU II (Paabo et al., EMBO J. 5:1921-1927 (1986)), pZip-Neo SV (Cepko et al., Cell 37:1053-1062 (1984)) and pSRa (DNAX, Palo Alto, Calif.). The introduction of genes into expression units and/or vectors can be accomplished using genetic engineering techniques, as described in manuals like Molecular Cloning and Current Protocols in Molecular Biology (Sambrook, J., et al., Molecular Cloning, Cold Spring Harbor Press (1989); Ausubel, F. M. et al., Current Protocols in Molecular Biology, Greene Publishing Associates and Wiley-Interscience (1989)). A resulting expressible nucleic acid can be introduced into cells of a human subject by any method capable of placing the nucleic acid into cells in an expressible form, for example as part of a viral vector such as described above, as naked plasmid or other DNA, or encapsulated in targeted liposomes or in erythrocyte ghosts (Friedman, T., *Science,* 244:1275-1281 (1989); Rabinovich, N. R. et al., *Science.* 265:1401-1404 (1994)). Methods of transduction include direct injection into tissues and tumors, liposomal transfection (Fraley et al., *Nature* 370:111-117 (1980)), receptor-mediated endocytosis (Zatloukal et al., *Ann. N.Y. Acad. Sci.* 660:136-153 (1992)), and particle bombardment-mediated gene transfer (Eisenbraun et al., *DNA & Cell. Biol.* 12:791-797 (1993)).

The amount of heat shock protein fusion and biotinylated components, or a non-covalent complex of the same, in the compositions of the present invention is an amount which produces an effective immunostimulatory response in a subject. An effective amount is an amount such that when administered, it induces an immune response. In addition, the amount of heat shock protein fusion and biotinylated components, or a non-covalent complex of the same, administered to the subject will vary depending on a variety of factors, including the heat shock protein fusion and biotinylated component employed, the size, age, body weight, general health, sex, and diet of the subject as well as on the subject's general immunological responsiveness. Adjustment and manipulation of established dose ranges are well within the ability of those skilled in the art. For example, the amount of heat shock protein fusion, biotinylated components, or a non-covalent complex of the same can be from about 1 microgram to about 1 gram, preferably from about 100 microgram to about 1 gram, and from about 1 milligram to about 1 gram. An effective amount of a composition comprising an expression vector is an amount such that when administered, it induces an immune response against the antigen against which the pharmaceutical composition is directed. Furthermore, the amount of expression vector administered to the subject will vary depending on a variety of factors, including the heat shock protein fusion expressed, the size, age, body weight, general health, sex, and diet of the subject, as well as on its general immunological responsiveness. Additional factors that need to be considered are the route of application and the type of vector used. For example, when prophylactic or therapeutic treatment is carried out with a viral vector containing a nucleic acid encoding heat shock protein fusion, the effective amount will be in the range of $10^4$ to $10^{12}$ helper-free, replication-defective virus per kg body weight, preferably in the range of $10^5$ to $10^{11}$ virus per kg body weight and most preferably in the range of $10^6$ to $10^{10}$ virus per kg body weight.

Determination of an effective amount of fusion protein and biotinylated components, or a non-covalent complex of the same, for inducing an immune response in a subject is well within the capabilities of those skilled in the art, especially in light of the detailed disclosure provided herein.

An effective dose can be estimated initially from in vitro assays. For example, a dose can be formulated in animal models to achieve an induction of an immune response using techniques that are well known in the art. One having ordinary skill in the art could readily optimize administration to humans based on animal data. Dosage amount and interval may be adjusted individually. For example, when used as a vaccine, the proteins and/or strains of the invention may be administered in about 1 to 3 doses for a 1-36 week period. Preferably, 3 doses are administered, at intervals of about 3-4 months, and booster vaccinations may be given periodically thereafter. Alternate protocols may be appropriate for individual patients. A suitable dose is an amount of protein or strain that, when administered as described above, is capable of raising an immune response in an immunized patient sufficient to protect the patient from the condition or infection for at least 1-2 years.

The compositions may also include adjuvants to enhance immune responses. In addition, such proteins may be further suspended in an oil emulsion to cause a slower release of the proteins in vivo upon injection. The optimal ratios of each component in the formulation may be determined by techniques well known to those skilled in the art.

Any of a variety of adjuvants may be employed in the vaccines of this invention to enhance the immune response. Most adjuvants contain a substance designed to protect the antigen from rapid catabolism, such as aluminum hydroxide or mineral oil, and a specific or nonspecific stimulator of immune responses, such as lipid A, or *Bortadella pertussis*. Suitable adjuvants are commercially available and include, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A, quil A, SBAS1c, SBAS2 (Ling et al., 1997, Vaccine 15:1562-1567), SBAS7, $Al(OH)_3$ and CpG oligonucleotide (WO96/02555).

In the vaccines of the present invention, the adjuvant may induce a Th1 type immune response. Suitable adjuvant systems include, for example, a combination of monophosphoryl lipid A, preferably 3-de-O-acylated monophosphoryl lipid A (3D-MPL) together with an aluminum salt. An enhanced system involves the combination of a monophosphoryl lipid A and a saponin derivative, particularly the combination of 3D-MLP and the saponin QS21 as disclosed in WO 94/00153, or a less reactogenic composition where the QS21 is quenched with cholesterol as disclosed in WO 96/33739. Previous experiments have demonstrated a clear synergistic effect of combinations of 3D-MLP and QS21 in the induction of both humoral and Th1 type cellular immune responses. A particularly potent adjuvant formation involving QS21, 3D-MLP and tocopherol in an oil-in-water emulsion is described in WO 95/17210 and may comprise a formulation.

7. Kits

The present invention provides kits for expressing an engineered fusion protein according to the invention. Such kits may be comprised of nucleic acids encoding an engineered fusion protein of the invention. The nucleic acids may be included in a plasmid or a vector, e.g., a bacterial plasmid or viral vector. Other kits comprise an engineered fusion polypeptide. Furthermore, the present invention provides kits for producing and/or purifying fusion polypeptides according to the invention.

The present invention provides kits for expressing or administering a fusion protein of the invention, either alone or in combination with a biotinylated or non-biotinylated antibody or fragment thereof that binds specifically to mesothelin. Such kits may be comprised of nucleic acids encoding the fusion protein of interest. The nucleic acids may be included in a plasmid or a vector, e.g., a bacterial plasmid or viral vector. Other kits comprise a heat shock protein fused to a biotin-binding protein or an antibody-binding protein. Furthermore, the present invention provides kits for producing and/or purifying a fusion protein of the invention. Such kits may optionally include biotinylated components or biotinylation reagents as described herein.

The present invention provides kits for preventing or treating infectious, inflammatory, autoimmune or malignant disease in a patient. For example, a kit may comprise one or more pharmaceutical compositions as described above and optionally instructions for their use. In still other embodiments, the invention provides kits comprising one more pharmaceutical composition and one or more devices for accomplishing administration of such compositions.

Kit components may be packaged for either manual or partially or wholly automated practice of the foregoing methods. In other embodiments involving kits, instructions for their use may be provided.

EXAMPLES

Example 1

Production of MTBhsp70/Huhsp70-Anti-Mesothelin Constructs

Figure 18A:
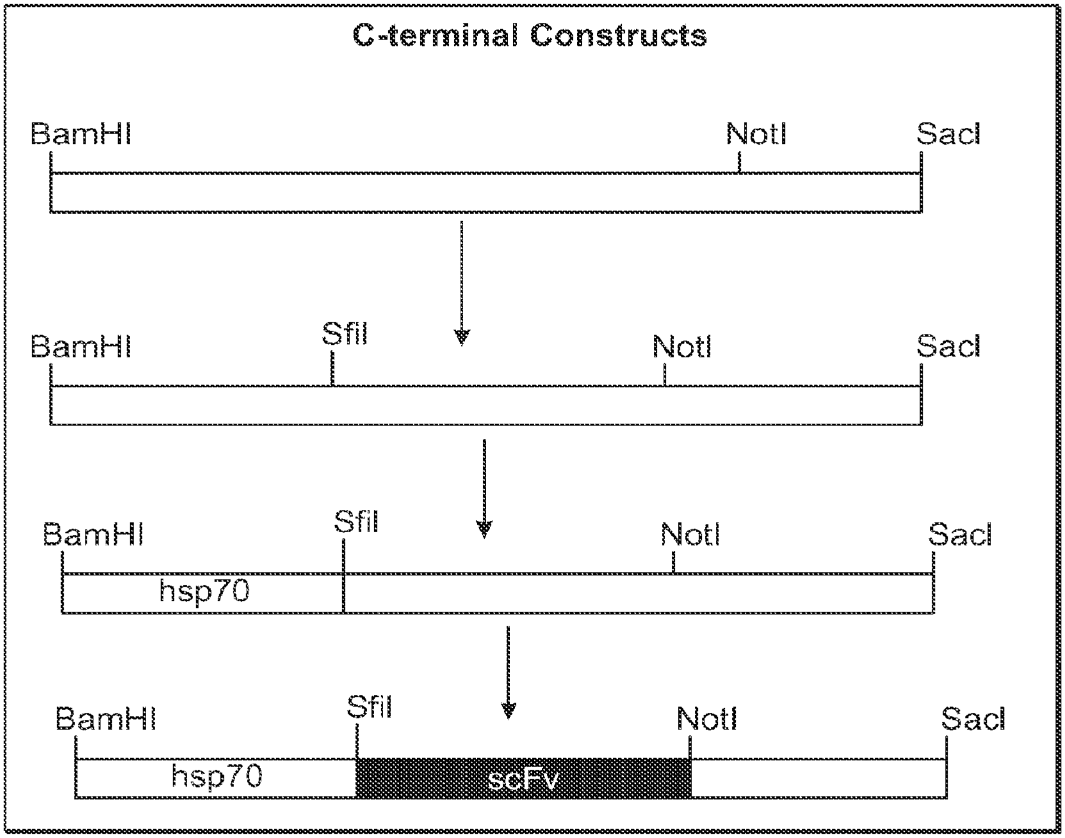
FIG. 18A presents a diagram of an hsp70-scFV fusion protein construct.
Figure 18B:
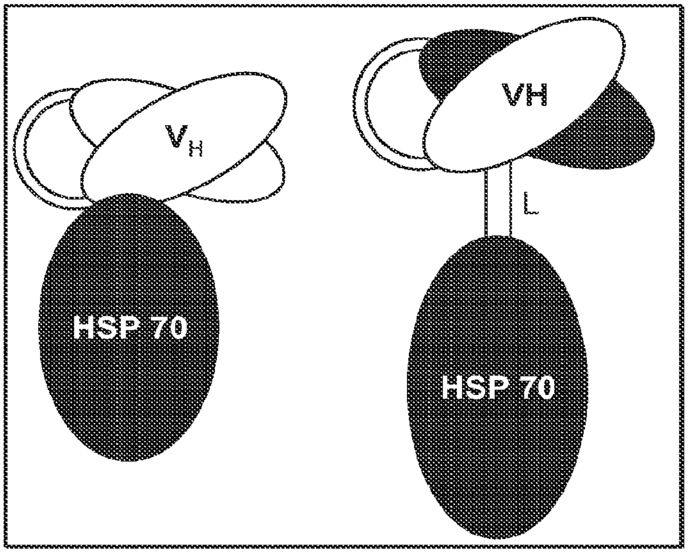
FIG. 18 B presents a diagram of an hsp70-scFV protein.

A fusion protein comprising a stress protein and an engineered mesothelin antibody can be prepared as follows. The anti-mesothelin scFv or mAb fragment is cloned, in frame, at the N-terminal end of a heat shock protein. The sequence encoding the scFv or mAb fragment can be separated from the N-terminus of the heat shock protein by a linker segment (for example a linker comprising (G4S)×3SEQ ID NO: 3).) Similarly, the construct is designed such that the scFv or the mAb fragment is cloned, in frame, at the C-terminal end of a heat shock protein, either directly or via a linker segment located between the heat shock protein C-terminal end and the scFv N-terminal segment. A sample scheme of this approach is depicted in FIG. 18A. FIG. 18B depicts the protein product of the construct described in this example.

Example 2

Production of Mesothelin Antibody (scFv) Binding Protein or Biotin-Binding Protein MTBhsp70/Huhsp70 Constructs The invention provides for constructs that encode 1) engineered mesothelin antibody-stress protein-biotin-binding protein fusions and 2) engineered mesothelin antibody-stress protein-antibody binding protein fusion proteins.

These constructs are designed such that an scFv or Ab binding protein (or peptide) such as Protein A, Protein G, Protein L, or a biotin-binding protein (Avidin, Streptavidin etc.), is cloned, in frame, at the N-terminal end of a heat shock protein. A linker segment may or may not be added between the C-terminal of the scFv/Ab binding protein or of the biotin-binding protein and the N-terminal of the heat shock protein.

In one embodiment the linker is (G4S)×3 (SEQ ID NO: 3).

Alternatively, a construct according to the invention comprises an scFv/Ab binding protein segment or a biotin-binding segment inserted at the C-terminal end of the heat shock protein with or without a linker segment between the C-terminus of the heat shock protein and the N-terminus of the scFv/Ab binding protein segment.

The invention also includes but is not limited to the following linkers. In one embodiment, a linker segment comprises the hinge region from a member of the immunoglobulin gene family such as the CD8α chain depicted below.

| Species | Amino Acid Sequences of CD8α chain Hinge region | SEQ ID NO |
|---|---|---|
| Human | DFLPTTAQPTKKSTLKKRVCRLPRPETQKGPLCSP | 5 |
| Guinea pig | DVLPTTAQPTTKTTPKKKKCQPPSPGPQKGLHCSL | 6 |
| Chicken | DVLPPLPSMSTLVPLTKKPMRCKPKNKAINKKGACTP | 7 |
| Axolotl | DSFPTTAILTTSTPCVGCKEHEETSKGSTKKKGARAGVACSS | 8 |
| rainbow trout | ETRPTLTPVTKPKPPGIPTGRCTKRNYQTPEGCGY | 9 |
| br. trout | ETRPTLTPVTKPKPPGIPTGRCTKRNDQTPKGCGS | 10 |
| salmon | ETRPTLTPVTKPKPPRIPTGRCTKRNDQTPKGCGS | 11 |

Adapted from Moore et al. (Characterization of salmon and trout CD8a and CD8β. Mol Immunol (2005)).

Figure 19A:
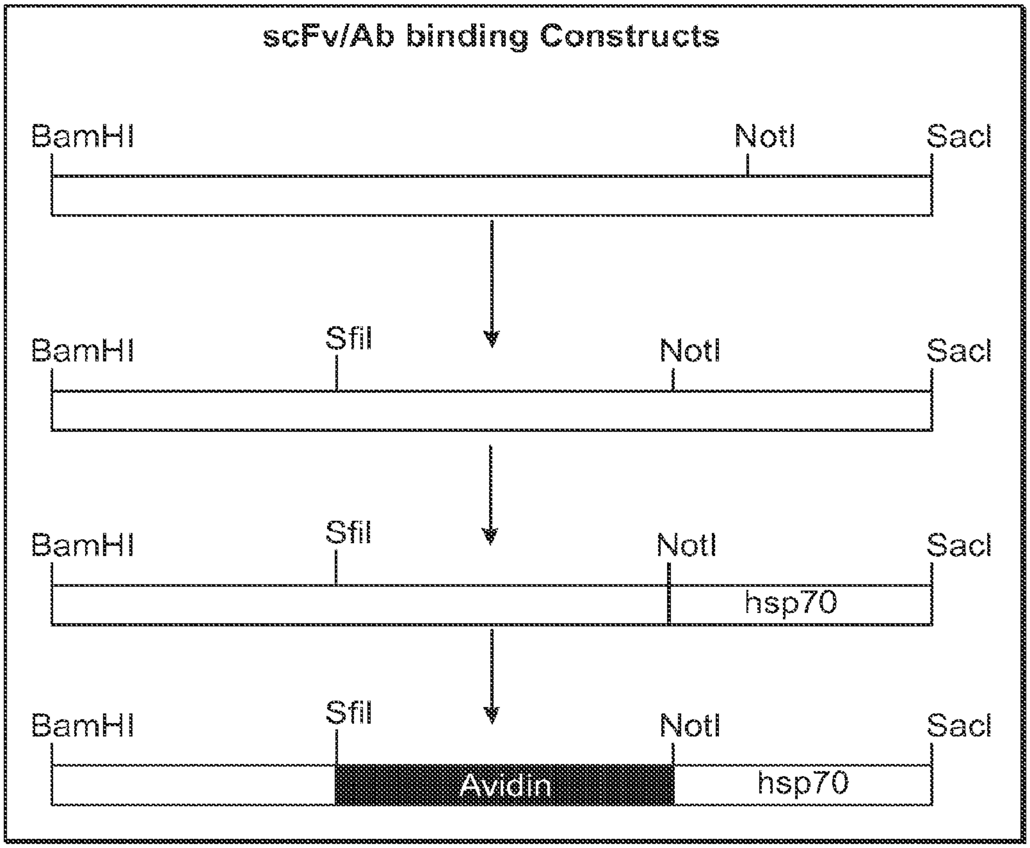
FIG. 19 A presents a diagram of an hsp70-avidin fusion protein construct.
Figure 19B:
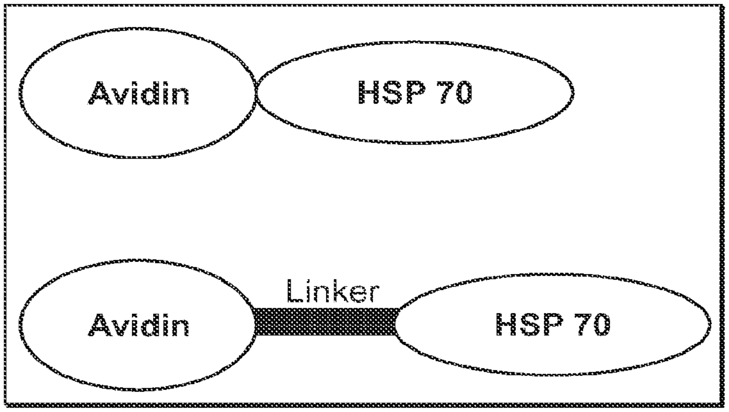

The constructs described herein and the resulting protein product are depicted in FIGS. 19A and 19B, respectively.

Example 3

Production of a Self-Assembling Vaccine

A self-assembling vaccine is prepared by reconstituting a lyophilized biotin-binding protein by the addition of biotinylated peptides, scFv, monoclonal antibodies, cells, and the like. The self-assembling vaccine can be administered to a subject, for example, via subcutaneous injection or intravenously, to induce an immune response. Alternatively, the self-assembling vaccine is administered via sublingual or nasal methods.

Example 4

Induction of an Immune Response

The fusion proteins of the invention are used to induce an immune response to mesothelin in an subject. In one embodiment, the anti-mesothelin antibody-stress protein is injected subcutaneously or intravenously to target tumors expressing high levels of mesothelin on the surface. An immune response to mesothelin is detected by any of the methods described herein, for example by ELISA or by immunohistochemical methods.

I claim:

1. A method for inducing an immune response to mesothelin in a subject comprising administering to the subject a fusion protein comprising a stress protein fused in frame with an engineered antibody or fragment thereof, that binds specifically to mesothelin to induce an immune response.

2. A method of treating cancer in a subject, comprising administering to the subject a fusion protein comprising a stress protein fused in frame with an engineered antibody or fragment thereof, that binds specifically to mesothelin to treat cancer, wherein the cancer is characterized by overexpression of mesothelin in cancer cells.

3. A method for inducing an immune response to mesothelin in a subject, comprising administering to said subject a fusion protein comprising a stress protein fused in frame with a biotin-binding protein in combination with a biotinylated engineered antibody or fragment thereof, that binds specifically to mesothelin, to induce an immune response.

4. A method of treating cancer in a subject, comprising administering to said subject a fusion protein comprising a stress protein fused in frame with a biotin-binding protein in combination with a biotinylated engineered antibody or fragment thereof, that binds specifically to mesothelin, to treat cancer, wherein the cancer is characterized by overexpression of mesothelin in cancer cells.

5. A method for inducing an immune response to mesothelin in a subject, comprising administering to said subject a fusion protein comprising an engineered antibody or fragment thereof, that binds specifically to mesothelin, fused in frame with a biotin binding protein to induce an immune response.

6. A method of treating cancer in a subject, comprising administering to said subject a fusion protein comprising an engineered antibody or fragment thereof, that binds specifically to mesothelin fused in frame with a biotin binding protein to treat cancer, wherein the cancer is characterized by overexpression of mesothelin in cancer cells.

7. The method of any one of claims 1-4 wherein the biotin-binding protein is selected from the group consisting of avidin, streptavidin, and neuravidin.

8. The method of any one of claims 1-4, wherein said biotin-binding protein is non-covalently bound to a biotinylated component.

9. The method of any one of claims 1-4, wherein the biotin binding protein is non-covalently bound to four biotinylated components, and further wherein at least two of the four biotinylated components are not identical.

10. The method of claim 9, wherein at least one of the four biotinylated components is a costimulatory molecule.

11. The method of anyone of claims 1-4, wherein said fusion protein further comprises a linker.

12. The method of claim 11, wherein said linker comprises an amino acid sequence selected from the group consisting of: GGSSRSSSEQ ID NO: 1), (GGGSGGG)×4 (SEQ ID NO: 2), or GGGGSGGGGSGGGGS (SEQ ID NO: 3).

13. A method for inducing an immune response to mesothelin in a subject, comprising administering to said subject a fusion protein comprising a stress protein fused in frame with an antibody binding protein in combination with an engineered antibody or fragment thereof, that binds specifically to mesothelin, to induce an immune response.

14. A method of treating cancer in a subject, comprising administering to said subject a fusion protein comprising a stress protein fused in frame with an antibody binding protein in combination with an engineered antibody or fragment thereof, that binds specifically to mesothelin, to treat cancer, wherein the cancer is characterized by overexpression of mesothelin in cancer cells.

15. A method for inducing an immune response to mesothelin in a subject, comprising administering to said subject a fusion protein comprising an engineered antibody or fragment thereof that binds specifically to mesothelin and an antibody binding protein, wherein the engineered antibody or fragment thereof is fused in frame with the antibody binding protein, to thereby induce an immune response.

16. A method of treating cancer in a subject, comprising administering to said subject a fusion protein comprising an engineered antibody or fragment thereof, that binds specifically to mesothelin fused in frame with an antibody binding protein to treat cancer, wherein the cancer is characterized by overexpression of mesothelin in cancer cells.

17. The method of claim 13 or 14, wherein said antibody binding protein is selected from the group consisting of: protein A, protein G, protein A/G and protein L.

18. The method of anyone of claims 13-14, wherein said fusion protein comprises a linker.

19. The method of claim 18, wherein said linker comprises an amino acid sequence selected from the group consisting of: GGSSRSSSEQ ID NO: 1), (GGGSGGG)×4 (SEQ ID NO: 2), or GGGGSGGGGSGGGGS (SEQ ID NO: 3).

20. The method of claim 2, wherein the cancer is selected from the group consisting of mesothelioma, pancreatic adenocarcinoma, ovarian cancer, lung adenocarcinoma, meningioma, glioma, metastasis to the leptomininges, uterine adenocarcinoma, malignant mesothelioma, and pancreatic cancer.

21. The method of claim 4, wherein the cancer is selected from the group consisting of mesothelioma, pancreatic adenocarcinoma, ovarian cancer, lung adenocarcinoma, meningioma, glioma, metastasis to the leptomininges, uterine adenocarcinoma, malignant mesothelioma, and pancreatic cancer.

22. The method of claim 6, wherein the cancer is selected from the group consisting of mesothelioma, pancreatic adenocarcinoma, ovarian cancer, lung adenocarcinoma, meningioma, glioma, metastasis to the leptomininges, uterine adenocarcinoma, malignant mesothelioma, and pancreatic cancer.

23. The method of claim 14, wherein the cancer is selected from the group consisting of mesothelioma, pancreatic adenocarcinoma, ovarian cancer, lung adenocarcinoma, meningioma, glioma, metastasis to the leptomininges, uterine adenocarcinoma, malignant mesothelioma, and pancreatic cancer.

24. The method of claim 16, wherein the cancer is selected from the group consisting of mesothelioma, pancreatic adenocarcinoma, ovarian cancer, lung adenocarcinoma, meningioma, glioma, metastasis to the leptomininges, uterine adenocarcinoma, malignant mesothelioma, and pancreatic cancer.

* * * * *